(12) United States Patent
Quan et al.

(10) Patent No.: US 6,949,550 B2
(45) Date of Patent: Sep. 27, 2005

(54) SUBSTITUTED AMINO METHYL FACTOR XA INHIBITORS

(75) Inventors: Mimi L. Quan, Newark, DE (US); Ruth R. Wexler, Chaddsford, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/304,810

(22) Filed: Nov. 26, 2002

(65) Prior Publication Data

US 2003/0212054 A1 Nov. 13, 2003

Related U.S. Application Data

(60) Provisional application No. 60/337,051, filed on Dec. 4, 2001.

(51) Int. Cl.[7] .................. A61K 31/4965; A61K 31/495; A61K 31/50; A01N 43/58; A01N 43/60
(52) U.S. Cl. ............. 514/249; 514/255.05; 514/266.23; 514/307; 514/314; 514/341; 514/379; 514/394; 514/397; 514/406; 544/283; 544/333; 544/405; 546/275.4; 548/241; 548/246; 548/306.1; 548/364.4; 548/369.7; 548/371
(58) Field of Search ........................... 514/249, 255.05, 514/266.23, 307, 314, 341, 379, 394, 397, 406; 544/283, 333, 405; 546/275.4; 548/241, 246, 306.1, 364.4, 369.7, 371

(56) References Cited

U.S. PATENT DOCUMENTS

| | | | |
|---|---|---|---|
| 3,340,269 A | 9/1967 | Blatter | 260/296 |
| 3,365,459 A | 1/1968 | Blatter | 260/294.7 |
| 3,423,414 A | 1/1969 | Blatter | 260/296 |
| 5,342,851 A | 8/1994 | Sanfilippo et al. | 514/370 |
| 5,998,424 A | 12/1999 | Galemmo et al. | 514/269 |
| 6,020,357 A | 2/2000 | Pinto et al. | 514/406 |
| 6,060,491 A | 5/2000 | Pruitt et al. | 514/355 |
| 6,191,159 B1 | 2/2001 | Pinto et al. | 514/406 |
| 6,271,237 B1 | 8/2001 | Galemmo et al. | 514/256 |
| 6,667,332 B2 * | 12/2003 | Li et al. | 514/379 |
| 6,706,730 B2 * | 3/2004 | Pinto | 514/303 |
| 2003/0018023 A1 * | 1/2003 | Pinto et al. | 514/215 |
| 2003/0191115 A1 * | 10/2003 | Pinto et al. | 514/224.2 |

FOREIGN PATENT DOCUMENTS

| | | |
|---|---|---|
| WO | WO 9828269 | 7/1998 |
| WO | WO 9828282 | 7/1998 |
| WO | WO 9857934 | 12/1998 |
| WO | WO 9857951 | 12/1998 |
| WO | WO 9932454 | 7/1999 |
| WO | WO 99/32477 | 7/1999 |
| WO | WO 9950255 | 10/1999 |
| WO | WO 0039108 | 7/2000 |
| WO | WO 0039131 | 7/2000 |
| WO | WO 0059902 | 10/2000 |
| WO | WO 0105784 | 1/2001 |
| WO | WO 0119798 | 3/2001 |
| WO | WO 0132628 | 5/2001 |

OTHER PUBLICATIONS

U.S. Appl. No. 60/284,614, filed Apr. 2001, Pinto.*
U.S. Appl. No. 60/324,165, filed Sep. 2001, Pinto et al.*
U.S. Appl. No. 60/278,165, filed Mar. 2001, Pinto et al.*
U.S. Appl. No. 60/234,622, filed Sep. 2000.*

* cited by examiner

Primary Examiner—James O. Wilson
Assistant Examiner—Zachary C. Tucker
(74) Attorney, Agent, or Firm—Jing G. Sun; David H. Vance

(57) ABSTRACT

The present application describes substituted-aminomethyl substituted compounds and derivatives thereof, or pharmaceutically acceptable salt forms thereof, which are useful as inhibitors of factor Xa.

40 Claims, No Drawings

SUBSTITUTED AMINO METHYL FACTOR XA INHIBITORS

CROSS-REFERENCE TO RELATED APPLICATIONS

The present application claims the priority benefit of U.S. Provisional Application No. 60/337,051, filed Dec. 4, 2001, the disclosure of which is incorporated herein by reference in its entirety.

FIELD OF THE INVENTION

This invention relates generally to substituted-aminomethyl substituted compounds, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

U.S. Pat. Nos. 3,365,459, 3,340,269, and 3,423,414 illustrate anti-inflammatory inhibitors of the following formula:

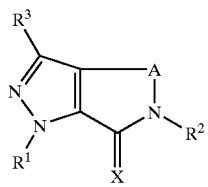

wherein A is 2–3 carbon atoms, X can be O, and $R^1$ and $R^3$ can be substituted or unsubstituted aromatic groups. None of these patents, however, exemplify or suggest compounds of the present invention.

U.S. Pat. No. 5,342,851 depicts thiazole platelet aggregation inhibitors including those of the following formula:

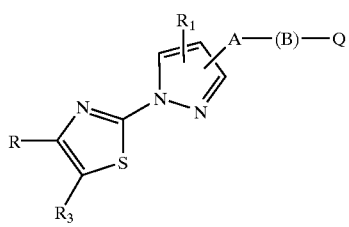

wherein A is a linker, B can be a linker or a ring, Q is a ring or an amino group, R, $R_1$, and $R_3$ are a variety of groups. This patent, however, does not exemplify or suggest compounds of the present invention.

WO00/39131 describes heterobicyclic Factor Xa inhibitors of which the following is an example formula:

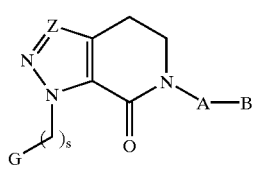

wherein Z is C or N, G is a mono- or bicyclic group, A is a cyclic moiety and B is a basic group or a cyclic moiety. Compounds specifically described in WO00/39131 are not considered to be part of the present invention.

WO98/28269, WO98/28282, WO99/32454, U.S. Pat. No. 6,020,357, and U.S. Pat No. 6,271,237 describe Factor Xa inhibitors of the following formula:

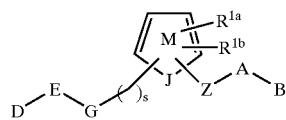

wherein ring M is a heterocycle, Z is a linker, A is a ring, B is a basic or cylic group, D is a basic moiety, and E is a ring. Compounds specifically described in WO098/28269, WO98/28282, WO99/32454, U.S. Pat. Nos. 6,020,357, and U.S. Pat. No. 6,271,237 are not considered to be part of the present invention.

WO98/57951 describes Factor Xa inhibitors of the following formula:

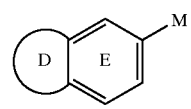

wherein ring M can be a variety of heterocycles and rings D-E represent a heterobicyclic group. Compounds specifically described in WO98/57951 are not considered to be part of the present invention.

WO98/57934 and U.S. Pat. No. 6,060,491 describe Factor Xa inhibitors of the following formula:

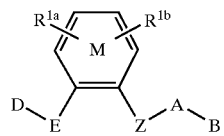

wherein ring M is a 6-membered heteroaryl, Z is a linker, A is a ring, B is a basic or cylic group, D is a basic moiety, and E is a ring. Compounds specifically described in WO98/57934 and U.S. Pat. No. 6,060,491 are not considered to be part of the present invention.

WO98/57937 and U.S. Pat. No. 5,998,424 describe Factor Xa inhibitors of the following formula:

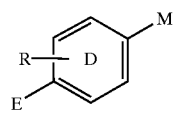

wherein ring M is a variety of rings, ring D is an aromatic ring, and R and E are non-basic groups. Compounds specifically described in WO98/57937 and U.S. Pat. No. 5,998,424 are not considered to be part of the present invention.

WO99/50255 and U.S. Pat. No. 6,191,159 describe pyrazoline and triazoline Factor Xa inhibitors of the following formulas:

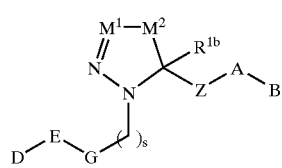

-continued

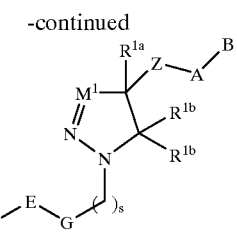

Compounds specifically described in WO99/50255 and U.S. Pat. No. 6,191,159 are not considered to be part of the present invention.

WO00/59902 describes Factor Xa inhibitors of the following formula:

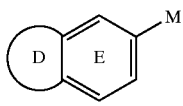

wherein ring M can be a variety of rings all of which are substituted with Z-A-B, Z is a linker, A is a ring, B is a sulfonyl-containing heterobicycle, and rings D-E represent a heterobicyclic group or a 6-membered ring. Compounds specifically described in WO00/59902 are not considered to be part of the present invention.

WO01/32628 describes cyano-pyrroles, cyano-imidazoles, cyano-pyrazoles, and cyano-triazoles that are Factor Xa inhibitors. Compounds specifically described in WO01/32628 are not considered to be part of the present invention.

WO01/05784 describes Factor Xa inhibitors of the following formulas:

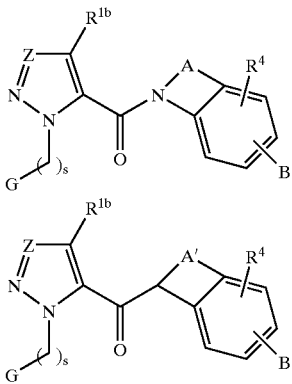

wherein Z is C or N, G is a mono- or bicyclic ring M, A is a linker, B is a basic or cyclic group. Compounds specifically described in WO01/05784 are not considered to be part of the present invention.

WO00/39108 describes Factor Xa inhibitors of the following formula:

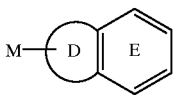

wherein ring M can be a variety of heterocycles and rings D-E represent a heterobicyclic group. Compounds specifically described in WO00/39108 are not considered to be part of the present invention.

WO01/19798 describes factor Xa inhibitors of the following formula:

A-Q-D-E-G-J-X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding, volume of distribution); (e) factors that decrease the liability for clinical drug-drug interactions (e.g., cytochrome P450 enzyme inhibition or induction); (f) factors that decrease the potential for adverse side-effects (e.g., pharmacological selectivity beyond serine proteases, potential chemical or metabolic reactivity, and limited CNS penetration); and, (g) factors that improve manufacturing costs or feasibility (e.g., difficulty of synthesis, number of chiral centers, chemical stability, and ease of handling).

SUMMARY OF THE INVENTION

Accordingly, the present invention provides novel substituted-aminomethyl substituted compounds that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel compounds for use in therapy.

The present invention provides the use of novel compounds for the manufacture of a medicament for the treatment of a thromboembolic disorder.

These and other objects, which will become apparent during the following detailed description, have been achieved by the inventors' discovery that the presently claimed substituted-aminomethyl substituted compounds, or pharmaceutically acceptable salt or prodrug forms thereof, are effective factor Xa inhibitors.

DETAILED DESCRIPTION OF PREFERRED EMBODIMENTS

[1] In an embodiment, the present invention provides a novel compound of formula I:

$$P^4\text{—P-M-M}_4 \qquad \qquad I$$

or a stereoisomer or pharmaceutically acceptable salt thereof, wherein;

M is a 3–10 membered carbocycle or a 4–10 membered heterocycle, consisting of: carbon atoms and 1–3 heteroatoms selected from O, $S(O)_p$, N, and $NZ^2$;

ring M is substituted with 0–3 $R^{1a}$ and 0–2 carbonyl groups, and there are 0–3 ring double bonds;

P is fused onto ring M and is a 5, 6, or 7 membered carbocycle or a 5, 6, or 7 membered heterocycle, consisting of: carbon atoms and 1–3 heteroatoms selected from O, $S(O)_p$, and N;

ring P is substituted with 0–3 $R^{1a}$ and 0–2 carbonyl groups, and there are 0–3 ring double bonds;

alternatively, ring P is absent and $P_4$ is directly attached to ring M;

one of $P_4$ and $M_4$ is -Z-A-B and the other $-G_1-G$, provided that $P_4$ and $M_4$ are attached to different rings when ring P is present;

G is a group of formula IIa or IIb:

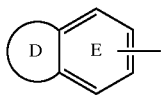

IIa

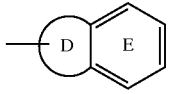

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–1 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

A is selected from:
 $C_{3-10}$ carbocycle substituted with 0–2 $R^4$, and
 5–12 membered heterocycle consisting of: carbon atoms and 1–4 heteroatoms selected from the group consisting of N, O, and $S(O)_p$ and substituted with 0–2 $R^4$;

B is Y or X—Y, provided that Z and B are attached to different atoms on A;

X is selected from $-(CR^2R^{2a})_{1-4}-$, $-CR^2(CR^2R^{2b})(CH_2)_t-$, $-C(O)-$, $-C(=NR^{1b})-$, $-CR^2(NR^{1b}R^2)-$, $-CR^2(OR^2)-$, $-CR^2(SR^2)-$, $-C(O)CR^2R^{2a}-$, $-CR^2R^{2a}C(O)$, $-S-$, $-S(O)-$, $-S(O)_2-$, $-SCR^2R^{2a}-$, $-S(O)CR^2R^{2a}-$, $-S(O)_2CR^2R^{2a}-$, $-CR^2R^{2a}S-$, $-CR^2R^{2a}S(O)-$, $-CR^2R^{2a}S(O)_2-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-NR^2C(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
 $C_{3-10}$ carbocycle substituted with 1 $R^{4a}$ and 0–2 $R^4$, and,
 5–10 membered heterocycle consisting of: carbon atoms and 1–4 heteroatoms selected from the group consisting of N, O, and $S(O)_p$ and substituted with 1 $R^{4a}$ and 0–2 $R^4$;

$G_1$ is absent or is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uN^{3b}(CR^3R^{3a})_w$, $(CR^3R^{3a})_uC(O)N^{3b}(CR^3R^{3a})_w$, $(CR^3R^{3a})_uN^{3b}C(O)(CR^3R^{3a})_w$, $(CR^3R^{3a})_uOC(O)N^{3b}(CR^3R^{3a})_w$, $(CR^3R^{3a})_uN^{3b}C(O)O(CR^3R^{3a})_w$, $(CR^3R^{3a})_uN^{3b}C(O)N^{3b}(CR^3R^{3a})_w$, $(CR^3R^{3a})_uN^{3b}C(S)N^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)N^{3b}(CR^3R^{3a})_w$, $(CR^3R^{3a})_uN^{3b}S(O)_2(CR^3R^{3a})_w$, $(CR^3R^{3a})_uS(O)_2N^{3b}(CR^3R^{3a})_w$, $(CR^3R^{3a})_uN^{3b}S(O)_2N^{3b}(CR^3R^{3a})_w$, $(CR^3R^{3a})_u NR^{3e}(CR^3R^{3a})_w$, $(CR^3R^{3a})_uC(O)(CR^3R^{3a})_uC(O)(CR^3R^{3a})_w$, $(CR^3R^{3a})_u NR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_u C(O)NR^{3b}$ $(CR^3R^{3a})_v$, $(CR^3R^{3a})_uNR^{3b}C(O)(CR^3R^{3a})_uC(O)NR^{3b}(CR^3R^{3a})_w$, $(CR^3R^{3a})_uS(O)NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w total 0, 1, 2, 3, or 4, provided that $G_1$ does not form a N—S, $NCH_2N$, $NCH_2O$, or $NCH_2S$ bond with either group to which it is attached;

Z is selected from a bond, $—(CR^3R^{3e})_{1-4}—$, $(CR^3R^{3e})_qO(CR^3R^{3e})_{q1}$, $(CR^3R^{3e})_qNR^{3b}(CR^3R^{3e})_{q1}$, $(CR^3R^{3e})_qC(O)(CR^3R^{3e})_{q1}$, $(CR^3R^{3e})_qC(O)O(CR^3R^{3e})_{q1}$, $(CR^3R^{3e})_qOC(O)(CR^3R^{3e})_{q1}$, $(CR^3R^{3e})_qC(O)NR^{3b}(CR^3R^{3e})_{q1}$, $(CR^3R^{3e})_qNR^{3b}C(O)(CR^3R^{3e})_{q1}$, $(CR^3R^{3e})_qOC(O)O(CR^3R^{3e})_{q1}$, $(CR^3R^{3e})_qOC(O)NR^{3b}(CR^3R^{3e})_{q1}$, $(CR^3R^{3e})_qNR^{3b}C(O)O(CR^3R^{3e})_{q1}$, $(CR^3R^{3e})_qNR^{3b}C(O)NR^{3b}(CR^3R^{3e})_{q1}$, $(CR^3R^{3e})_qC(O)(CR^3R^{3e})_qC(O)(CR^3R^{3e})_{q1}$, $(CR^3R^{3e})_qNR^{3b}(CR^3R^{3e})_qC(O)NR^{3b}(CR^3R^{3e})_{q1}$, $(CR^3R^{3e})_qNR^{3b}C(O)(CR^3R^{3e})_qC(O)(CR^3R^{3e})_{q1}$, $(CR^3R^{3e})_qC(O)(CR^3R^{3e})_qC(O)NR^{3b}(CR^3R^{3e})_{q1}$, $(CR^3R^{3e})_qNR^{3b}C(O)(CR^3R^{3e})_qC(O)NR^{3b}(CR^3R^{3e})_{q1}$, $(CR^3R^{3e})_qS(CR^3R^{3e})_{q1}$, $(CR^3R^{3e})_qS(O)(CR^3R^{3e})_{q1}$, $(CR^3R^{3e})_qS(O)_2(CR^3R^{3e})_{q1}$, $(CR^3R^{3e})_qSO_2NR^{3b}(CR^3R^{3e})_{q1}$, $(CR^3R^{3e})_qNR^{3b}SO_2(CR^3R^{3e})_{q1}$, $(CR^3R^{3e})_qS(O)NR^{3b}C(O)(CR^3R^{3e})_{q1}$, $(CR^3R^{3e})_qC(O)NR^{3b}S(O)_2(CR^3R^{3e})_{q1}$, and $(CR^3R^{3e})_qNR^{3b}SO_2NR^{3b}(CR^3R^{3e})_{q1}$, wherein q+q1 total 0, 1, 2, 3, or 4, provided that Z does not form a N—S, $NCH_2N$, $NCH_2O$, or $NCH_2S$ bond with either group to which it is attached;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $—(C_{0-4}$ alkyl)-cycloalkyl substituted with 0–3 $R^{1a}$, $—(C_{0-4}$ alkyl)-heterocycle substituted with 0–3 $R^{1a}$, $—(C_{0-4}$ alkyl)-aryl substituted with 0–3 $R^{1a}$, and, $—(C_{0-4}$ alkyl)-heteroaryl substituted with 0–3 $R^{1a}$;

$R^{1a}$, at each occurrence, is selected from H, $—(CR^3R^{3a})_r—R^{1b}$, $—(CR^3R^{3a})_r—CR^3R^{1b}R^{1b}$, $—(CR^3R^{3a})_r—O—(CR^3R^{3a})_r—R^{1b}$, $—(CR^3R^{3a})_r—NR^2—(CR^3R^{3a})_r—R^{1b}$, $—(CR^3R^{3a})_r—S(O)_p—(CR^3R^{3a})_r—R^{1b}$, $—(CR^3R^{3a})_r—CO_2—(CR^3R^{3a})_r—R^{1b}$, $—(CR^3R^{3a})_r—C(O)NR^2—(CR^3R^{3a})_r—R^{1b}$, $—(CR^3R^{3a})_r—C(O)—(CR^3R^{3a})r—R^{1b}$, $—C_{2-6}$ alkenylene-$R^{1b}$, $—C_{2-6}$ alkynylene-$R^{1b}$, and $—(CR^3R^{3a})_r—C(=NR^{1b})NR^3R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, —CN, $—NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, benzyl, $—(CH_2)_r—C_{3-10}$ carbocycle substituted with 0–2 $R^{4b}$, and $—(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl, benzyl, $—(CH_2)_r—C_{3-10}$ carbocycle substituted with 0–2 $R^{4b}$, and $—(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $C_{1-6}$ alkyl substituted with 0–2 $R^{4b}$, $—(CH_2)_r—C_{3-10}$ carbocycle substituted with 0–2 $R^{4b}$, and $—(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, $—(CH_2)_r—C_{3-10}$ carbocycle substituted with 0–2 $R^{4b}$, and $—(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-6}$ alkyl substituted with 0–2 $R^{4c}$, $—(CR^3R^{3a})_r—C_{3-10}$ carbocycle substituted with 0–2 $R^{4c}$, and $—(CR^3R^{3a})_r$-5–10 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N,—$S(O)_pS(O)_p$, S—O, O—N, O—S, or O—O moiety;

$R^{2e}$, at each occurrence, is selected from H, $R^{4c}$, $C_{1-6}$ alkyl substituted with 0–2 $R^{4c}$, $—(CR^3R^{3a})_r—C_{3-10}$ carbocycle substituted with 0–2 $R^{4c}$, and $—(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from $CF_3$, $C_{1-4}$ alkoxy substituted with 0–2 $R^{4b}$, $C_{1-6}$ alkyl substituted with 0–2 $R^{4b}$, $—(CH_2)_r—C_{3-10}$ carbocycle substituted with 0–2 $R^{4b}$, and $—(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_r$-3–6 membered carbocycle, and —$(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_r$ $OR^2$, F, Cl, Br, I, $C_{1-4}$ alkyl, $(CR^3R^{3a})_rCN$, $(CR^3R^{3a})_r$ $NO_2$, $(CR^3R^{3a})_rNR^2R^{2a}$, $(CR^3R^{3a})_rC(O)R^{2c}$, $(CR^3R^{3a})_r$ $NR^2C(O)R^{2b}$, $(CR^3R^{3a})_rC(O)NR^2R^{2a}$, $(CR^3R^{3a})_rNR^2C$ $(O)NR^2R^{2a}$, $(CR^3R^{3a})_rC(=NR^2)NR^2R^{2a}$, $(CR^3R^{3a})_rC$ $(=NS(O)_2R^{5a})NR^2R^{2a}$, $(CR^3R^{3a})_rNHC(=NR^2)NR^2R^{2a}$, $(CR^3R^{3a})_rC(O)NHC(=NR^2)NR^2R^{2a}$, $(CR^3R^{3a})_r$ $SO_2NR^2R^{2a}$, $(CR^3R^{3a})_rNR^2SO_2NR^2R^{2a}$, $(CR^3R^{3a})_r$ $NR^2SO_2$—$C_{1-4}$ alkyl, $(CR^3R^{3a})_rNR^2SO_2R^{5a}$, $(CR^3R^{3a})_r$ $S(O)_pR^{5a}$, $(CR^3R^{3a})_r(CF_2)_rCF_3$, $NHCH_2R^{1b}$, $OCH_2R^{1b}$, $SCH_2R^{1b}$, $N(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $(CR^3R^{3g})_rN(\rightarrow O)R^{2d}R^{2d}$, $(CR^3R^{3g})_v$—$NR^{2d}C(O)R^{2e}$, $(CR^{3R3g})_v$—$C(O)NR^{2d}R^{2d}$, $(CR^3R^{3g})_v$—$NR^{2d}C(O)NR^{2d}R^{2d}$, $(CR^3R^{3g})_v$—$NR^{2d}C(O)OR^{2d}$, $(CR^3R^{3g})_v$—$SO_2NR^{2d}R^{2d}$, $(CR^3R^{3g})_v$—$NR^{2d}SO_2NR^{2d}R^{2d}$, $(CR^3R^{3g})_v$—$C(O)NR^{2d}SO_2R^{2d}$, $(CR^3R^{3g})_v$—$NR^{2d}SO_2R^{2d}$, and $(CR^3R^{3g})_v$—$S(O)_pR^{2d}$, provided that $S(O)_pR^{2d}$ forms other than $S(O)_2H$ or $S(O)H$;

alternatively, $R^{4a}$ is selected from $(CR^3R^{3g})_rNR^{2d}R^{2d}$, $NR^{2d}C(O)R^{2e}$, $C(O)NR^{2d}R^{2d}$, $NR^{2d}C(O)NR^{2d}R^{2d}$, $NR^{2d}C(O)OR^{2d}$, $SO_2NR^{2d}R^{2d}$, $NR^{2d}SO_2NR^{2d}R^{2d}$, $C(O)NR^{2d}SO_2R^{2d}$, $NR^{2d}SO_2R^{2d}$, and $S(O)_pR^{2d}$, provided that at least one of $R^{2d}$ and $R^{2e}$ is alkyl substituted with at least one $R^{4c}$ that is other than alkyl, provided that $S(O)_pR^{2d}$ forms other than $S(O)_2H$ or $S(O)H$;

$R^{4b}$, at each occurrence, is selected from H, =O, $(CH_2)_r$ $OR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r$—$C(O)$ $NR^3R^{3a}$, $(CH_2)_rNR^3C(O)NR^3R^{3a}$, $(CH_2)_r$—$C(=NR^3)$ $NR^3R^{3a}$, $(CH_2)_rNR^3C(=NR^3)NR^3R^{3a}$, $(CH_2)_r$ $SO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rC(O)NHSO_2$—$C_{1-4}$ alkyl, $(CR^3R^{3a})_rNR^2SO_2R^{5a}$, $(CR^3R^{3a})_rS(O)_pR^{5a}$, $(CF_2)_rCF_3$, $(CR^3R^{3a})_r$ $C_{3-10}$ carbocycle substituted with 0–2 $R^{4b}$, and $(CR^3R^{3a})_r$ 5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rCH(=NOR^{3d})$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, $(CF_2)_r$ $CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_r$ $OR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—$C(O)$ bond;

$R^6$, at each occurrence, is selected from H, OH, $(CH_2)_rOR^2$, halo $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2$—$C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-CH_2—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-NH_2—C(O)—, phenyl-NH_2—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

t, at each occurrence, is selected from 0, 1, 2, and 3;

v, at each, occurrence, is selected from 1, 2, 3, 4, 5, and 6; and, provided that when ring M is phenyl and is substituted 1,2 by $M_4$ and $P_4$ and $G_1$ is present, then Z-A is other than NHC(O)-thienyl, $NHCH_2$-thienyl, NHC(O)-benzothienyl, and $NHCH_2$-benzothienyl;

further provided that when (a) P is absent, (b) ring M is a non-aromatic ring with at least one ring N, (c) G-G$_1$ is attached via a ring N, and (d) Z is at least two atoms in length, then Y is other than phenyl or pyridyl.

[2] In a preferred embodiment, the present invention provides a novel compound of Formula II:

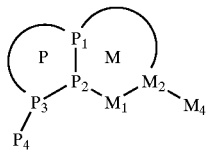

II or a stereoisomer or pharmaceutically acceptable salt thereof, wherein;

ring M, including P$_1$, P$_2$, M$_1$, and M$_2$, is a 5, 6, or 7 membered carbocycle or a 5, 6, or 7 membered heterocycle, consisting of: carbon atoms and 1–3 heteroatoms selected from O, S(O)$_p$, N, and NZ$^2$;

ring M is substituted with 0–2 R$^{1a}$ and 0–2 carbonyl groups, and there are 0–3 ring double bonds;

ring P, including P$_1$, P$_2$, and P$_3$, is a 5 or 6 membered aromatic heterocycle, consisting of: carbon atoms and 1–3 heteroatoms selected from O, S(O)$_p$, and N;

alternatively, ring P, including P$_1$, P$_2$, and P$_3$, is a 5 or 6 membered dihydro-aromatic heterocycle, consisting of: carbon atoms and 1–3 heteroatoms selected from O, S(O)$_p$, and N;

ring P is substituted with 0–2 R$^{1a}$; one of P$_4$ and M$_4$ is -Z-A-B and the other -G$_1$-G;

G is a group of formula IIa or IIb:

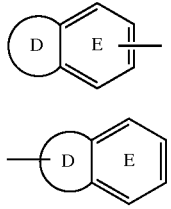

ring D, including the two atoms of Ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with 1 R and with a 5 membered heterocycle consisting of: carbon atoms and 1–4 heteroatoms selected from the group consisting of N, O, and S(O)$_p$, wherein the 5 membered heterocycle is substituted with 0–1 carbonyls and 1–2 R and there are 0–3 ring double bonds;

R is selected from H, C$_{1-4}$ alkyl, F, Cl, OH, OCH$_3$, OCH$_2$CH$_3$, OCH(CH$_3$)$_2$, CN, C(=NH)NH$_2$, C(=NH)NHOH, C(=NH)NHOCH$_3$, NH$_2$, NH(C$_{1-3}$ alkyl), N(C$_{1-3}$ alkyl)$_2$, C(=NH)NH$_2$, CH$_2$NH$_2$, CH$_2$NH(C$_{1-3}$ alkyl), CH$_2$N(C$_{1-3}$ alkyl)$_2$, (CR$^8$R$^9$)$_r$NR$^7$R$^8$, C(O)NR$^7$R$^8$, CH$_2$C(O)NR$^7$R$^8$, S(O)$_2$R$^3$, S(O)$_p$NR$^7$R$^8$, CH$_2$S(O)$_p$NR$^7$R$^8$, and OCF$_3$;

alternatively, when 2 R groups are attached to adjacent atoms, they combine to form methylenedioxy or ethylenedioxy;

A is selected from:
C$_{5-10}$ carbocycle substituted with 0–2 R$^4$, and
5–10 membered heterocycle consisting of: carbon atoms and 1–4 heteroatoms selected from the group consisting of N, O, and S(O)$_p$ and substituted with 0–2 R$^4$;

X is selected from —(CR$^2$R$^{2a}$)$_{1-4}$—, —C(O)—, —C(=NR$^{1b}$)—, —CR$^2$(NR$^{1b}$R$^2$)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from one of the following carbocyclic and heterocycles that are substituted with 1 R$^{4a}$ and 0–2 R$^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

Z is selected from a bond, CH$_2$, CH$_2$CH$_2$, CH$_2$O, OCH$_2$, C(O), NH, CH$_2$NH, NHCH$_2$, CH$_2$C(O), C(O)CH$_2$, C(O)NH, NHC(O), NHC(O)CH$_2$C(O)NH, S(O)$_2$, CH$_2$S(O)$_2$, S(O)$_2$(CH$_2$), SO$_2$NH, and NHSO$_2$, provided that Z does not form a N—S, NCH$_2$N, NCH$_2$O, or NCH$_2$S bond with either group to which it is attached;

Z$^2$ is selected from H, C$_{1-4}$ alkyl, phenyl, benzyl, C(O)R$^{3b}$, S(O)R$^{3f}$, and S(O)$_2$R$^{3f}$;

R$^{1a}$, at each occurrence, is selected from H, —(CH$_2$)$_r$—R$^{1b}$, —(CH(CH$_3$))$_r$—R$^{1b}$, —(C(CH$_3$)$_2$)$_r$—R$^{1b}$, —O—(CR$^3$R$^{3a}$)$_r$—R$^{1b}$, —NR$^2$—(CR$^3$R$^{3a}$)$_r$—R$^{1b}$, and —S—(CR$^3$R$^{3a}$)$_r$—R$^{1b}$, provided that R$^{1a}$ forms other than an N-halo, N—S, O—O, or N—CN bond;

alternatively, when two R$^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and S(O)$_p$, this ring being substituted with 0–2 R$^{4b}$ and comprising: 0–3 double ring bonds;

R$^{1b}$ is selected from H, CH$_3$, CH$_2$CH$_3$, CH$_2$CH$_2$CH$_3$, CH(CH$_3$)$_2$, F, Cl, Br, I, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, NR$^2$C(O)NHR$^2$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, C$_{5-6}$ carbocycle substituted with 0–2 R$^{4b}$, and 5–6 membered heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

R$^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, a C$_{5-6}$ carbocyclic-CH$_2$-group substituted with 0–2 R$^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p-S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or $C(O)-S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence; is selected from H, $CH_3$, $CH_2CH_3$, $CH_2CH_2CH_3$, $CH(CH_3)_2$, cyclopropyl, cyclopropylmethyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4a}$ is selected from $(CR^3R^{3g})_v N(\rightarrow O)R^{2d}R^{2d}$, $(CR^3R^{3g})_v-NR^{2d}C(O)R^{2e}$, $(CR^3R^{3g})_v-NR^{2d}C(O)NR^{2d}R^{2d}$, $(CR^3R^{3g})_v-NR^{2d}C(O)OR^{2d}$, $(CR^3R^{3g})_v-NR^{2d}SO_2NR^{2d}R^{2d}$, and $(CR^3R^{3g})_v-NR^{2d}SO_2R^{2d}$;

alternatively, $R^{4a}$ is selected from $(CR^3R^{3g})_r NR^{2d}R^{2d}$, $NR^{2d}C(O)R^{2e}$, $NR^{2d}C(O)NR^{2d}R^{2d}$, $NR^{2d}C(O)OR^{2d}$, $NR^{2d}SO_2NR^{2d}R^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2R^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2-C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2-C_{1-4}$ alkyl, $CH_2NR^3SO_2-C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, $CF_3$, and $CH_2-CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2-C_{1-4}$ alkyl;

r, at each occurrence, is selected from 0, 1, and 2; and, v, at each occurrence, is selected from 1, 2, and 3.

[3] In another preferred embodiment, the present invention provides a novel compound, wherein:

ring M is substituted with 0–2 $R^{1a}$ and is selected from the group:

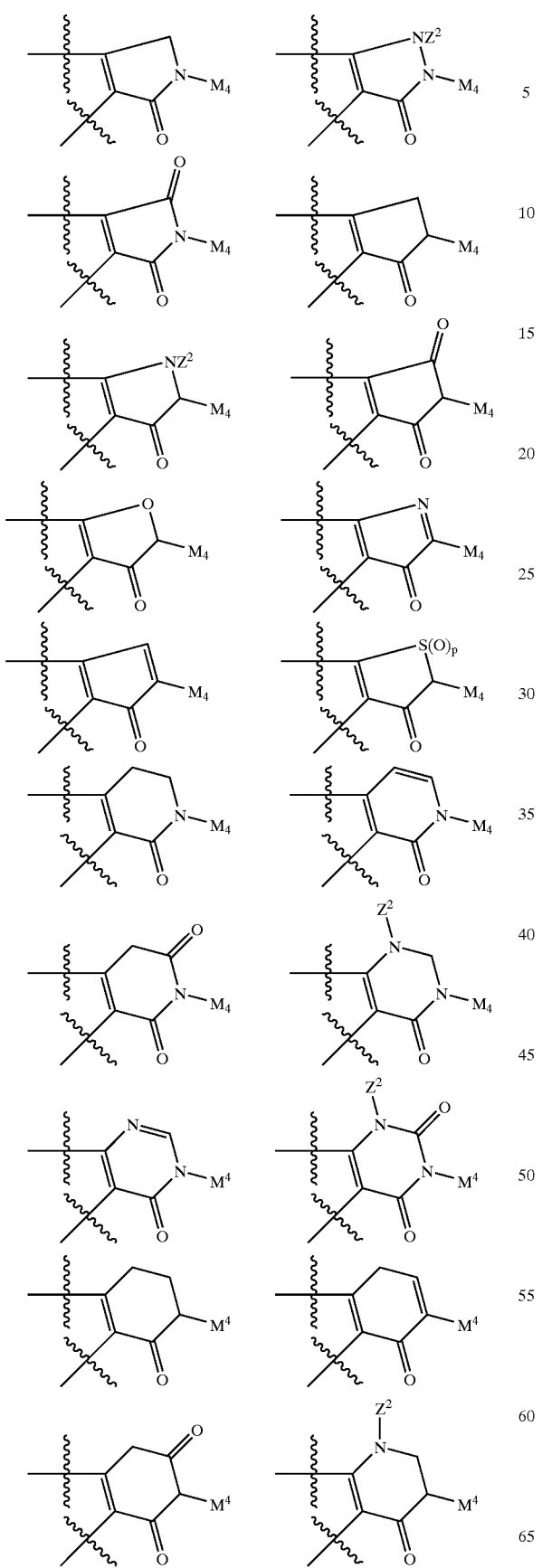
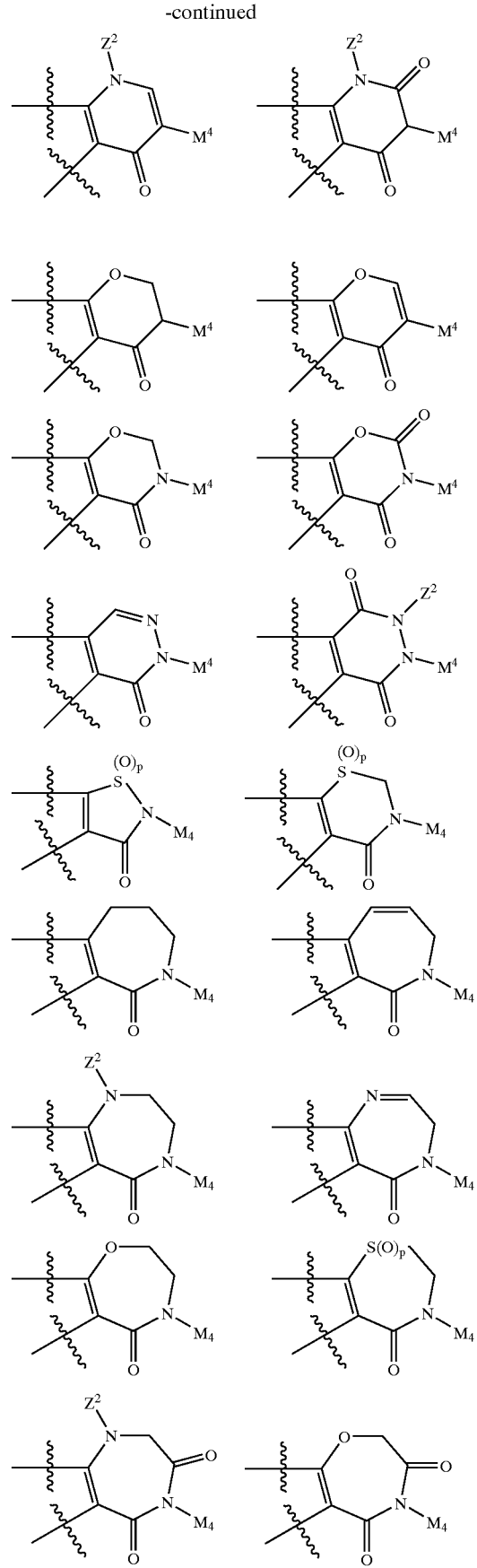

-continued

-continued
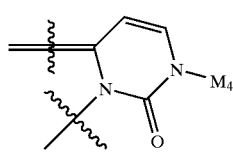 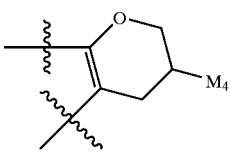
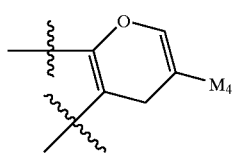 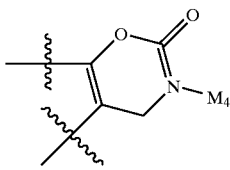
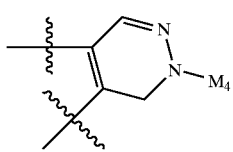 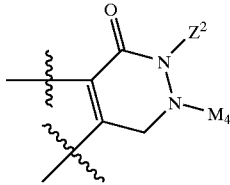
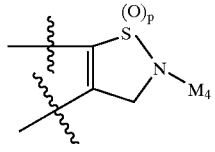 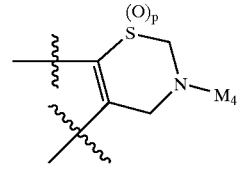
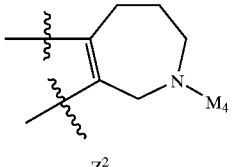 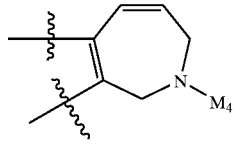
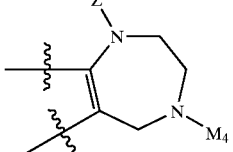 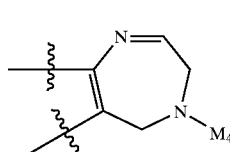
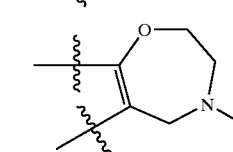 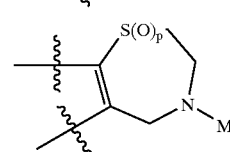
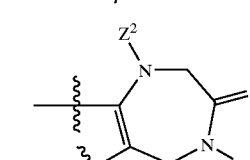 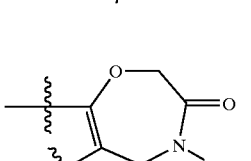
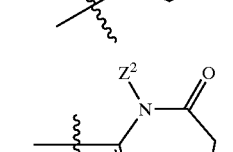 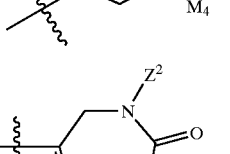
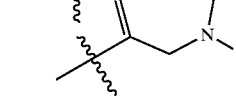 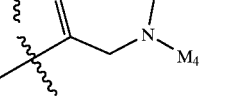
-continued
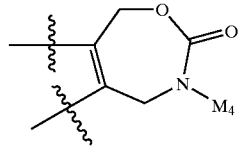 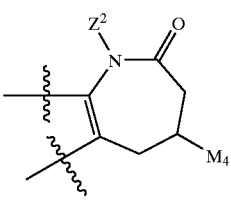
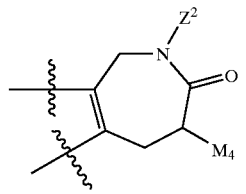 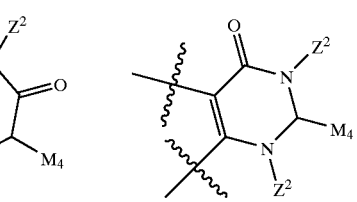
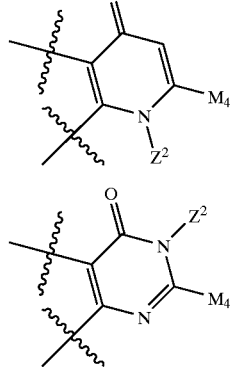 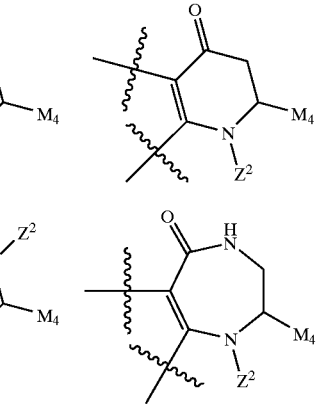
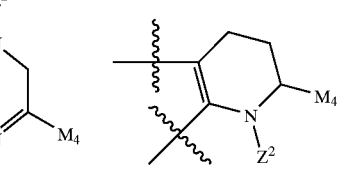
ring P, including $P_1$, $P_2$, $P_3$, and $P_4$ is selected from group:
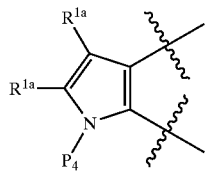 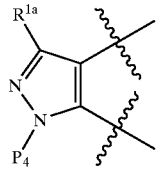
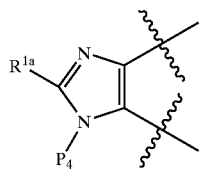 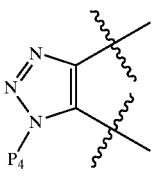

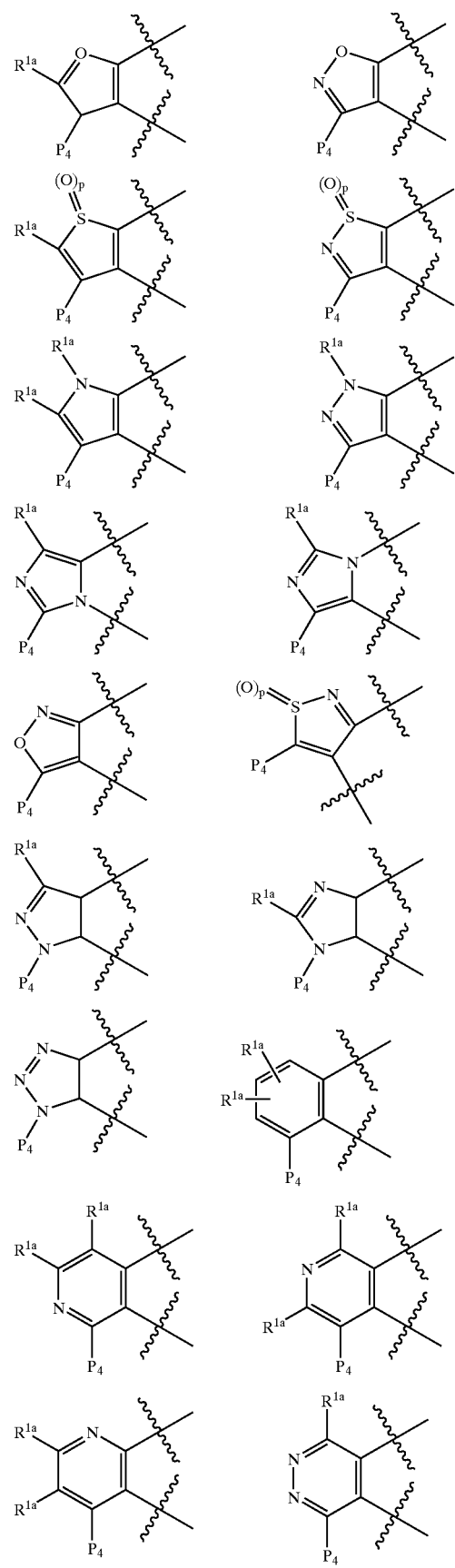
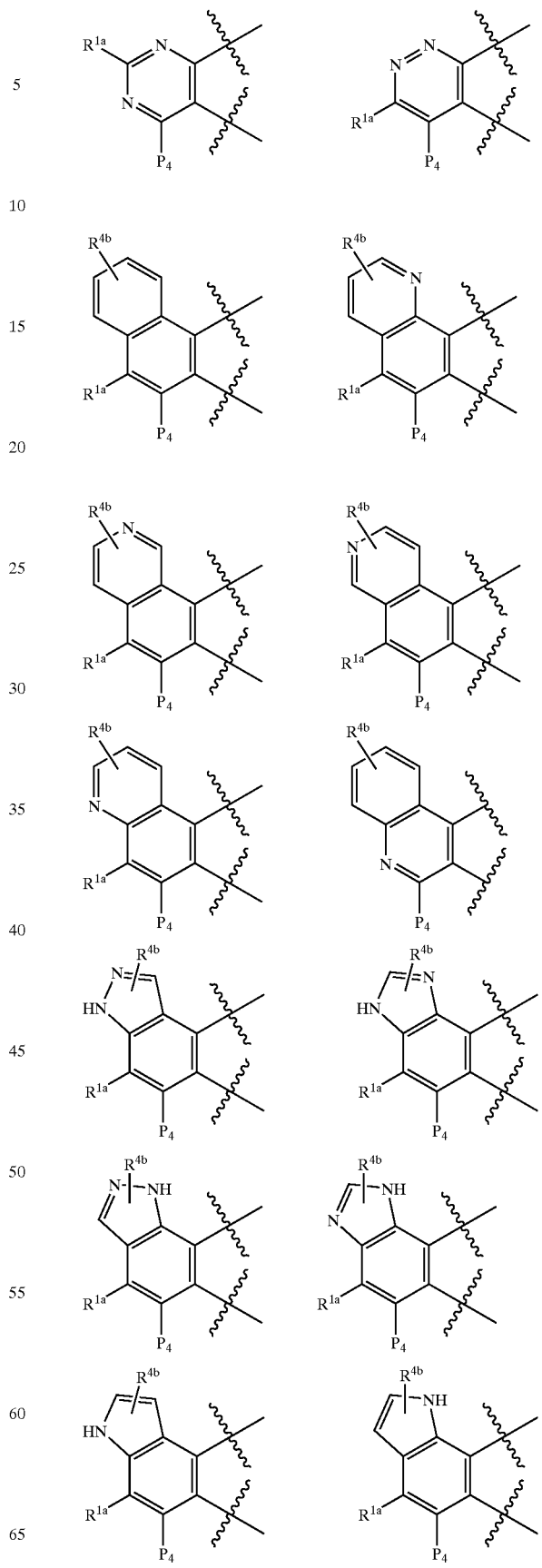

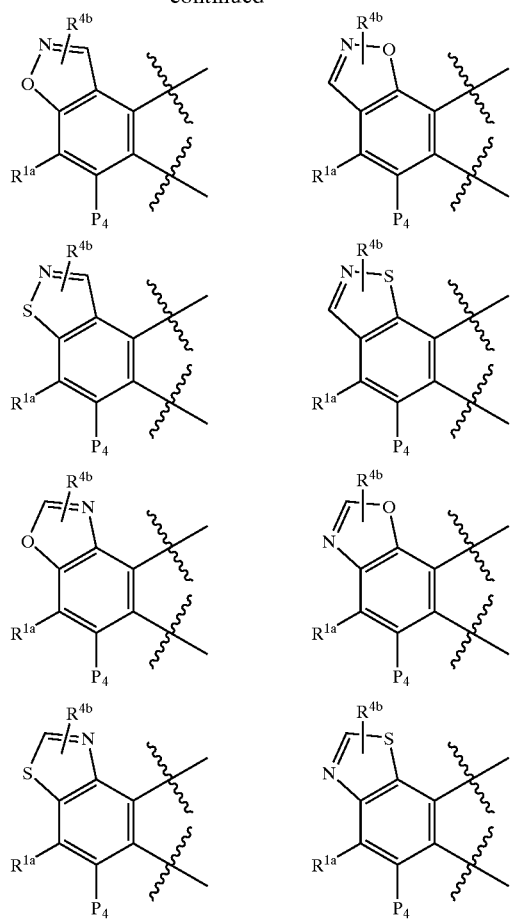
one of $P_4$ and $M_4$ is -Z-A-B and the other -$G_1$-G;
G is selected from the group:
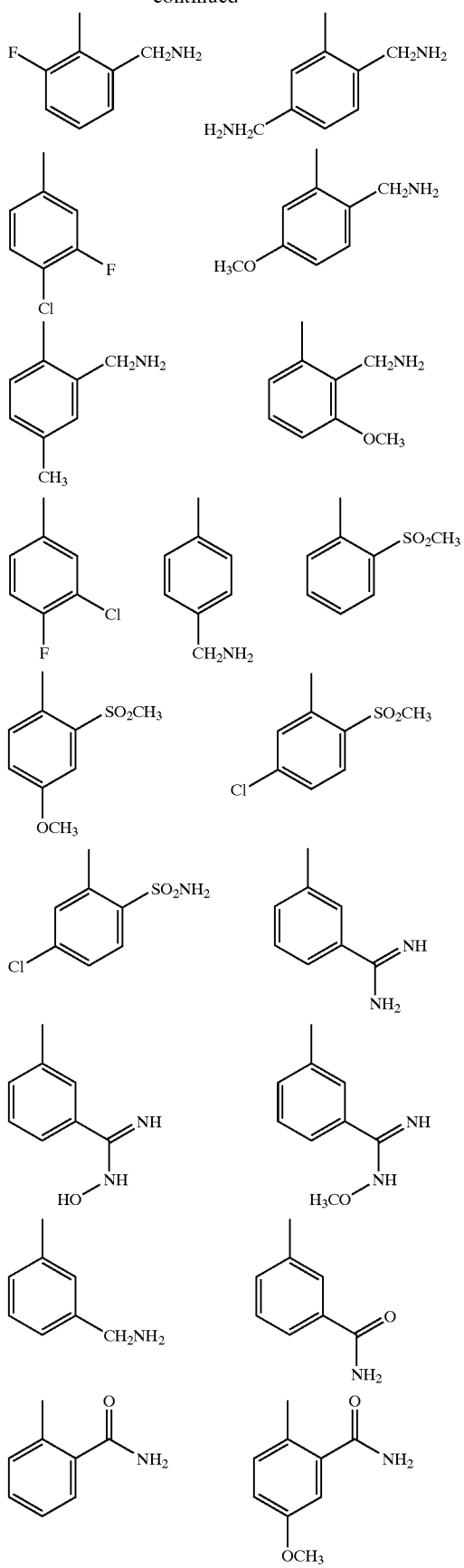

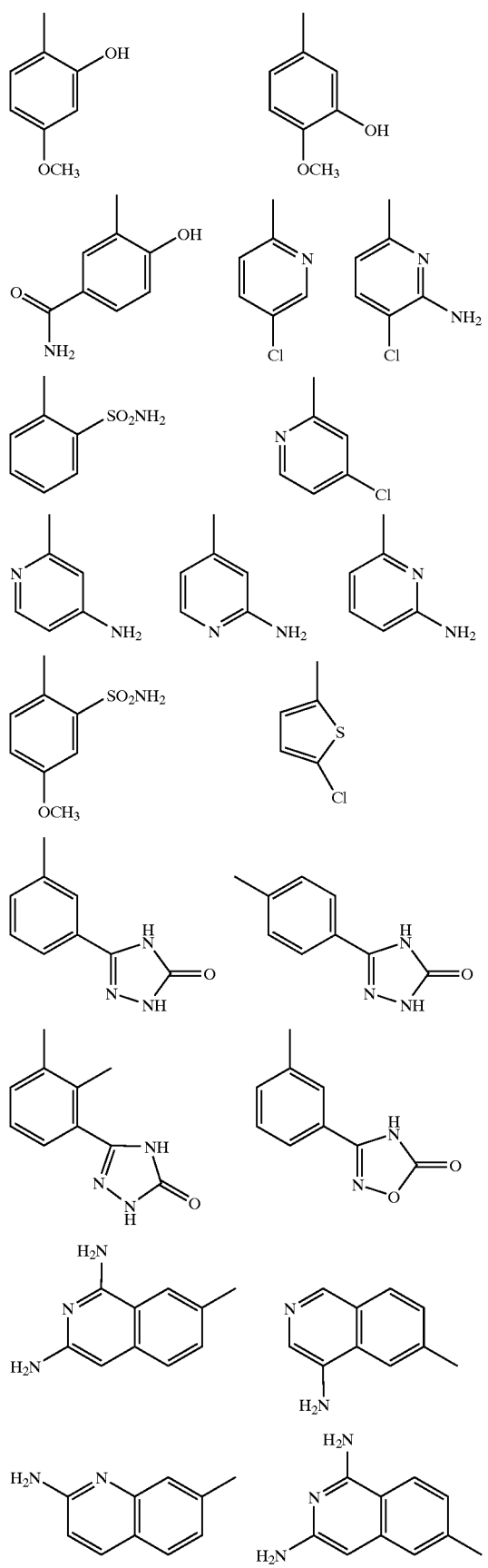
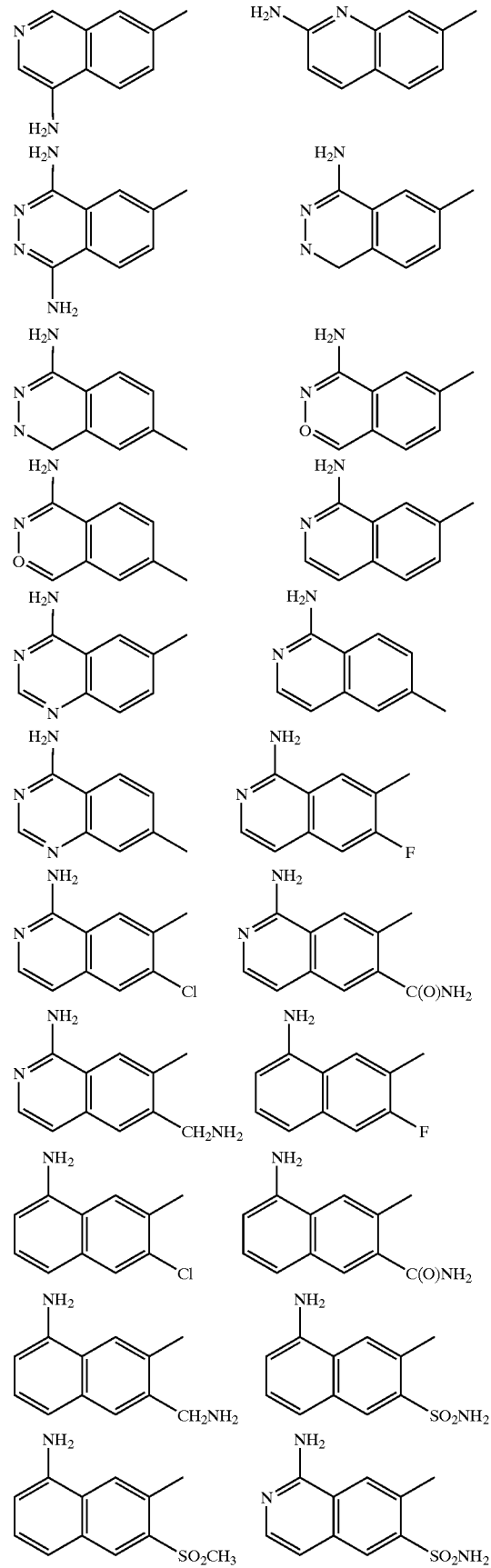

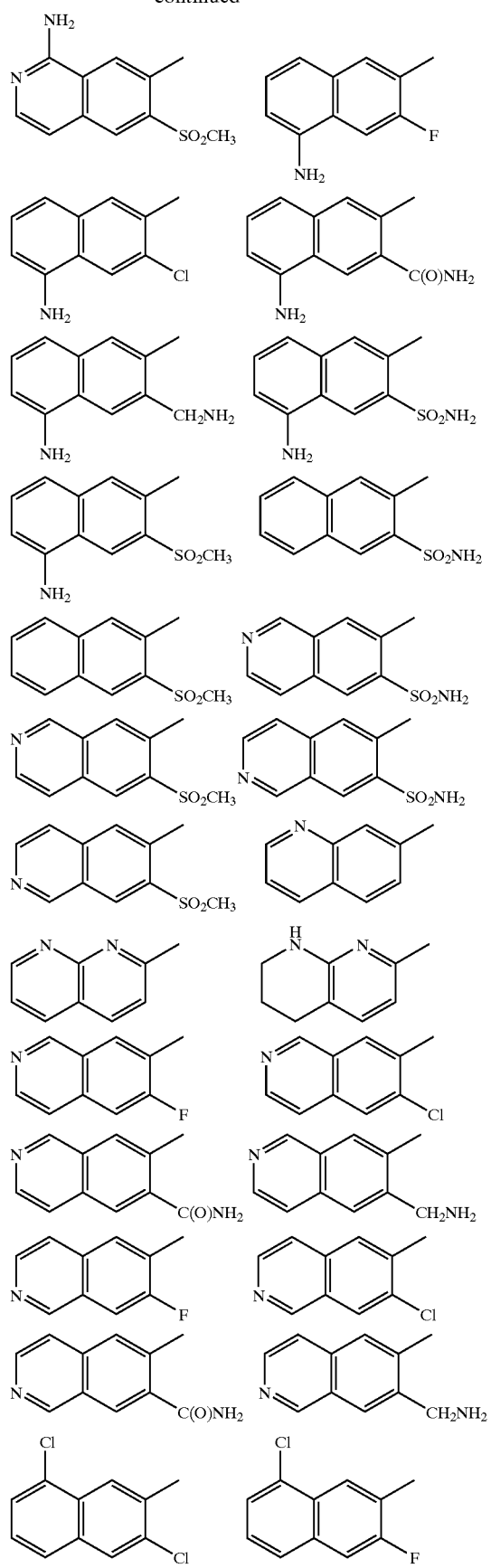
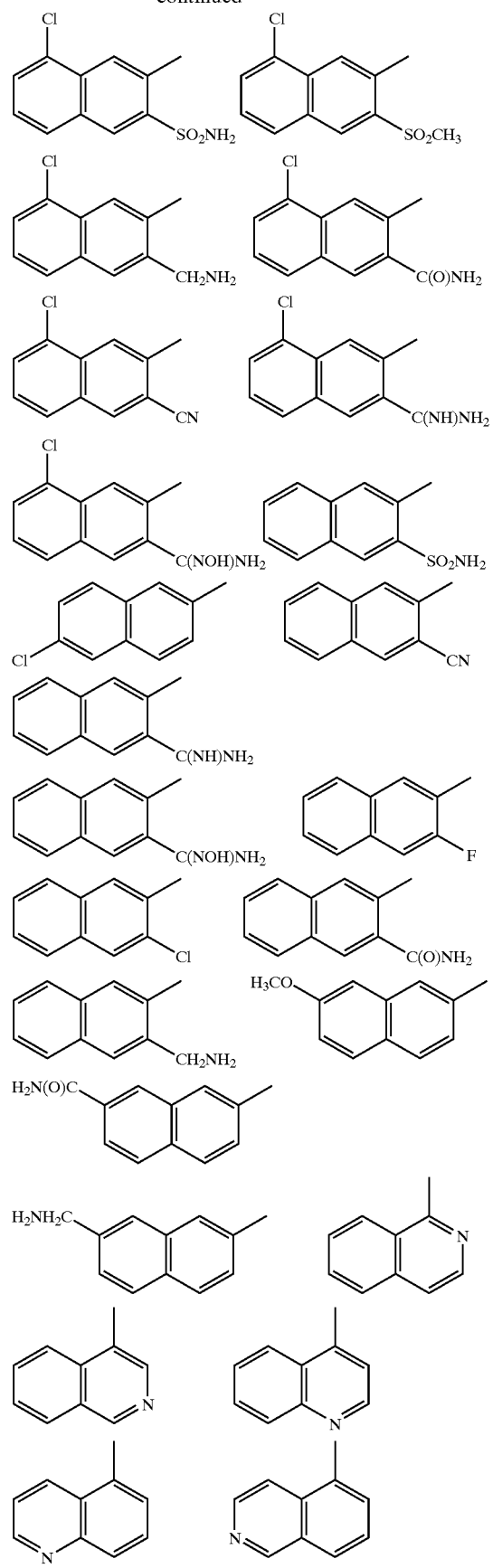

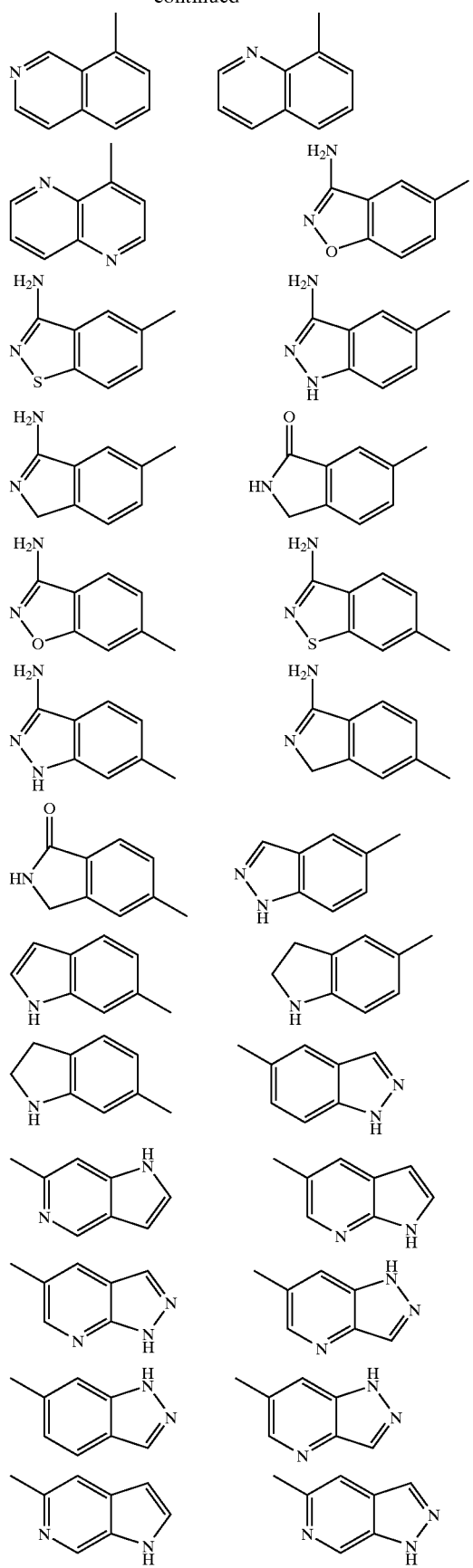
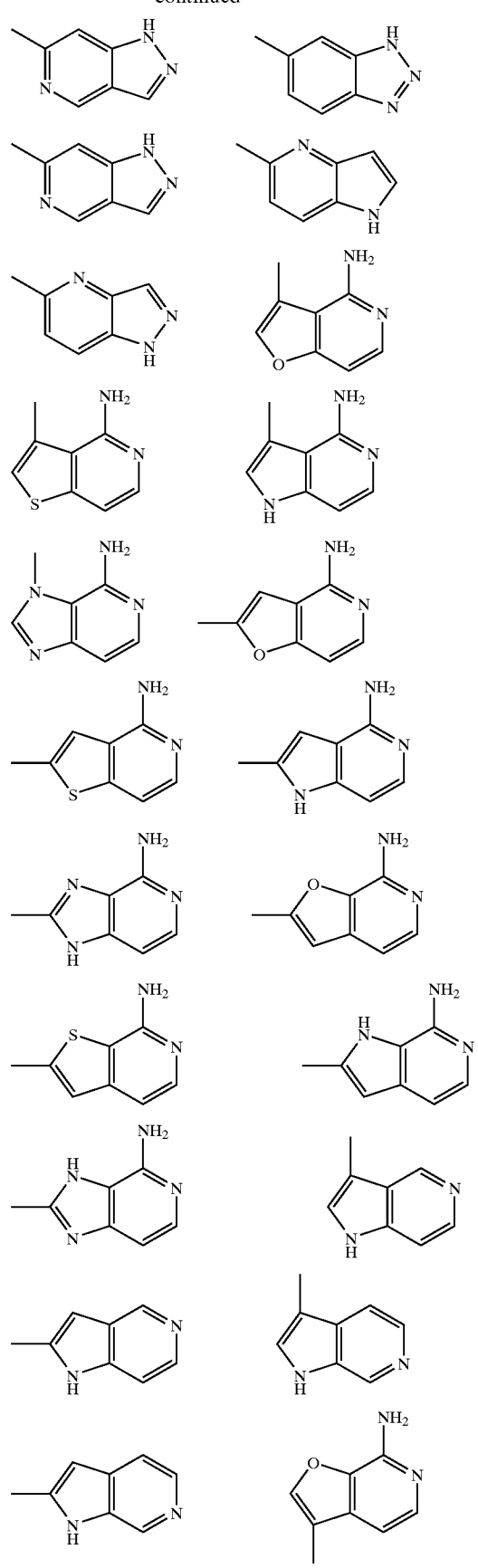

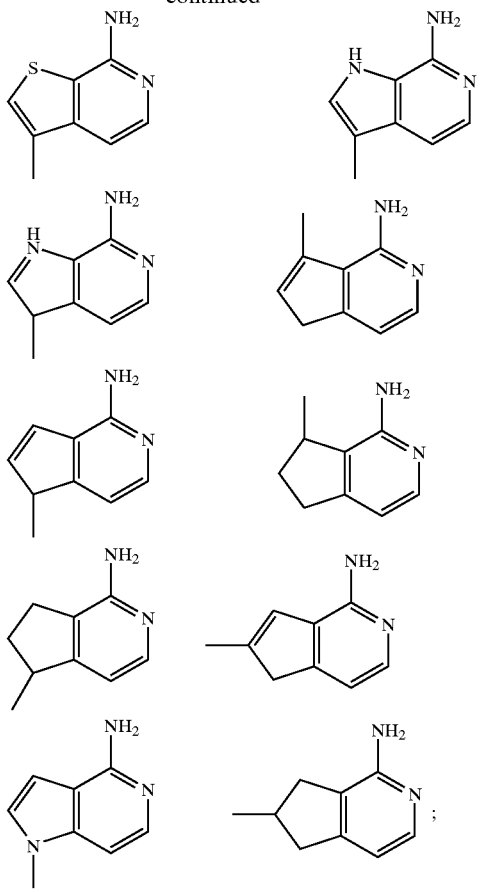

G$_1$ is absent or is selected from (CR$^3$R$^{3a}$)$_{1-3}$, (CR$^3$R$^{3a}$)$_u$C(O)(CR$^3$R$^{3a}$)$_w$, (CR$^3$R$^{3a}$)$_u$O(CR$^3$R$^{3a}$)$_w$, (CR$^3$R$^{3a}$)$_u$NR$^{3b}$(CR$^3$R$^{3a}$)$_w$, (CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_w$, (CR$^3$R$^{3a}$)$_u$NR$^{3b}$C(O)(CR$^3$R$^{3a}$)$_u$C(O)NR$^{3b}$(CR$^3$R$^{3a}$)$_w$, (CR$^3$R$^{3a}$)$_u$S(CR$^3$R$^{3a}$)$_w$, (CR$^3$R$^{3a}$)$_u$S(O)(CR$^3$R$^{3a}$)$_w$, (CR$^3$R$^{3a}$)$_u$S(O)$_2$(CR$^3$R$^{3a}$)$_w$, (CR$^3$R$^{3a}$)$_u$S(O)NR$^{3b}$(CR$^3$R$^{3a}$)$_w$, (CR$^3$R$^{3a}$)$_u$NR$^{3b}$S(O)$_2$(CR$^3$R$^{3a}$)$_w$, and (CR$^3$R$^{3a}$)$_u$S(O)$_2$NR$^{3b}$(CR$^3$R$^{3a}$)$_w$, wherein u+w total 0, 1, or 2, provided that G$_1$ does not form a N—S, NCH$_2$N, NCH$_2$O, or NCH$_2$S bond with either group to which it is attached;

R$^{1a}$ is selected from H, R$^{1b}$, CH(CH$_3$)R$^{1b}$, C(CH$_3$)$_2$R$^{1b}$, CH$_2$R$^{1b}$, and CH$_2$CH$_2$R$^{1b}$, provided that R$^{1a}$ forms other than an N-halo, N—S, or N—CN bond;

alternatively, when two R$^{1a}$ groups are attached to adjacent atoms, together with the atoms to which they are attached they form a 5–6 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, CH$_3$, CH$_2$CH$_3$, F, Cl, Br, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, C(O)NR$^2$R$^{2a}$, SO$_2$NR$^2$R$^{2a}$, NR$^2$SO$_2$R$^2$, phenyl substituted with 0–2 R$^{4b}$, and 5–6 membered aromatic heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

A is selected from one of the following carbocyclic and heterocyclic groups which are substituted with 0–2 R$^4$;

phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

X is selected from —C(O)—, —C(=NR$^{1b}$)—, —C(O)NR$^2$—, —NR$^2$C(O)—, —NR$^2$C(O)CR$^2$R$^{2a}$—, —NR$^2$C(O)NR$^2$—, and O;

Y is selected from one of the following carbocyclic and heterocycles that are substituted with 1 R$^{4a}$ and 0–1 R$^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

R$^2$, at each occurrence, is selected from H, CF$_3$, CH$_3$, CH$_2$CH$_3$, CH$_2$CH$_2$CH$_3$, CH(CH$_3$)$_2$, phenyl substituted with 0–2 R$^{4b}$, a benzyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

R$^{2a}$, at each occurrence, is selected from H, CF$_3$, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–2 R$^{4b}$, and 5–6 membered aromatic heterocycle containing from 1–4 heteroatoms selected from the group consisting of N, O, and S(O)$_p$ and substituted with 0–2 R$^{4b}$;

R$^{2d}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CR$^3$R$^{3a}$)—C$_{3-6}$ carbocycle substituted with 0–2 R$^{4c}$, 5–6 membered heterocycle consisting of: carbon atoms and 1–4 heteroatoms selected from the group consisting of N, O, and S(O)$_p$ and substituted with 0–2 R$^{4c}$, and —(CR$^3$R$^{3a}$)-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—S $(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from $(CH_2)_vN(\rightarrow O)R^{2d}R^{2d}$, $(CH_2)_v$—$NR^{2d}C(O)R^{2e}$, $(CH_2)_v$—$NR^{2d}C(O)NR^{2d}R^{2d}$, $(CH_2)_v$—$NR^{2d}C(O)OR^{2d}$, and $(CH_2)_v$—$NR^{2d}SO_2R^{2d}$;

alternatively, $R^{4a}$ is selected from $(CH_2)_vNR^{2d}R^{2d}$, $NR^{2d}C(O)R^{2e}$, $NR^{2d}C(O)NR^{2d}R^{2d}$, $NR^{2d}C(O)OR^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3_1$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$-alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$ 5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2$—$C_{1-4}$ alkyl; and, v, at each occurrence, is selected from 1 and 2.

[4] In another preferred embodiment, the present invention provides a novel compound, wherein:

ring M is substituted with 0–2 $R^{1a}$ and is selected from the group:

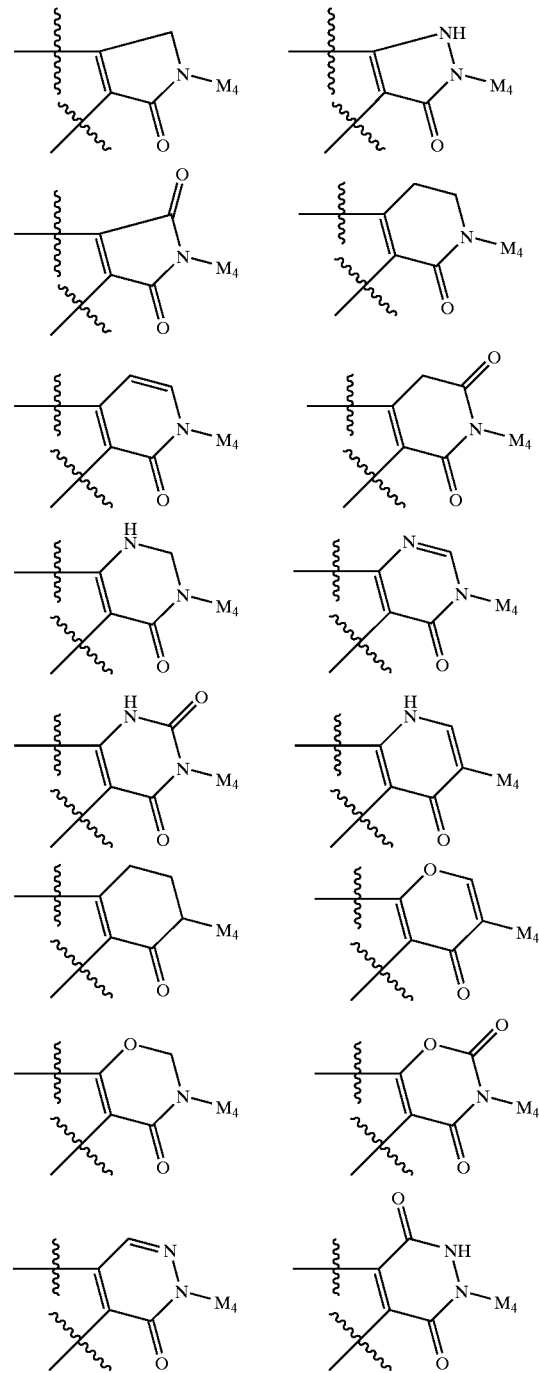

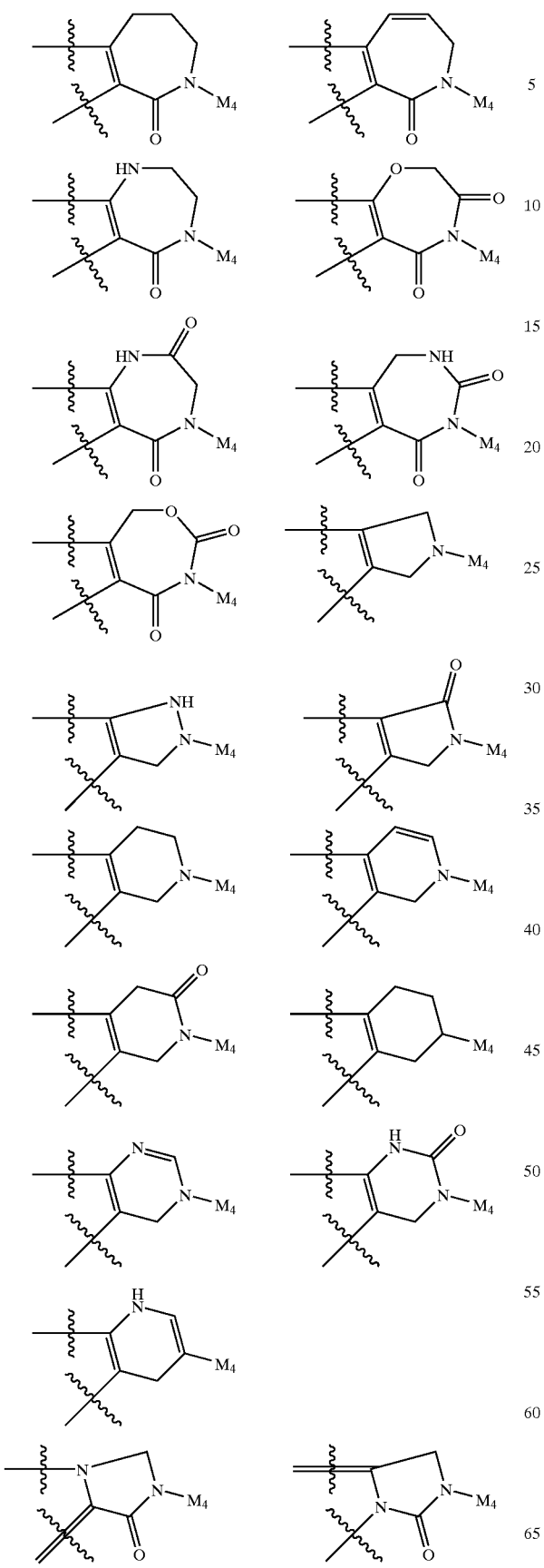
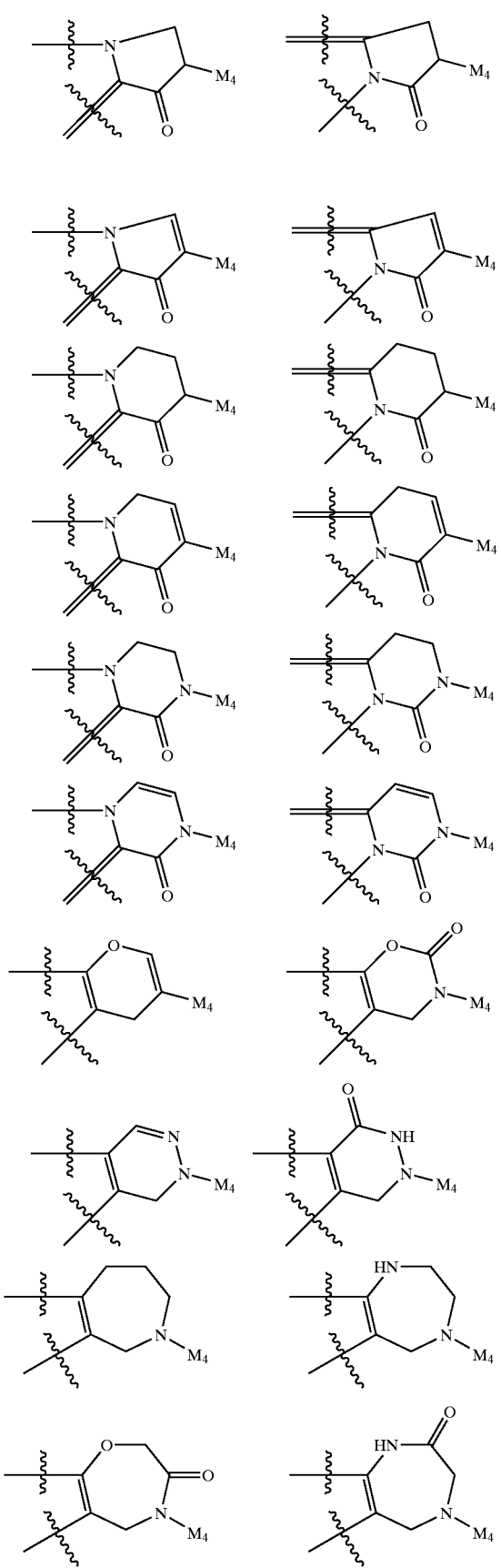

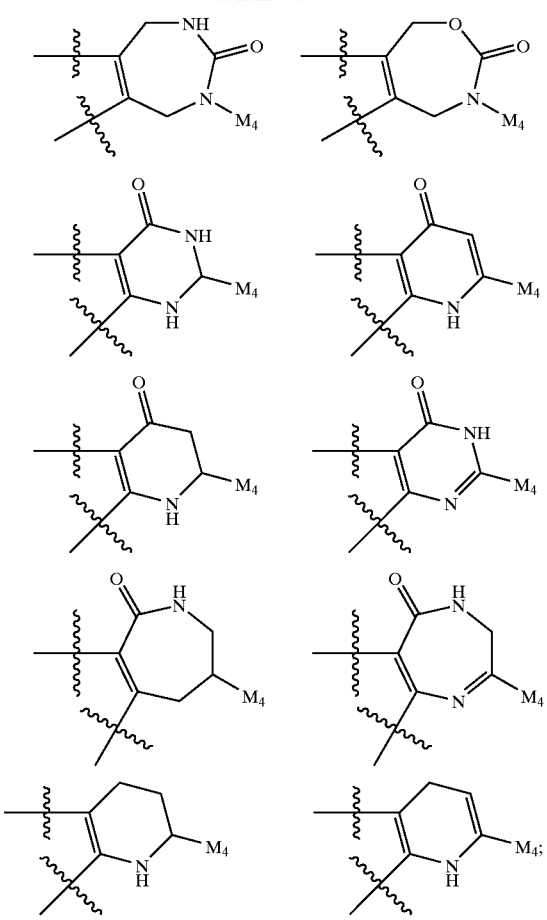
ring P, including $P_1$, $P_2$, $P_3$, and $P_4$ is selected from group:
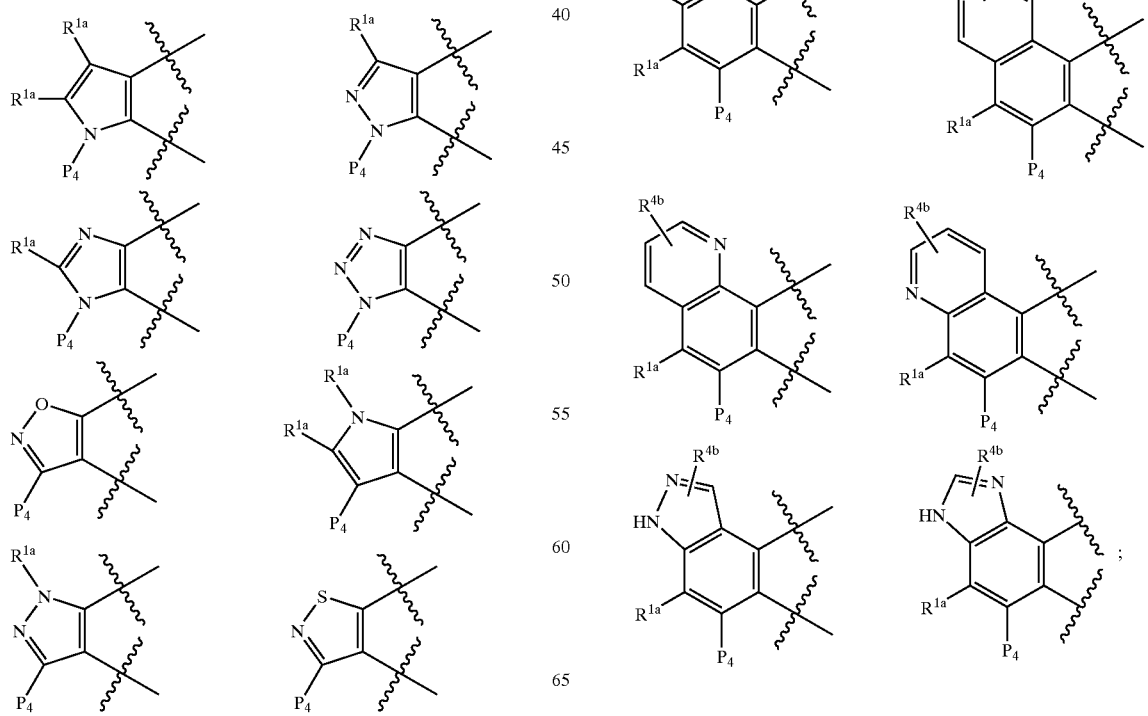
one of $P_4$ and $M_4$ is -A-B and the other -G;

G is selected from the group:
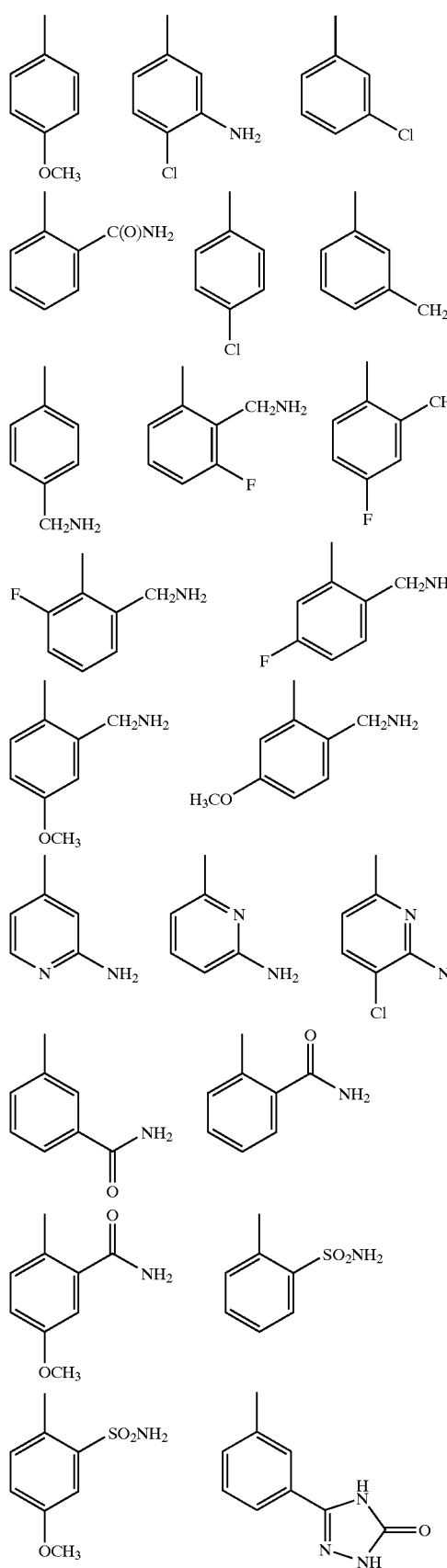
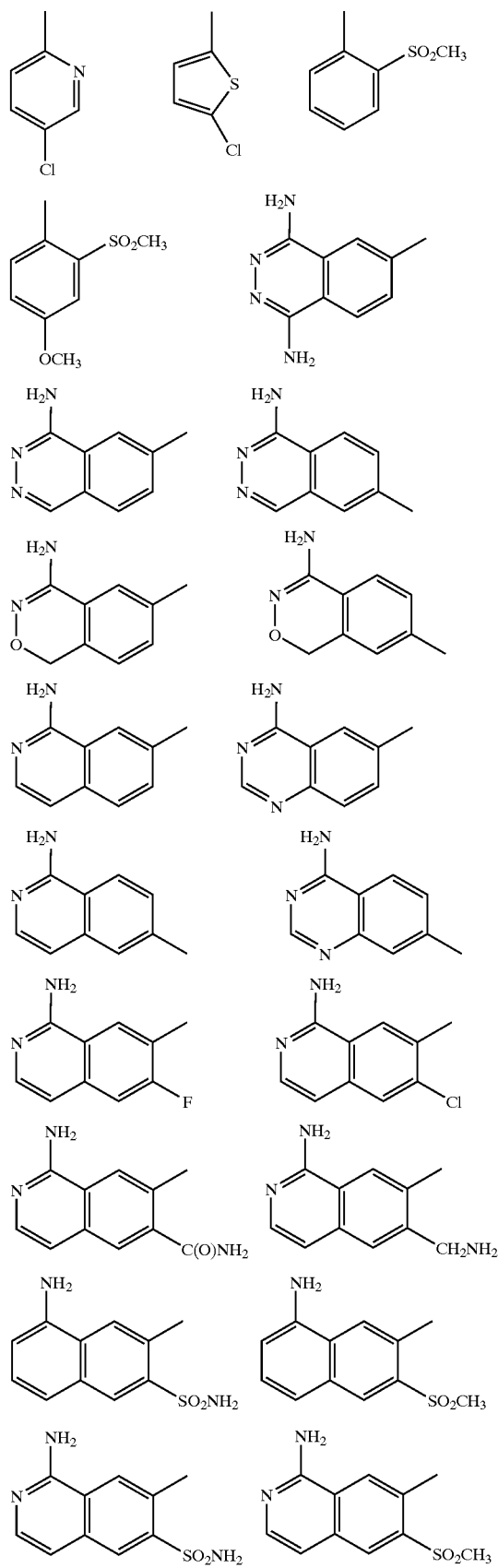

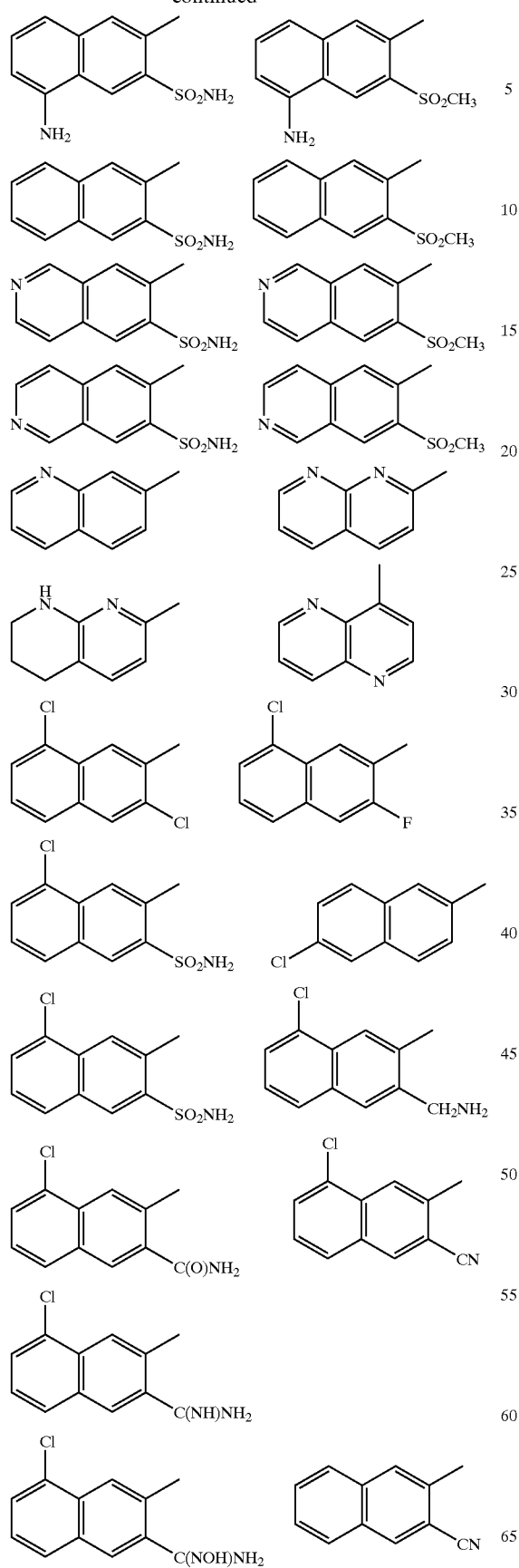
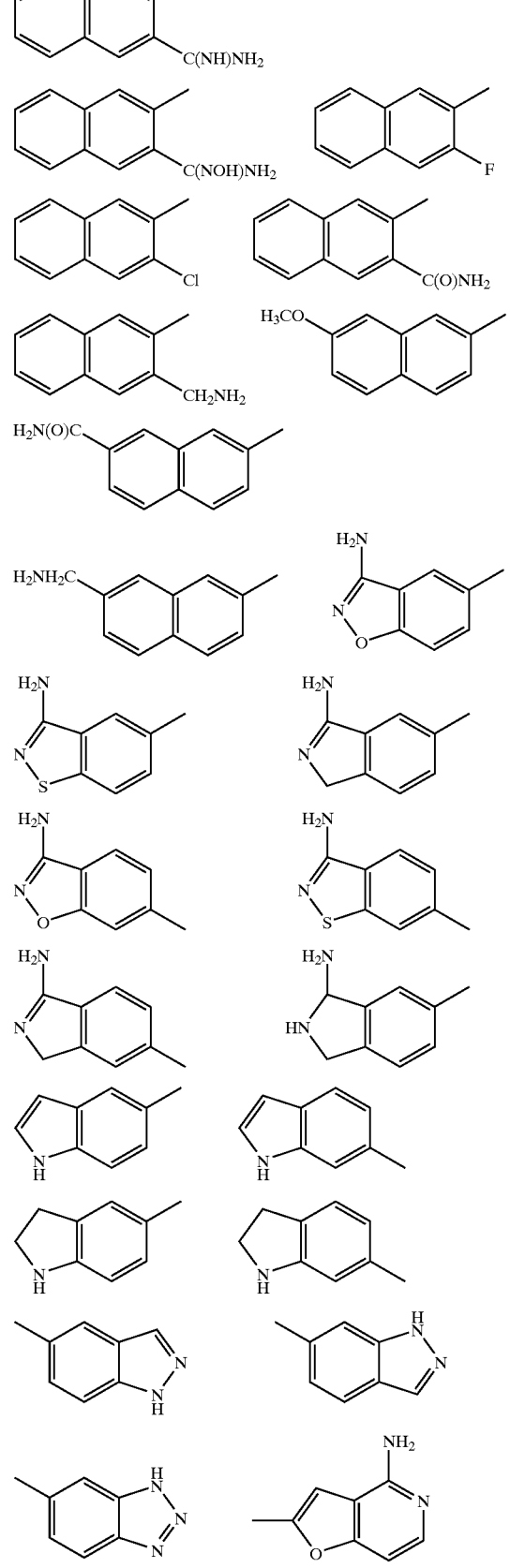

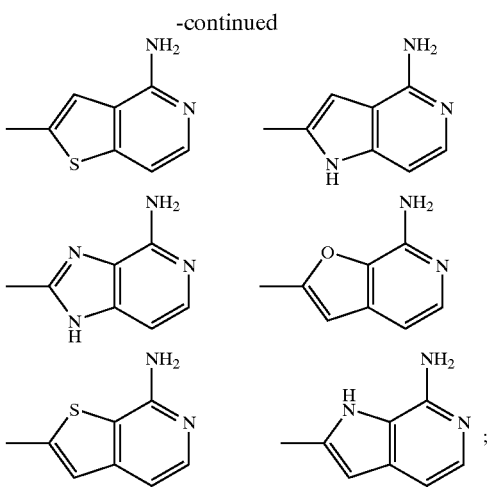

G₁ is absent or is selected from CH₂, CH₂CH₂, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, provided that G₁ does not form a N—S, NCH₂N, NCH₂O, or NCH₂S bond with either group to which it is attached;

A is selected from piperidinyl, phenyl, pyridyl, and pyrimidyl, and is substituted with 0–2 R⁴;

B is selected from phenyl, pyridyl, pyrrolidino, N-pyrrolidino-carbonyl, morpholino, N-morpholino-carbonyl, 1,2,3-triazolyl, imidazolyl, and benzimidazolyl, and is substituted with 1 R⁴ᵃ and 0–1 R⁴;

R¹ᵃ is selected from H, R¹ᵇ, C(CH₃)₂R¹ᵇ, and CH₂R¹ᵇ, provided that R¹ᵃ forms other than an N-halo, N—S, or N—CN bond;

R¹ᵇ is selected from CH₃, CH₂CH₃, F, Cl, Br, —CN, CF₃, OR², NR²R²ᵃ, C(O)R²ᵇ, CO₂R²ᵇ, CO₂R²ᵃ, S(O)ₚR², C(O)NR²R²ᵃ, SO₂NR²R²ᵃ, NR²SO₂R², and 5–6 membered aromatic heterocycle consisting of carbon atoms and from 1–4 heteroatoms selected from the group consisting of N, O, and S(O)ₚ and substituted with 0–2 R⁴ᵇ, provided that R¹ᵇ forms other than an O—O, N-halo, N—S, or N—CN bond;

R², at each occurrence, is selected from H, CH₃, CH₂CH₃, CH₂CH₂CH₃, CH(CH₃)₂, phenyl substituted with 0–1 R⁴ᵇ, benzyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

R²ᵃ, at each occurrence, is selected from H, CH₃, CH₂CH₃, CH₂CH₂CH₃, CH(CH₃)₂, benzyl, phenyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

alternatively, R² and R²ᵃ, together with the atom to which they are attached, combine to form a 5 or 6 membered saturated, partially saturated or unsaturated ring substituted with 0–1 R⁴ᵇ and consisting of: 0–1 additional heteroatoms selected from the group consisting of N, O, and S(O)ₚ;

R²ᵇ, at each occurrence, is selected from OCH₃, OCH₂CH₃, OCH₂CH₂CH₃, OCH(CH₃)₂, CH₃, CH₂CH₃, CH₂CH₂CH₃, CH(CH₃)₂, benzyl, phenyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

R²ᶜ, at each occurrence, is selected from OH, OCH₃, OCH₂CH₃, OCH₂CH₂CH₃, OCH(CH₃)₂, CH₃, CH₂CH₃, CH₂CH₂CH₃, CH(CH₃)₂, benzyl, phenyl substituted with 0–1 R⁴ᵇ, and 5–6 membered aromatic heterocycle containing from 1–4 heteroatoms selected from the group consisting of N, O, and S(O)ₚ and substituted with 0–1 R⁴ᵇ;

R²ᵈ, at each occurrence, is selected from H, R⁴ᶜ, C₁₋₄ alkyl substituted with 0–2 R⁴ᶜ, C₃₋₆ carbocycle substituted with 0–2 R⁴ᶜ, —(CH₂)—C₃₋₆ carbocycle substituted with 0–2 R⁴ᶜ, 5–6 membered heterocycle consisting of: carbon atoms and 1–4 heteroatoms selected from the group consisting of N, O, and S(O)ₚ and substituted with 0–2 R⁴ᶜ, and —(CH₂)-5–6 membered heterocycle consisting of: carbon atoms and 1–4 heteroatoms selected from the group consisting of N, O, and S(O)ₚ and substituted with 0–2 R⁴ᶜ, provided that R²ᵈ forms other than a N-halo, N—C-halo, S(O)ₚ-halo, O-halo, N—S, S—N, S(O)ₚ—S(O)ₚ, S—O, O—N, O—S, or O—O moiety;

R²ᵉ, at each occurrence, is selected from H, R⁴ᶜ, C₁₋₄ alkyl substituted with 0–2 R⁴ᶜ, C₃₋₆ carbocycle substituted with 0–2 R⁴ᶜ, —(CH₂)—C₃₋₆ carbocycle substituted with 0–2 R⁴ᶜ, 5–6 membered heterocycle consisting of: carbon atoms and 1–4 heteroatoms selected from the group consisting of N, O, and S(O)ₚ and substituted with 0–2 R⁴ᶜ, and —(CH₂)-5–6 membered heterocycle consisting of: carbon atoms and 1–4 heteroatoms selected from the group consisting of N, O, and S(O)ₚ and substituted with 0–2 R⁴ᶜ, provided that R²ᵉ forms other than a C(O)-halo or C(O)—S(O)ₚ moiety;

R⁴, at each occurrence, is selected from OH, OR², CH₂OR², (CH₂)₂OR², F, Br, Cl, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, NR²R²ᵃ, CH₂NR²R²ᵃ, (CH₂)₂NR²R²ᵃ, CF₃, and CF₂CF₃;

R⁴ᵃ is selected from (CH₂)ᵣN(→O)R²ᵈR²ᵈ, (CH₂)ᵥ—NR²ᵈC(O)R²ᵉ, (CH₂)ᵥ—NR²ᵈC(O)NR²ᵈR²ᵈ, (CH₂)ᵥ—NR²ᵈC(O)OR²ᵈ, and (CH₂)ᵥ—NR²ᵈSO₂R²ᵈ;

alternatively, R⁴ᵃ is selected from (CH₂)ᵣNR²ᵈR²ᵈ, NR²ᵈC(O)R²ᵉ, NR²ᵈC(O)NR²ᵈR²ᵈ, NR²ᵈC(O)OR²ᵈ, and NR²ᵈSO₂R²ᵈ, provided that at least one of R²ᵈ and R²ᵉ is alkyl substituted with at least one R⁴ᶜ that is other than alkyl;

R⁴ᵇ, at each occurrence, is selected from H, =O, OR³, CH₂OR³, F, Cl, CH₃, CH₂CH₃, CH₂CH₂CH₃, CH(CH₃)₂, —CN, NO₂, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)ₚ—C₁₋₄ alkyl, S(O)ₚ-phenyl, and CF₃;

R⁴ᶜ, at each occurrence, is selected from =O, OR², CH₂OR², F, Br, Cl, CF₃, C₁₋₄ alkyl, —CN, NO₂, NR²R²ᵃ, CH₂NR²R²ᵃ, N(→O)R²R²ᵃ, CH₂N(→O)R²R²ᵃ, C(O)R²ᶜ, CH₂C(O)R²ᶜ, NR²C(O)R²ᵇ, CH₂NR²C(O)R²ᵇ, C(O)NR²R²ᵃ, CH₂C(O)NR²R²ᵃ, SO₂NR²R²ᵃ, CH₂SO₂NR²R²ᵃ, NR²SO₂R⁵ᵃ, CH₂NR²SO₂R⁵ᵃ, S(O)ₚR⁵ᵃ, CH₂S(O)ₚR⁵ᵃ, CF₃, CF₂CF₃, C₃₋₆ carbocycle substituted with 0–2 R⁴ᵇ, (CH₂)C₃₋₆ carbocycle substituted with 0–2 R⁴ᵇ, 5–6 membered heterocycle consisting of carbon atoms and from 1–4 heteroatoms selected from the group consisting of N, O, and S(O)ₚ and substituted with 0–2 R⁴ᵇ, and (CH₂)-5–6 membered heterocycle consisting of carbon atoms and from 1–4 heteroatoms selected from the group consisting of N, O, and S(O)ₚ and substituted with 0–2 R⁴ᵇ;

R⁵, at each occurrence, is selected from H, =O, CH₃, CH₂CH₃, CH₂CH₂CH₃, CH(CH₃)₂, OR³, CH₂OR³, F, Cl, —CN, NO₂, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)ₚ—C₁₋₄ alkyl, S(O)ₚ-phenyl, CF₃, phenyl substituted with 0–2 R⁶, naphthyl substituted with 0–2 R⁶, and benzyl substituted with 0–2 R⁶; and, R⁶, at each occurrence, is selected from H, OH, OR², F, Cl, CH₃, CH₂CH₃, CH₂CH₂CH₃, CH(CH₃)₂, —CN, NO₂, NR²R²ᵃ, CH₂NR²R²ᵃ, C(O)R²ᵇ, CH₂C(O)R²ᵇ, NR²C(O)R²ᵇ, and SO₂NR²R²ᵃ.

[5] In another preferred embodiment, the present invention provides a novel compound, wherein:

ring M is substituted with 0–1 R¹ᵃ and is selected from the group:

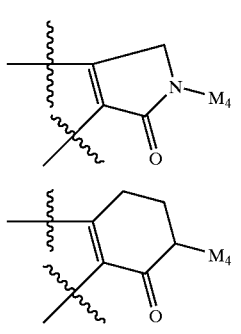 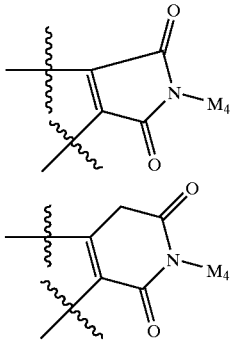
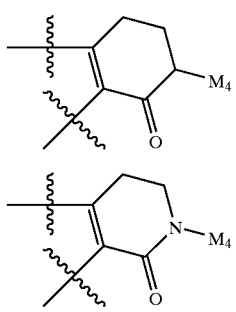 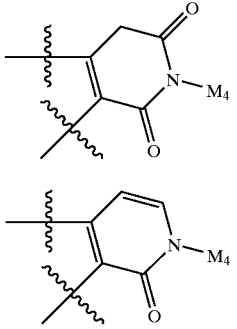
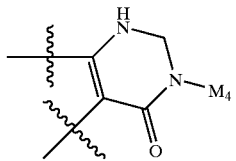 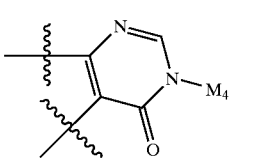
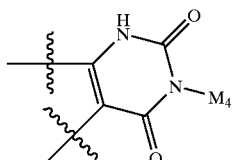 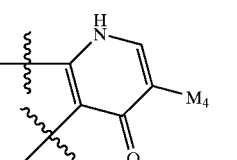
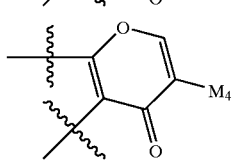 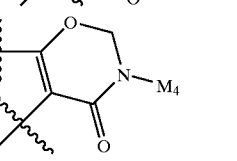
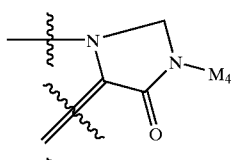 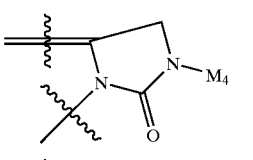
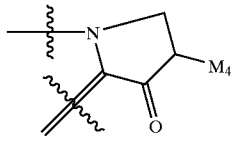 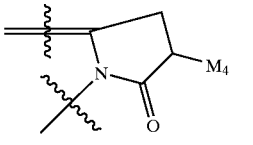

-continued

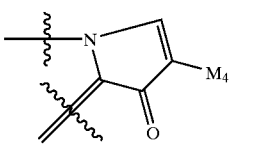 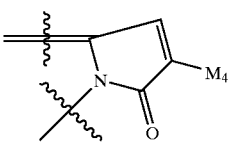
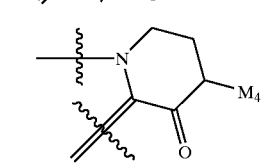 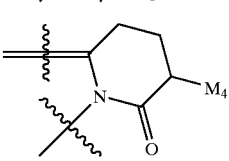
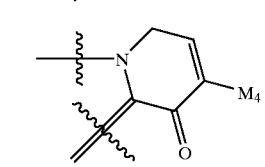 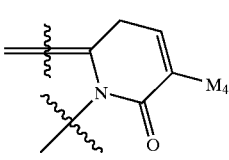
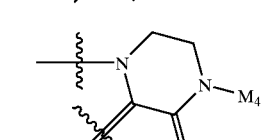 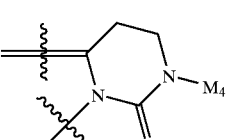
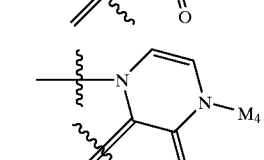 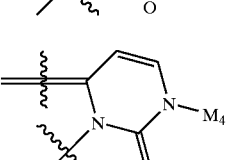
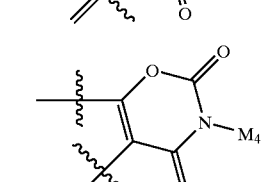 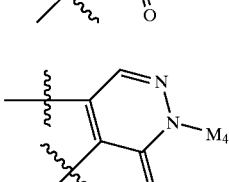
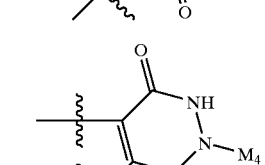 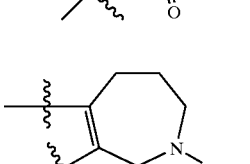
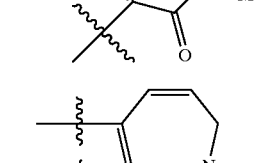 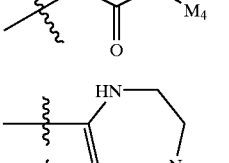
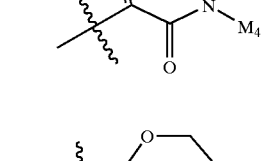 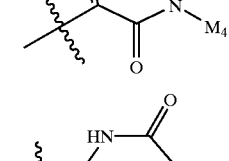
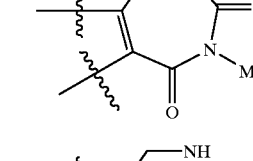 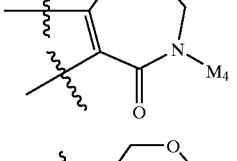
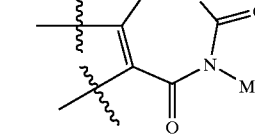 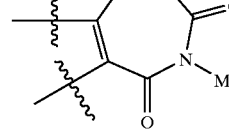

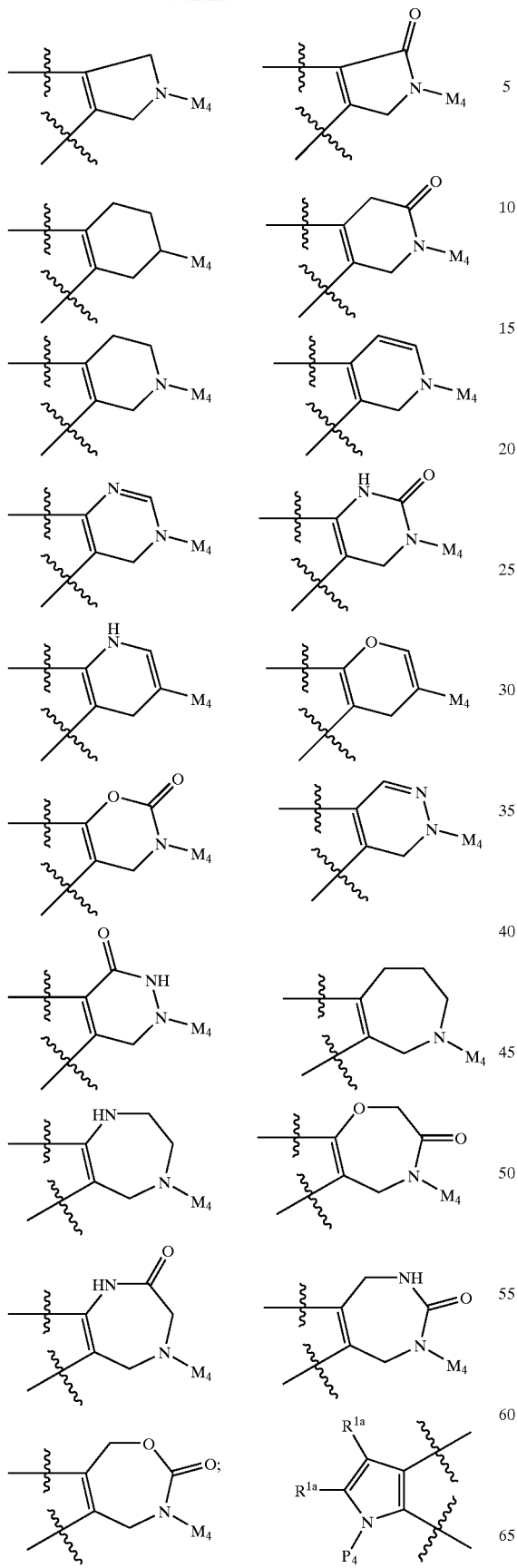
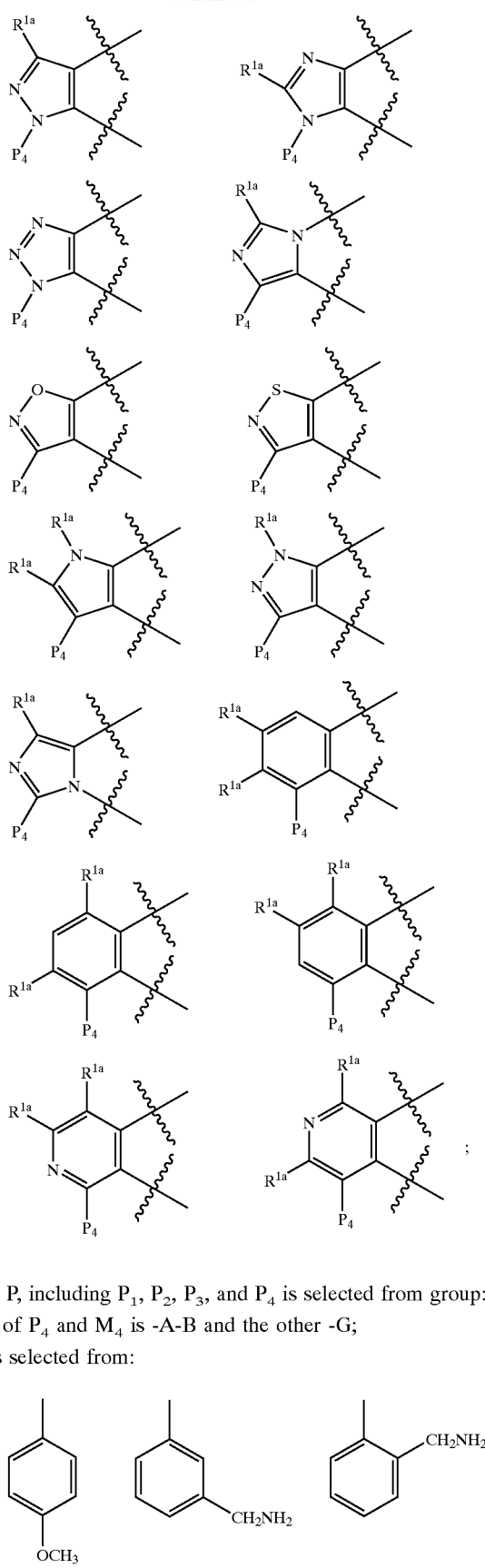
ring P, including $P_1$, $P_2$, $P_3$, and $P_4$ is selected from group:
one of $P_4$ and $M_4$ is -A-B and the other -G;
G is selected from:
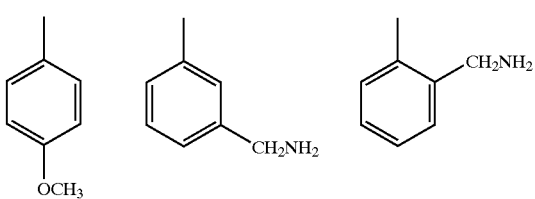

-continued

-continued

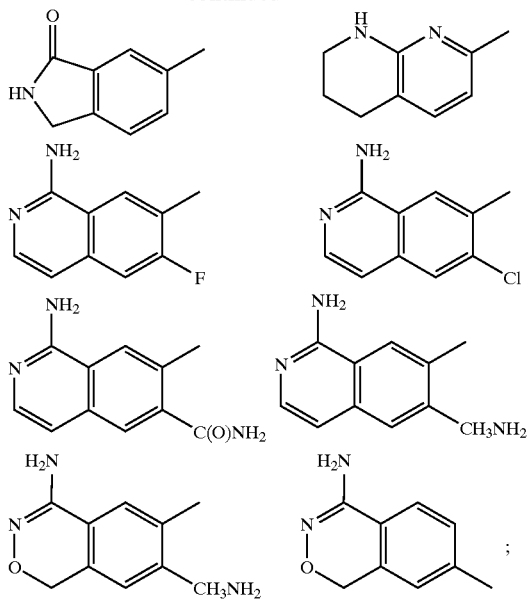

A is selected from the group: piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from phenyl, pyridyl, 1,2,3-triazolyl, imidazolyl, and benzimidazolyl, and is substituted with 1 $R^{4a}$;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^{4a}$ is selected from $CH_2N(\rightarrow O)R^{2d}R^{2d}$, $CH_2NR^{2d}C(O)R^{2e}$, $CH_2NR^{2d}C(O)NR^{2d}R^{2d}$, $CH_2NR^{2d}C(O)OR^{2d}$, and $CH_2NR^{2d}SO_2R^{2d}$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[6] In another preferred embodiment, the present invention provides a novel compound, wherein the compound is selected from:

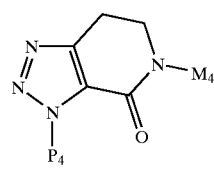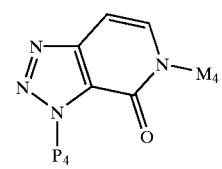

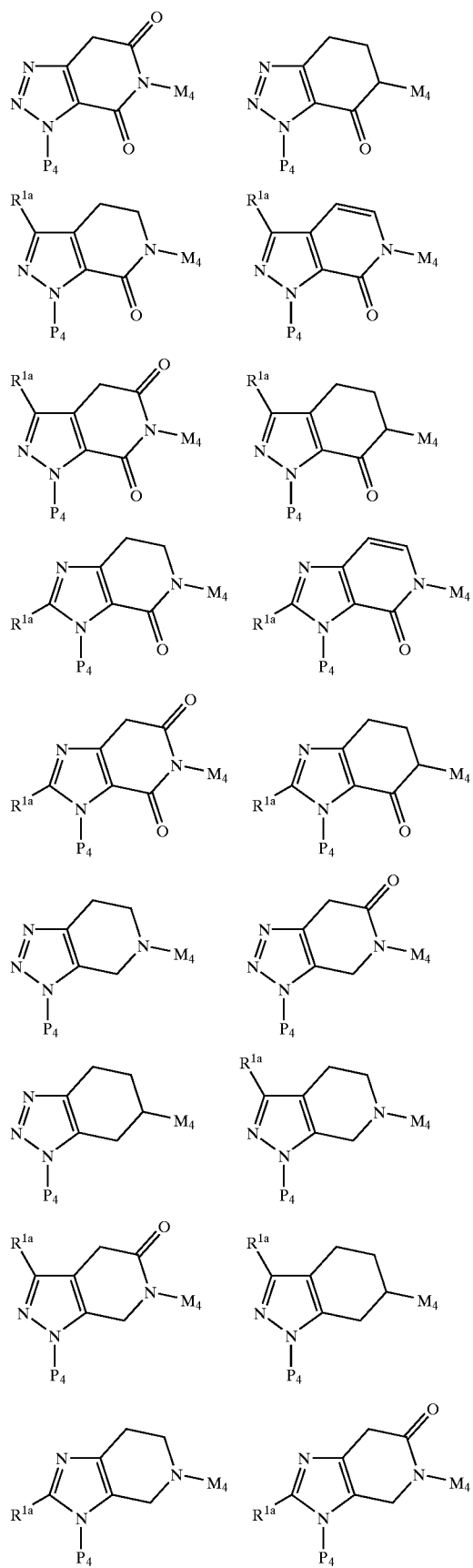
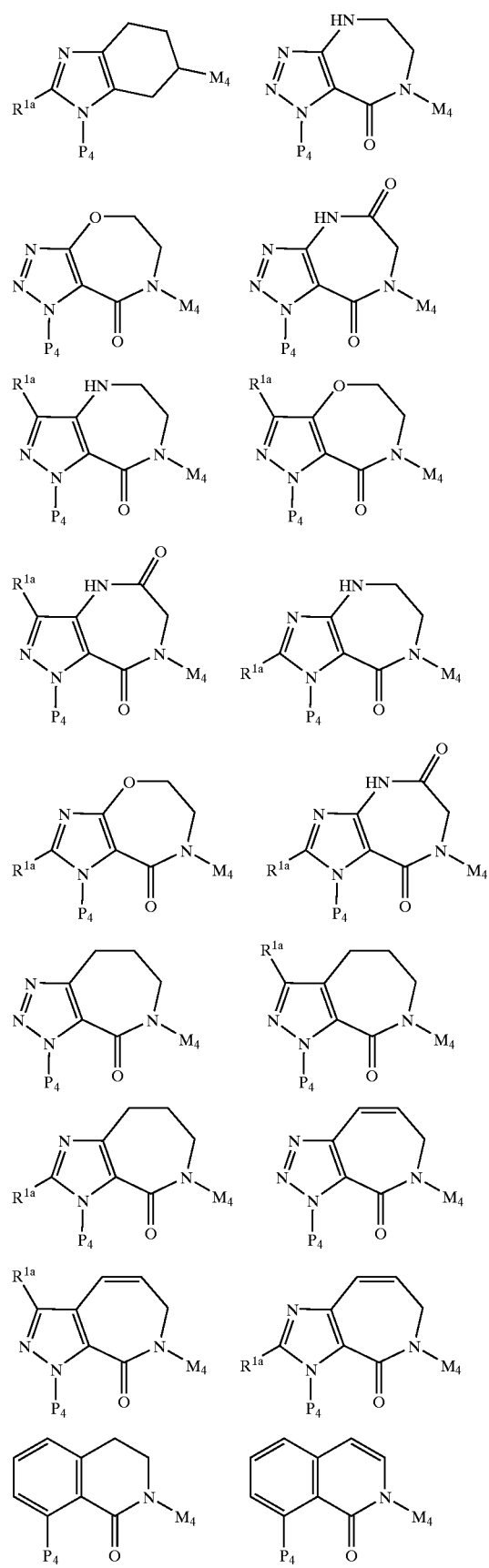

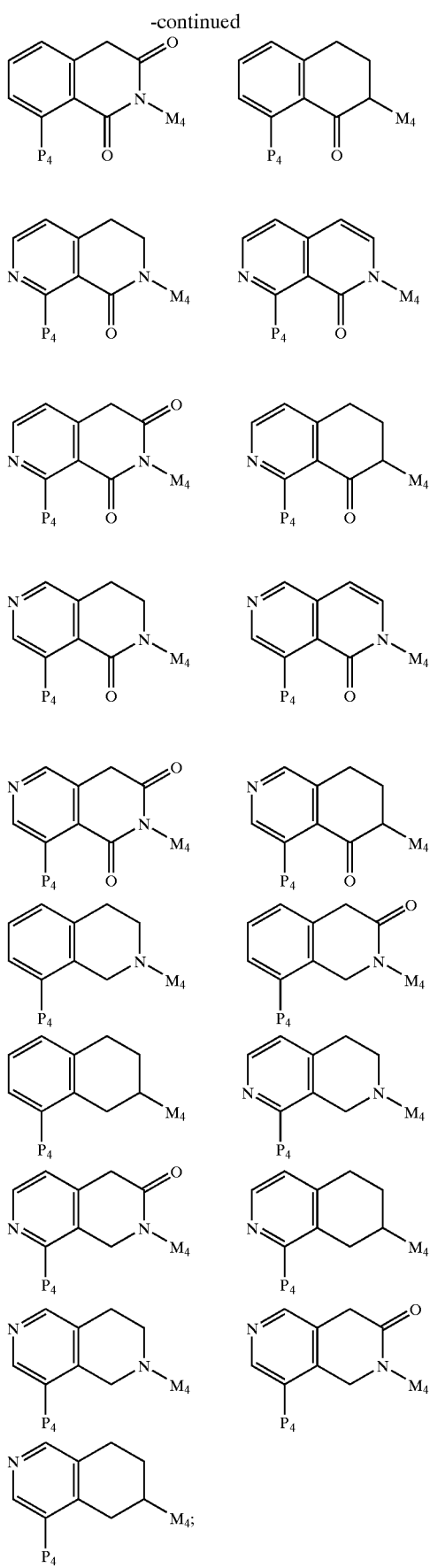
P$_4$ is -G;
M$_4$ is -A-B;
G is selected from:
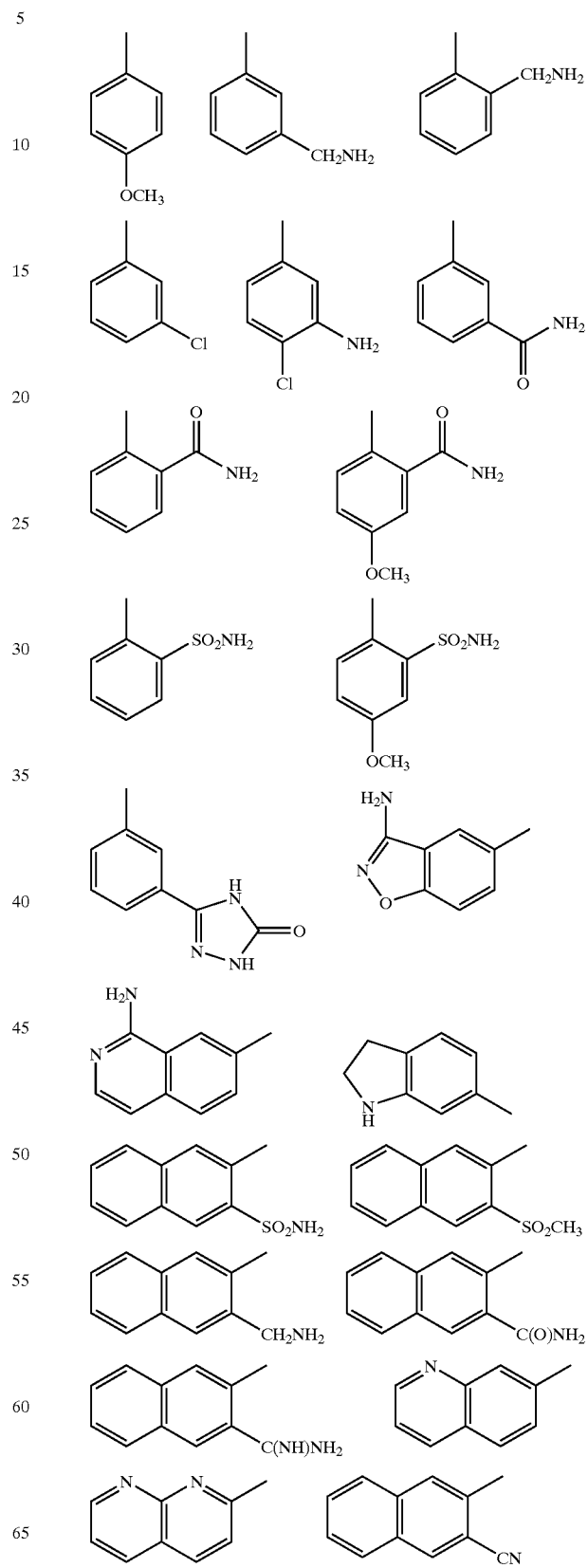

-continued

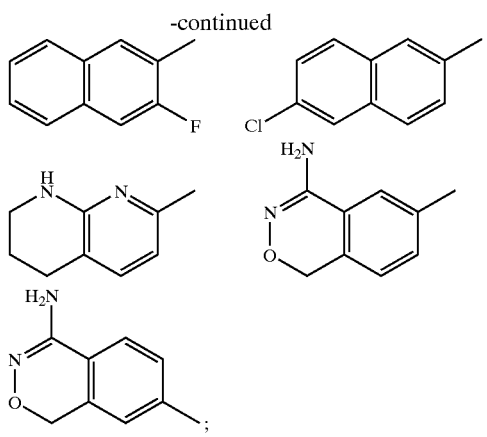

A-B is selected from:

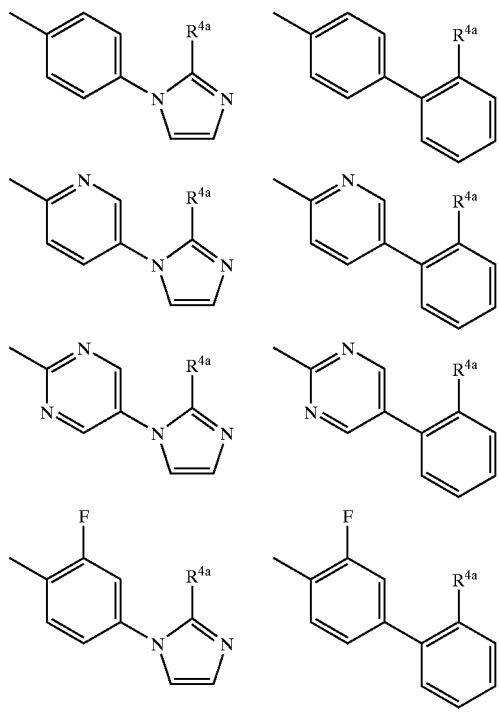

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $CH_2N(\rightarrow O)R^{2d}R^{2d}$, $CH_2NR^{2d}C(O)R^{2e}$, $CH_2NR^{2d}C(O)OR^{2d}$, and $CH_2NR^{2d}SO_2R^{2d}$; and, $R^4c$ is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

[7] In another preferred embodiment, the present invention provides a novel compound, wherein the compound is of the formula:

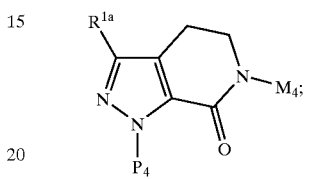

$P_4$ is -G;

$M_4$ is -A-B;

A-B is selected from:

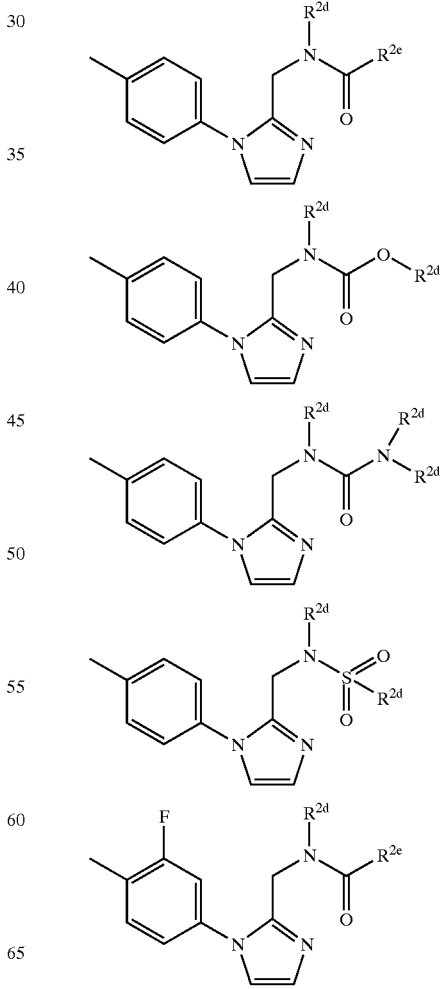

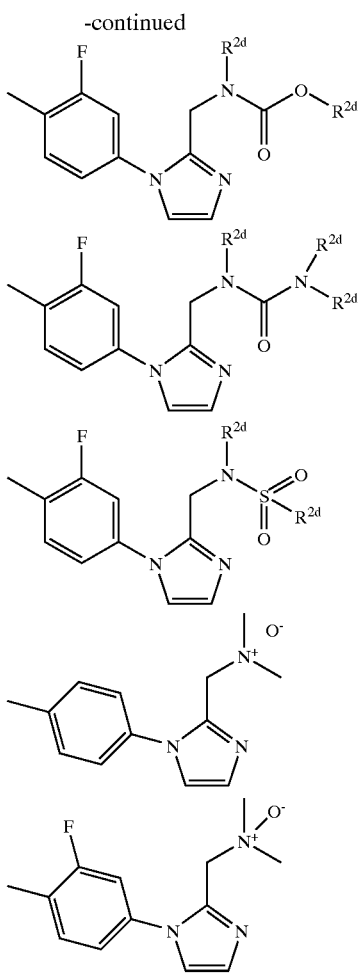

$R^{2d}$, at each occurrence, is selected from H, CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl; and, $R^{2e}$, at each occurrence, is selected from CH$_3$, CH$_2$CH$_3$, CH$_2$CH$_2$CH$_3$, CH(CH$_3$)$_2$, CH$_2$CH(CH$_3$)$_2$, CH$_2$CH$_2$CH(CH$_3$)$_2$, CH$_2$-cyclopropyl, cyclopropyl, and cyclopentyl.

[8] In another preferred embodiment, the present invention provides a novel compound, wherein the compound is selected from the group:

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylacetamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylacetamide;

methyl (1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl(methyl)carbamate;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylmethanesulfonamide;

N-[(1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N,3,5-trimethyl-4-isoxazolesulfonamide;

6-[4-(2-{[acetyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[ethylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[n-propylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[i-propylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[i-butylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

1-(4-methoxyphenyl)-6-{4-[2-({methyl[(methylamino)carbonyl]-amino}methyl)-1H-imidazol-1-yl]phenyl}-7-oxo-4,5,6,7-tetrahydro-1H-pyrazolo[3,4-c]pyridine-3-carboxamide;

methyl (1-{4-[3-(aminocarbonyl)-1-(4-methoxyphenyl)-7-oxo-1,4,5,7-tetrahydro-6H-pyrazolo[3,4-c]pyridin-6-yl]phenyl}-1H-imidazol-2-yl)methyl(methyl)carbamate;

ethyl (1-{4-[3-(aminocarbonyl)-1-(4-methoxyphenyl)-7-oxo-1,4,5,7-tetrahydro-6H-pyrazolo[3,4-c]pyridin-6-yl]phenyl}-1H-imidazol-2-yl)methyl(methyl)carbamate;

1-(4-methoxyphenyl)-6-[4-(2-{[methyl(methylsulfonyl)amino]-methyl}-1H-imidazol-1-yl)phenyl]-7-oxo-4,5,6,7-tetrahydro-1H-pyrazolo[3,4-c]pyridine-3-carboxamide;

1-(4-methoxyphenyl)-6-[4-(2-{[methyl(n-propylsulfonyl)amino]-methyl}-1H-imidazol-1-yl)phenyl]-7-oxo-4,5,6,7-tetrahydro-1H-pyrazolo[3,4-c]pyridine-3-carboxamide;

6-[4-(2-{[[(3,5-dimethyl-4-isoxazolyl)sulfonyl](methyl)amino]methyl}-1H-imidazol-1-yl)phenyl]-1(4-methoxyphenyl)-7-oxo-4,5,6,7-tetrahydro-1H-pyrazolo[3,4-c]pyridine-3-carboxamide;

1-(4-methoxyphenyl)-6-[4-(2-{[methyl(phenylsulfonyl)amino]-methyl}-1H-imidazol-1-yl)phenyl]-7-oxo-4,5,6,7-tetrahydro-1H-pyrazolo[3,4-c]pyridine-3-carboxamide;

6-[4-(2-{[acetyl(ethyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

6-[4-(2-{[ethylcarbonylamino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylacetamide;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylpropanamide;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylbutanamidetrifluoroacetic acid salt;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N,2-dimethylpropanamide;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylcyclopropanecarboxamide;

methyl (1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl(methyl)carbamate;

N-ethyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide;

N-isopropyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide;

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-propylacetamide;

1-(4-methoxyphenyl)-6-[2'-({methyl[(methylamino)carbonyl]-amino}methyl)-1,1'-biphenyl-4-yl]-7-oxo-4,5,6,7-tetrahydro-1H-pyrazolo[3,4-c]pyridine-3-carboxamide;

1-(4-methoxyphenyl)-6-(2'-{[methyl(methylsulfonyl)amino]-methyl}-1,1'-biphenyl-4-yl)-7-oxo-4,5,6,7-tetrahydro-1H-pyrazolo[3,4-c]pyridine-3-carboxamide;

N-(2-{4-[3-cyano-1-(4-methoxyphenyl)-7-oxo-1,4,5,7-tetrahydro-6H-pyrazolo[3,4-c]pyridin-6-yl]-1-piperidinyl}benzyl)-N-methylacetamide;

6-[1-(2-{[acetyl(methyl)amino]methyl}phenyl)-4-piperidinyl]-1-(4-methoxyphenyl)-7-oxo-4,5,6,7-tetrahydro-1H-pyrazolo[3,4-c]pyridine-3-carboxamide;

1-(4-methoxyphenyl)-6-[1-(2-{[methyl(methylsulfonyl)amino]methyl}phenyl)-4-piperidinyl]-7-oxo-4,5,6,7-tetrahydro-1H-pyrazolo[3,4-c]pyridine-3-carboxamide;

6-(4-{2-[(dimethylnitroryl)methyl]-1H-imidazol-1-yl}phenyl)-1-(4-methoxyphenyl)-3-(trifluoromethyl)-1,4,5,6-tetrahydro-7H-pyrazolo[3,4-c]pyridin-7-one;

1-(3-amino-1,2-benzisoxazol-5-yl)-6-(2'-{[bis(2-hydroxyethyl)amino]methyl}-1,1'-biphenyl-4-yl)-3-(trifluoromethyl)-1,4,5,6-tetrahydro-7H-pryazolo[3,4-c]pyridin-7-one;

1-(3-amino-1,2-benzisoxazol-5-yl)-6-(2'-{[(3-aminopropyl)(methyl)amino]methyl}-1,1'-biphenyl-4-yl)-3-(trifluoromethyl)-1,4,5,6-tetrahydro-7H-pryazolo[3,4-c]pyridin-7-one;

6-(2'-{[(2-hydroxyethyl)(methyl)amino]methyl}-1,1'-biphenyl-4-yl)-1-(4-methoxyphenyl)-7-oxo-4,5,6,7-tetrahydro-1H-pryazolo[3,4-c]pyridine-3-carboxamide;

6-(2'-{[bis(2-hydroxyethyl)amino]methyl}-1,1'-biphenyl-4-yl)-1-(4-methoxyphenyl)-7-oxo-4,5,6,7-tetrahydro-1H-pryazolo[3,4-c]pyridine-3-carboxamide;

6-(2'-{[(3-aminopropyl)(methyl)amino]methyl}-1,1'-biphenyl-4-yl)-1-(4-methoxyphenyl)-7-oxo-4,5,6,7-tetrahydro-1H-pryazolo[3,4-c]pyridine-3-carboxamide;

6-(2'-{[(2-hydroxyethyl)(methyl)amino]methyl}-1,1'-biphenyl-4-yl)-1-(4-methoxyphenyl)-3-(methylsulfonyl)-1,4,5,6-tetrahydro-1H-pryazolo[3,4-c]pyridin-7-one;

or a pharmaceutically acceptable salt form thereof.

[9] In another preferred embodiment, the present invention provides a novel compound, wherein the compound is of Formula IIIa, IIIb, or IIIc:

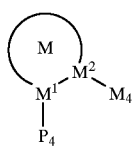

IIIa

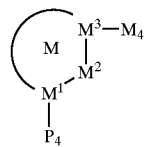

IIIb

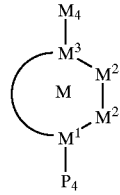

IIIc or a stereoisomer or pharmaceutically acceptable salt thereof, wherein;

ring M, including $M_1$, $M_2$, and, if present, $M_3$, is phenyl or a 3–10 membered carbocyclic or 4–10 membered heterocyclic ring consisting of: carbon atoms and 1–4 heteroatoms selected from O, $S(O)_p$, N, and $NZ^2$;

ring M is substituted with 0–3 $R^{1a}$ and 0–2 carbonyl groups, and there are 0–3 ring double bonds;

one of $P_4$ and $M_4$ is -Z-A-B and the other -$G_1$-G;

G is a group of formula IIa or IIb:

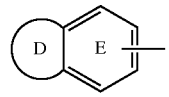

IIa

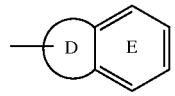

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with 1 R and with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and there are 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)NHOH$, $C(=NH)NHOCH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_2R^3$, $S(O)_pNR^7R^8$, $CH_2S(O)_pNR^7R^8$, and $OCF_3$;

alternatively, when 2 R groups are attached to adjacent atoms, they combine to form methylenedioxy or ethylenedioxy;

A is selected from:
C$_{5-10}$ carbocycle substituted with 0–2 R$^4$, and
5–10 membered heterocycle consisting of: carbon atoms and 1–4 heteroatoms selected from the group consisting of N, O, and S(O)$_p$ and substituted with 0–2 R$^4$;

X is selected from —(CR$^2$R$^{2a}$)$_{1-4}$—, —C(O)—, —C(=NR$^{1b}$)—, —CR$^2$(NR$^{1b}$R$^2$)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from one of the following carbocyclic and heterocycles that are substituted with 1 R$^{4a}$ and 0–2 R$^4$: cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

Z is selected from a bond, CH$_2$, CH$_2$CH$_2$, CH$_2$O, OCH$_2$, C(O), NH, CH$_2$NH, NHCH$_2$, CH$_2$C(O), C(O)CH$_2$, C(O)NH, NHC(O), NHC(O)NH, NHC(O)CH$_2$C(O)NH, C(O)NHS(O)$_2$, S(O)$_2$, CH$_2$S(O)$_2$, S(O)$_2$(CH$_2$), SO$_2$NH, and NHSO$_2$, provided that Z does not form a N—S, NCH$_2$N, NCH$_2$O, or NCH$_2$S bond with either group to which it is attached;

Z$^2$ is selected from H, C$_{1-4}$ alkyl, phenyl, benzyl, C(O)R$^{3b}$, S(O)R$^{3f}$, and S(O)$_2$R$^{3f}$;

R$^{1a}$, at each occurrence, is selected from H, —(CH$_2$)$_r$—R$^{1b}$, —(CH(CH$_3$))$_r$—R$^{1b}$, —(C(CH$_3$)$_2$)$_r$—R$^{1b}$, —O—(CR$^3$R$^{3a}$)$_r$—R$^{1b}$, —NR$^2$—(CR$^3$R$^{3a}$)$_r$—R$^{1b}$, and —S—(CR$^3$R$^{3a}$)$_r$—R$^{1b}$, provided that R$^{1a}$ forms other than an N-halo, N—S, O—O, or N—CN bond;

alternatively, when two R$^{1a}$ groups are attached to adjacent atoms or to the same carbon atom, together with the atoms to which they are attached they form a 5–7 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, CH$_3$, CH$_2$CH$_3$, CH$_2$CH$_2$CH$_3$, CH(CH$_3$)$_2$, F, Cl, Br, I, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, NR$^2$C(O)NHR$^2$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, C$_{5-6}$ carbocycle substituted with 0–2 R$^{4b}$, and 5–6 membered heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

R$^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, a C$_{5-6}$ carbocyclic-CH$_2$-group substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

R$^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, C$_{5-6}$ carbocycle substituted with 0–2 R$^{4b}$, and 5–6 membered heterocycle containing from 1–4 heteroatoms selected from the group consisting of N, O, and S(O)$_p$ and substituted with 0–2 R$^{4b}$;

R$^{2d}$, at each occurrence, is selected from H, R$^{4c}$, C$_{1-4}$ alkyl substituted with 0–2 R$^{4c}$, —(CR$^3$R$^{3a}$)$_r$—C$_{3-6}$ carbocycle substituted with 0–2 R$^{4c}$, and —(CR$^3$R$^{3a}$)$_r$-5–6 membered heterocycle consisting of: carbon atoms and 1–4 heteroatoms selected from the group consisting of N, O, and S(O)$_p$ and substituted with 0–2 R$^{4c}$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, —(CR$^3$R$^{3a}$)$_r$—C$_{3-6}$ carbocycle substituted with 0–2 R$^{4c}$, and —(CR$^3$R$^{3a}$)$_r$-5–6 membered heterocycle consisting of: carbon atoms and 1–4 heteroatoms selected from the group consisting of N, O, and S(O)$_p$ and substituted with 0–2 R$^{4c}$, provided that R$^{2e}$ forms other than a C(O)-halo or C(O)—S(O)$_p$ moiety;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms and the nitrogen atom to which R$^3$ and R$^{3a}$ are attached;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^{3g}$, at each occurrence, is selected from H, CH$_3$, CH$_2$CH$_3$, CH$_2$CH$_2$CH$_3$, CH(CH$_3$)$_2$, cyclopropyl, cyclopropylmethyl, benzyl, and phenyl;

alternatively, when R$^3$ and R$^{3g}$ are attached to the same carbon atom, they combine with the attached carbon atom to form a cyclopropyl group;

R$^4$, at each occurrence, is selected from H, =O, OR$^2$, CH$_2$OR$^2$, (CH$_2$)$_2$OR$^2$, F, Cl, Br, I, C$_{1-4}$ alkyl, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, S(O)$_p$R$^{5a}$, CF$_3$, CF$_2$CF$_3$, 5–6 membered carbocycle substituted with 0–1

R⁵, and a 5–6 membered heterocycle consisting of: carbon atoms and 1–4 heteroatoms selected from the group consisting of N, O, and S(O)$_p$ and substituted with 0–1 R⁵;

R$^{4a}$ is selected from (CR³R$^{3g}$)$_v$N(→O)R$^{2d}$R$^{2d}$, (CR³R$^{3g}$)$_v$—NR$^{2d}$C(O)R$^{2e}$, (CR³R$^{3g}$)$_v$—NR$^{2d}$C(O)NR$^{2d}$R$^{2d}$, (CR³R$^{3g}$)$_v$—NR$^{2d}$C(O)OR$^{2d}$, (CR³R$^{3g}$)$_v$—NR$^{2d}$SO₂NR$^{2d}$R$^{2d}$, and (CR³R$^{3g}$)$_v$—NR$^{2d}$SO₂R$^{2d}$;

alternatively, R$^{4a}$ is selected from (CR³R$^{3g}$)$_r$NR$^{2d}$R$^{2d}$, NR$^{2d}$C(O)R$^{2e}$, NR$^{2d}$C(O)NR$^{2d}$R$^{2d}$, NR$^{2d}$C(O)OR$^{2d}$, NR$^{2d}$SO₂NR$^{2d}$R$^{2d}$, and NR$^{2d}$SO₂R$^{2d}$, provided that at least one of R$^{2d}$ and R$^{2e}$ is alkyl substituted with at least one R$^{4c}$ that is other than alkyl;

R$^{4b}$, at each occurrence, is selected from H, =O, OR³, CH₂OR³, F, Cl, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —CN, NO₂, NR³R$^{3a}$, CH₂NR³R$^{3a}$, C(O)R³, CH₂—C(O)R³, C(O)OR$^{3c}$, CH₂C(O)OR$^{3c}$, NR³C(O)R$^{3a}$, CH₂NR³C(O)R$^{3a}$, C(O)NR³R$^{3a}$, CH₂C(O)NR³R$^{3a}$, NR³C(O)NR³R$^{3a}$, CH₂NR³C(O)NR³R$^{3a}$, C(=NR³)NR³R$^{3a}$, CH₂C(=NR³)NR³R$^{3a}$, NR³C(=NR³)NR³R$^{3a}$, CH₂NR³C(=NR³)NR³R$^{3a}$, SO₂NR³R$^{3a}$, CH₂SO₂NR³R$^{3a}$, NR³SO₂NR³R$^{3a}$, CH₂NR³SO₂NR³R$^{3a}$, NR³SO₂—C$_{1-4}$ alkyl, CH₂NR³SO₂—C$_{1-4}$ alkyl, NR³SO₂CF₃, CH₂NR³SO₂CF₃, NR³SO₂-phenyl, CH₂NR³SO₂-phenyl, S(O)$_p$CF₃, CH₂S(O)$_p$CF₃, S(O)$_p$—C$_{1-4}$ alkyl, CH₂S(O)$_p$—C$_{1-4}$ alkyl, S(O)$_p$-phenyl, CH₂S(O)$_p$-phenyl, CF₃, and CH₂—CF₃;

R$^{4c}$, at each occurrence, is selected from =O, (CR³R$^{3a}$)$_r$OR², (CR³R$^{3a}$)$_r$F, (CR³R$^{3a}$)$_r$Br, (CR³R$^{3a}$)$_r$Cl, (CR³R$^{3a}$)$_r$CF₃, C$_{1-4}$ alkyl, (CR³R$^{3a}$)$_r$CN, (CR³R$^{3a}$)$_r$NO₂, (CR³R$^{3a}$)$_r$NR²R$^{2a}$, (CR³R$^{3a}$)$_r$N(→O)R²R$^{2a}$, (CR³R$^{3a}$)$_r$C(O)R$^{2c}$, (CR³R$^{3a}$)$_r$NR²C(O)R$^{2b}$, (CR³R$^{3a}$)$_r$C(O)NR²R$^{2a}$, (CR³R$^{3a}$)$_r$NR²C(O)NR²R$^{2a}$, (CR³R$^{3a}$)$_r$SO₂NR²R$^{2a}$, (CR³R$^{3a}$)$_r$NR²SO₂NR²R$^{2a}$, (CR³R$^{3a}$)$_r$NR²SO₂R$^{5a}$, (CR³R$^{3a}$)$_r$S(O)$_p$R$^{5a}$, (CF₂)$_r$CF₃, (CR³R$^{3a}$)$_r$C$_{3-10}$ carbocycle substituted with 0–2 R$^{4b}$, and (CR³R$^{3a}$)$_r$5–10 membered heterocycle consisting of carbon atoms and from 1–4 heteroatoms selected from the group consisting of N, O, and S(O)$_p$ and substituted with 0–2 R$^{4b}$;

R⁵, at each occurrence, is selected from H, =O, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, OR³, CH₂OR³, F, Cl, —CN, NO₂, NR³R$^{3a}$, CH₂NR³R$^{3a}$, C(O)R³, CH₂C(O)R³, C(O)OR$^{3c}$, CH₂C(O)OR$^{3c}$, NR³C(O)R$^{3a}$, C(O)NR³R$^{3a}$, NR³C(O)NR³R$^{3a}$, CH(=NOR$^{3d}$), C(=NR³)NR³R$^{3a}$, NR³C(=NR³)NR³R$^{3a}$, SO₂NR³R$^{3a}$, NR³SO₂NR³R$^{3a}$, NR³SO₂—C$_{1-4}$ alkyl, NR³SO₂CF₃, NR³SO₂-phenyl, S(O)$_p$CF₃, S(O)$_p$—C$_{1-4}$ alkyl, S(O)$_p$-phenyl, CF₃, phenyl substituted with 0–2 R⁶, naphthyl substituted with 0–2 R⁶, and benzyl substituted with 0–2 R⁶;

R⁶, at each occurrence, is selected from H, OH, OR², F, Cl, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —CN, NO₂, NR²R$^{2a}$, CH₂NR²R$^{2a}$, C(O)R$^{2b}$, CH₂C(O)R$^{2b}$, NR²C(O)R$^{2b}$, NR²C(O)NR²R$^{2a}$, C(=NH)NH₂, NHC(=NH)NH₂, SO₂NR²R$^{2a}$, NR²SO₂NR²R$^{2a}$, and NR²SO₂—C$_{1-4}$ alkyl;

r, at each occurrence, is selected from 0, 1, and 2; and, v, at each occurrence, is selected from 1, 2, and 3.

[10] In another preferred embodiment, the present invention provides a novel compound, wherein:

ring M, including M₁, M₂, and, if present, M₃, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran=1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran=1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopentene, cyclopentane, cyclohexene, cyclohexane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, and tetrahydro-1,2,3,4-tetrazine;

ring M is substituted with 0–3 R$^{1a}$ and 0–1 carbonyl group;

G is selected from the group:

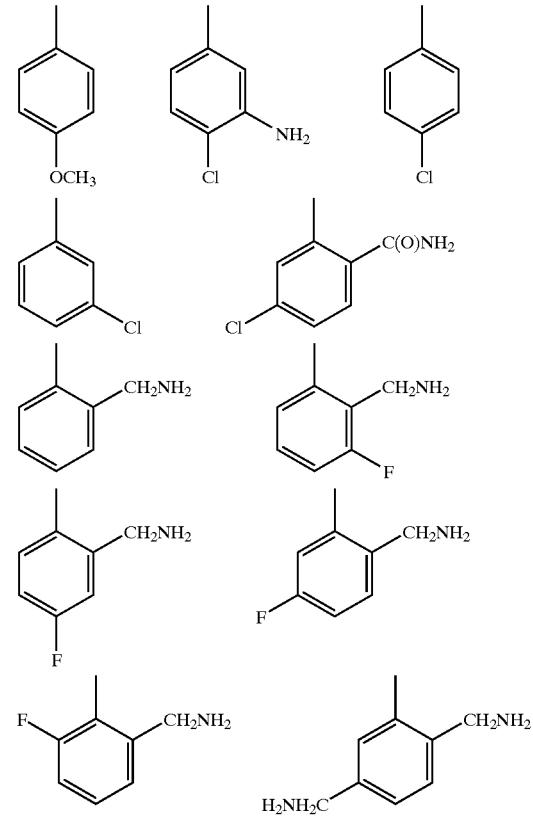

-continued
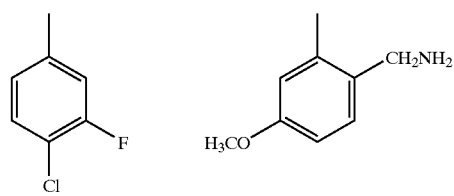
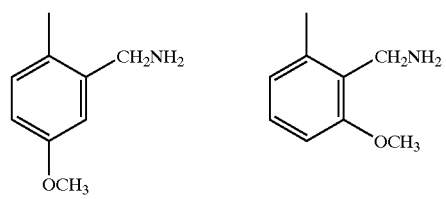
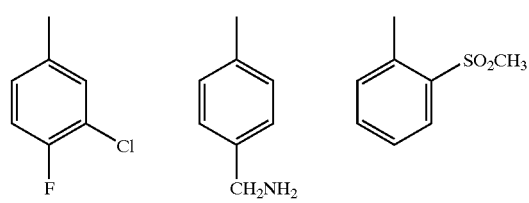
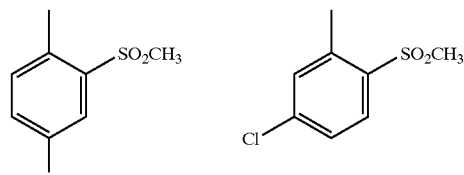
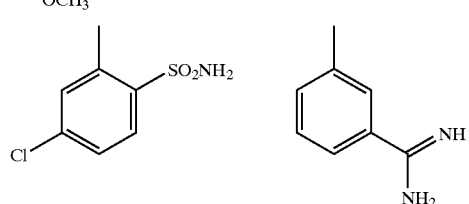
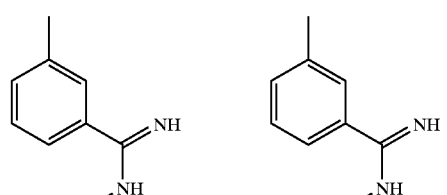
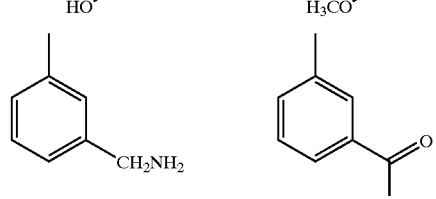
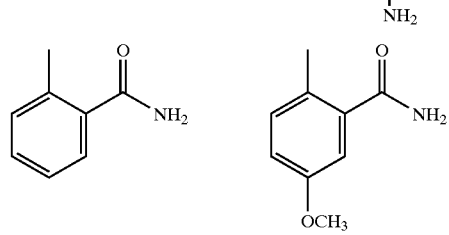
-continued
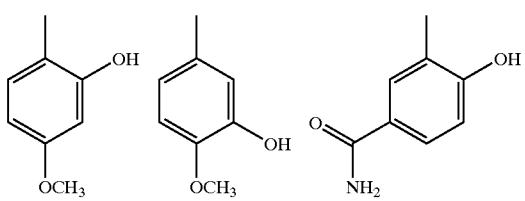
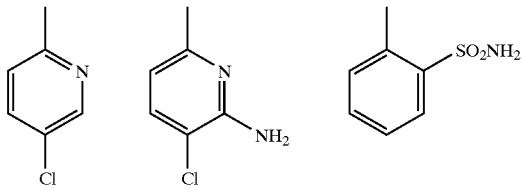
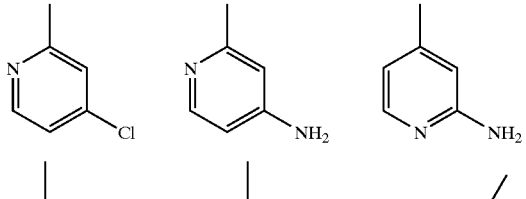
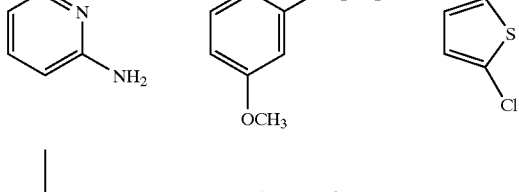
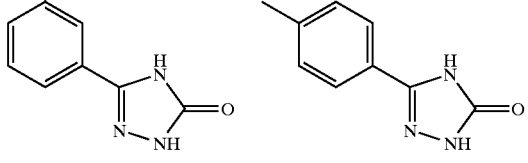
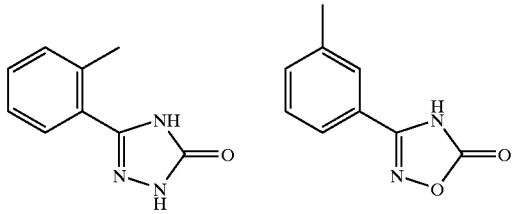
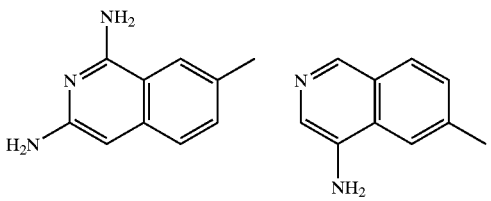
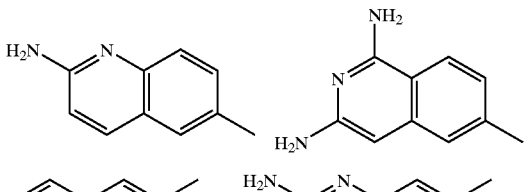
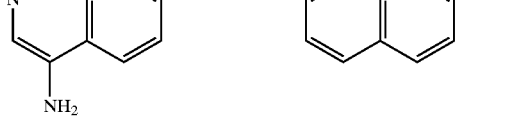

-continued
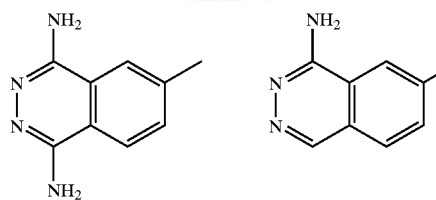
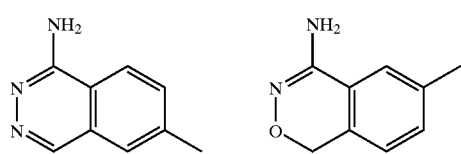
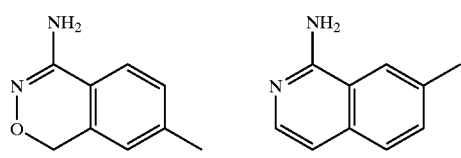
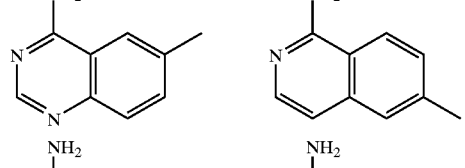
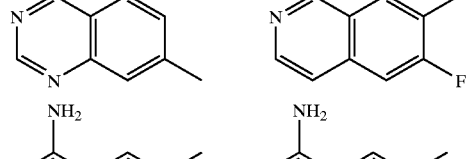
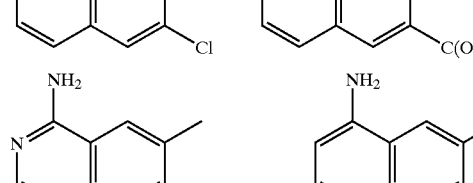
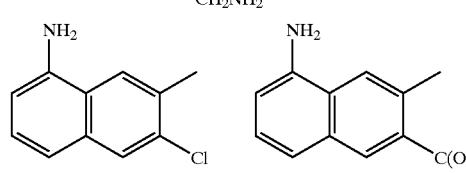
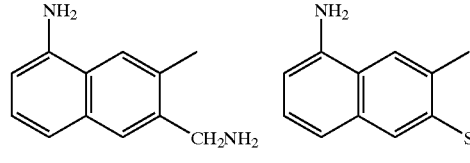
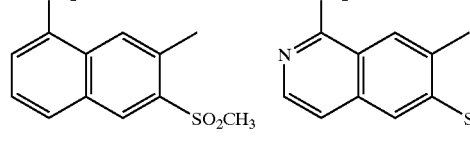
-continued
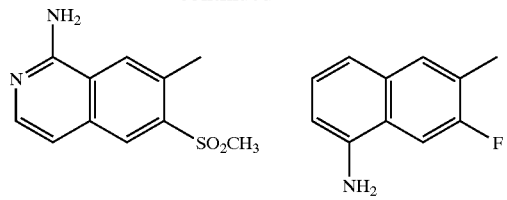
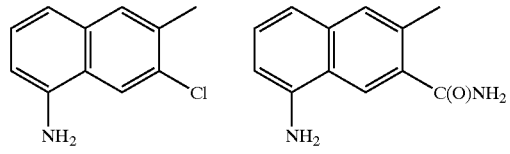
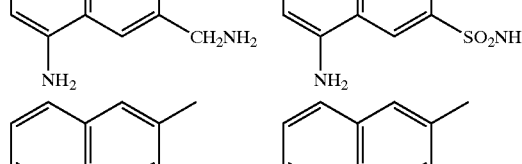
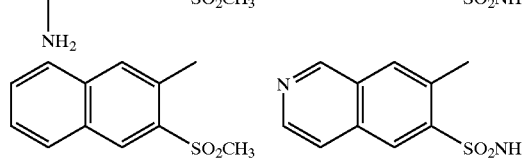
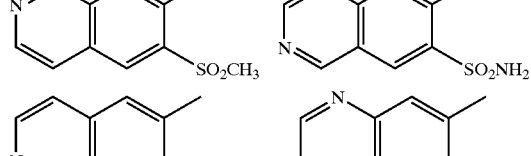
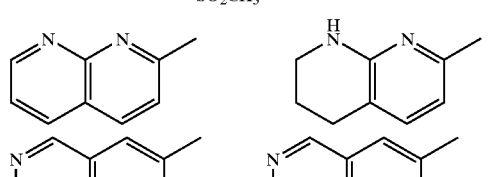
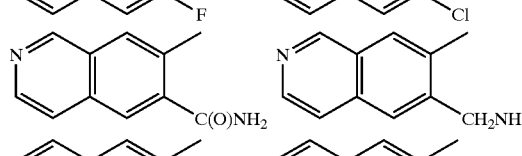
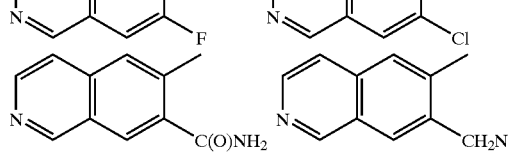
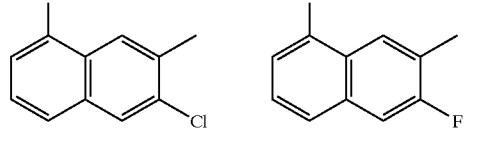

-continued
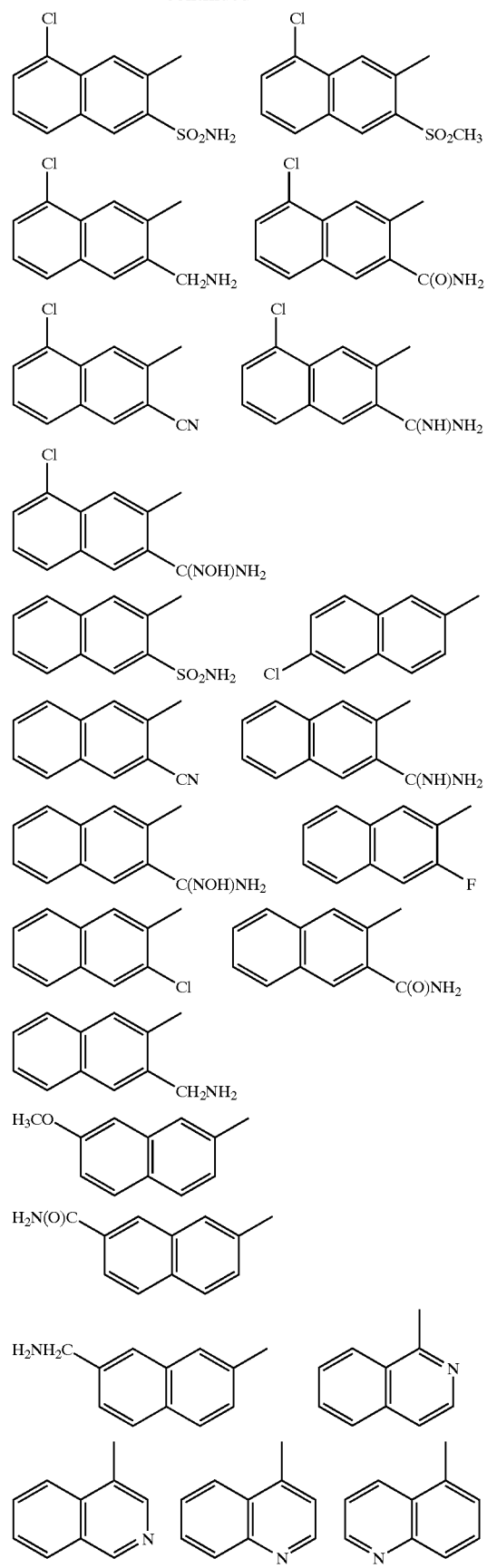
-continued
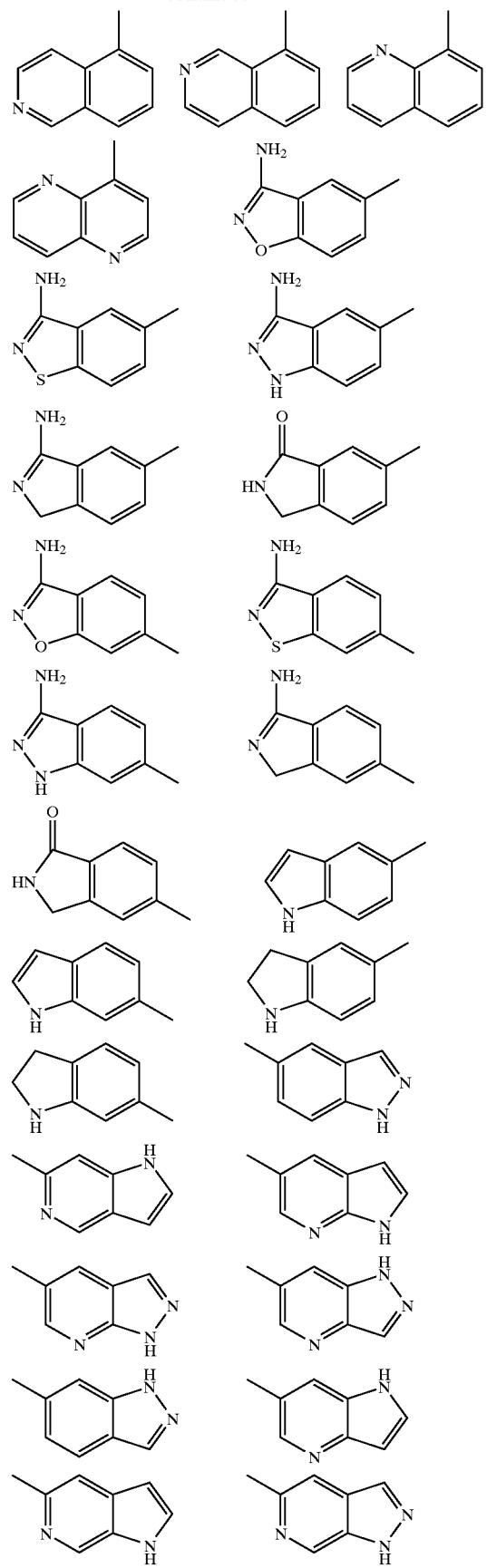

-continued
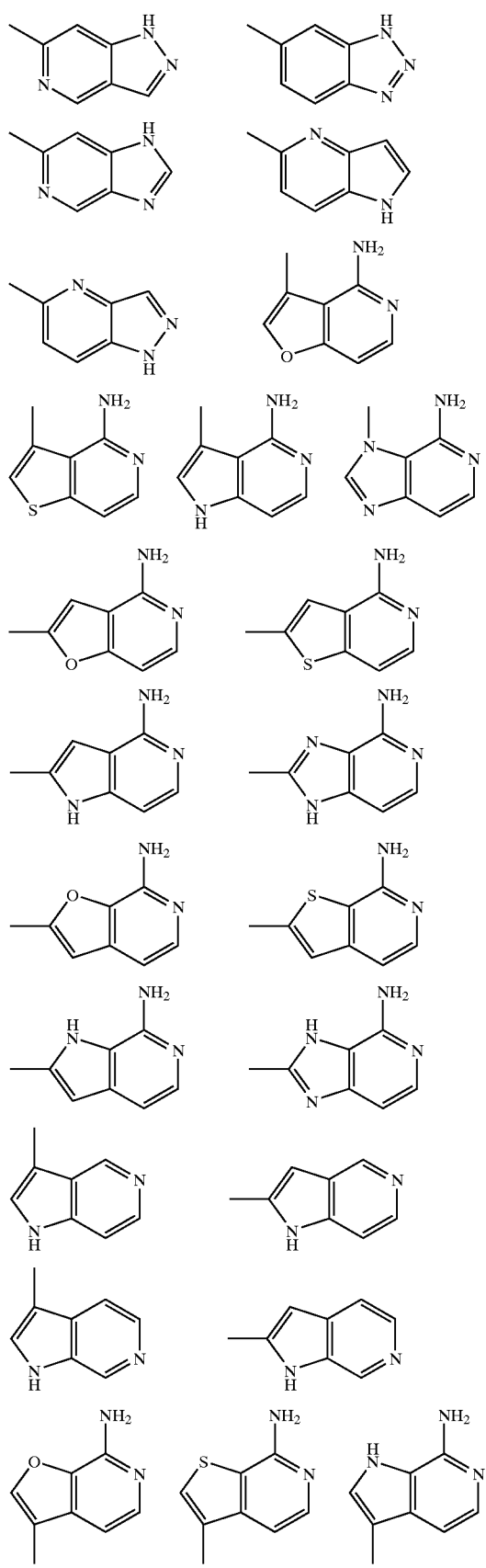
-continued
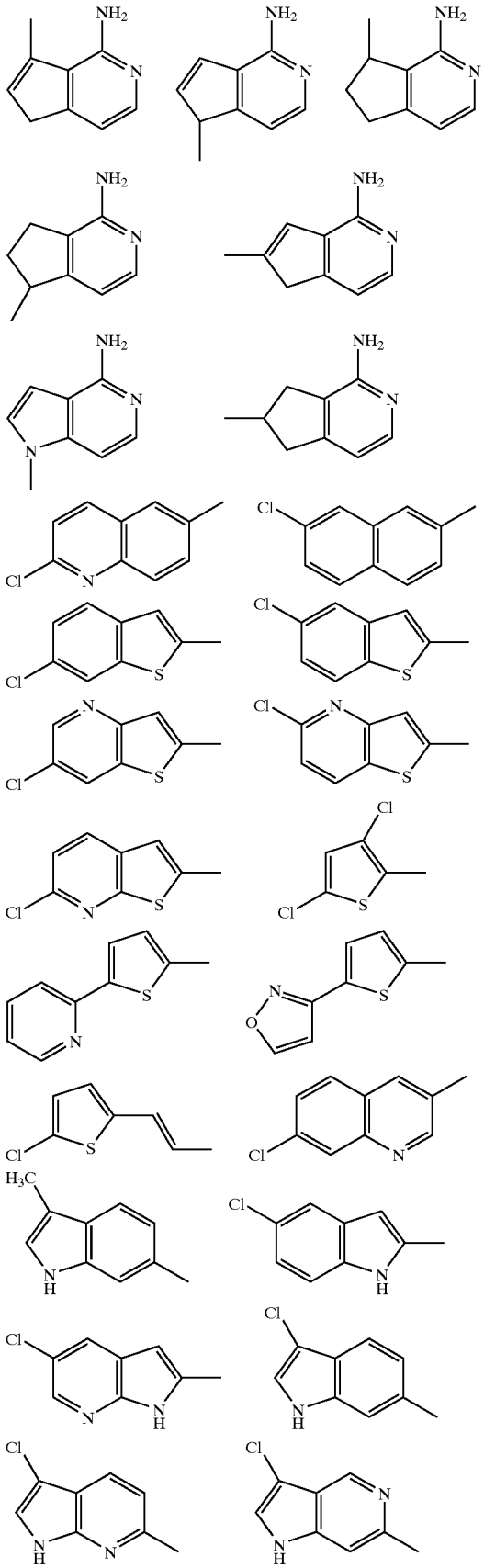

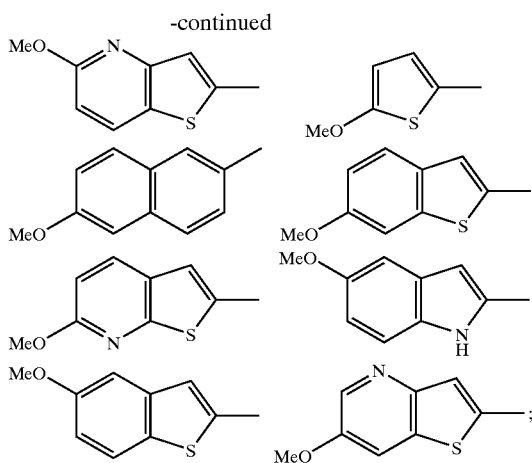

G₁ is absent or is selected from (CR³R³ᵃ)₁₋₃, (CR³R³ᵃ)ᵤC(O)(CR³R³ᵃ)ᵥ, (CR³R³ᵃ)ᵤO(CR³R³ᵃ)ᵥ, (CR³R³ᵃ)ᵤNR³ᵇ(CR³R³ᵃ)ᵥ, (CR³R³ᵃ)ᵤC(O)NR³ᵇ(CR³R³ᵃ)ᵥ, (CR³R³ᵃ)ᵤNR³ᵇC(O)(CR³R³ᵃ)ᵥ, (CR³R³ᵃ)ᵤNR³ᵇC(O)NR³ᵇ(CR³R³ᵃ)ᵥ, (CR³R³ᵃ)ᵤS(CR³R³ᵃ)ᵥ, (CR³R³ᵃ)ᵤS(O)(CR³R³ᵃ)ᵥ, (CR³R³ᵃ)ᵤS(O)₂(CR³R³ᵃ)ᵥ, (CR³R³ᵃ)ᵤS(O)NR³ᵇ(CR³R³ᵃ)ᵥ, (CR³R³ᵃ)ᵤNR³ᵇS(O)₂(CR³R³ᵃ)ᵥ, (CR³R³ᵃ)ᵤS(O)₂NR³ᵇ(CR³R³ᵃ)ᵥ, and (CR³R³ᵃ)ᵤC(O)NR³ᵇS(O)₂(CR³R³ᵃ)ᵥ, wherein u+w total 0, 1, or 2, provided that G₁ does not form a N—S, NCH₂N, NCH₂O, or NCH₂S bond with either group to which it is attached;

R¹ᵃ is selected from H, R¹ᵇ, CH(CH₃)R¹ᵇ, C(CH₃)₂R¹ᵇ, CH₂R¹ᵇ, and CH₂CH₂R¹ᵇ, provided that R¹ᵃ forms other than an N-halo, N—S, or N—CN bond;

alternatively, when two R¹ᵃ groups are attached to adjacent atoms, together with the atoms to which they are attached they form a 5–6 membered ring consisting of: carbon atoms and 0–2 heteroatoms selected from the group consisting of N, O, and S(O)ₚ, this ring being substituted with 0–2 R⁴ᵇ and 0–3 ring double bonds;

R¹ᵇ is selected from H, CH₃, CH₂CH₃, F, Cl, Br, —CN, —CHO, CF₃, OR²; NR²R²ᵃ, C(O)R²ᵇ, CO₂R²ᵇ, OC(O)R², CO₂R²ᵃ, S(O)ₚR², NR²(CH₂)ᵣOR², NR²C(O)R²ᵇ, C(O)NR²R²ᵃ, SO₂NR²R²ᵃ, NR²SO₂R², phenyl substituted with 0–2 R⁴ᵇ, and 5–6 membered aromatic heterocycle consisting of carbon atoms and from 1–4 heteroatoms selected from the group consisting of N, O, and S(O)ₚ and substituted with 0–2 R⁴ᵇ, provided that R¹ᵇ forms other than an O—O, N-halo, N—S, or N—CN bond;

A is selected from one of the following carbocyclic and heterocyclic groups which are substituted with 0–2 R⁴;

phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,24-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

X is selected from —C(O)—, —C(=NR¹ᵇ)—, —C(O)NR²—, —NR²C(O)—, —NR²C(O)CR²R²ᵃ—, —NR²C(O)NR²—, and O;

Y is selected from one of the following carbocyclic and heterocycles that are substituted with 1 R⁴ᵃ and 0–1 R⁴;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzimidazolone, benzoxazole, benzthiazole, indazole, benzisoxazole, benzisothiazole, and isoindazole;

R², at each occurrence, is selected from H, CF₃, CH₃, CH₂CH₃, CH₂CH₂CH₃, CH(CH₃)₂, phenyl substituted with 0–2 R⁴ᵇ, a benzyl substituted with 0–2 R⁴ᵇ, and 5–6 membered aromatic heterocycle consisting of: carbon atoms and 1–4 heteroatoms selected from the group consisting of N, O, and S(O)ₚ and substituted with 0–2 R⁴ᵇ;

R²ᵃ, at each occurrence, is selected from H, CF₃, CH₃, CH₂CH₃, CH₂CH₂CH₃, CH(CH₃)₂, benzyl, phenyl substituted with 0–2 R⁴ᵇ, and 5–6 membered aromatic heterocycle consisting of: carbon atoms and 1–4 heteroatoms selected from the group consisting of N, O, and S(O)ₚ and substituted with 0–2 R⁴ᵇ;

alternatively, R² and R²ᵃ, together with the atom to which they are attached, combine to form a 5 or 6 membered saturated, partially saturated or unsaturated ring substituted with 0–2 R⁴ᵇ and consisting of: 0–1 additional heteroatoms selected from the group consisting of N, O, and S(O)ₚ;

R²ᵇ, at each occurrence, is selected from CF₃, C₁₋₄ alkoxy, CH₃, CH₂CH₃, CH₂CH₂CH₃, CH(CH₃)₂, benzyl, phenyl substituted with 0–2 R⁴ᵇ, and 5–6 membered aromatic heterocycle consisting of: carbon atoms and 1–4 heteroatoms selected from the group consisting of N, O, and S(O)ₚ and substituted with 0–2 R⁴ᵇ;

R²ᶜ, at each occurrence, is selected from CF₃, OH, OCH₃, OCH₂CH₃, OCH₂CH₂CH₃, OCH(CH₃)₂, CH₃, CH₂CH₃, CH₂CH₂CH₃, CH(CH₃)₂, benzyl, phenyl substituted with 0–2 R⁴ᵇ, and 5–6 membered aromatic heterocycle containing from 1–4 heteroatoms selected from the group consisting of N, O, and S(O)ₚ and substituted with 0–2 R⁴ᵇ;

R²ᵈ, at each occurrence, is selected from H, R⁴ᶜ, C₁₋₄ alkyl substituted with 0–2 R⁴ᶜ, C₃₋₆ carbocycle substituted with 0–2 R⁴ᶜ, —(CR³R³ᵃ)—C₃₋₆ carbocycle substituted with 0–2 R⁴ᶜ, 5–6 membered heterocycle consisting of: carbon atoms and 1–4 heteroatoms selected from the group consisting of N, O, and S(O)ₚ and substituted with 0–2 R⁴ᶜ, and —(CR³R³ᵃ)-5–6 membered heterocycle consisting of: carbon atoms and 1–4 heteroatoms selected from the group consisting of N, O, and S(O)ₚ and substituted with 0–2 R⁴ᶜ, provided that R²ᵈ forms other than a N-halo, N—C-halo, S(O)ₚ-halo, O-halo, N—S, S—N, S(O)ₚ—S(O)ₚ, S—O, O—N, O—S, or O—O moiety;

R²ᵉ, at each occurrence, is selected from H, R⁴ᶜ, C₁₋₄ alkyl substituted with 0–2 R⁴ᶜ, C₃₋₆ carbocycle substituted with 0–2 R⁴ᶜ, —(CR³R³ᵃ)—C₃₋₆ carbocycle substituted with 0–2 R⁴ᶜ, 5–6 membered heterocycle consisting of: carbon atoms and 1–4 heteroatoms selected from the group consisting of N, O, and S(O)ₚ and substituted with 0–2 R⁴ᶜ, and —(CR³R³ᵃ)-5–6 membered heterocycle consisting of: carbon atoms and 1–4 heteroatoms selected from the group consisting of N, O, and S(O)ₚ and substituted with 0–2 R⁴ᶜ, provided that R²ᵉ forms other than a C(O)-halo or C(O)—S(O)ₚ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from $(CH_2)_vN(\rightarrow O)R^{2d}R^{2d}$, $(CH_2)_v$—$NR^{2d}C(O)R^{2e}$, $(CH_2)_v$—$NR^{2d}C(O)NR^{2d}R^{2d}$, $(CH_2)_v$—$NR^{2d}C(O)OR^{2d}$, and $(CH_2)_v$—$NR^{2d}SO_2R^{2d}$;

alternatively, $R^{4a}$ is selected from $(CH_2)_vNR^{2d}R^{2d}$, $NR^{2d}C(O)R^{2e}$, $NR^{2d}C(O)NR^{2d}R^{2d}$, $NR^{2d}C(O)OR^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$5–0 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2$—$C_{1-4}$ alkyl; and, v, at each occurrence, is selected from 1 and 2.

[11] In another preferred embodiment, the present invention provides a novel compound, wherein the compound is selected from:

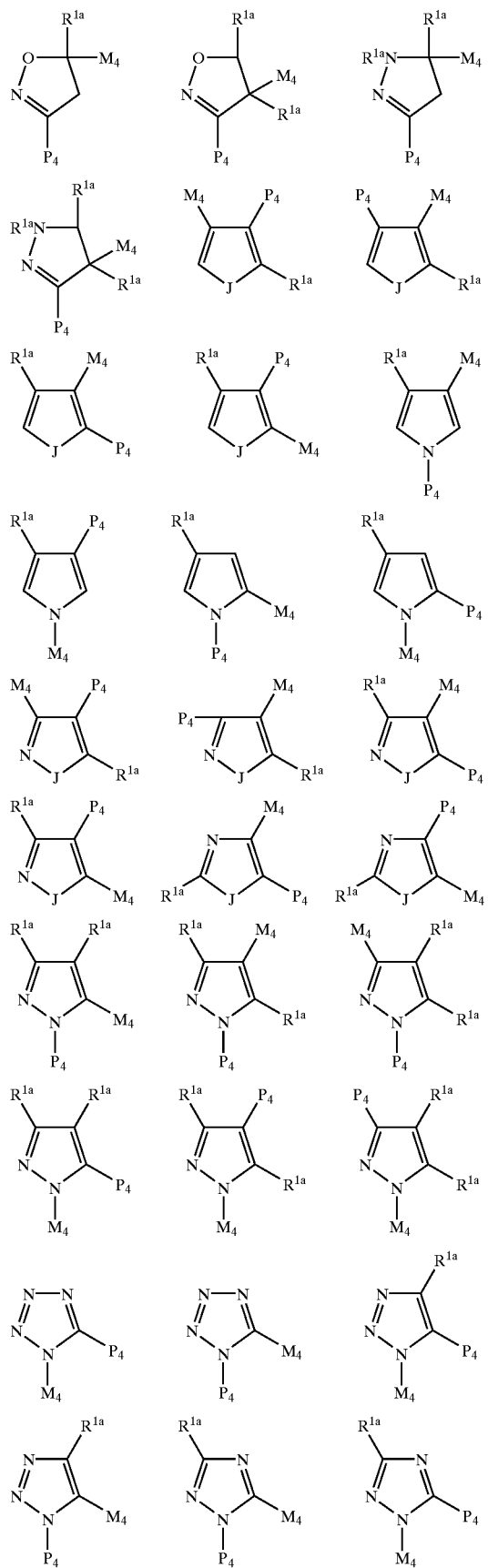

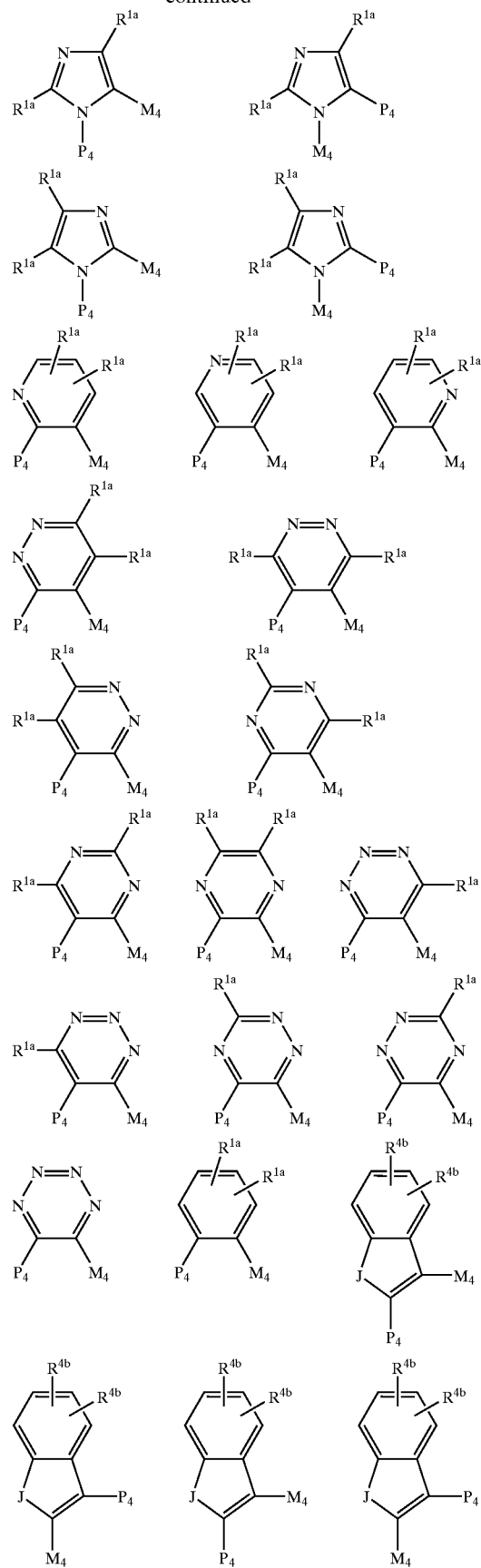
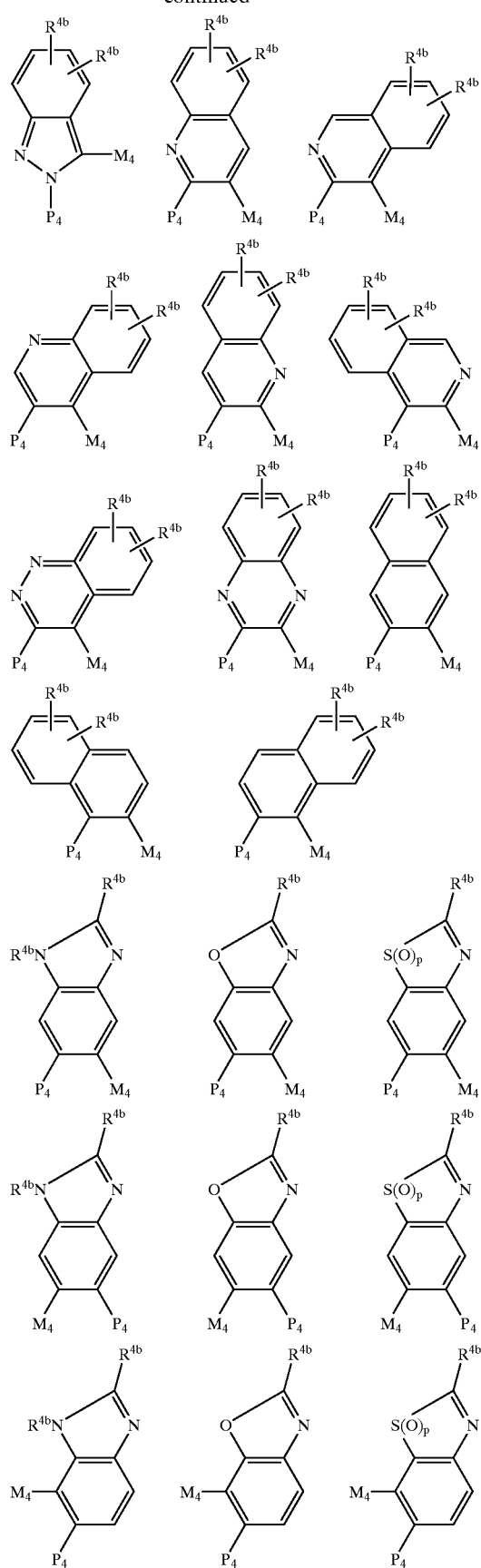

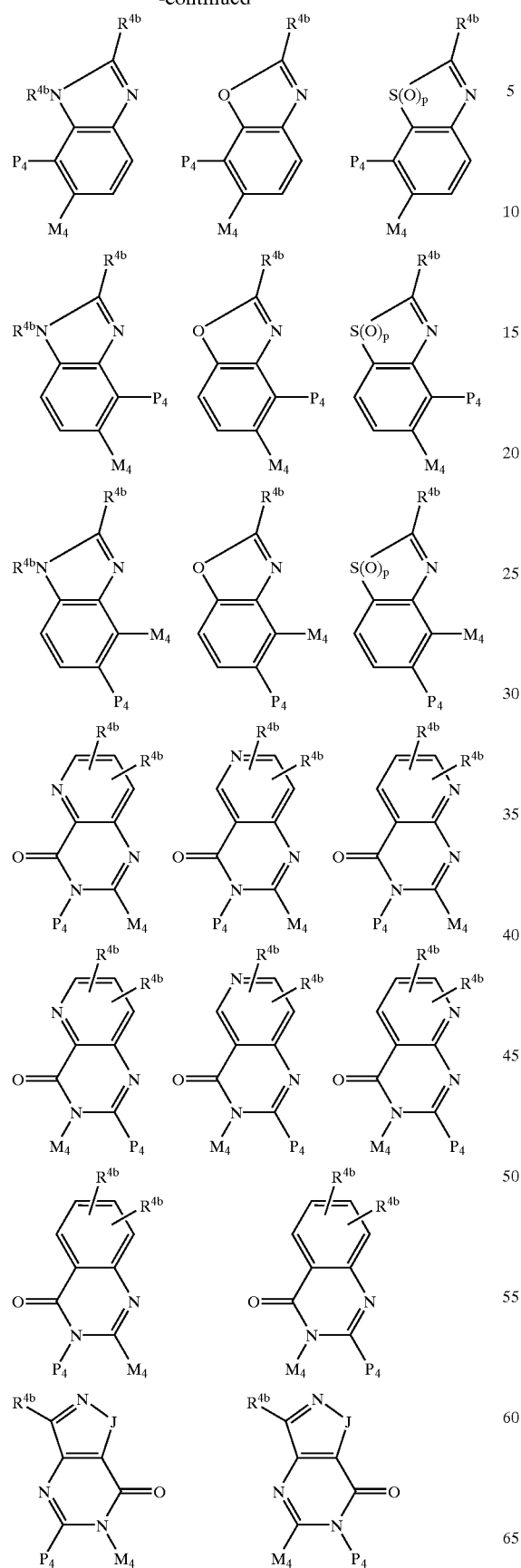
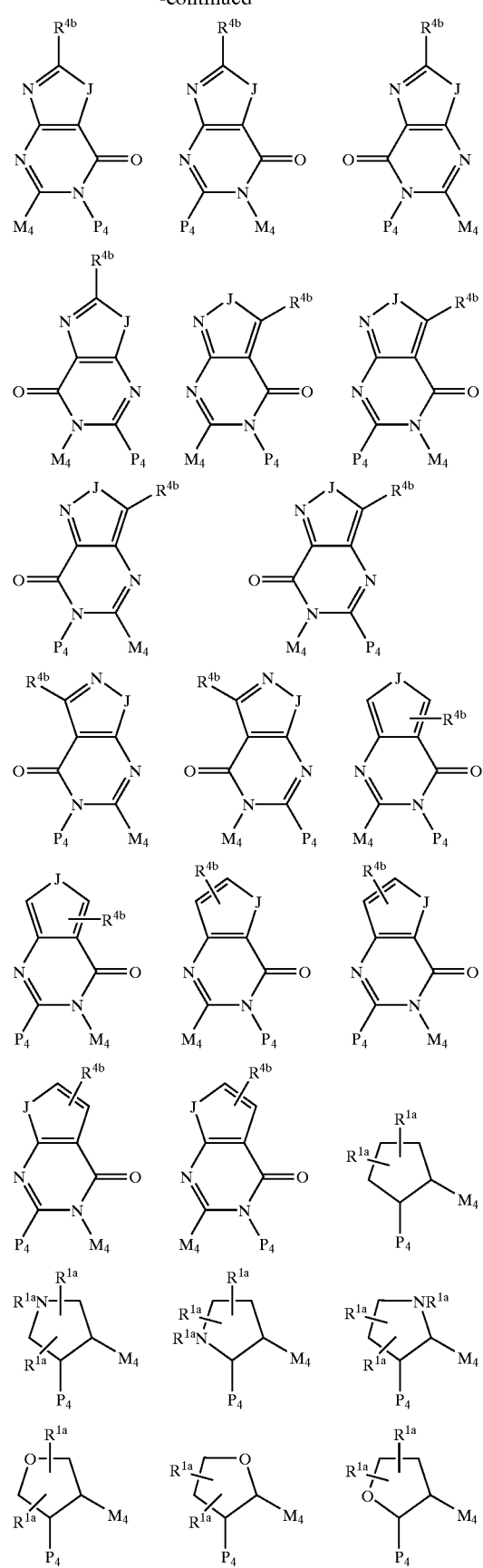

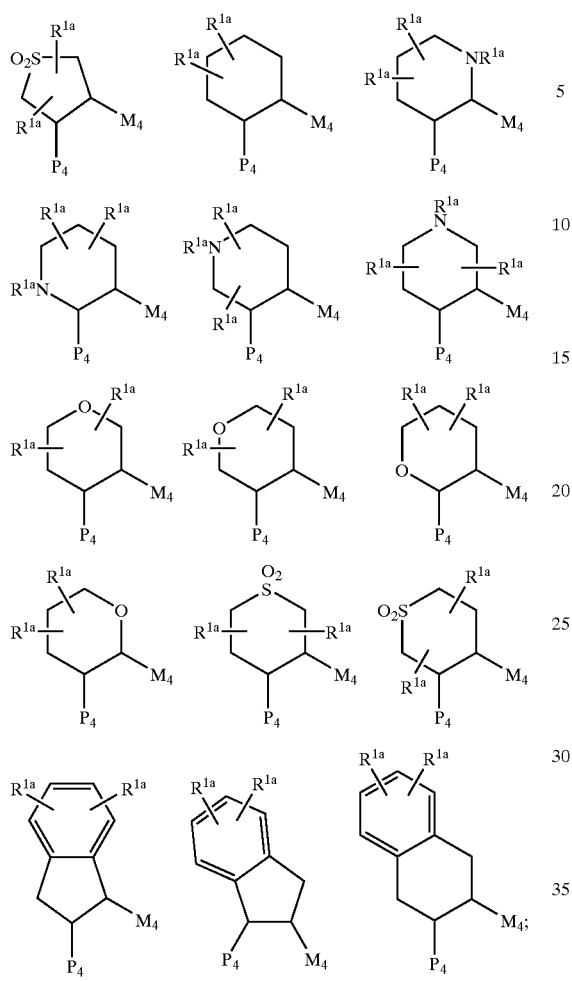
J is selected from O, S, NH, and $NR^{1a}$;
G is selected from the group:
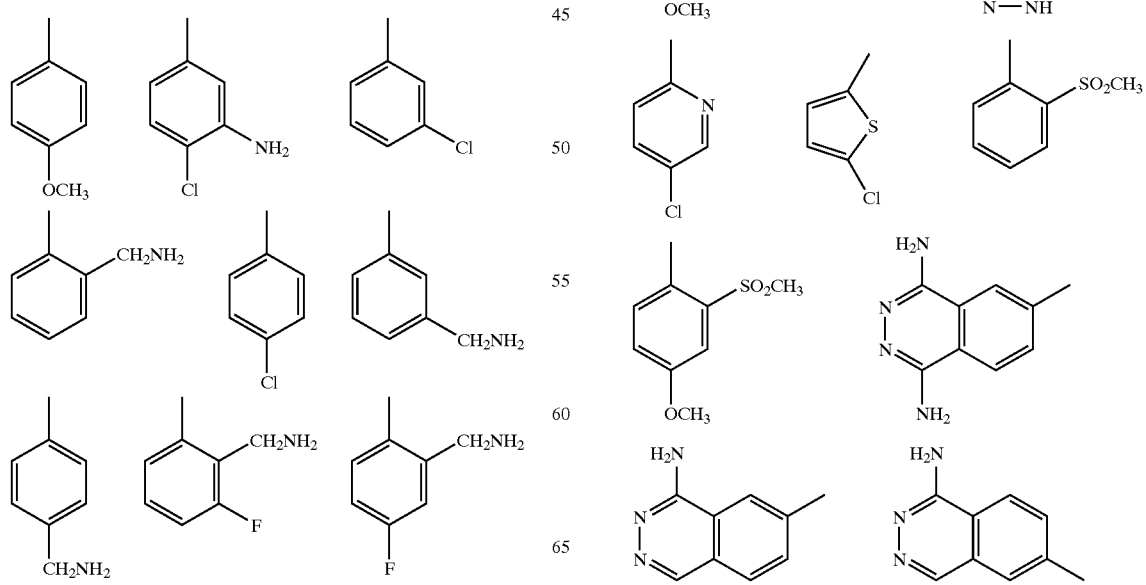
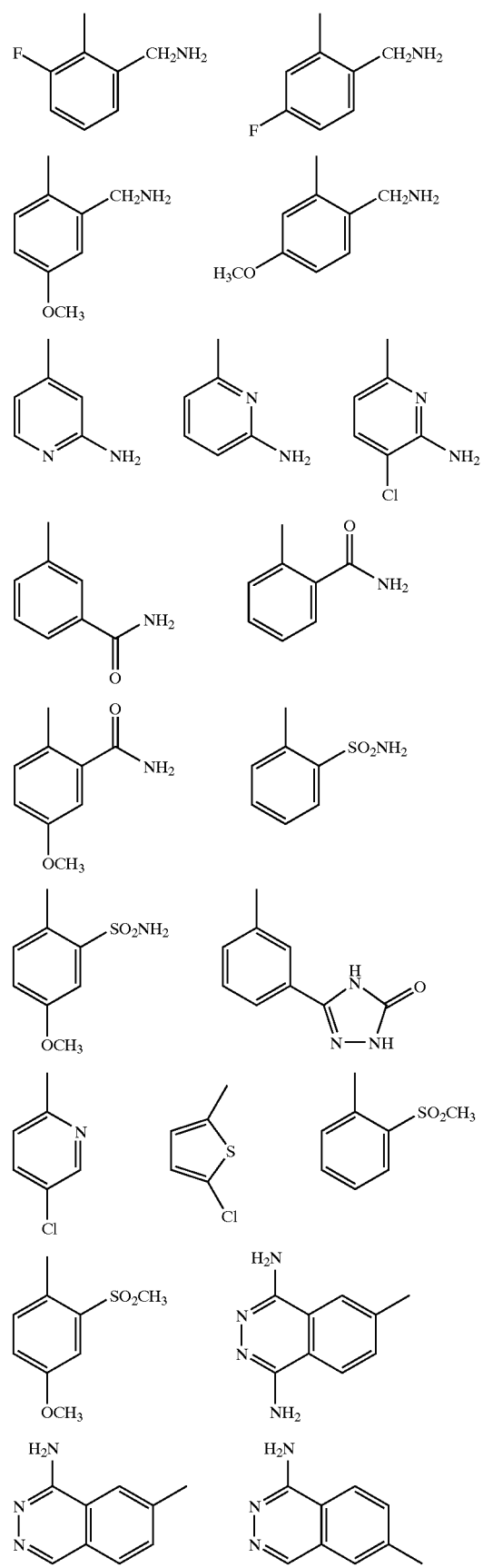

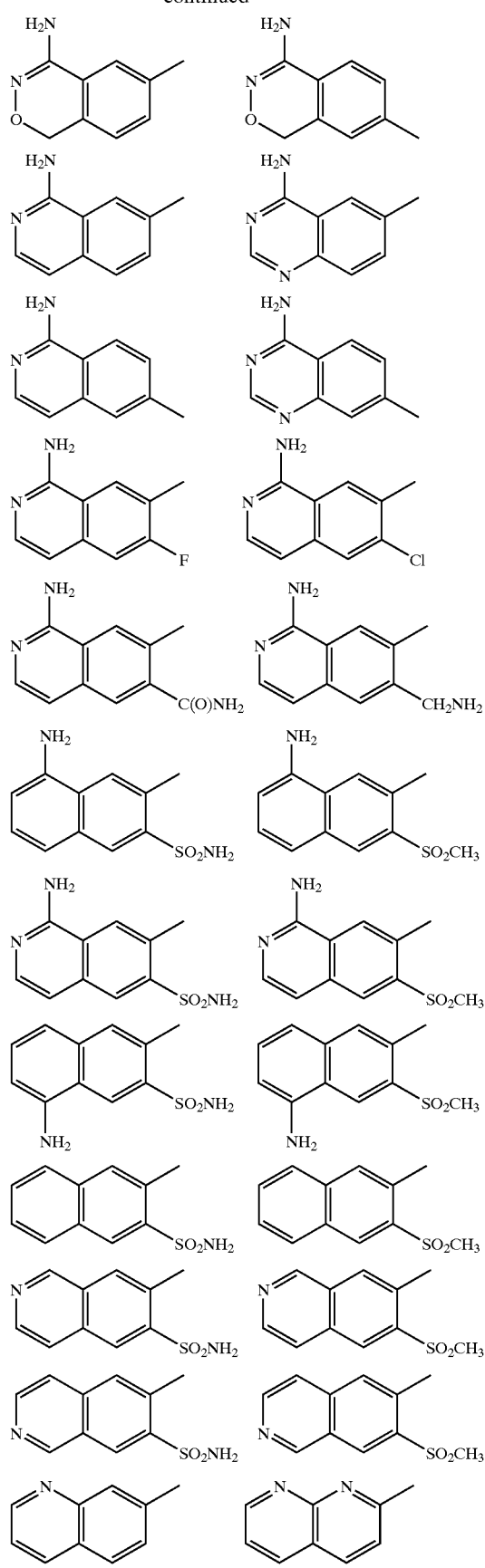
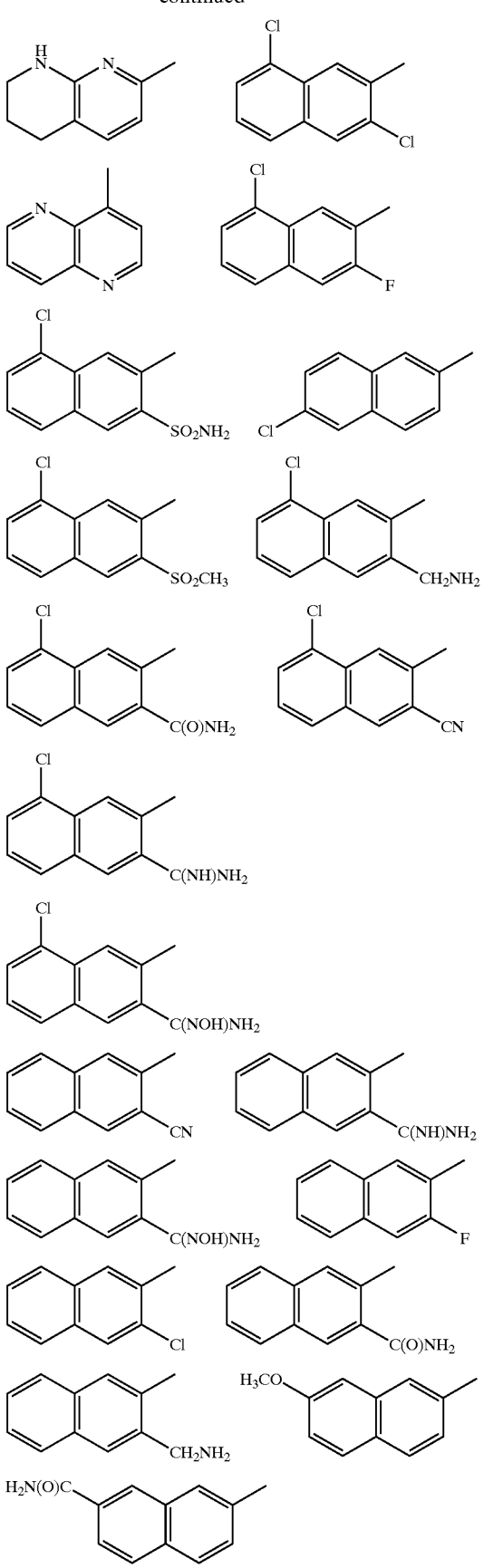

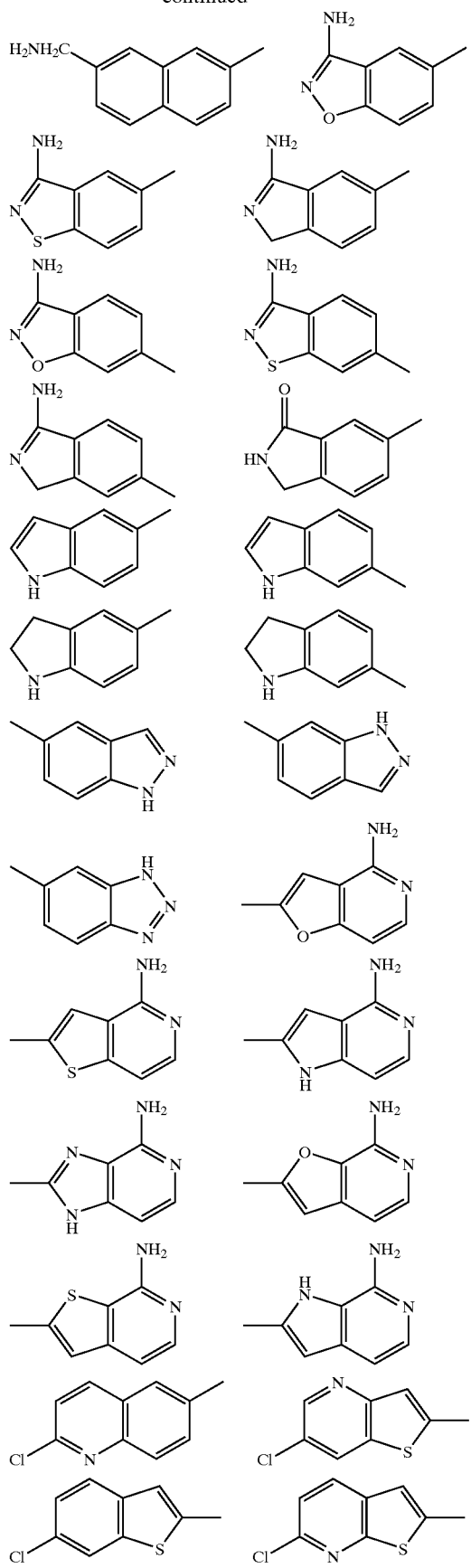
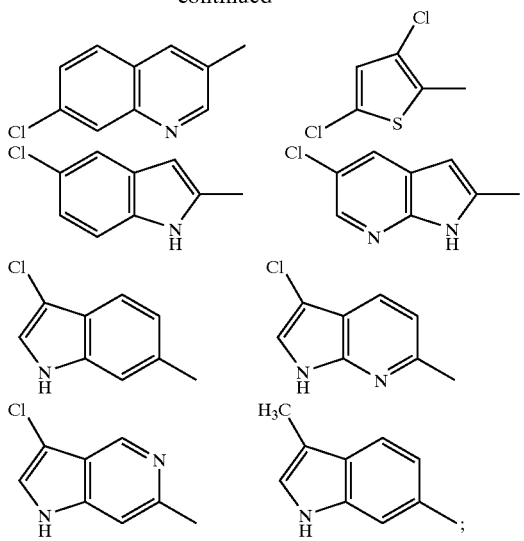

G₁ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $NHC(O)NH$, $C(O)NHS(O)_2$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from indolinyl, piperidinyl, phenyl, pyridyl, and pyrimidyl, and is substituted with 0–2 $R^4$;

B is selected from phenyl, pyridyl, pyrrolidino, N-pyrrolidino-carbonyl, morpholino, N-morpholino-carbonyl, 1,2,3-triazolyl, imidazolyl, and benzimidazolyl, and is substituted with 1 $R^{4a}$ and 0–1 $R^4$;

$R^{1a}$ is selected from H, $R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CH_2)$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N-C-halo, $S(O)_p$-halo, O-halo, N—S, S—N, $S(O)_p$—S $(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle consisting of:

carbon atoms and 1–4 heteroatoms selected from the group consisting of N, O, and $S(O)_p$ and substituted with 0–2 $R^{4c}$, and —$(CH_2)$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$ is selected from $(CH_2)_vN(\rightarrow O)R^{2d}R^{2d}$, $(CH_2)_v$—$NR^{2d}C(O)R^{2e}$, $(CH_2)_v$—$NR^{2d}C(O)NR^{2d}R^{2d}$, $(CH_2)_v$—$NR^{2d}C(O)OR^{2d}$, and $(CH_2)_v$—$NR^{2d}SO_2R^{2d}$, alternatively, $R^{4a}$ is selected from $(CH_2)_vNR^{2d}R^{2d}$, $NR^{2d}C(O)R^{2e}$, $NR^{2d}C(O)NR^{2d}R^{2d}$, $NR^{2d}C(O)OR^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $C_{1-4}$ alkyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}S(O)_p R^{5a}$, $CH_2S(O)_p R^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[12] In another preferred embodiment, the present invention provides a novel compound, wherein the compound is selected from:

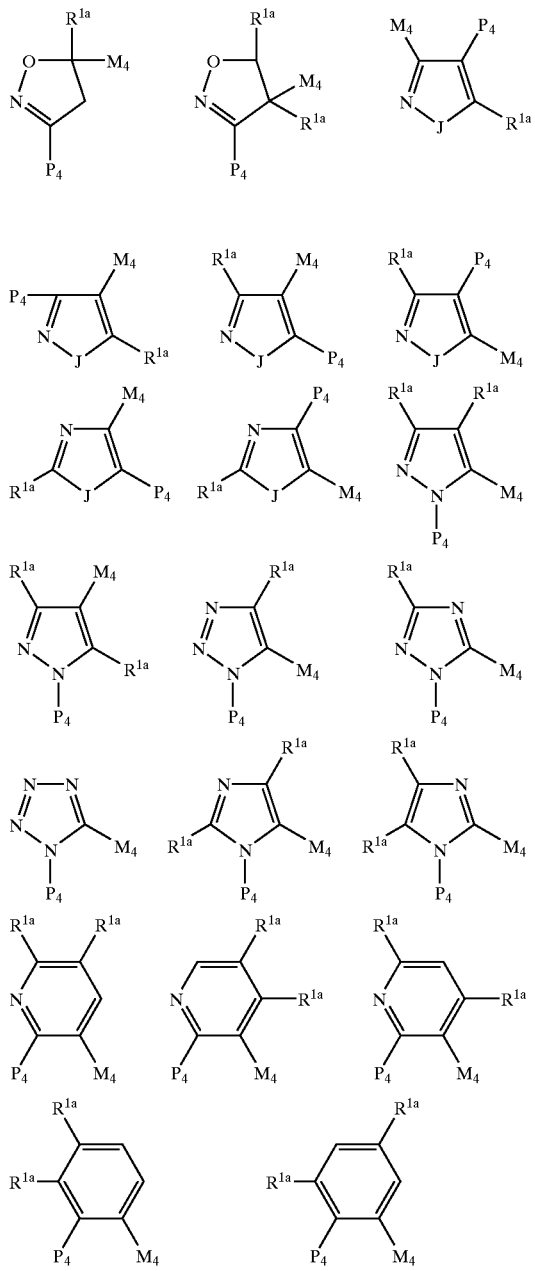

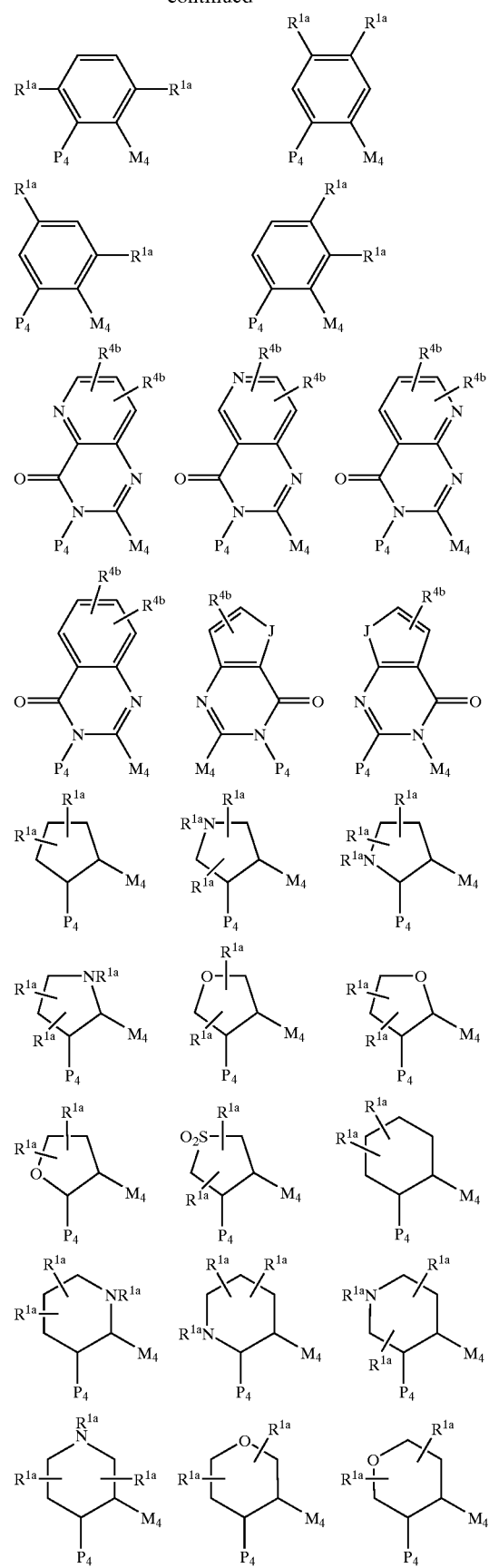
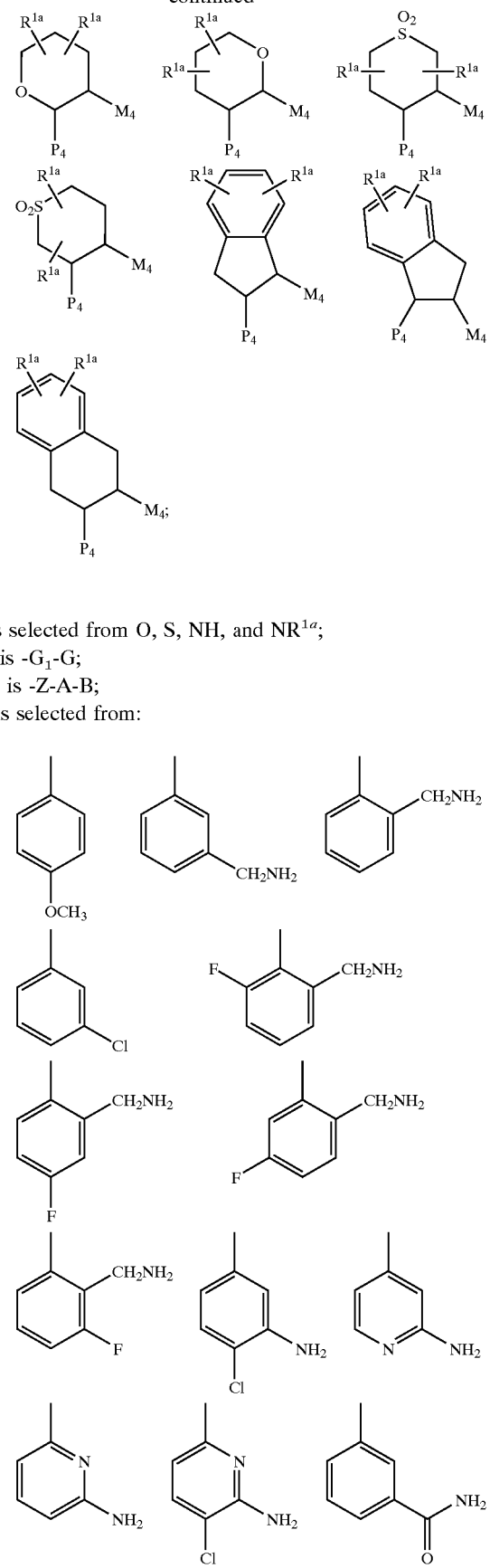
J is selected from O, S, NH, and $NR^{1a}$;
$P_4$ is $-G_1-G$;
$M_4$ is $-Z-A-B$;
G is selected from:
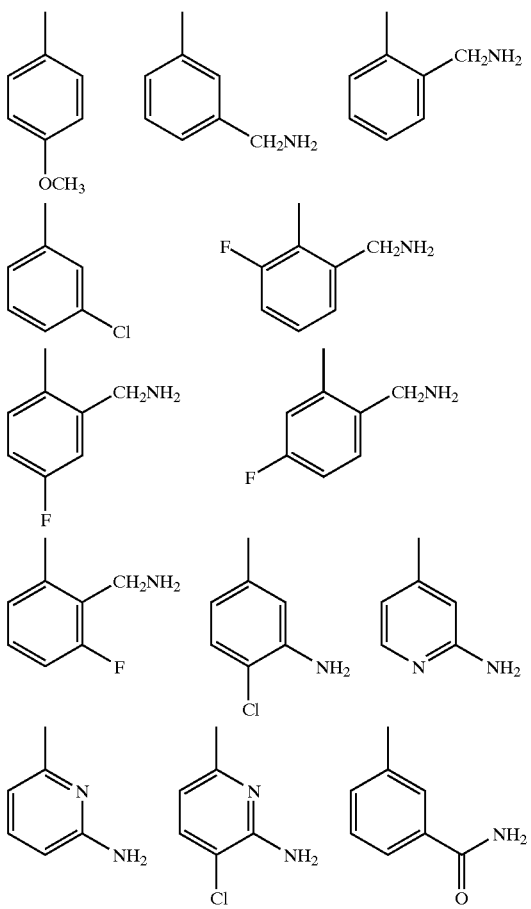

-continued
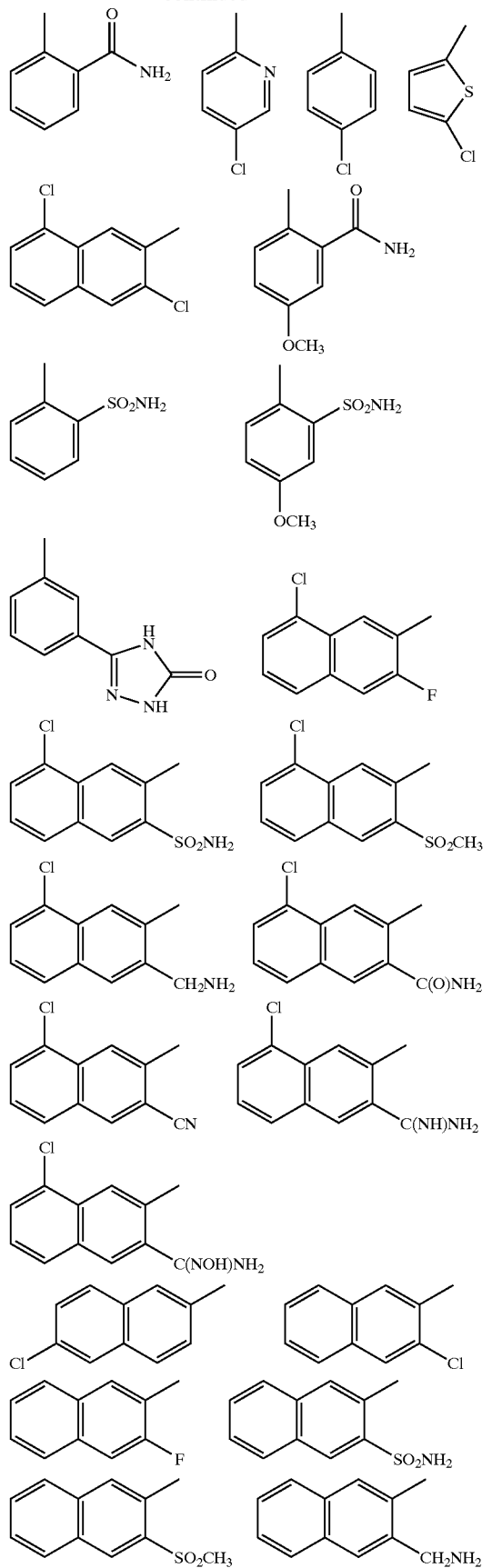
-continued
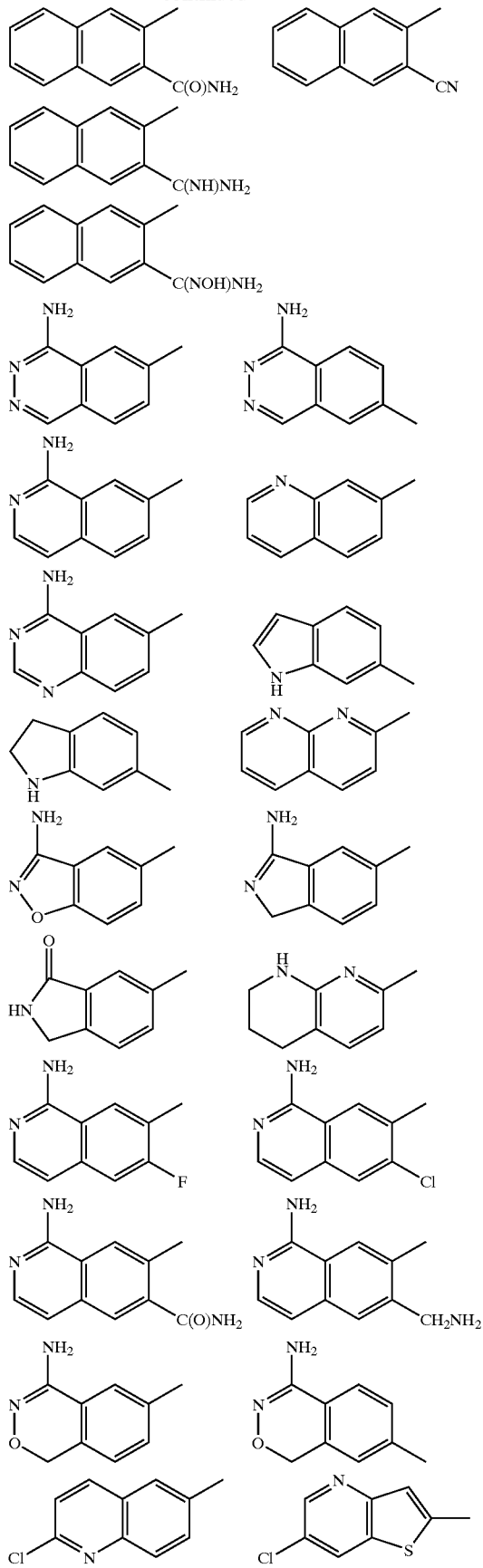

-continued

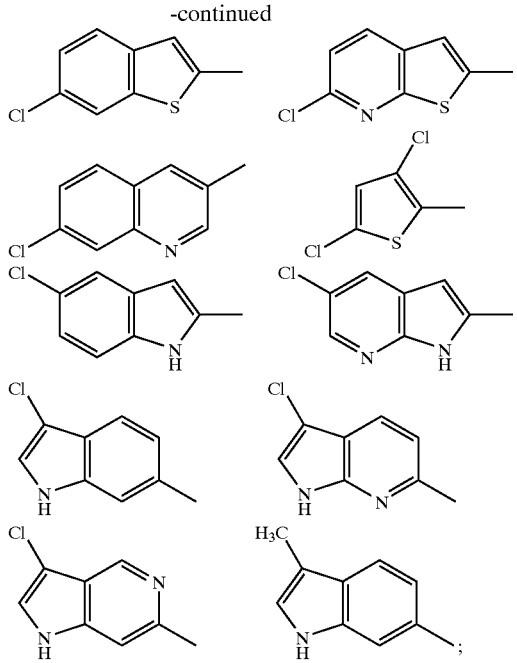

G₁ is absent or is selected from CH₂NH, NHCH₂, CH₂C(O), C(O)CH₂, C(O)NH, NHC(O), NHC(O)NH, CH₂S(O)₂, S(O)₂(CH₂), SO₂NH, and NHSO₂, provided that G₁ does not form a N—S, NCH₂N, NCH₂O, or NCH₂S bond with either group to which it is attached;

A is selected from the group: indolinyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from phenyl, pyridyl, 1,2,3-triazolyl, imidazolyl, and benzimidazolyl, and is substituted with 1 $R^{4a}$;

$R^{1a}$ is selected from H, CH₃, CH₂CH₃, CH₂CH₂CH₃, CH₂F, CH₂Cl, Br, CH₂Br, —CN, CH₂CN, CF₃, CH₂CF₃, OCH₃, CH₂OH, C(CH₃)₂OH, CH₂OCH₃, NH₂, CH₂NH₂, NHCH₃, CH₂NHCH₃, N(CH₃)₂, CH₂N(CH₃)₂, CO₂H, COCH₃, CO₂CH₃, CH₂CO₂CH₃, SCH₃, CH₂SCH₃, S(O)CH₃, CH₂S(O)CH₃, S(O)₂CH₃, CH₂S(O)₂CH₃, C(O)NH₂, CH₂C(O)NH₂, SO₂NH₂, CH₂SO₂NH₂, NHSO₂CH₃, CH₂NHSO₂CH₃, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH₂-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, CH₂-1,2,3,4-tetrazol-1-yl, and CH₂-1,2,3,4-tetrazol-5-yl, provided that $R^1a$ forms other than an N-halo, N—S, or N—CN bond;

$R^2$, at each occurrence, is selected from H, CH₃, CH₂CH₃, CH₂CH₂CH₃, CH(CH₃)₂, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and S(O)$_p$ and substituted with 0–1 $R^{4b}$;

$R^{2a}$, at each occurrence, is selected from H, CH₃, and CH₂CH₃;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and S(O)$_p$;

$R^{2b}$, at each occurrence, is selected from OH, OCH₃, OCH₂CH₃, CH₃, and CH₂CH₃;

$R^{2c}$, at each occurrence, is selected from OH, OCH₃, OCH₂CH₃, CH₃, and CH₂CH₃;

$R^{2d}$, at each occurrence, is selected from H, $R^{4c}$, C₁₋₄ alkyl substituted with 0–2 $R^{4c}$, C₃₋₆ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and S(O)$_p$ and substituted with 0–2 $R^{4c}$, provided that $R^{2d}$ forms other than a N-halo, N—C-halo, S(O)$_p$-halo, O-halo, N—S, S—N, S(O)$_p$—S(O)$_p$, S—O, O—N, O—S, or O—O moiety;

$R^{2e}$, at each occurrence, is selected from H, $R^{4c}$, C₁₋₄ alkyl substituted with 0–2 $R^{4c}$, C₃₋₆ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and S(O)$_p$ and substituted with 0–2 $R^{4c}$, provided that $R^{2e}$ forms other than a C(O)-halo or C(O)—S(O)$_p$ moiety;

$R^{4a}$ is selected from CH₂N(→O)$R^{2d}R^{2d}$, CH₂N$R^{2d}$C(O)$R^{2e}$, CH₂N$R^{2d}$C(O)NR$^{2d}R^{2d}$, CH₂N$R^{2d}$C(O)O$R^{2d}$, and CH₂N$R^{2d}$SO₂$R^{2d}$;

$R^{4b}$, at each occurrence, is selected from H, =O, O$R^3$, CH₂O$R^3$, F, Cl, CH₃, CH₂CH₃, NR³R$^{3a}$, CH₂NR³R$^{3a}$, C(O)$R^3$, C(O)O$R^{3c}$, NR³C(O)$R^{3a}$, C(O)NR³R$^{3a}$, SO₂NR³R$^{3a}$, NR³SO₂-phenyl, S(O)₂CH₃, S(O)₂-phenyl, and CF₃;

$R^{4c}$, at each occurrence, is selected from =O, OH, OCH₃, OCH₂CH₃, OCH₂CH₂CH₃, OCH(CH₃)₂, CH₃, CH₂CH₃, CH₂CH₂CH₃, CH(CH₃)₂, CH₂OH, CH₂OCH₃, CH₂OCH₂CH₃, CH₂OCH₂CH₂CH₃, CH₂OCH(CH₃)₂, F, Br, Cl, CF₃, NR²R$^{2a}$, CH₂NR²R$^{2a}$, N(→O)R²R$^{2a}$, CH₂N(O)R²R$^{2a}$, C(O)R$^{2c}$, CH₂C(O)R$^{2c}$, NR²C(O)R$^{2b}$, CH₂NR²C(O)R$^{2b}$, C(O)NR²R$^{2a}$, CH₂C(O)NR²R$^{2a}$, SO₂NR²R$^{2a}$, CH₂SO₂NR²R$^{2a}$, NR²SO₂R$^{5a}$, CH₂NR²SO₂R$^{5a}$, S(O)$_p$R$^{5a}$, CH₂S(O)$_p$R$^{5a}$, CF₃, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, CH₂-cyclopropyl substituted with 0–1 $R^{4b}$, CH₂-cyclobutyl substituted with 0–1 $R^{4b}$, —CH₂-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and S(O)$_p$ and substituted with 0–2 $R^{4b}$, and (CH₂)-5–6 membered aromatic heterocycle consisting of carbon atoms and from 1–4 heteroatoms selected from the group consisting of N, O, and S(O)$_p$ and substituted with 0–2 $R^{4b}$;

$R^5$, at each occurrence, is selected from H, =O, CH₃, CH₂CH₃, O$R^3$, CH₂O$R^3$, F, Cl, NR³R$^{3a}$, CH₂NR³R$^{3a}$, C(O)$R^3$, C(O)O$R^{3c}$, NR³C(O)$R^{3a}$, C(O)NR³R$^{3a}$, SO₂NR³R$^{3a}$, NR³SO₂—C₁₋₄ alkyl, NR³SO₂-phenyl, S(O)₂—CH₃, S(O)₂-phenyl, CF₃, phenyl substituted with 0–2 $R^6$, naphthyl substituted with 0–2 $R^6$, and benzyl substituted with 0–2 $R^6$; and, $R^6$, at each occurrence, is selected from H, OH, O$R^2$, F, Cl, CH₃, CH₂CH₃, NR²R$^{2a}$, CH₂NR²R$^{2a}$, C(O)R$^{2b}$, CH₂C(O)R$^{2b}$, NR²C(O)R$^{2b}$, and SO₂NR²R$^{2a}$.

[13] In another preferred embodiment, the present invention provides a novel compound, wherein the compound is selected from:

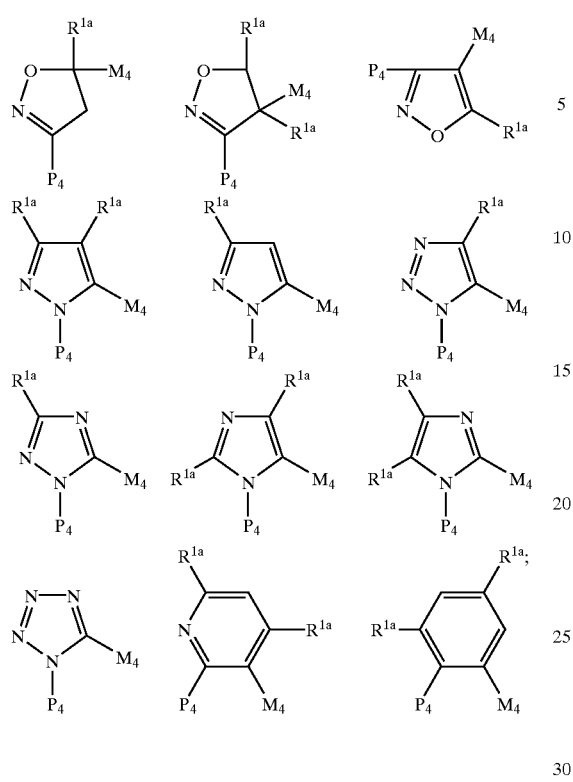
G is selected from:
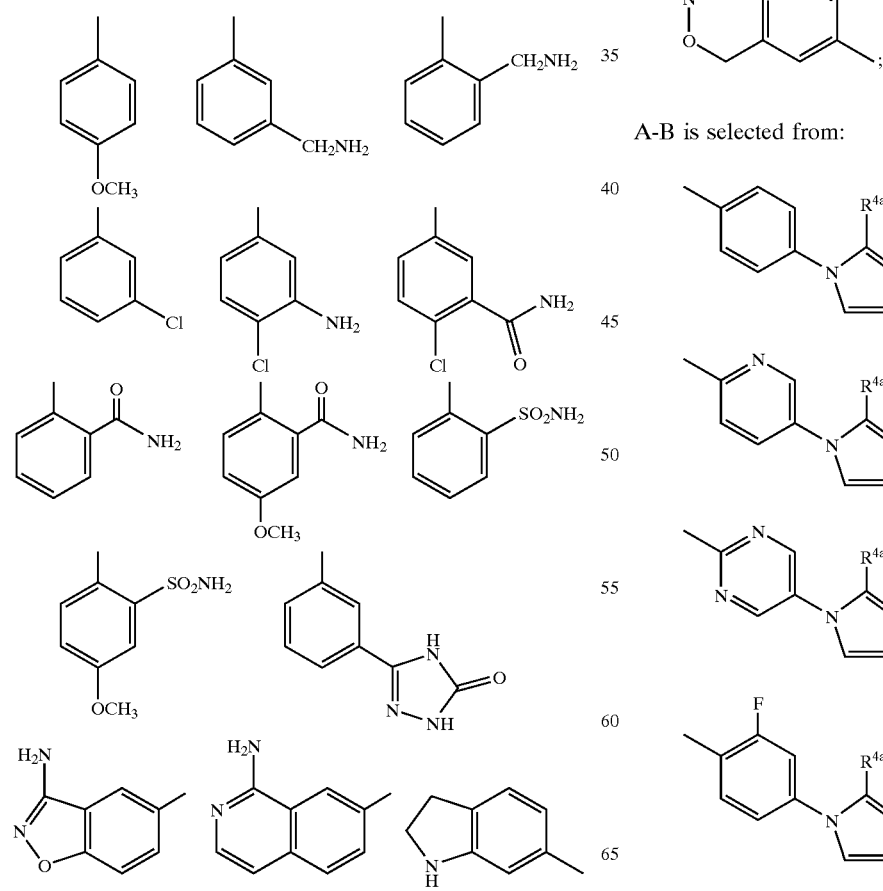
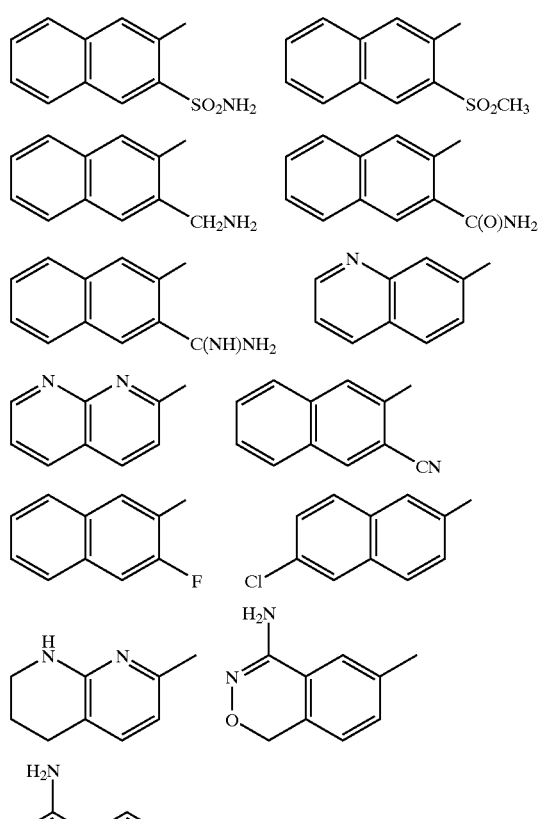
A-B is selected from:
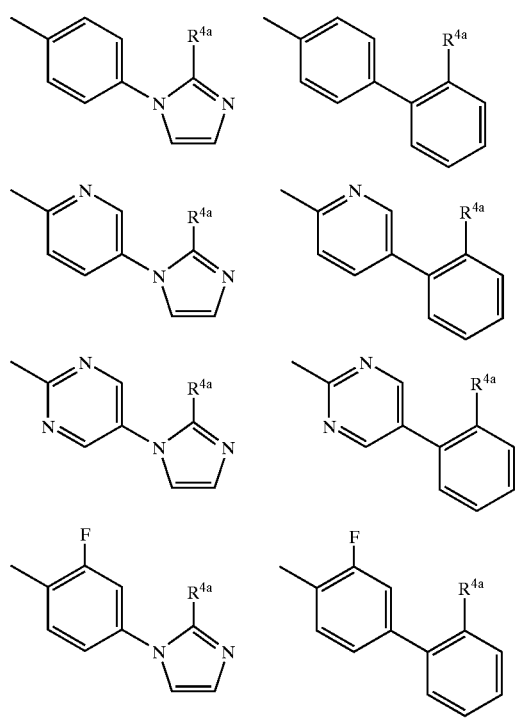

-continued

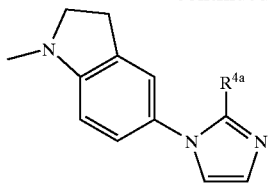

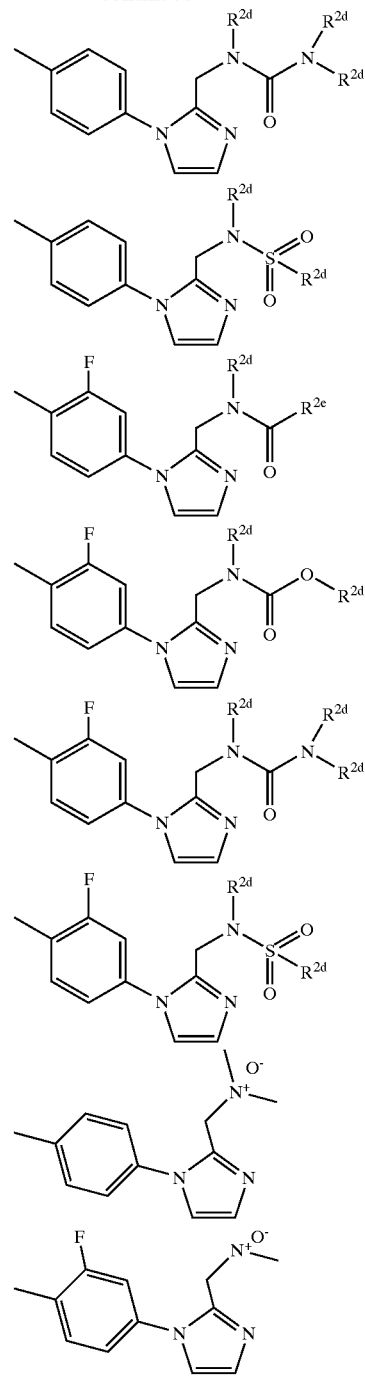

$R^{2d}$, at each occurrence, is selected from H, $C_{1-4}$ alkyl substituted with 0–1 $R^{4c}$, $C_{3-6}$ cycloalkyl substituted with 0–2 $R^{4c}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $CH_2N(\rightarrow O)R^{2d}R^{2d}$, $CH_2NR^{2d}C(O)R^{2e}$, $CH_2NR^{2d}C(O)OR^{2d}$, and $CH_2NR^{2d}SO_2R^{2d}$; and, $R^{4c}$ is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_p R^{5a}$, and $CH_2S(O)_p R^{5a}$.

[14] In another preferred embodiment, the present invention provides a novel compound, wherein the compound is selected from:

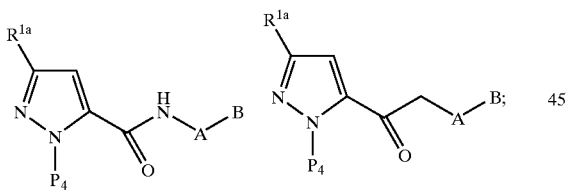

$P_4$ is -G; and
A-B is selected from:

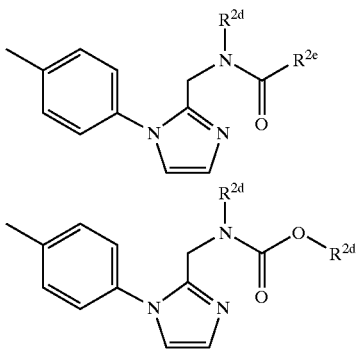

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl; and, $R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl.

[15] In another preferred embodiment, the present invention provides a novel compound, wherein the compound is selected from the group:

N-[4-(2-{[acetyl(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide;

N-[4-(2-{[acetyl(methyl)amino]methyl}-1H-imidazol-1-yl)-2-fluorophenyl]-1-(3-amino-1,2-benzisoxazol-5-yl)-3-(methylsulfonyl)-1H-pyrazole-5-carboxamide;

N-[4-(2-{[methylsulfonylamino]methyl}-1H-imidazol-1-yl)-2-fluorophenyl]-1-(4-methoxyphenyl)-3-(methylsulfonyl)-1H-pyrazole-5-carboxamide;

N-[4-(2-{[methylsulfonylamino]methyl}-1H-imidazol-1-yl)-2-fluorophenyl]-1-(4-methoxyphenyl)-3-(aminocarbonyl)-1H-pyrazole-5-carboxamide;

5-{[5-(2-{[acetyl(methyl)amino]methyl}-1H-imidazol-1-yl)-2,3-dihydro-1H-indol-1-yl]carbonyl}-1-(3-amino-1,2-benzisoxazol-5-yl)-1H-pyrazole-3-carboxamide;

1-(3-amino-1,2-benzisoxazol-5-yl)-5-{[5-(2-{[methyl(methylsulfonyl)amino]methyl}-1H-imidazol-1-yl)-2,3-dihydro-1H-indol-1-yl]carbonyl}-1H-pyrazole-3-carboxamide;

2-(3-aminobenzo[d]isoxazol-5-yl)-5-trifluoromethyl-2H-pyrazole-3-carboxylic acid (1-{2-[(acetylmethylamino)-methyl]phenyl}-piperidin-4-yl)amide;

2-(3-aminobenzo[d]isoxazol-5-yl)-5-trifluoromethyl-2H-pyrazole-3-carboxylic acid (1-{2-[(methanesulfonylmethyl-amino)methyl]phenyl}piperidin-4-yl)amide;

2-(4-methoxyphenyl)-5-trifluoromethyl-2H-pyrazole-3-carboxylic acid [1-(2-{[(2-hydroxyethyl)methylamino]-methyl}phenyl)piperidin-4-yl]amide;

or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be-isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and SO$_2$H.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with an oxidizing agent (e.g., MCPBA and/or hydrogen peroxides) to afford other compounds of this invention. Thus, all shown and claimed amines are considered to cover both the shown amine and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)) Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_3$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]

bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2] bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of the present invention of formula I (Scheme 1) where P is not fused onto ring M could be prepared as outlined in Scheme 2 to Scheme 8 and via standard methods known to those skilled in the art.

Scheme 1

Formula I

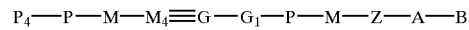

The compounds of the present invention of formula I where B is imidazole can be prepared as shown in Scheme 2. Commercially available imidazole 2-carboxaldehyde can be used as the starting material. Reductive amination, followed by protection of the amino group can produce the imidazole intermediate 2. Ullman coupling of imidazole 2 with iodide 3 can give the biaryl A-B precursor 4, which can be coupled with 5 using standard coupling conditions to provide 6. Deprotection of the CBZ group, followed by reaction with acid chlorides, carbamoyl chloride, sulfonyl chlorides, and isocyanates can provide compounds of the invention with structures 7, 8, 9, and 10. Similarly, other compounds of the present invention where B is an imidazole derivative could be prepared as shown in Scheme 3 using 2-aminomethylimidazole (JOC, 43 (8), 1978, 1603) as the starting material.

Scheme 2
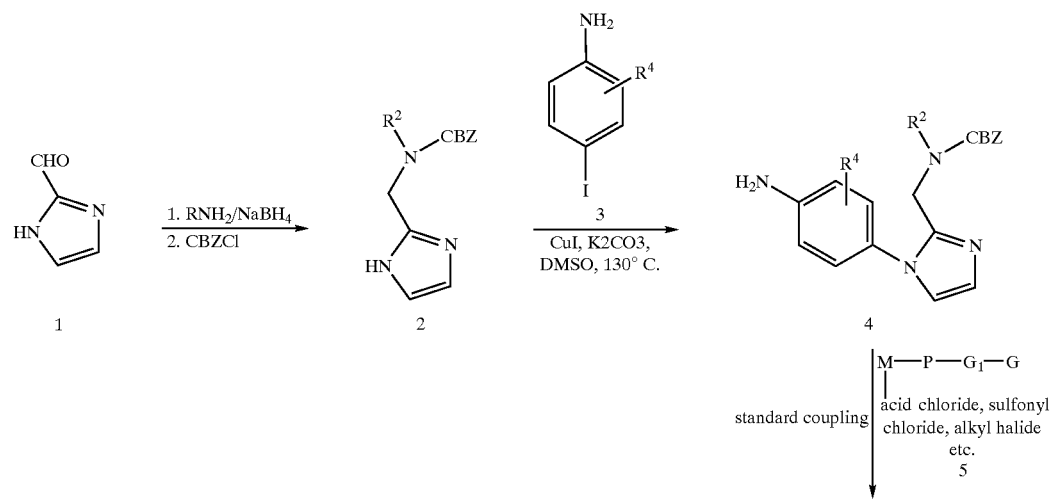
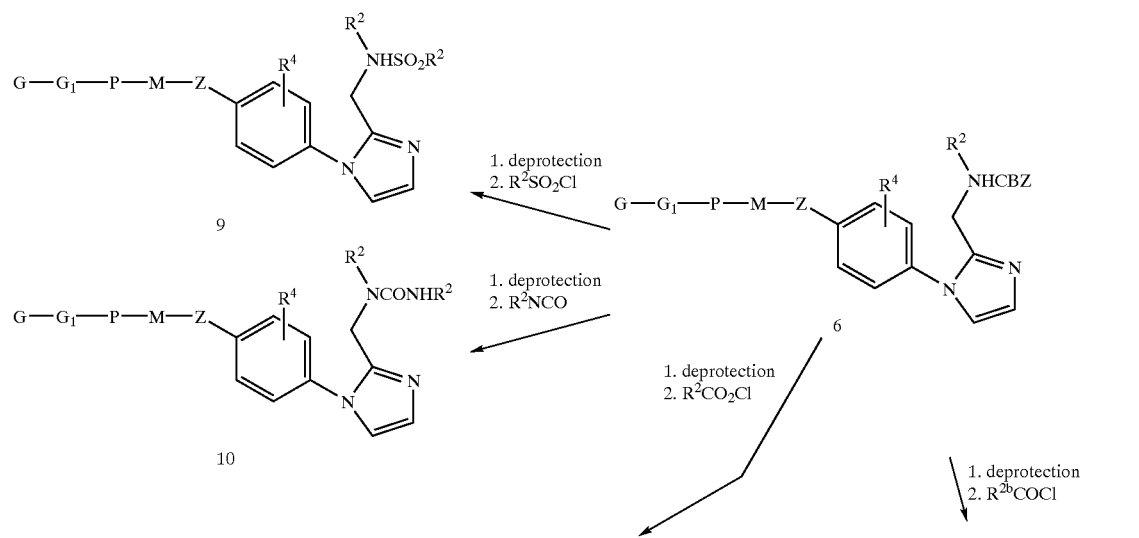

Scheme 3

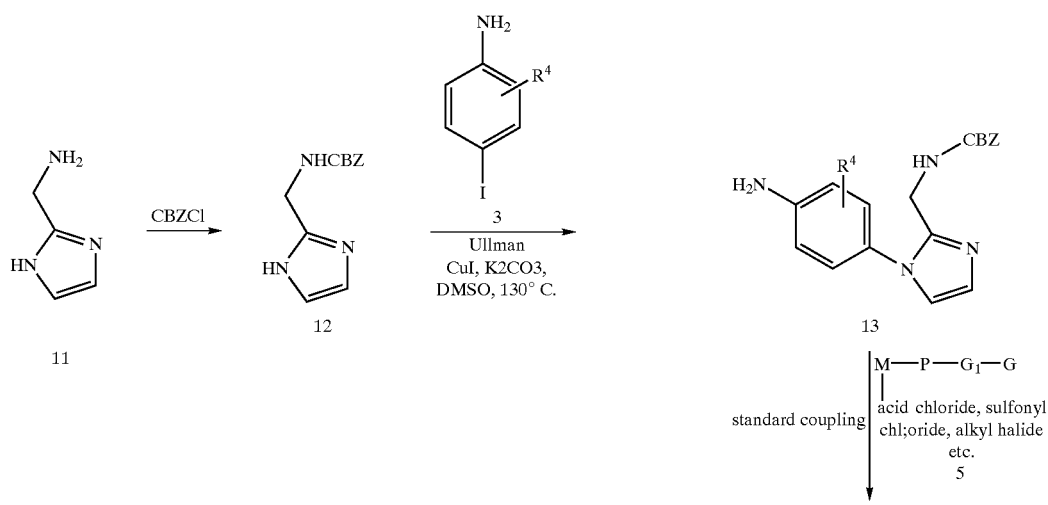

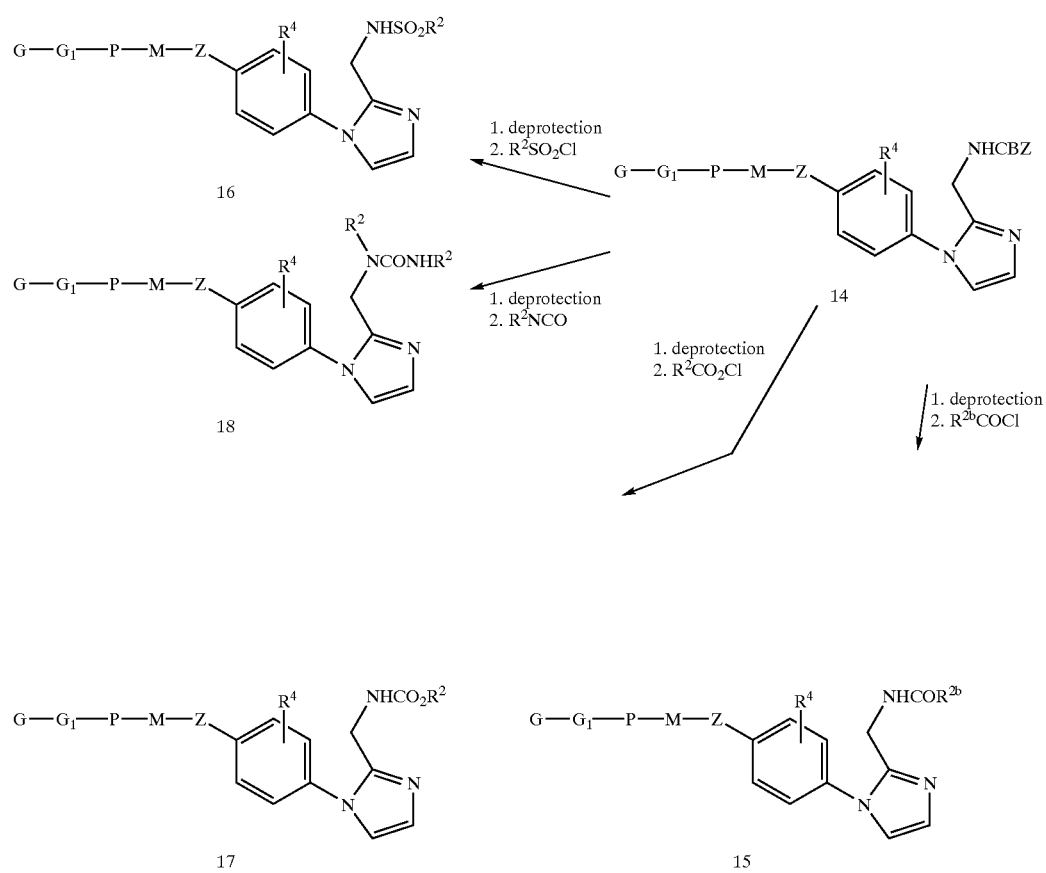

Compounds of formula I where B is a phenyl derivative can be prepared as shown in Scheme 4. Suzuki coupling of iodide 19 with boric acid 20 can afford the biaryl intermediate 21, which can be coupled with 5 through standard coupling conditions to give 22. Reductive amination, followed by reactions with acid chlorides, carbamates, sulfonyl chlorides, and isocyanates can provide compounds of this invention having structures 23–26.

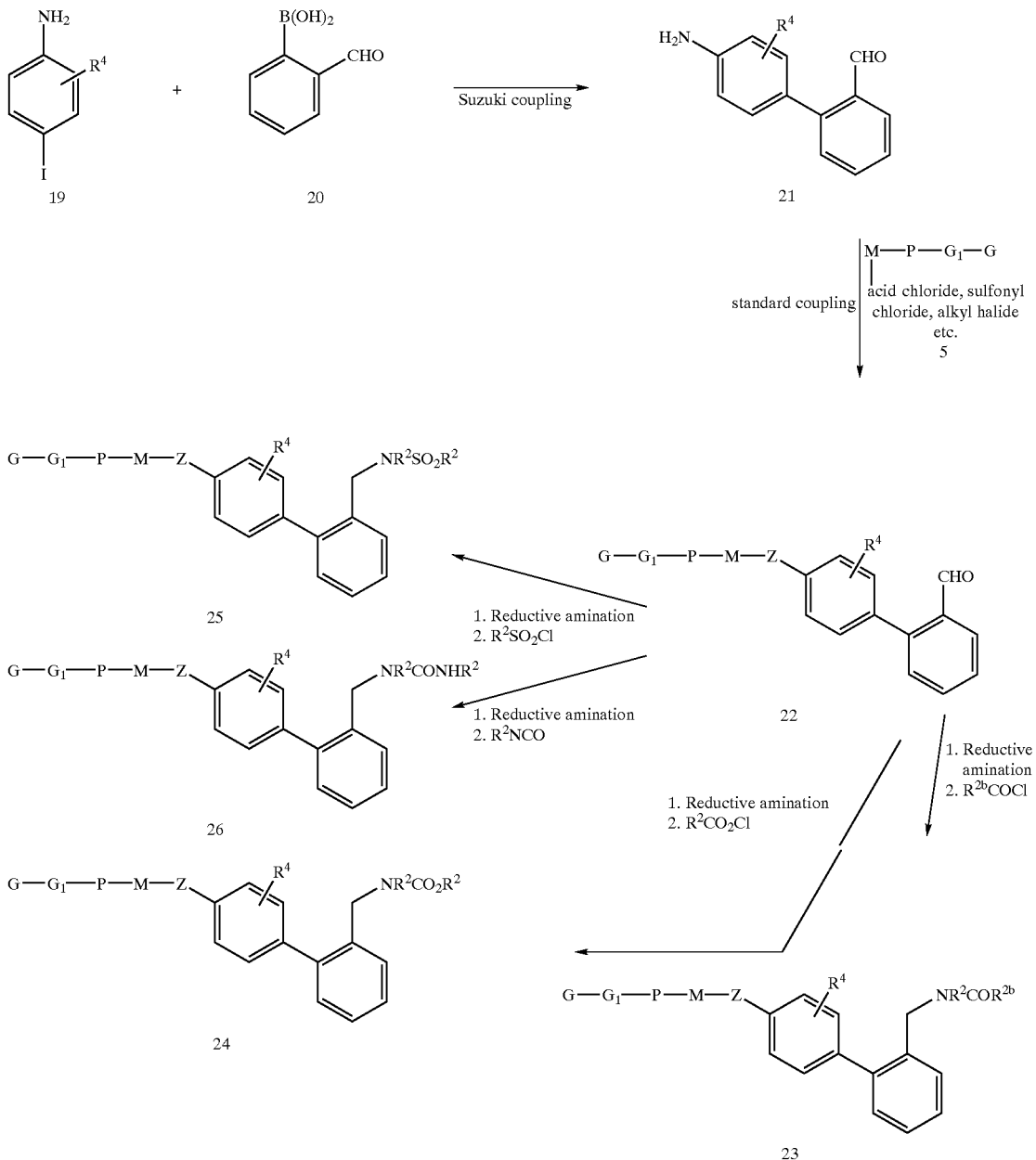
Aminopyridyl and aminopyrimidyl A-B analogs (see structures in Scheme 5) can be prepared using routes similar to those of Scheme 4.
Scheme 5
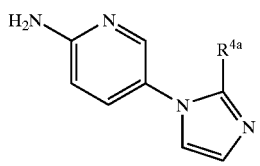
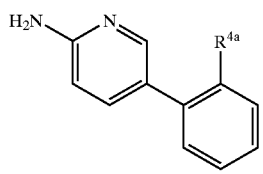
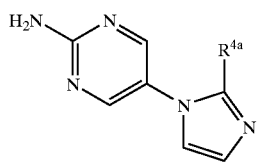

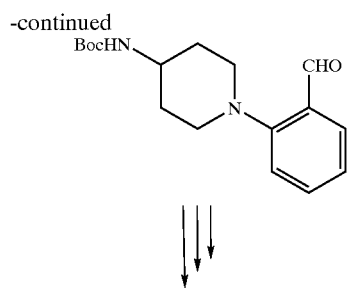

Additional Z-linkers to the A-B intermediates can be synthesized by the chemical manipulation of the amino functionality (Scheme 6) of the compounds described above.

Scheme 6

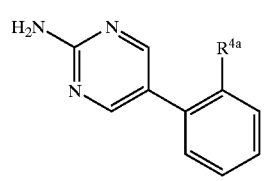

R = I, OH, SH or $SO_2Cl$

Other possible A-B intermediates with various Z-linkers can be synthesized by the methods shown in Scheme 7. The iodo-ester intermediate can be subjected to Ullman and/or Suzuki coupling methodologies to afford A-B intermediates. These intermediates in turn can be homologated via the Arndt Eistert methodology to afford other A-B intermediates. Alternatively, the ester functionality can be reduced to the alcohol that in turn can be converted to a variety of A-B intermediates by procedures known to those skilled in the art.

The compounds of formula I (Scheme 1) where P is fused onto ring M can be prepared as outlined in Schemes 9 to 11 and via standard methods known to those skilled in the art. The halogenated intermediates illustrated in these Schemes can be subjected to the Ullman or the Suzuki coupling methodologies to afford the intermediates shown. Further elaboration of these intermediates using the methods described above and by those skilled in the art should provide compounds of the present invention.

Scheme 7

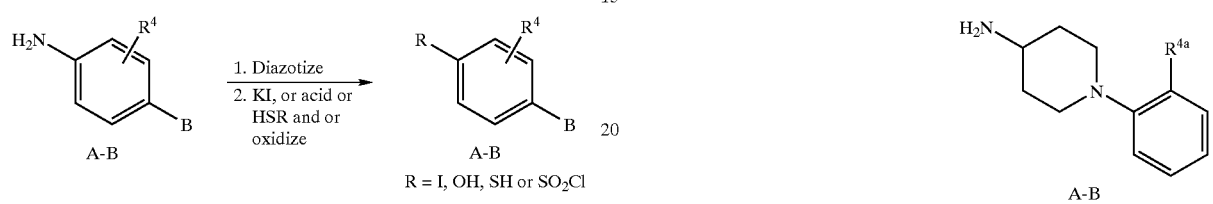
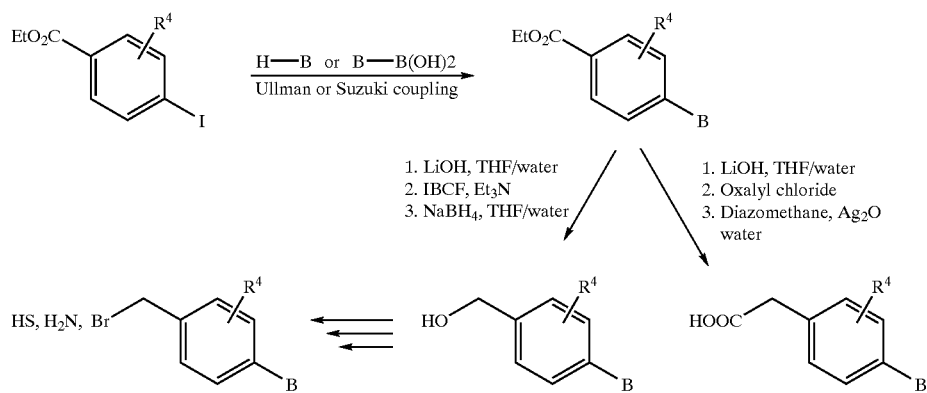

Non-aromatic intermediates as shown in Scheme 8 can be synthesized via procedures known to those skilled in the art. These intermediates can than be further manipulated to incorporate $R^{4a}$ via procedures previously described.

Scheme 8

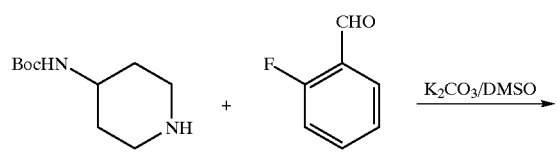

Scheme 9

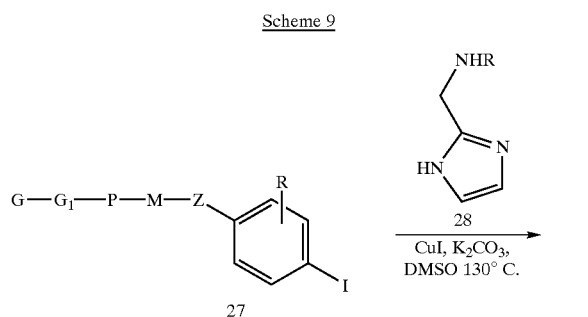

Scheme 10

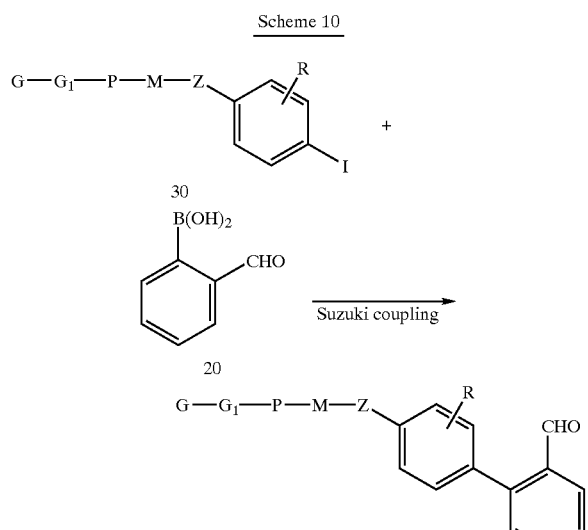

Scheme 11

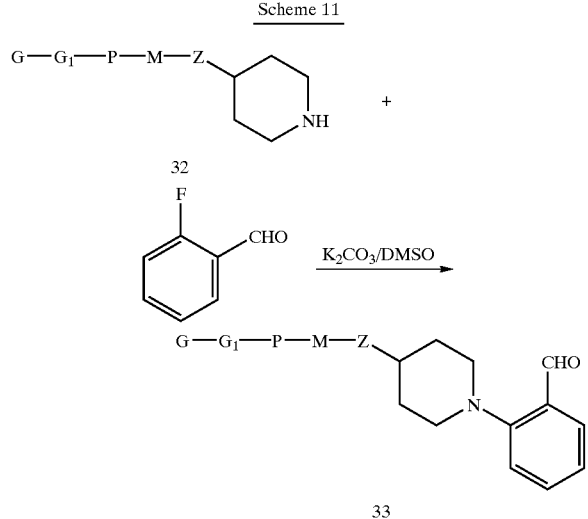

The compounds of this invention and the intermediates described above wherein the B group contains an oxidizable group can be oxidized, e.g. N to N-oxide.

Schemes 2–11 describe how to make the A-B moieties of the present invention and how to couple them to prepare compounds of the present invention. In the above Schemes, the Z group may or may not be present depending on how the A-B group is coupled. The coupling portion of the A-B group could (a) be displaced by the incoming Z or M group, (b) become the Z group, or (c) be incorporated into ring M.

The remaining portions of the compounds of the present invention, $G-G_1-P-M-Z$, $G-G_1-M-P-Z$, $G-G_1-P-M$, $G-G_1-M-P$, $G-G_1-M-Z$, and $G-G_1-M$, can be prepared using methods known to those of ordinary skill in the art. All of the following patents and publications are incorporated herein by reference. For compounds wherein ring P is absent and ring M is a 5-, 6-, or 7-membered ring, one of ordinary skill in the art can look to U.S. Pat. Nos. 5,939,418, 5,925,635, 6,057,342, 6,187,797, 6,020,357, 6,060,491, 5,998,424, 6,191,159, WO98/57951, WO99/32454, WO00/039108, WO00/059902, WO01/32628, WO01/005785, U.S. Ser. Nos. 09/892,319, U.S. Ser. Nos. 60/313,552, 60/246,108, and U.S. Ser. No. 09/887,936 for starting materials and intermediates to which the present B and/or A-B groups can be coupled. For compounds wherein ring P is fused to ring M (i.e., a bicyclic moiety is present), one of ordinary skill in the art can look to WO00/39131, U.S. Ser. Nos. 60/246,125, 60/292,665, 60/278,173, 60/278,165, and U.S. Ser. No. 09/887,850 for starting materials and intermediates to which the present B and/or A-B groups can be coupled.

For compounds wherein G is a ring substituted with a basic moiety, one of ordinary skill in the art can look to U.S. Pat. Nos. 5,939,418, 5,925,635, 6,057,342, 6,187,797, 6,020,357, 6,060,491, 6,191,159, WO98/57951, WO99/32454, WO00/059902, WO01/32628, WO00/39131, U.S. Ser. No. 09/892,319, U.S. Ser. Nos. 60/313,552, 60/246,108, 60/246,125, 60/292,665, 60/278,173, and U.S. Ser. No. 60/278,165 for starting materials and intermediates to form the present $G-G_1-P-M-Z$, $G-G_1-M-P-Z$, $G-G_1-P-M-Z-A$, and/or $G-G_1-M-P-Z-A$ groups to which the present B and/or A-B groups can be coupled. For compounds wherein G is a ring substituted with a non-basic group, one of ordinary skill in the art can look to U.S. Pat. No. 5,998,424, WO00/39131, WO00/059902, WO01/32628, U.S. Ser. Nos. 09/892,319, 60/313,552, U.S. Ser. Nos. 60/246,108, 60/246,125, 60/292, 665, 60/278,173, and U.S. Ser. No. 60/278,165 for starting materials and intermediates to form the present $G-G_1-P-M-Z$, $G-G_1-P-Z$, $G-G_1-P-M-Z-A$, and/or $G-G_1-M-P-Z-A$ groups to which the present B and/or A-B groups can be coupled. For compounds wherein G is a bicyclic moiety, one of ordinary skill in the art can look to WO98/57951, WO00/039108, WO00/39131, U.S. Ser. No. 09/892,319, U.S. Ser. Nos. 60/313,552, 60/246,108, 60/246,125, 60/292, 665, 60/278,173, and U.S. Ser. No. 60/278,165 for starting materials and intermediates to form the present $G-G_1-P-M-Z$, $G-G_1-M-P-Z$, $G-G_1-P-M-Z-A$, and/or $G-G_1-M-P-Z-A$ groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed. Scheme 12 illustrates some of the numerous pyrrole intermediates that can be used to prepare compounds of the present invention ($R_Z$ is the point of attachment for Z-A-B and can be H, a protecting group, a group modifiable to Z or Z-A, Z, Z-A, or A). These intermediates are described in the above-noted patents and publications.

Scheme 12

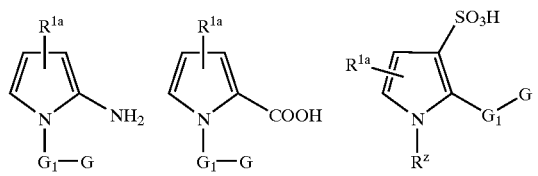

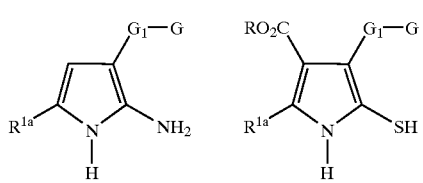

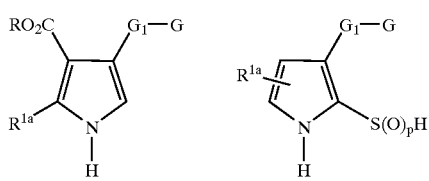

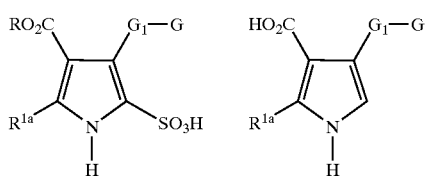

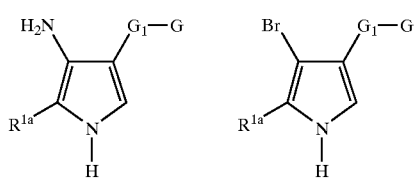

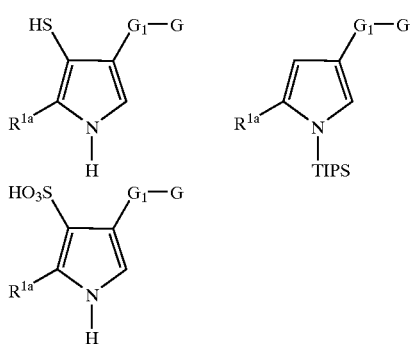

Scheme 13 illustrates some of the numerous imidazole, triazole, and tetrazole intermediates that can be used to prepare compounds of the present invention. These intermediates are described in the above-noted patents and publications. In Scheme 13, V is nitro, amino, thio, hydroxy, sulfonic acid, sulfonic ester, sulfonyl chloride, ester, acid, or halide. In Scheme 13, U is aldehyde, ester, acid, amide, amino, thiol, hydroxy, sulfonic acid, sulfonic ester, sulfonyl chloride, or methylene halide.

Scheme 13

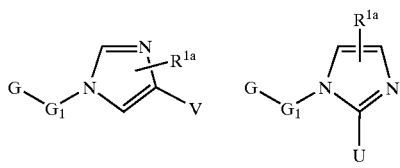

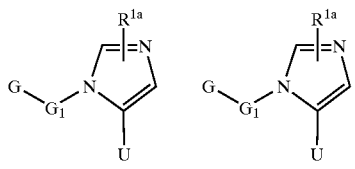

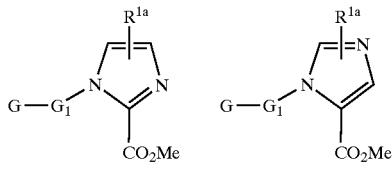

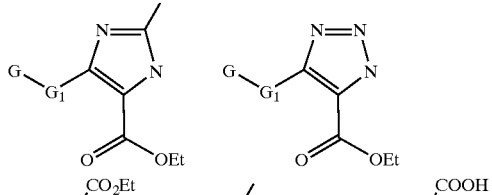

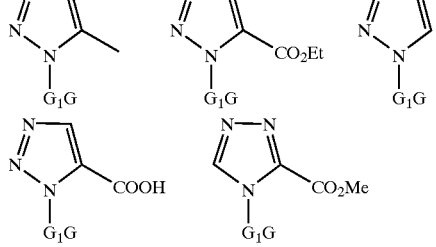

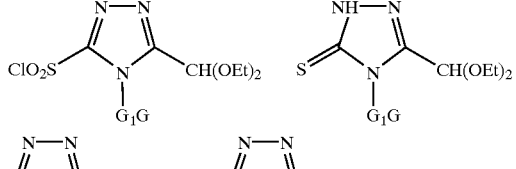

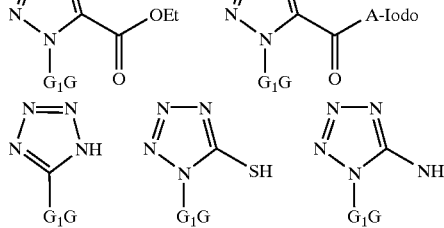

Scheme 14 shows some of the numerous pyrazole intermediates that can be used to prepare compounds of the present invention. These intermediates are described in the above-noted patents and publications.

Scheme 14

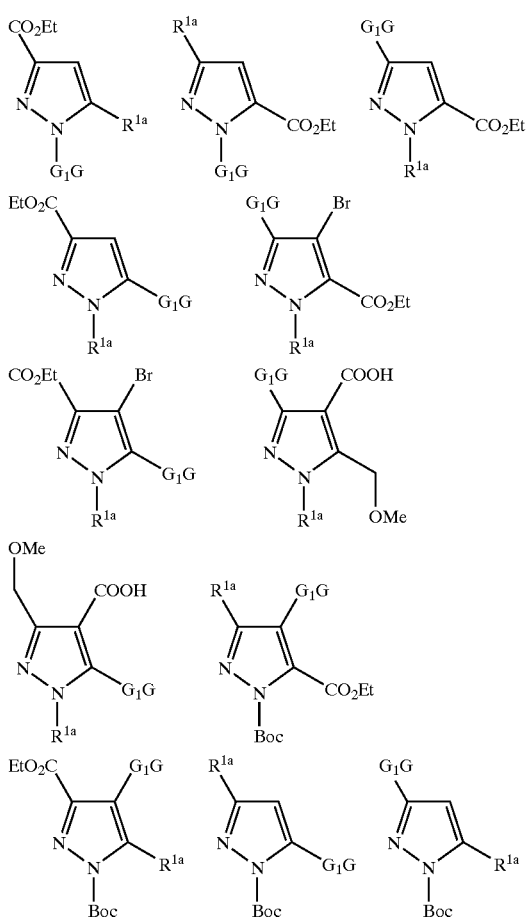

Scheme 15 depicts some of the numerous oxazole, thiazole, isoxazole, oxadiazole, and thiadiazole intermediates that can be used to prepare compounds of the present invention. These intermediates are described in the above-noted patents and publications. In Scheme 15, V is nitro, amino, ester, or acid.

Scheme 15

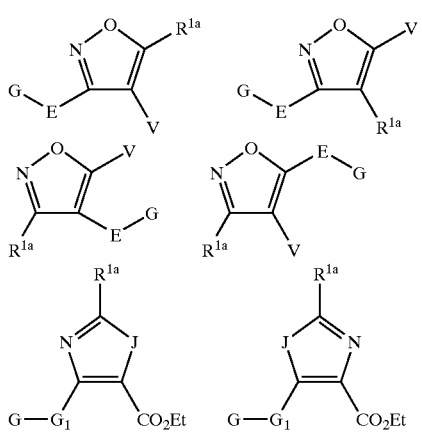

-continued

Scheme 16 illustrates two intermediates useful for making a compound of the present invention wherein ring P is fused to ring M. Scheme 16 also illustrates a number of bicyclic compounds that can be made from these intermediates or derivatives thereof. These intermediates and their modification are described in the above-noted patents and publications.

Scheme 16

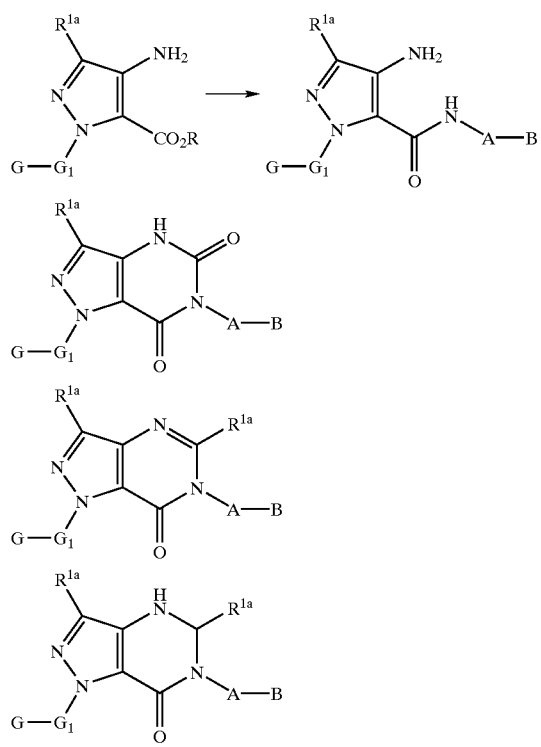

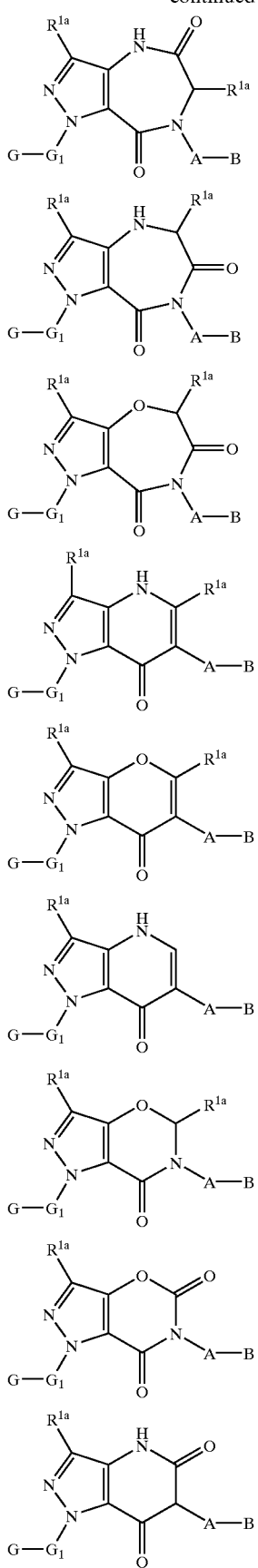
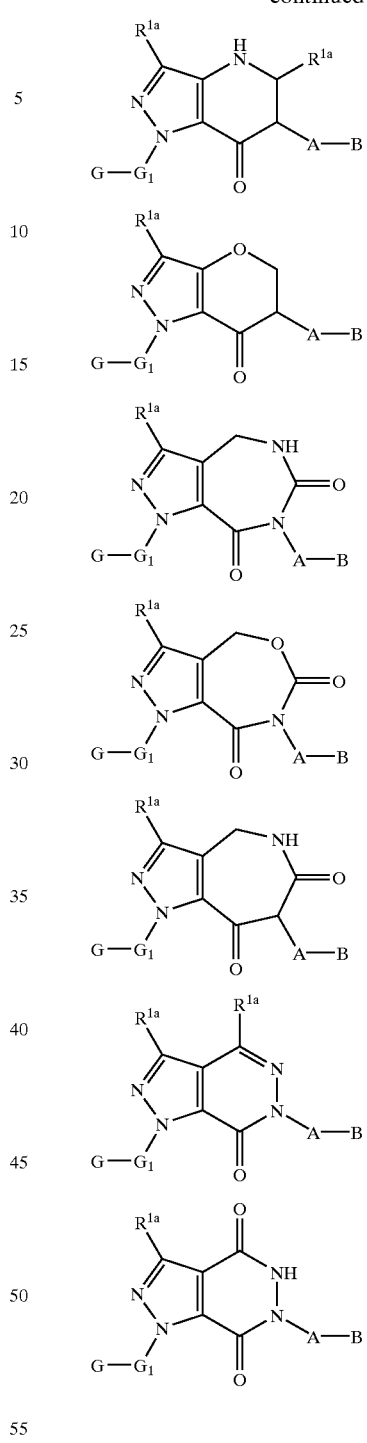

Scheme 17 depicts another intermediate useful for making a compound of the present invention wherein ring P is fused to ring M. Scheme 17 also illustrates a number of bicyclic compounds that can be made from this intermediate or derivatives thereof (e.g., the corresponding cyclohexenone). In Scheme 17, U is OH or morpholine and V is H or $C(O)R^{1a}$. This intermediate, derivatives thereof, and their modification are described in the above-noted patents and publications.

Scheme 17

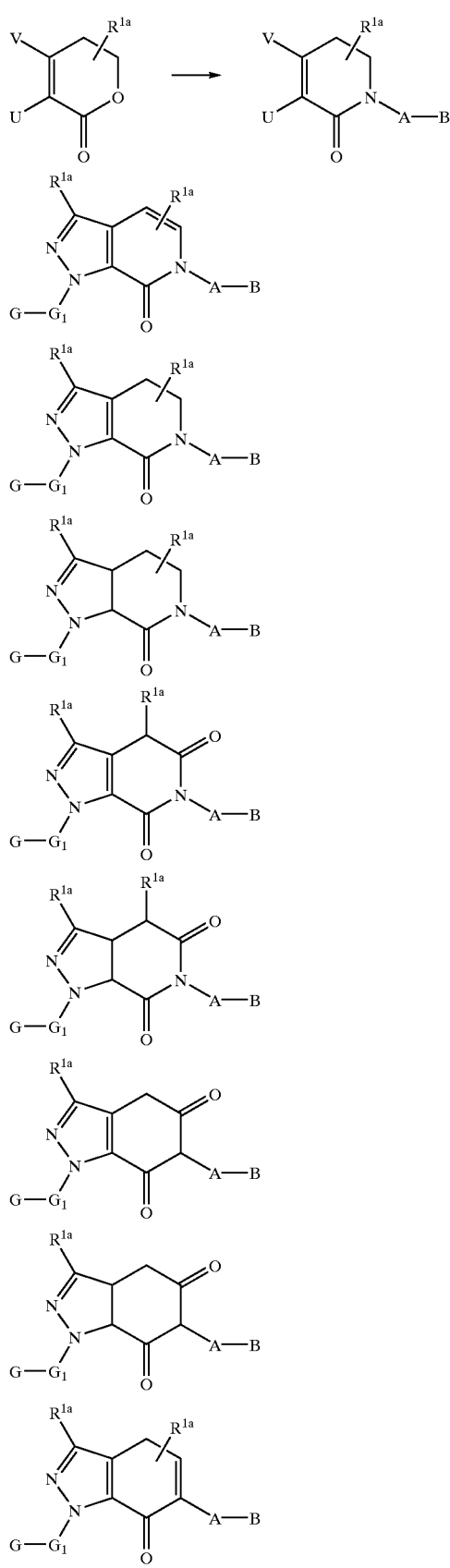
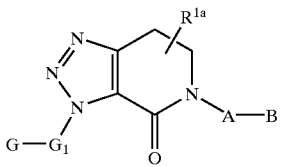
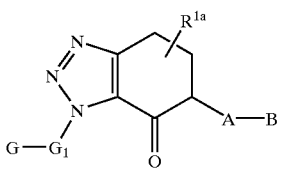
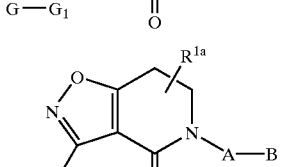
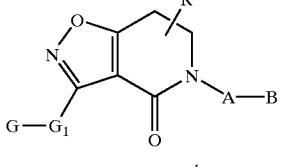
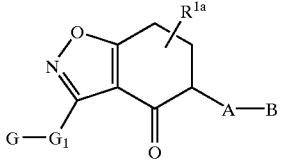
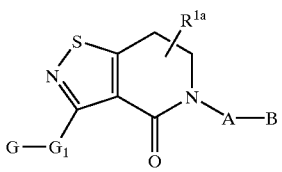
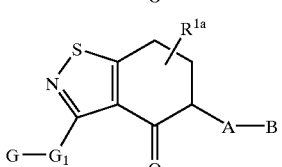
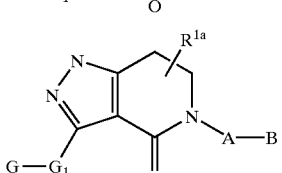
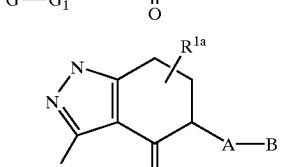
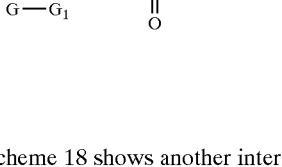

Scheme 18 shows another intermediate useful for making a compound of the present invention wherein ring P is fused to ring M. Scheme 18 also illustrates a number of bicyclic compounds that can be made from this intermediate or derivatives thereof. This intermediate, derivatives thereof, and their modification are described in the above-noted patents and publications.

Scheme 18
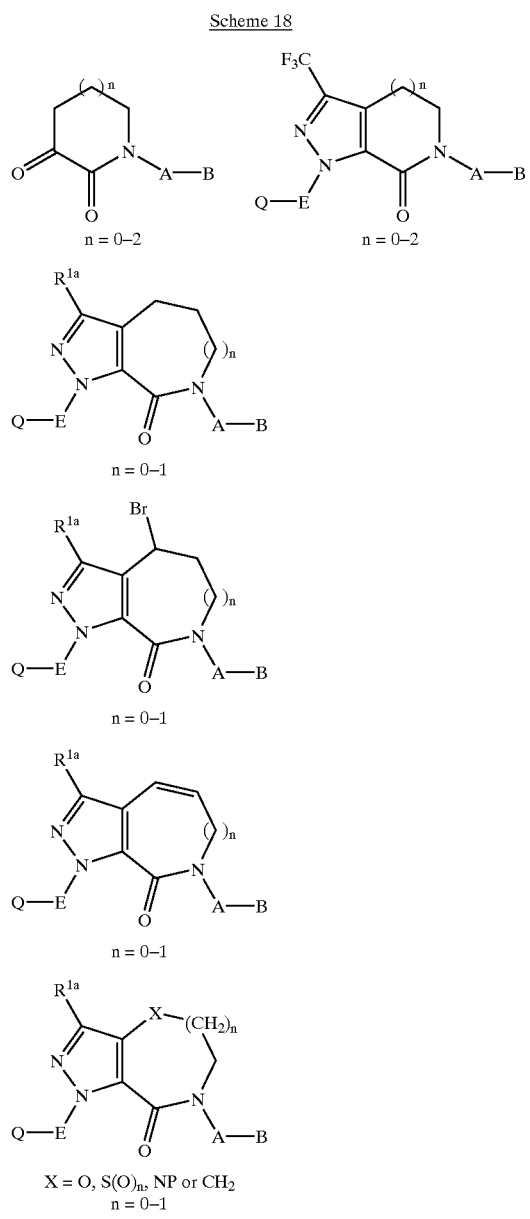
Scheme 19 illustrates a number of other bicyclic rings that are considered to be part of the present bicyclic group, rings P-M. Scheme 19 also describes a method of converting the shown rings to compounds of the present invention. As one of ordinary skill in the art would recognize, this method would be applicable to other heterobicyclics not shown.
Scheme 19
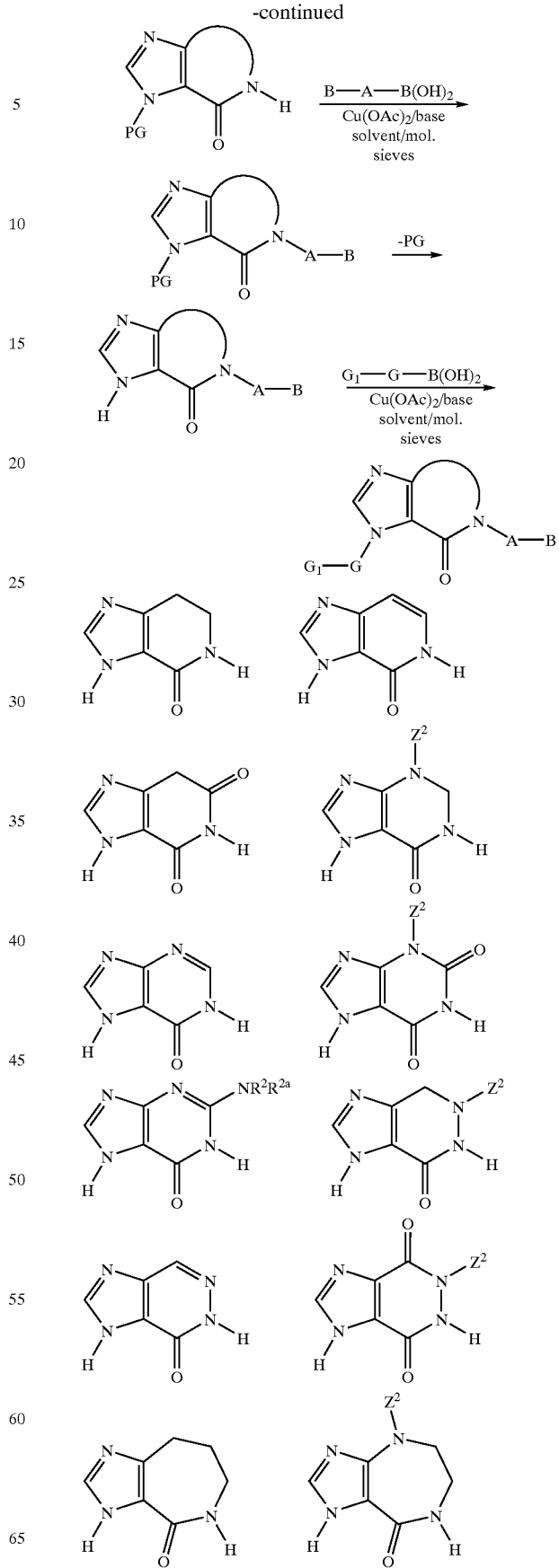

129

-continued

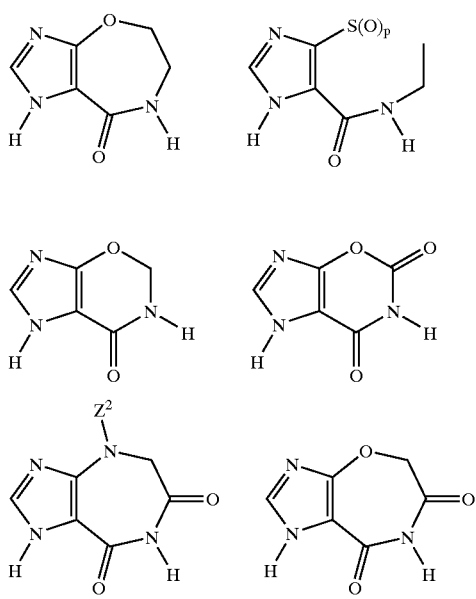

130

-continued

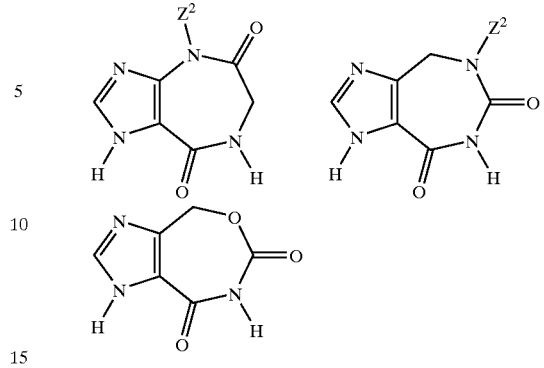

Other useful pyrazole intermediates wherein $G_1$ is an amide are exemplified in Scheme 20. Compounds of the present invention wherein the $G_1$ group is other than an amide can be easily manipulated to other linker functionalities according to the methodologies known in the art, including the methodologies outlined in WO98/28269 and WO98/28282, the contents of both are incorporated herein by reference.

Scheme 20

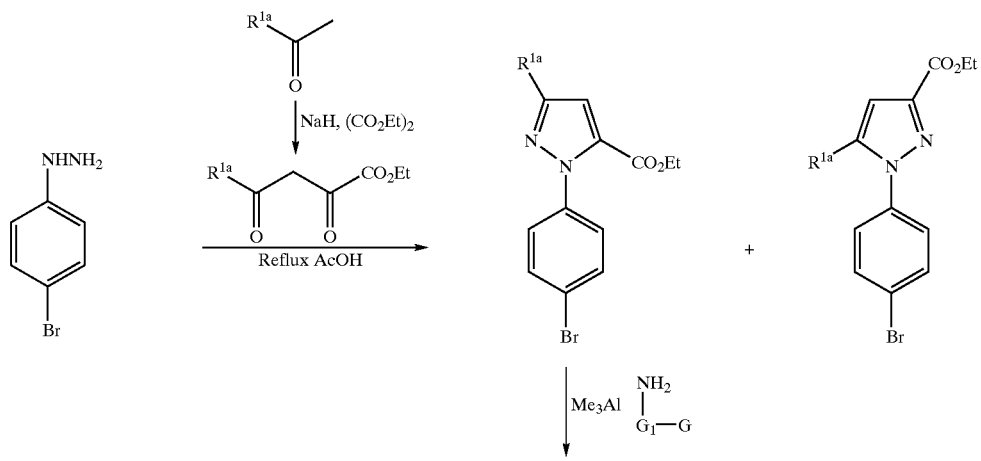

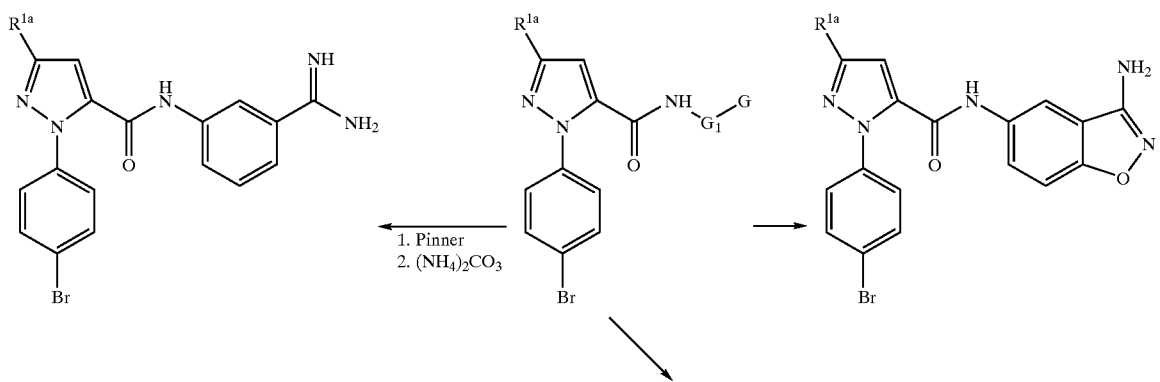

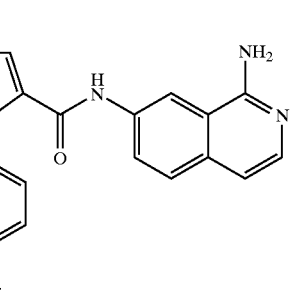

Scheme 21 depicts some of the numerous 6-membered aromatic ring intermediates that can be used to prepare compounds of the present invention. These intermediates are described in the above-noted patents and publications. In Scheme 21, V is nitro, protected sulfonamide, or ester group and is a precursor of group Z of the present invention.

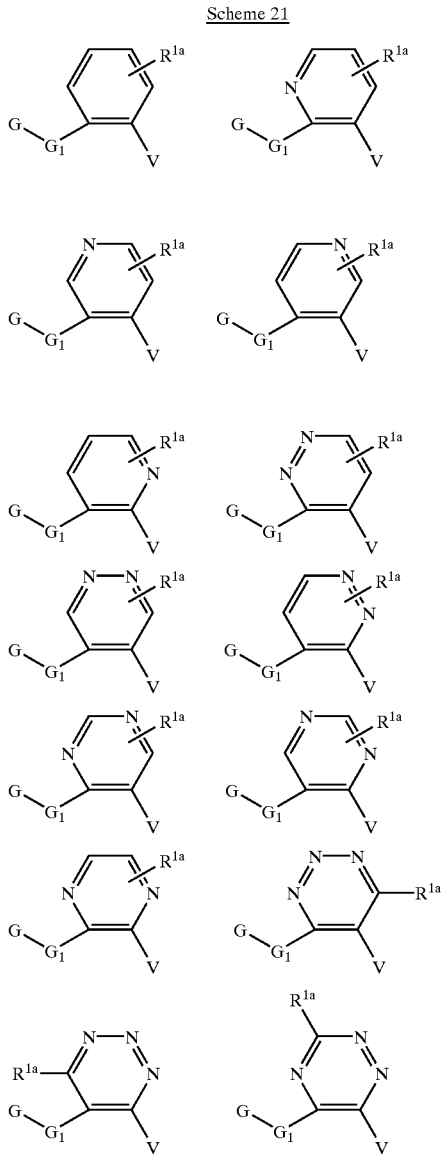

Benzo fused dihydro-pyridone intermediates of the present invention can be prepared from readily available starting materials as shown in Scheme 22.

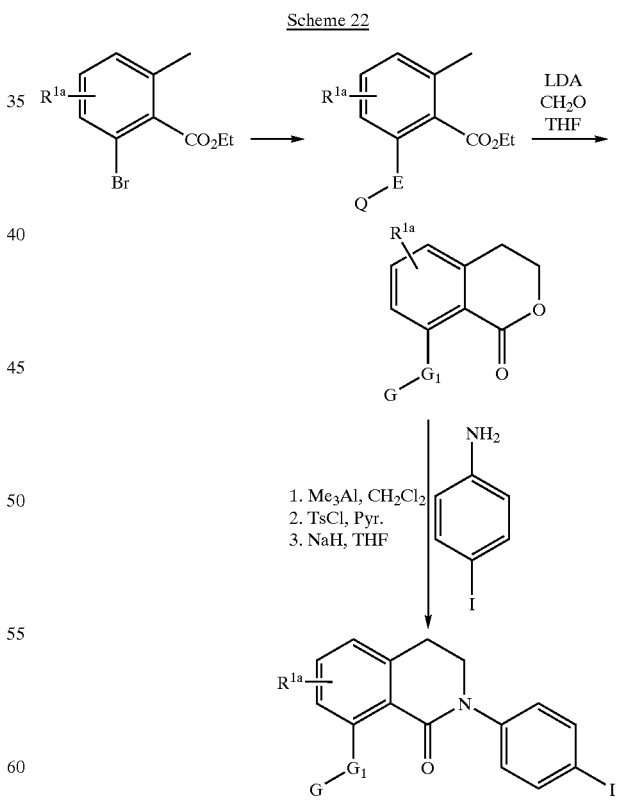

Other benzo-bicyclics can also be obtained as shown in Schemes 23 and 24.

Scheme 23
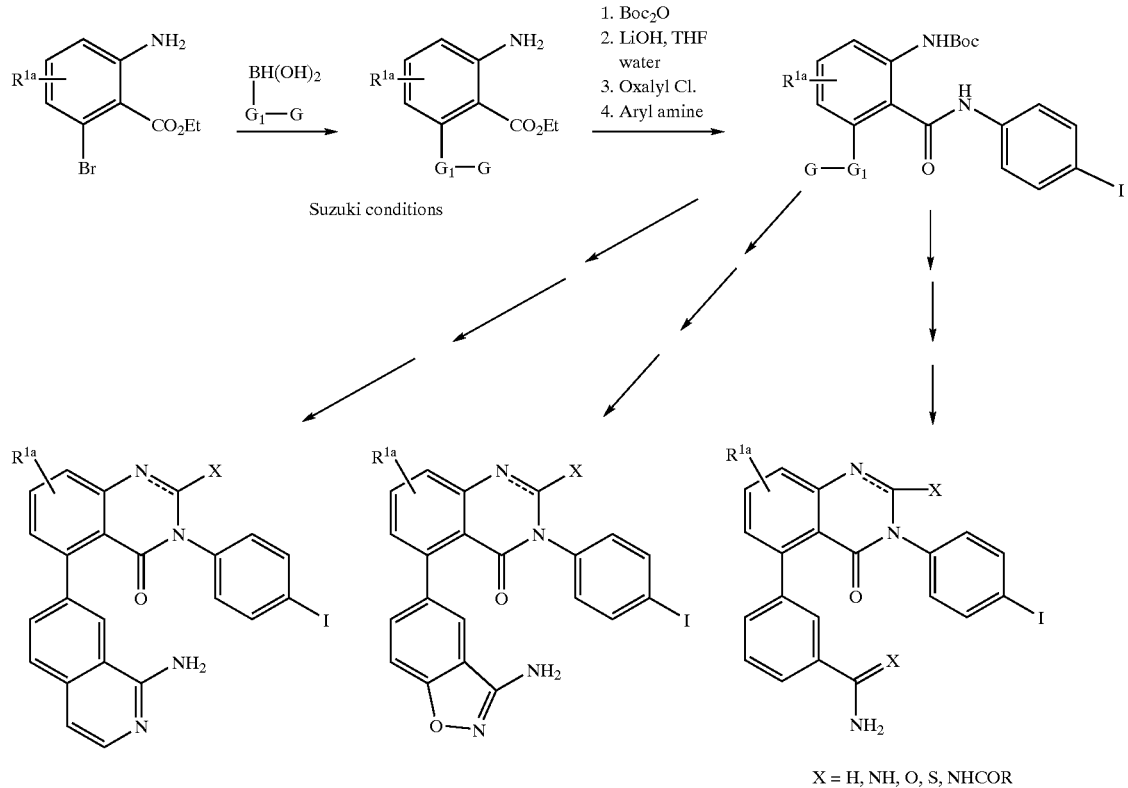
X = H, NH, O, S, NHCOR
Scheme 24
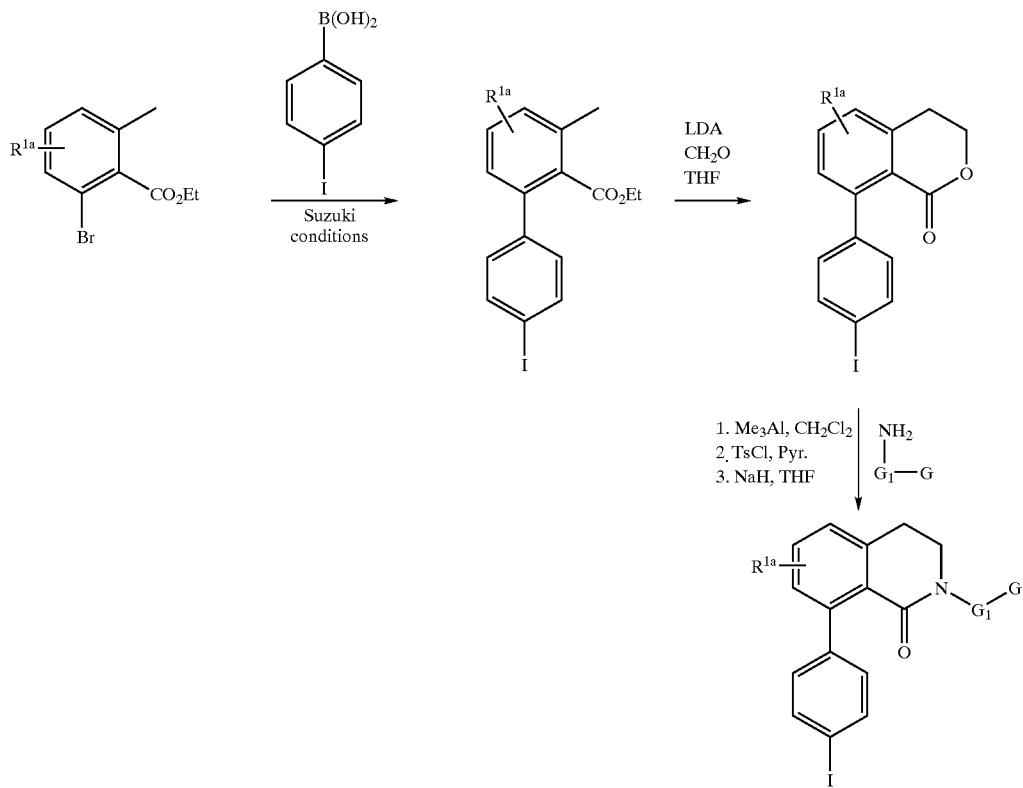

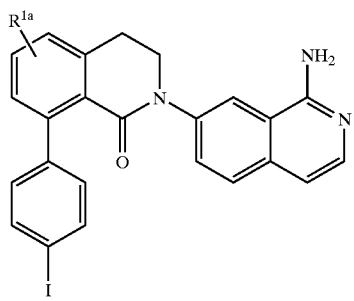
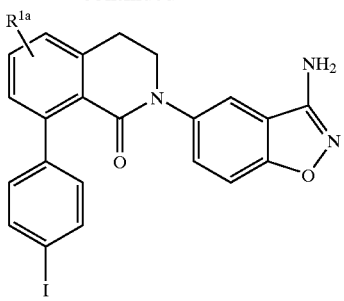
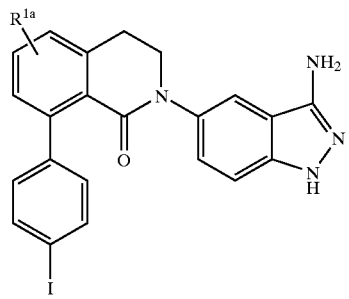

When M is a non-aromatic ring, the compounds of this invention with general structure of Formula I can be synthesized by using similar methods as described previously and by those skilled in the art. One diastereomer of a compound of Formula I may display better activity compared with the others. Thus, the following stereochemistries are considered to be a part of the present invention.

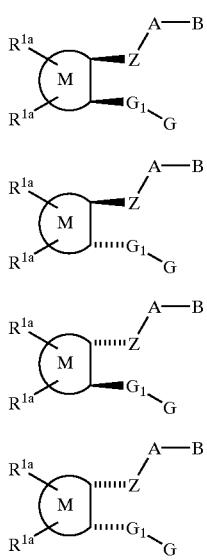

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio.) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:

v_o is the velocity of the control in the absence of inhibitor;

v_s is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10\,\mu M$. Preferred compounds of the present invention have $K_i$'s of $\leq 1\,\mu M$. More preferred compounds of the present invention have $K_i$'s of $\leq 0.1\,\mu M$. Even more preferred compounds of the present invention have $K_i$'s of $\leq 0.01\,\mu M$. Still more preferred compounds of the present invention have $K_i$'s of $\leq 0.001\,\mu M$. Using the methodology described above, a number of compounds of the present invention were found to exhibit $K_i$'s of $\leq 10\,\mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM.

After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $10\,\mu m$, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. No. 5,612,359 and U.S. Pat. No. 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping; and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLE 1

N-[(1-{4-[1-(4-Methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylacetamide, trifluoroacetic acid salt

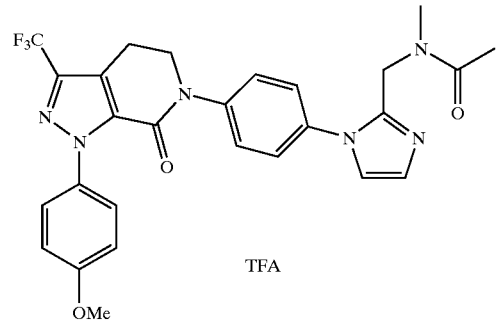

Part A: Preparation of 6-[4-Iodophenyl]-1,4,5,6-tetrahydropyrazolo-[3,4-c]-pyridin-7-one 4-Iodoaniline (45.82 g, 209.2 mmol) and triethylamine (65.61 mL, 470.7 mmol) were dissolved into THF (800 mL) and cooled to 0 °C. 5-Bromovaleryl chloride (50.0 g, 251.1 mmol) dissolved in THF (200 mL) was added dropwise to the reaction mixture. The reaction was warmed to room temperature and stirred overnight. It was then cooled to 0° C. and potassium tert-butoxide (70.43 g, 627.6 mmol) was slowly added. The reaction was warmed to room temperature and stirred overnight. The reaction mixture was concentrated and then re-dissolved in ethyl acetate (500 mL) and 3N HCl (500 mL), extracted with ethyl acetate (2×250 mL), washed with 1N HCl (3×250 mL), washed with brine (1×250 mL), and dried ($Na_2SO_4$). Purification by silica gel chromatography using 0%–100% ethyl acetate/hexane gradient as eluent afforded 51.03 g of the desired product (81%). $^1$HNMR ($CDCl_3$) δ 7.70 (d, 2H), 7.03 (d, 2H), 3.62 (t, 2H), 2.56 (t, 2H), 2.50–1.88 (m, 4H) ppm.

Part B: Preparation of 1-(4-iodophenyl)-3-(4-morpholinyl)-5,6-dihydro-2(1H)-pyridinone 6-[4-Iodophenyl]-1,4,5,6-tetrahydropyrazolo-[3,4-c]-pyridin-7-one (85.17 g, 282.8 mmol) and phosphorus pentachloride (205.91 g, 990.0 mmol) were dissolved into $CHCl_3$ (750 mL) and refluxed for 3½ hours. The reaction mixture was poured over ice and then quenched further with water. It was extracted with $CHCl_3$ (3×400 mL), washed with brine (1×400 mL), dried ($MgSO_4$), and concentrated. This residue was dissolved in morpholine (400 mL) and refluxed overnight. The reaction mixture was concentrated and purified by silica gel chromatography using 0%–100% ethyl acetate/hexane gradient as eluent to afford 68 g of the morpholine-enamine (63%). $^1$HNMR ($CDCl_3$) δ 7.68 (d, 2H), 7.11 (d, 2H), 5.66 (t, 1H), 3.82 (t, 4H), 3.77 (t, 2H), 2.89 (t, 4H), 2.53–2.47 (m, 2H) ppm.

Part C: Preparation of 1-(4-iodophenyl)-4-(trifluoroacetyl)-2,3-piperidinedione

4-Dimethylaminopyridine (3.92 g, 32.01 mmol) was dissolved into $CH_2Cl_2$ (130 mL) and cooled to 0° C. Trifluoroacetic anhydride (4.54 g, 32.01 mmol) was added and the mixture was stirred at 0° C. for 30 min. A solution of the above morpholine-enamine from part B (10.25 g, 26.68 mmol) in $CH_2Cl_2$ (370 mL) was added slowly. The reaction mixture was warmed to room temperature and stirred overnight. The reaction mixture was concentrated and purified by silica gel chromatography using 0%–50% ethyl acetate/hexane gradient to isolate the intermediate. The intermediate was dissolved in 20% HCl (50 mL) and diethyl ether (200 mL) and stirred at room temperature overnight. It was then quenched with water, extracted with ether (3×100 mL), washed with brine (1×100 mL), and dried ($Na_2SO_4$). The residue was re-dissolved in petroleum ether and the undissolved solid was filtered off. The filtrate was concentrated to afford 9.99 g of the desired product (78%). $^1$HNMR ($CDCl_3$) δ 7.77 (d, 2H), 7.11 (d, 2H), 3.93 (t, 2H), 2.92 (t, 2H) ppm.

Part D: Preparation of 1-[4-methoxyphenyl]-3-trifluoromethyl-6-[4-iodophenyl]-1,4,5,6-tetrahydropyrazolo-[3,4-c]-pyridin-7-one 1-(4-iodophenyl)-4-(trifluoroacetyl)-2,3-piperidinedione from Part C (10.0 g, 24.3 mmol) and 4-methoxyphenylhydrazine hydrochloride (4.28 g, 24.3 mmol) were dissolved in HCl (1N, 200 mL) and methanol (400 mL). The mixture was refluxed overnight. The reaction mixture was cooled to room temperature and quenched with water. It was extracted with ethyl acetate, washed with brine, and dried ($Na_2SO_4$). Purification by silica gel chromatography using 0%–100% ethyl acetate/hexane gradient as eluent afforded the desired pyrazole 9.28 g (74%). $^1$HNMR ($CDCl_3$) δ 7.69 (d, 2H), 7.45 (d, 2H), 7.06 (d, 2H), 6.92 (d, 2H), 4.11 (t, 2H), 3.81 (s, 3H), 3.15 (t, 2H) ppm; Mass Spec $(M+H)^+$ 514.3.

Part E: Preparation of benzyl 1H-imidazol-2-yl-methyl-(methyl)carbamate

2-Imidazolecarboxyaldehyde (5.0 g, 52.0 mmol) was suspended in 200 mL of methanol. Methylamine (20 mL of 33% solution in methanol) was added. After stirred for 15 minutes, $NaBH_4$ (3.95 g, 0.10 mol) was added portion-wise. The reaction mixture was then heated at 50° C. for 2 h under $N_2$. The solvent was removed. The solid was washed with $CH_2Cl_2$ and filtered. The $CH_2Cl_2$ solution was dried over $MgSO_4$, concentrated, and dried under vacuum to give the methylamine as a yellow oil. This oil was dissolved in a 1:1 solution of $CH_2Cl_2$ and THF. To it was added $Et_3N$ (7.94 mL, 57.0 mmol) and benzylchloroformate (7.4 mL, 52.0 mmol). The mixture was stirred at room temperature under $N_2$ for 1 h. The solvent was removed and the residue was partitioned between EtOAc and $H_2O$. The EtOAc layer was washed with brine, dried over $MgSO_4$, and concentrated. The mixture was refluxed with 15 mL of TFA for 30 minutes to convert most of the bis-acylated byproduct to the desired product. The TFA was removed. It was dissolved in EtOAc and washed with Saturated aqueous $NaHCO_3$ and brine. The mixture was dried over $MgSO_4$, concentrated, and chromatographed with 1:1 EtOAc/hexane to give 6.56 g off-white solid (51.4% yield). MS $(AP^+)$: 246.3, $(M+H)^+$. $^1$HNMR ($CDCl_3$): δ 7.35 (s, 6H), 6.90 (s, 1H), 5.14 (s, 2H), 4.48 (s, 2H), 3.00 (s, 3H).

Part F: Preparation of benzyl (1-{4-[1-(4-methoxyphenyl)-7-methylene-3-(trifluoromethyl)-1,4,5,7-tetrahydro-6H-pyrazolo[3,4-c]pyridin-6-yl]phenyl}-1H-imidazol-2-yl)methyl(methyl)carbamate Benzyl 1H-imidazol-2-ylmethyl(methyl)carbamat (1.17 g, 4.76 mmol) from Part E, 1-[2-trifluoroacetamidomethyl-phenyl]-3-trifluoromethyl-6-[4-Iodo-2-fluorophenyl]-1,4,5,6-tetrahydropyrazolo-[3,4-c]-pyridin-7-one from Part D (1.63 g, 3.18 mmol), CuI (0.12 9, 20%), $K_2CO_3$ (0.66 g, 4.76 mmol), 1,10-phenanthroline (56 mg, 20%) were added together with 100 mL of DMSO. The mixture was degassed and then heated at 130° C. under $N_2$ for 12 h. The mixture was cooled and aqueous $NH_4OH$ (200 mL of of 10% $NH_4OH$) was added. The mixture was filtered through Celite® and washed with EtOAc. The two layers were separated and the aqueous layer was extracted with EtOAc. The combined EtOAc mixture was washed with brine, dried over $MgSO_4$, concentrated, and chromatographed with EtOAc to give 1.34 g of the desired product (66.9%). MS (ES+): 631.3, $(M+H)^+$.

Part G: Preparation of 1-(4-methoxyphenyl)-6-(4-{2-[(methylamino)methyl]-1H-imidazol-1-yl}phenyl)-3-(trifluoromethyl)-1,4,5,6-tetrahydro-7H-pyrazolo[3,4-c]pyridin-7-one bis(trifluoroacetic acid)salt Benzyl (1-{4-[1-(4-methoxyphenyl)-7-methylene-3-(trifluoromethyl)-1,4,5,7-tetrahydro-6H-pyrazolo[3,4-c]pyridin-6-yl]phenyl}-1H-imidazol-2-yl)methyl(methyl)carbamate (100 mg) was heated with 5 mL of TFA at 80° C. for 1 h. The solvent was removed and dried under vacuum. The crude product was purified by reverse phase HPLC (C18 reverse phase column, eluted with a $H_2O/CH_3CN$ gradient with 0.05% TFA) to give 20.0 mg of the desired product as the bis-TFA salt. MS $(ES^+)$: 497.5, $(M+H)^+$. $^1$HNMR ($CDCl_3$): δ 7.53–7.39 (m, 6H), 7.27 (s, 1H), 7.20 (s, 1H), 6.95 (d, 2H), 4.25 (s, 2H), 4.23 (t, 2H), 3.84 (s, 3H), 3.22 (t, 2H), 2.74 (s, 3H).

Part H: Preparation of N-[(1-{4-[1-(4-Methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylacetamide, trifluoroacetic acid salt The crude product Part G (100 mg, 0.20 mmol) was dissolved in $CH_2Cl_2$ (10 mL). Triethylamine (0.11 mL, 0.80 mmol) was added, followed by acetyl chloride (0.03 mL, 0.40 mmol). The mixture was stirred at room temperature under $N_2$ for 2 h. It was diluted with $CH_2Cl_2$ and washed with $H_2O$ and brine. The organic solution was then dried over $MgSO_4$ and concentrated. The crude product was purified by reverse phase HPLC (C18 reverse phase column, eluted with a $H_2O/CH_3CN$ gradient with 0.05% TFA) to give 20.0 mg of the desired product as the TFA salt. MS $(ES^+)$: 539.5, $(M+H)^+$. $^1$HNMR ($CDCl_3$): δ 7.58–7.44 (m, 7H), 7.17 (s, 1H), 6.95 (d, 2H), 4.61 (s, 2H), 4.23 (t, 2H), 3.83 (s, 3H), 3.23 (t, 2H), 3.18 (s, 3H), 2.08 (s, 3H).

EXAMPLE 2

N-[(1-{4-[1-(4-Methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylacetamide, trifluoroacetic acid salt

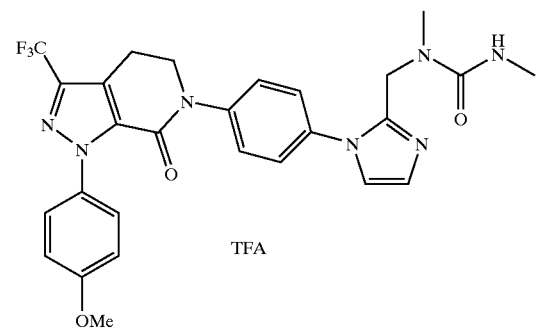

The crude product from Part G of Example 1 (100 mg, 0.20 mmol) was dissolved in $CH_2Cl_2$ (10 mL). Methyl isocyanate (26.0 mg, 2.0 mmol) was added and the mixture was stirred at room temperature under $N_2$ for ½ h. It was diluted with $CH_2Cl_2$ and washed with $H_2O$ and brine. The organic solution was then dried over $MgSO_4$ and concentrated. The crude product was purified by reverse phase HPLC (C18 reverse phase column, eluted with a $H_2O/$ CH₃CN gradient with 0.05% TFA) to give 20.0 mg of the desired product as the TFA salt. MS (ES⁺): 554.5, (M+H)⁺. ¹HNMR (CDCl₃): δ 7.56 (s, 3H), 7.45 (d, 3H), 7.31 (s, 1H), 7.19 (s, 1H), 6.96 (d, 2H), 4.59 (s, 2H), 4.23 (t, 2H), 3.84 (s, 3H), 3.23 (t, 2H), 2.98 (s, 3H), 2.70 (s, 3H).

EXAMPLE 3

Methyl (1-{4-[1-(4-methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl (methyl)carbamate, trifluoroacetic acid salt

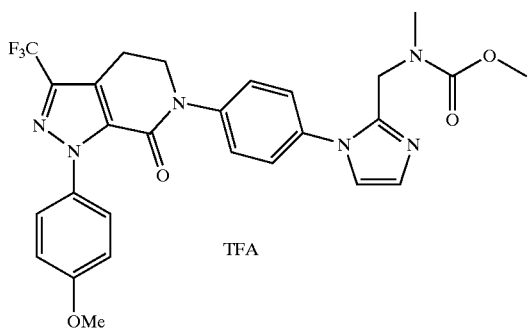

The crude product from Part G of Example 1 (120 mg, 0.24 mmol) was dissolved in CH₂Cl₂ (10 mL). Triethylamine (0.15 mL, 1.08 mmol) was added, followed by methyl chloroformate (0.075 mL, 0.96 mmol). The mixture was stirred at room temperature under N₂ for 1 h. It was diluted with CH₂Cl₂ and washed with H₂O and brine. The organic solution was then dried over MgSO₄ and concentrated. The crude product was purified by reverse phase HPLC (C18 reverse phase column, eluted with a H₂O/CH₃CN gradient with 0.05% TFA) to give 32.5 mg of the desired product as the TFA salt. MS (ES⁺): 555.2, (M+H)⁺. ¹HNMR (DMSO, 90° C.): δ 7.64 (s, 1H), 7.58 (m, 4H), 7.50 (d, 2H), 7.01 (d, 2H), 4.60 (s, 2H), 4.15 (t, 2H), 3.81 (s, 3H), 3.50 (s, 3H), 3.15 (t, 2H), 2.75 (s, 3H).

EXAMPLE 4

N-[(1-{4-[1-(4-Methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N-methylmethanesulfonamide, trifluoroacetic acid salt

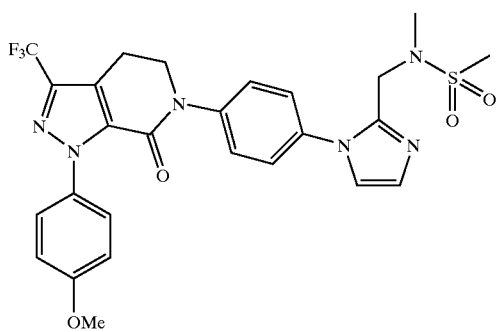

The crude product from Part G of Example 1 (200 mg, 0.40 mmol) was dissolved in CH₂Cl₂ (10 mL). Triethylamine (0.25 mL, 1.6 mmol) was added, followed by meth-anesulfonyl chloride (0.06 mL, 0.80 mmol). The mixture was stirred at room temperature under N₂ for 2 h. It was diluted with CH₂Cl₂ and washed with H₂O and brine. The organic solution was then dried over MgSO₄ and concentrated. The crude product was purified by reverse phase HPLC (C18 reverse phase column, eluted with a H₂O/CH₃CN gradient with 0.05% TFA) to give 50.0 mg of the desired product as the TFA salt. MS (ES⁺): 575.4, (M+H)⁺. ¹HNMR (CDCl₃): δ 7.57–7.44 (m, 7H), 7.25 (s, 1H), 6.96 (d, 2H), 4.68 (s, 2H), 4.22 (t, 2H), 3.83 (s, 3H), 3.22 (t, 2H), 2.88 (s, 3H), 2.81 (s, 3H).

EXAMPLE 5

N-[(1-{4-[1-(4-Methoxyphenyl)-7-oxo-3-(trifluoromethyl)-1,4,5,7-tetrahydro-6H-pyrazolo[3,4-c]pyridin-6-yl]phenyl}-1H-imidazol-2-yl)methyl]-N,3,5-trimethyl-4-isoxazolesulfonamide, trifluoroacetic acid salt

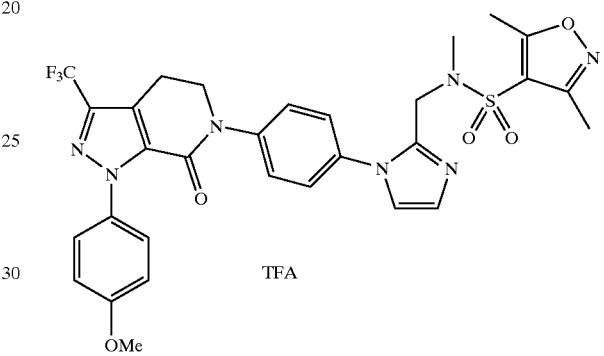

This compound was prepared using the same methods as described in Example 4. MS (ES⁺): 656.4, (M+H)⁺. ¹HNMR (CD₃OD): δ 7.79 (s, 1H), 7.71 (s, 1H), 7.61 (m, 4H), 7.46 (d, 2H), 6.99 (d, 2H), 4.59 (s, 2H), 4.21 (t, 2H), 3.82 (s, 3H), 3.20 (t, 2H), 2.79 (s, 3H), 2.49 (s, 3H), 2.23 (s, 3H).

EXAMPLE 6

6-[4-(2-{[Acetyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

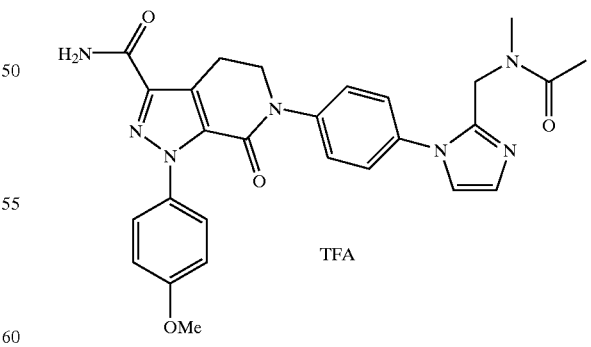

Part A: Preparation of ethyl (2Z)-chloro[(4-methoxyphenyl)hydrazono]ethanoate

To p-anisidine (16 g, 0.129 mol) in conc. HCL (40 mL), 100 mL) H₂O, cooled to −5° C. and sodium nitrite (9.4 g, 0.136 mol) in H₂O (60 mL) was added. The reaction mixture was stirred at −5° C. for 20 min and a mixture of ethylchloroacetoacetate (22 g, 0.133 mol), ethanol (100 mL), sodiumacetate (32 g, 0.389 mmol), and H₂O (400 mL) was added. The reaction was allowed to warm up to room temperature and stirred for 2h. The product precipitated as a black solid. It was filtered and dried (30 g). ¹HNMR (CDCl₃) δ 8.28 (s, 1H), 7.18 (d, 2H), 6.90 (d, 2H), 4.41 (q, 2H), 3.80 (s, 3H), 1.42 (t, 3H) ppm.

Part B: Preparation of ethyl 6-(4-iodophenyl)-1-(4-methoxyphenyl)-7-oxo-4,5,6,7-tetrahydro-1H-pyrazolo[3,4-c]pyridine-3-carboxylate The product of Part A (30 g, 0.117 mol) was stirred with 1-(4-iodophenyl)-3-(4-morpholinyl)-5,6-dihydro-2(1H)-pyridinone (29.9 g, 0.078 mol) prepared in Part B of Example 1 and triethylamine (74 mL, 0.53 mol) at reflux in toluene (400 mL) for 24 h. The reaction mixture was cooled, washed with water, and dried (Na₂SO₄). It was concentrated and chromatographed with 1:1 EtOAc/hexane to afford 28.8 g (71%) of the ester-iodo product. Mass Spec (M+H)⁺517.9; ¹HNMR (CDCl₃) δ 7.70 (d, 2H), 7.47 (d, 2H), 7.09 (d, 2H), 6.93 (d, 2H), 4.49 (q, 2H), 4.18 (t, 2H), 3.81 (s, 3H), 3.37 (t, 2H), 1.45 (t, 3H) ppm.

Part C: Preparation of 2-(methylaminomethyl)imidazole

2-Imidazolecarboxaldehyde (50.0 g, 52.5 mmol) and MeOH (700 mL) were added together in a 2 L round-bottomed flask. A solution of methylamine in EtOH (200 mL of 33%) was added. The mixture was stirred at RT under N₂ for 30 minutes and NaBH₄ (37 g, 100 mmol) was added portion wise in 35 minutes. The resulting mixture was stirred at RT for 1 h, then heated at 55° C. for 2 h. The solvents were removed in vacuo. The residue was washed with CH₂Cl₂ and filtered. The filtrate was washed with brine, dried over MgSO₄. It was concentrated and dried under vacuum to give 42.7 g of the desired product as a yellow oil. ¹HNMR (CDCl₃) δ 6.95 (s, 2H), 3.85 (s, 2H), 2.42 (s, 3H) ppm.

Part D: Preparation of ethyl 1-(4-methoxyphenyl)-6-(4-{2-[(methylamino)methyl]-1H-imidazol-1-yl}phenyl)-7-oxo-4,5,6,7-tetrahydro-1H-pyrazolo[3,4-]pyridine-3-carboxylate 2-(methylaminomethyl)imidazole (2.22 g, 20 mmol), the product from Part B (5.17 g, 10 mmol), CuI (1.9 g, 10 mmol), K₂CO₃ (5.53 g, 40 mmol) were added together with 60 mL of DMSO. The mixture was degassed and then heated at 130° C. under N₂ for 4 h. The mixture was cooled and aqueous NH₄OH (10 mL) was added. The mixture was filtered through Celite® and washed with EtOAc. The two layers were separated and the aqueous layer was extracted with EtOAc. The combined EtOAc mixture was washed with brine, dried over MgSO4, concentrated in vacuo, and chromatographed with MeOH:CHCl₃ (2% to 4% to 7%) to give 2.1 g of the desired product (41.2%). MS (ES⁺): 501.5, (M+H)⁺; ¹HNMR (CDCl₃) δ 7.49–7.44 (m, 6H), 7.09 (d, 1H), 7.01 (d, 1H), 6.96–6.91 (m, 2H), 4.47 (q, 2H), 4.19 (t, 2H), 3.82 (s, 3H), 3.71 (s, 2H), 3.37 (t, 2H), 2.4 (s, 3H), 1.44 (t, 3H) ppm.

Part E: Preparation ethyl 6-[4-(2-{[acetyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxylate Product from Part D (500 mg, 0.40 mmol) was acylated with acetyl chloride (66 mg, 0.84 mmol) in CH₂Cl₂ (10 mL) and Et₃N (120 mg, 1.68 mmol) to give the desired product. The crude product was purified by flash chromatography to give the final product (89 mg). MS (ES⁺): 543.5, (M+H)⁺. ¹HNMR (CDCl₃) δ 7.58–7.44 (m, 7H), 7.09 (d, 1H), 6.92 (d, 2H), 4.58 (s, 2H), 4.47 (q, 2H), 4.19 (t, 2H), 3.82 (s, 3H), 3.41–3.38 (m, 5H), 2.12 (s, 3H), 1.44 (t, 3H) ppm.

Part F: Preparation of 6-[4-(2-{[Acetyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt Product from Part E (115 mg, 0.21 mmol) was dissolved in dioxane (20 mL) and treated with NH₄OH (20 mL). The flask was stoppered and the mixture stirred at room temperature for 54 hours. The solvents were removed in vacuo and the residue purified away from remaining starting material by flash chromatography using MeOH:CHCl₃:NH₄OH (20:1000:2 to 10:100:1). It was then was further purified by reverse phase HPLC (C18 reverse phase column, eluted with a H₂O/CH₃CN gradient with 0.05% TFA) to give 113 mg of the final product as the TFA salt. MS (ES⁺): 514.4, (M+H)⁺. ¹HNMR (CD₃OD) δ 7.69 (d, 2H), 7.65–7.57 (m, 5H), 7.47 (d, 2H), 6.95 (d, 2H), 4.68 (s, 2H), 4.16 (t, 2H), 3.80 (s, 3H), 3.32 (t, 2H), 2.96 (s, 3H), 2.01 (s, 3H) ppm.

EXAMPLE 7

6-[4-(2-{[ethylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

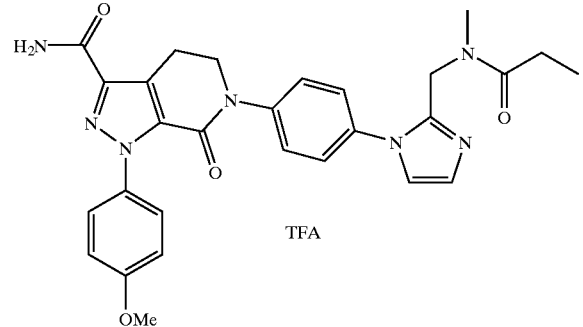

Part A: Preparation of 1-(4-methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxamide Ethyl 1-(4-methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxylate from Part D of Example 6 (500 mg, 1 mmol) was dissolved in 8% NH3 in ethylene glycol (10 mL) in a 50 mL pressure tube. The mixture was heated at 85° C. for 18 hours. Water was added and the precipitate filtered. This solid was dissolved in EtOAc, washed with water, dried over MgSO₄, and concentrated in vacuo. The crude product was purified by reverse phase HPLC (C18 reverse phase column, eluted with a H₂O/CH₃CN gradient with 0.05% TFA) to give the final product as the bis-TFA salt. MS (ES+): 472.5, (M+H)⁺. ¹HNMR (CD₃OD) δ 7.55 (d, 2H), 7.49–7.43 (m, 4H), 7.38 (d, 1H), 7.17 (d, 1H), 6.95 (d, 2H), 4.24 (s, 2H), 4.14 (t, 2H), 3.80 (s, 3H), 3.32 (t, 2H), 2.70 (s, 3H) ppm.

Part B: Preparation of 6-[4-(2-{[ethylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt Product from Part A (250 mg, 0.53 mmol), propionic acid (111 mg, 1.5 mmol), and triethylamine (500 mg, 5 mmol) in EtOAc (20 mL) were treated with O-benzotriazol-1-yl-N,N,N',N'-tetramethyluronium hexafluorophosphate (569 mg, 1.5 mmol) and the mixture was stirred at room temperature for 18 hours. The mixture was diluted with EtOAc, washed with water and brine, dried over MgSO4, and concentrated in vacuo. The residue was purified by reverse phase HPLC (C18 reverse phase column, eluted with a H₂O/CH₃CN gradient with 0.05% TFA) to give 183 mg of the final product as the TFA salt. MS (ES+): 528.5, (M+H)+. ¹HNMR (CD₃OD) δ 7.72 (d, 1H), 7.65–7.63 (m, 5H), 7.51 (d, 2H), 7.00 (d, 2H), 4.73 (s, 2H), 4.20 (t, 2H), 3.84 (s, 3H), 3.36–3.34 (m, 2H), 2.97 (s, 3H), 2.34 (q, 2H), 1.03 (s, 3H) ppm.

EXAMPLE 8

6-[4-(2-{[n-propylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

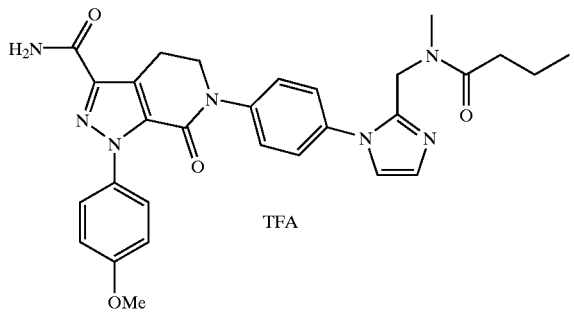

TFA

This compound was prepared by the same methods described in Example 7. MS (ES⁺): 542.5, (M+H)⁺. ¹HNMR (CD₃OD) δ 7.68 (d, 1H), 7.64–7.56 (m, 5H), 7.47 (d, 2H), 6.96 (d, 2H), 4.84 (s, 2H), 4.16 (t, 2H), 3.80 (s, 3H), 3.32 (t, 2H), 2.94 (s, 3H), 2.25 (t, 2H), 1.50 (q, 2H), 0.88 (t, 3H) ppm.

EXAMPLE 9

6-[4-(2-{[i-propylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

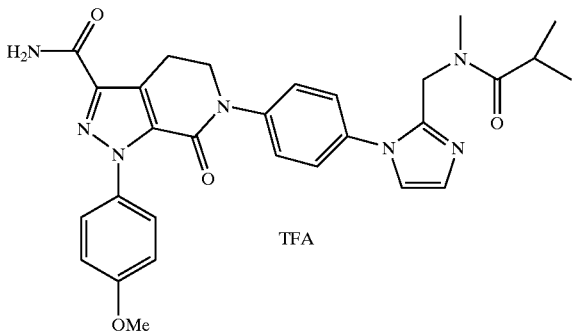

TFA

This compound was prepared by the same methods described in Example 6. MS (ES⁺): 486.5, (M+H)⁺. ¹HNMR (CD₃OD) δ 7.68 (d, 1H), 7.65–7.60 (m, 5H), 7.49–7.46 (m, 2H), 6.97–6.94 (m, 2H), 4.67 (s, 2H), 4.16 (t, 2H), 3.80 (s, 3H), 3.32 (t, 2H), 3.00 (s, 3H), 2.82–2.78 (m, 1H), 0.98 (d, 6H) ppm.

EXAMPLE 10

6-[4-(2-{[i-butylcarbonyl(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

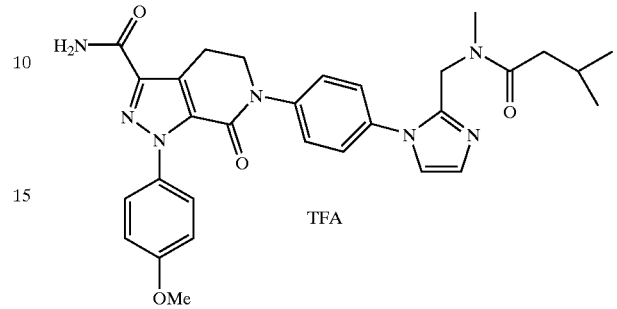

TFA

This compound was prepared by the same methods described in Example 7. MS (ES+): 556.5, (M+H)⁺. ¹HNMR (CD₃OD) δ 7.70 (d, 1H), 7.66–7.59 (m, 5H), 7.51–7.48 (m, 2H), 6.99–6.96 (m, 2H), 4.70 (s, 2H), 4.18 (t, 2H), 3.82 (s, 3H), 3.34 (t, 2H), 2.97 (s, 3H), 2.18 (d, 2H), 2.12–1.95 (m, 1H), 0.89 (d, 6H) ppm.

EXAMPLE 11

1-(4-Methoxyphenyl)-6-{4-[2-({methyl[(methylamino)carbonyl]-amino}methyl)-1H-imidazol-1-yl]phenyl}-7-oxo-4,5,6,7-tetrahydro-1H-pyrazolo[3,4-c]pyridine-3-carboxamide, trifluoroacetic acid salt

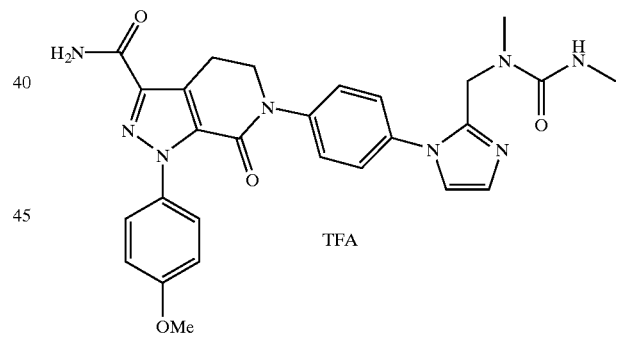

TFA

Part A: Preparation of ethyl 1-(4-methoxyphenyl)-6-{4-[2-({methyl[(methylamino)carbonyl]amino}methyl)-1H-imidazol-1-yl]phenyl}-7-oxo-4,5,6,7-tetrahydro-1H-pyrazolo[3,4-c]pyridine-3-carboxylate The product from Part D of Example 6 (200 mg, 0.40 mmol) was dissolved in CH₂Cl₂ (10 mL). Methyl isocyanate (228 mg, 4.0 mmol) was added and the mixture was stirred at room temperature under N₂ for 18 h. It was diluted with CH₂Cl₂ and washed with H₂O and brine. The organic solution was then dried over MgSO₄ and concentrated in vacuo. The crude product was purified by flash chromatography using MeOH:CHCl₃ (1% to 3%) to give 86 mg of the final product. MS (ES⁺): 558.5, (M+H)⁺. ¹HNMR (CDCl₃) δ 7.56–7.45 (m, 8H), 6.94–6.90 (m, 2H), 4.62 (s, 2H), 4.47 (q, 2H), 4.19 (t, 2H), 3.82 (s, 3H), 3.42–3.38 (m, 2H), 3.22 (s, 3H), 2.74 (s, 3H), 1.44 (t, 3H) ppm.

Part B: Preparation of 1-(4-methoxyphenyl)-6-{4-[2-({methyl[(methylamino)carbonyl]-amino}methyl)-1H-imidazol-1-yl]phenyl}-7-oxo-4,5,6,7-tetrahydro-1H-pyrazolo[3,4-c]pyridine-3-carboxamide, trifluoroacetic acid salt This compound was prepared using the same methods as described in Part F of Example 6 using the product from Part A as the starting material. MS (ES+): 529.4, (M+H)+. 1HNMR (CD3OD) δ 7.69 (d, 1H), 7.65–7.61 (m, 5H), 7.49 (d, 2H), 6.98 (d, 2H), 4.65 (s, 2H), 4.18 (t, 2H), 3.82 (s, 3H), 3.34 (t, 2H), 2.78 (s, 3H), 2.65 (s, 3H) ppm.

EXAMPLE 12

Methyl (1-{4-[3-(aminocarbonyl)-1-(4-methoxyphenyl)-7-oxo-1,4,5,7-tetrahydro-6H-pyrazolo[3,4-c]pyridin-6-yl]phenyl}-1H-imidazol-2-yl)methyl(methyl)carbamate, trifluoroacetic acid salt

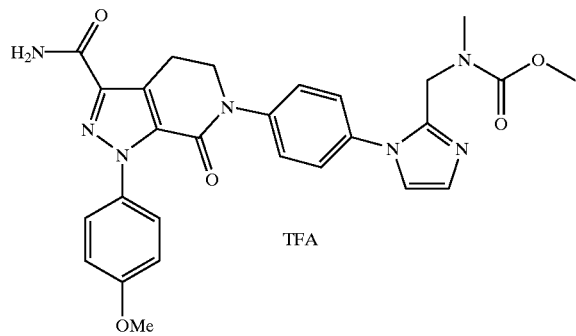

Part A: Preparation of ethyl 6-[4-(2-{[(methoxycarbonyl)(methyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxylate Ethyl 1-(4-methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxylate from Part D of Example 6 (200 mg, 0.4 mmol) was dissolved in CH2Cl2 (10 mL). Triethylamine (191 mg, 1.9 mmol) was added, followed by methyl chloroformate (159 mg, 1.68 mmol). The mixture was stirred at room temperature under N2 for 18 h. It was diluted with CH2Cl2 and washed with H2O and brine. The organic solution was then dried over MgSO4 and concentrated. The crude product was purified by flash chromatography using MeOH:CHCl3 (1% to 3%) as elutent to give 84 mg of the final product. MS (ES+): 559.5, (M+H)+. 1HNMR (CD3OD) δ 7.51–7.38 (m, 8H), 6.86 (d, 2H), 4.67 (bs, 2H), 4.41 (q, 2H), 4.13 (t, 2H), 3.76 (s, 3H), 3.53 (bs, 3H), 3.32 (t, 2H), 3.08 (bs, 3H), 1.38 (t, 3H) ppm.

Part B: Preparation of Methyl (1-{4-[3-(aminocarbonyl)-1-(4-methoxyphenyl)-7-oxo-1,4,5,7-tetrahydro-6H-pyrazolo[3,4-c]pyridin-6-yl]phenyl}-1H-imidazol-2-yl)methyl(methyl)carbamate, trifluoroacetic acid salt This compound was prepared using the same methods as described in Part F of Example 6 using the product from Part A as the starting material. MS (ES+): 530.4, (M+H)+. 1HNMR (CD3OD) δ 7.70 (d, 1H), 7.65–7.61 (m, 5H), 7.49 (d, 2H), 6.98 (d, 2H), 4.75–4.68 (m, 2H), 4.18 (t, 2H), 3.82 (s, 3H), 3.68–3.13 (m, 3H), 3.34 (t, 2H), 2.84 (s, 3H) ppm.

EXAMPLE 13

Ethyl (1-{4-[3-(aminocarbonyl)-1-(4-methoxyphenyl)-7-oxo-1,4,5,7-tetrahydro-6H-pyrazolo[3,4-c]pyridin-6-yl]phenyl}-1H-imidazol-2-yl)methyl(methyl)carbamate, trifluoroacetic acid salt

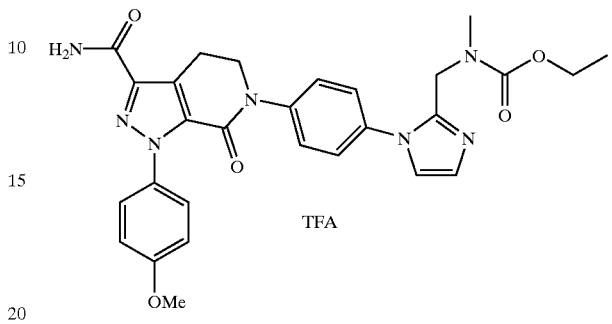

1-(4-Methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxamide from Part A of Example 7 (25 mg, 0.036 mmol) was suspended in CH2Cl2 (5 mL). Triethylamine (36 mg, 0.36 mmol) was added, followed by ethyl chloroformate (4.3 mg, 0.04 mmol). The mixture was stirred at room temperature under N2 for 18 h. The solvent was removed in vacuo. The crude product was purified by reverse phase HPLC (C18 reverse phase column, eluted with a H2O/CH3CN gradient with 0.05% TFA) to give 18 mg of the final product as the TFA salt. MS (ES+): 544.5, (M+H)+. 1HNMR (CD3OD) δ 7.72–7.59 (m, 6H), 7.48 (d, 2H), 6.96 (d, 2H), 4.75–4.63 (m, 2H), 4.16 (t, 2H), 4.10–4.00 (m, 2H), 3.80 (s, 3H), 3.32 (t, 2H), 2.83 (s, 3H), 1.22–1.02 (m, 3H) ppm.

EXAMPLE 14

1-(4-Methoxyphenyl)-6-[4-(2-{[methyl(methylsulfonyl)amino]-methyl}-1H-imidazol-1-yl)phenyl]-7-oxo-4,5,6,7-tetrahydro-1H-pyrazolo[3,4-c]pyridine-3-carboxamide, trifluoroacetic acid salt

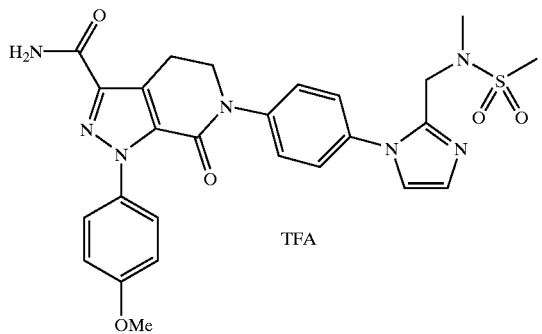

Part A: Preparation of ethyl 1-(4-methoxyphenyl)-6-[4-(2-{[methyl(methylsulfonyl)amino]methyl}-1H-imidazol-1-yl)phenyl]-7-oxo-4,5,6,7-tetrahydro-1H-pyrazolo[3,4-c]pyridine-3-carboxylate Ethyl 1-(4-methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxylate from Part D of Example 6 (200 mg, 0.40 mmol) was dissolved in CH2Cl2 (10 mL). Triethylamine (170 mg, 1.68 mmol) was added, followed by methanesulfonyl chloride (96 mg, 0.84 mmol). The mixture was stirred at room temperature under $N_2$ for 18 h. It was diluted with $CH_2Cl_2$ and washed with $H_2O$ and brine. The organic solution was then dried over $MgSO_4$ and concentrated in vacuo. The residue was purified by flash chromatography using MeOH:$CHCl_3$ (1% to 3%) to 82 mg of the final product. MS (ES$^+$): 579.5, (M+H)$^+$. $^1$HNMR (CDCl$_3$) δ 7.58–7.42 (m, 8H), 6.93 (d, 2H), 4.77 (s, 2H), 4.47 (q, 2H), 4.19 (t, 2H), 3.82 (s, 3H), 3.38 (t, 2H), 2.96 (s, 3H), 2.91 (s, 3H), 1.44 (t, 3H) ppm.

Part B: Preparation of 1-(4-Methoxyphenyl)-6-[4-(2-{[methyl(methylsulfonyl)amino]-methyl}-1H-imidazol-1-yl)phenyl]-7-oxo-4,5,6,7-tetrahydro-1H-pyrazolo[3,4-c]pyridine-3-carboxamide, trifluoroacetic acid salt This compound was prepared using the same methods as described in Part F of Example 6 using the product from Part A as the starting material. MS (ES$^+$): 550.4, (M+H)$^+$. $^1$HNMR (CD$_3$OD) δ 7.78 (d, 1H), 7.70–7.61 (m, 5H), 7.52 (d, 2H), 7.09 (d, 2H), 4.62 (s, 2H), 4.19 (t, 2H), 3.84 (s, 3H), 3.36 (t, 2H), 2.89 (s, 3H), 2.84 (s, 3H) ppm.

EXAMPLE 15

1-(4-Methoxyphenyl)-6-[4-(2-{[methyl(n-propylsulfonyl)amino]-methyl}-1H-imidazol-1-yl)phenyl]-7-oxo-4,5,6,7-tetrahydro-1H-pyrazolo[3,4-c]pyridine-3-carboxamide, trifluoroacetic acid salt

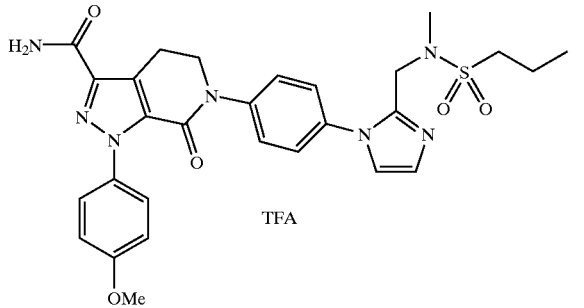

1-(4-Methoxyphenyl)-6-(4-{2-[(methylamino)methyl]-1H-imidazol-1-yl}phenyl)-7-oxo-4,5,6,7-tetrahydro-1H-pyrazolo[3,4-c]pyridine-3-carboxamide from Part A of Example 7 (25 mg, 0.03 mmol) was suspended in $CH_2Cl_2$ (5 mL). Triethylamine (36 mg, 0.36 mmol) was added, followed by propanesulfonyl chloride (16.8 mg, 0.12 mmol). The mixture was stirred at room temperature under $N_2$ for 18 h. The solvent was removed in vacuo. The crude product was purified by reverse phase HPLC (C18 reverse phase column, eluted with a $H_2O/CH_3CN$ gradient with 0.05% TFA) to give 14 mg of the final product as the TFA salt. MS (ES$^+$): 578.4 (M+H)$^+$. $^1$HNMR (CD$_3$OD) δ 7.72–7.56 (m, 6H), 7.47 (d, 2H), 6.95 (d, 2H), 4.61 (s, 2H), 4.15 (t, 2H), 3.80 (s, 3H), 3.32 (t, 2H), 3.00–2.95 (m, 2H), 2.79 (s, 3H), 1.74–1.67 (m, 2H), 0.97 (t, 2H) ppm.

EXAMPLE 16

6-[4-(2-{[[(3,5-dimethyl-4-isoxazolyl)sulfonyl](methyl)-amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

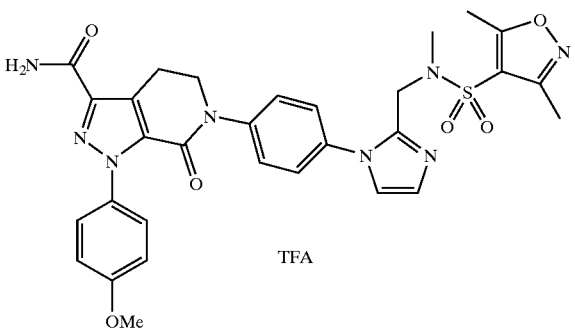

This compound was prepared using the same methods as described in Example 14. MS (ES$^+$): 631.4, (M+H)$^+$. $^1$HNMR (CD$_3$OD) δ 7.81 (d, 1H), 7.73 (d, 1H), 7.66–7.58 (m, 4H), 7.50 (d, 2H), 6.99 (d, 2H), 4.59 (s, 2H), 4.18 (t, 2H), 3.82 (s, 3H), 3.35 (t, 2H), 2.80 (s, 3H), 2.50 (s, 3H), 2.25 (s, 3H) ppm.

EXAMPLE 17

1-(4-Methoxyphenyl)-6-[4-(2-{[methyl(phenylsulfonyl)amino]-methyl}-1H-imidazol-1-yl)phenyl]-7-oxo-4,5,6,7-tetrahydro-1H-pyrazolo[3,4-c]pyridine-3-carboxamide, trifluoroacetic acid salt

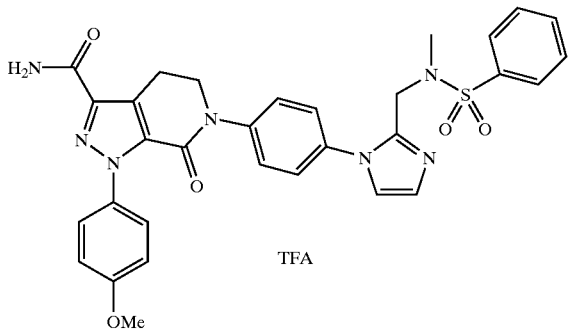

This compound was prepared using the same methods as described in Example 14. MS (ES$^+$): 612.4, (M+H)$^+$. $^1$HNMR (CD$_3$OD) δ 7.82 (d, 1H), 7.75 (d, 1H), 7.69–7.57 (m, 9H), 7.53 (d, 2H), 7.00 (d, 2H), 4.40 (s, 2H), 4.21 (t, 2H), 3.85 (s, 3H), 3.37 (t, 2H), 2.72 (s, 3H) ppm.

EXAMPLE 18

6-[4-(2-{[Acetyl(ethyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

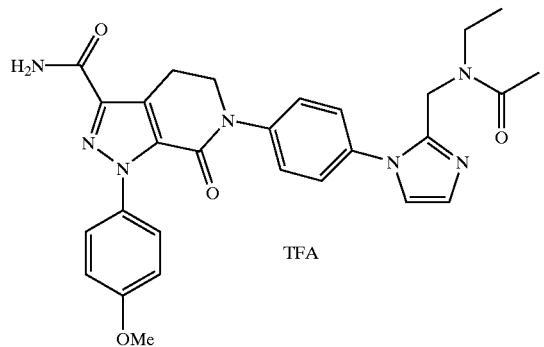

Part A: Preparation of N-[2-(ethylaminomethyl)]-1H-imidazole

2-Imidazolecarboxyaldehyde (2.5 g, 26 mmol) was suspended in 100 mL of methanol. Ethylamine (2.0 M in THF) was added. After stirring for 30 minutes at room temperature, NaBH$_4$ (1.98 g, 52 mmol) was added portion-wise. The reaction mixture was then heated at 50° C. for 2 h under N$_2$. The solvent was removed. The solid was washed with CH$_2$Cl$_2$ and filtered. The CH$_2$Cl$_2$ solution was dried over MgSO$_4$, concentrated, and dried under vacuum to afford 3.4 g of final product as a yellow oil. $^1$HNMR (CDCl$_3$) δ 7.04 (s, 2H), 3.91 (s, 2H), 2.69 (q, 2H), 1.12 (t, 3H) ppm.

Part B: Preparation of 6-(4-iodophenyl)-1-(4-methoxyphenyl)-7-oxo-4,5,6,7-tetrahydro-1H-pyrazolo[3,4-c]pyridine-3-carboxamide Ethyl 6-(4-iodophenyl)-1-(4-methoxyphenyl)-7-oxo-4,5,6,7-tetrahydro-1H-pyrazolo[3,4-c]pyridine-3-carboxylate from Part B of example 6 (3.0 g, 5.8 mmol) was suspended in 8% NH$_3$ in ethylene glycol (30 mL) in a 100 mL pressure tube. The mixture was heated at 85° C. for 18 hours. Water was added, and the precipitate was filtered and washed with water. The crude product was dried under vacuum to afford 3.2 g of final product. MS (ES$^+$): 489.2 (M+H)$^+$. $^1$HNMR (DMSO-d$_6$) δ 7.72–7.68 (m, 3H), 7.49–7.41 (m, 3H), 7.15 (d, 2H), 6.97 (d, 2H), 4.00 (t, 2H), 3.77 (s, 3H), 3.16 (t, 2H) ppm.

Part C: Preparation of 6-(4-{2-[(ethylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid)salt 2-(Ethylaminomethyl)imidazole (250 mg, 2 mmol), 6-(4-iodophenyl)-1-(4-methoxyphenyl)-7-oxo-4,5,6,7-tetrahydro-1H-pyrazolo[3,4-c]pyridine-3-carboxamide from Part B (488 mg, 1.02 mmol), CuI (190 mg, 1 mmol), K$_2$CO$_3$ (552 mg, 4 mmol) were added together with 6 mL of DMSO. The mixture was degassed and then heated at 130° C. under N$_2$ for 4 h. The mixture was cooled and aqueous NH$_4$OH (1 mL) was added. The mixture was filtered through Celite® and washed with EtOAc. The two layers were separated and the aqueous layer was extracted with EtOAc. The combined EtOAc mixture was washed with brine, dried over MgSO$_4$, concentrated in vacuo, and chromatographed with MeOH:CHCl$_3$:NH$_4$OH (20:1000:2 to 70:1000:7) to give the desired product. The product was further purified by reverse phase HPLC (C18 reverse phase column, eluted with a H$_2$O/CH$_3$CN gradient with 0.05% TFA) to give 170 mg of the final product as the TFA salt. MS (ES$^+$): 486.5, (M+H)$^+$. $^1$HNMR (CD$_3$OD) δ 7.56 (d, 2H), 7.49–7.44 (m, 4H), 7.38 (d, 1H), 7.18 (d, 1H), 6.96 (d, 2H), 4.25 (s, 2H), 4.14 (t, 2H), 3.80 (s, 3H), 3.32 (t, 2H), 3.08 (q, 2H), 1.25 (t, 2H) ppm.

Part D: Preparation of 6-[4-(2-{[Acetyl(ethyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt This compound was prepared by the same methods described in Example 7 using the product from Part A as the starting material. MS (ES$^+$): 528.5, (M+H)$^+$. $^1$HNMR (CD$_3$OD) δ 7.68 (d, 1H), 7.63–7.59 (m, 5H), 7.48 (d, 2H), 6.96 (d, 2H), 4.64 (s, 2H), 4.16 (t, 2H), 3.80 (s, 3H), 3.36–3.28 (t, 4H), 2.05 (s, 3H), 1.10 (t, 3H) ppm.

EXAMPLE 19

6-[4-(2-{[Acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

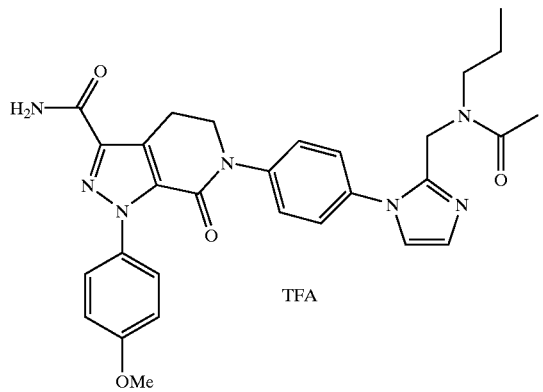

Part A: Preparation of N-[2-(n-propylaminomethyl)]-1H-imidazole

2-Imidazolecarboxyaldehyde (2.5 g, 26.0 mmol) was suspended in 100 mL of methanol. N-Propylamine (1.53 g, 26 mmol) was added. After stirring for 30 minutes, NaBH$_4$ (1.97 g, 52 mmol) was added portion-wise. The reaction mixture was then heated at 50° C. for 2 h under N$_2$. The solvent was removed. The solid was washed with CH$_2$Cl$_2$ and filtered. The CH$_2$Cl$_2$ solution was dried over MgSO$_4$, concentrated, and dried under vacuum to give 3.39 g of final product as a yellow oil. MS (AP$^+$): 140.1, (M+H)$^+$. $^1$HNMR (CDCl$_3$ w/CD$_3$OD) δ 6.95 (s, 2H), 3.82 (s, 2H), 2.56 (t, 2H), 1.56–1.47 (m, 2H), 0.93 (t, 3H) ppm.

Part B: Preparation of 1-(4-methoxyphenyl)-7-oxo-6-(4-{2-[(propylamino)methyl]-1H-imidazol-1-yl}phenyl)-4,5,6,7-tetrahydro-1H-pyrazolo[3,4-c]pyridine-3-carboxamide, bis(trifluoroacetic acid)salt 2-(Propylaminomethyl)imidazole (562 mg, 4.1 mmol), the product from Part B of Example 18 (1.0 g, 2.05 mmol), CuI (390 mg, 2.65 mmol), K$_2$CO$_3$ (1.13 g, 8.2 mmol) were added together with 12 mL of DMSO. The mixture was degassed and then heated at 130° C. under N$_2$ for 4 h. The mixture was cooled and aqueous NH$_4$OH was added. The mixture was filtered through Celite® and washed with EtOAc. The two layers were separated and the aqueous layer was extracted with EtOAc. The combined EtOAc mixture was washed with brine, dried over MgSO$_4$, concentrated in vacuo, and chromatographed with MeOH:CHCl$_3$:NH$_4$OH (20:1000:2 to 70:1000:7) to give the desired product. The product was further purified by reverse phase HPLC (C18 reverse phase column, eluted with a H$_2$O/CH$_3$CN gradient with 0.05% TFA) to give 342 mg of the final product as the TFA salt. MS (ES$^+$): 500.5, (M+H)$^+$. $^1$HNMR (C$_3$OD) δ 7.56 (d, 2H), 7.49–7.44 (m, 4H), 7.41 (d, 1H), 7.22 (d, 1H), 6.95 (d, 2H), 4.27 (s, 2H), 4.14 (t, 2H), 3.80 (s, 3H), 3.32 (t, 2H), 3.01–2.95 (m, 2H), 1.75–1.60 (m, 2H), 0.95 (t, 3H) ppm.
Part C: Preparation of 6-[4-(2-{[Acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt This compound was prepared by the same methods described in Example 7 using the product from Part B as the starting material. MS (ES$^+$): 542.4, (M+H)$^+$. $^1$HNMR (CD$_3$OD) δ 7.69 (d, 1H), 7.65–7.57 (m, 5H), 7.48 (d, 2H), 6.96 (d, 2H), 4.64 (s, 2H), 4.17 (t, 2H), 3.80 (s, 3H), 3.33 (t, 2H), 3.23–3.18 (m, 2H), 2.04 (s, 3H), 1.58–1.43 (m, 2H), 0.84 (t, 3H) ppm.

EXAMPLE 20

6-[4-(2-{[Acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

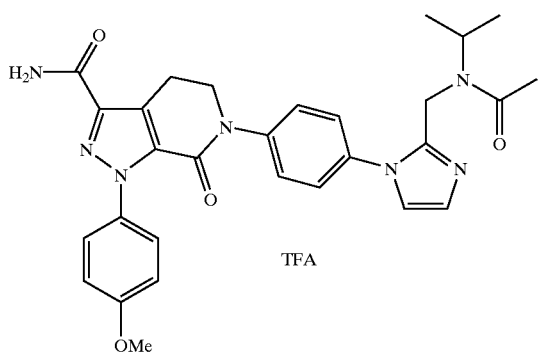

Part A: Preparation of N-[2-(i-propylaminomethyl)]-1H-imidazole

2-Imidazolecarboxyaldehyde (2.5 g, 26.0 mmol) was suspended in 100 mL of methanol. Isopropylamine (1.54 g, 26 mmol) was added. After stirring for 30 minutes, NaBH$_4$ (1.97 g, 52 mmol) was added portion-wise. The reaction mixture was then heated at 50° C. for 2 h under N$_2$. The solvent was removed. The solid was washed with CH$_2$Cl$_2$ and filtered. The CH$_2$Cl$_2$ solution was dried over MgSO$_4$, concentrated, and dried under vacuum to give 3.7 g of final product as a yellow oil. MS (AP$^+$): 140.1, (M+H)$^+$. $^1$HNMR (CDCl$_3$ w/CD$_3$OD) δ 6.82 (s, 2H), 3.69 (s, 2H), 2.73–2.65 (m, 1H), 0.97 (s, 6H) ppm.
Part B: Preparation of 6-(4-{2-[(isopropylamino)methyl]-1H-imidazol-1-yl}phenyl)-1-(4-methoxyphenyl)-7-oxo-4,5,6,7-tetrahydro-1H-pyrazolo[3,4-c]pyridine-3-carboxamide, bis(trifluoroacetic acid)salt 2-(Isopropylaminomethyl)imidazole (562 mg, 4.1 mmol), the product from Part B of Example 18 (1.0 g, 2.05 mmol), CuI (390 mg, 2.65 mmol), K$_2$CO$_3$ (1.13 g, 8.2 mmol) were added together with 12 mL of DMSO. The mixture was degassed and then heated at 130° C. under N$_2$ for 4 h. The mixture was cooled and aqueous NH$_4$OH was added. The mixture was filtered through Celite® and washed with EtOAc. The two layers were separated and the aqueous layer was extracted with EtOAc. The combined EtOAc mixture was washed with brine, dried over MgSO$_4$, concentrated in vacuo, and chromatographed with MeOH:CHCl$_3$:NH$_4$OH (20:1000:2 to 70:1000:7) to elute desired product. The product was further purified by reverse phase HPLC (C18 reverse phase column, eluted with a H$_2$O/CH$_3$CN gradient with 0.05% TFA) to give 359 mg of the final product as the TFA salt. MS (ES$^+$): 500.4, (M+H)$^+$ $^1$HNMR (CD$_3$OD) δ 7.56 (d, 2H), 7.49–7.44 (m, 4H), 7.38 (s, 1H), 7.18 (s, 1H), 6.96 (d, 2H), 4.24 (s, 2H), 4.15 (t, 2H), 3.80 (s, 3H), 3.42–3.38 (m, 1H), 3.32 (t, 2H), 1.26 (d, 6H) ppm.
Part C: Preparation of 6-[4-(2-{[Acetyl(n-propyl)amino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt This compound was prepared by the same methods described in Example 7. MS (ES$^+$): 542.5, (M+H)$^+$. $^1$HNMR (CD$_3$OD) δ 7.70–7.60 (m, 6H), 7.48 (d, 2H), 6.96 (d, 2H), 4.51 (s, 2H), 4.28–4.21 (m, 1H), 4.17 (t, 2H), 3.80 (s, 3H), 3.33 (t, 2H), 2.17 (s, 3H), 1.16 (d, 6H) ppm.

EXAMPLE 21

6-[4-(2-{[ethylcarbonylamino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt

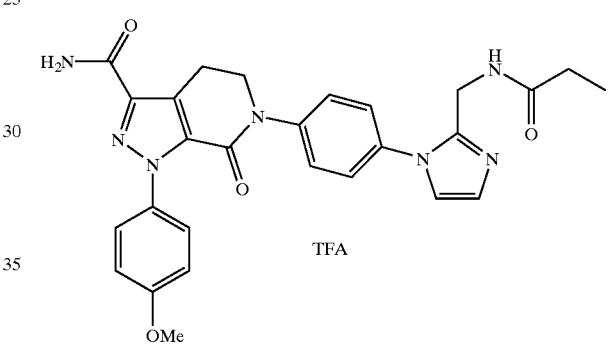

Part A: Preparation of N-[2-(aminomethyl)]-1H-imidazole bis(hydrochloric acid)salt Imidazole (6.8 g, 100 mmol) and benzoyl chloride were added together in acetonitrile (200 mL). Triethylamine (40.4 g, 400 mmol) was added dropwise and the mixture stirred at room temperature for 18 hours. The precipitate was filtered off and washed with water and then dried under vacuum to afford 12.3 g of white solid. This solid was suspended in MeOH (150 mL). Iso-propanol saturated with HCl (30 mL) was then added and the mixture stirred at reflux for 18 hours. The solvents were removed in vacuo and the solid washed with acetone and dried under vacuum to afford 2.81 g of off-white solid as final product. $^1$HNMR (CD$_3$OD) δ 7.66 (s, 2H), 4.89 (bs, 2H) ppm.
Part B: Preparation of 6-{4-[2-(aminomethyl)-1H-imidazol-1-yl]phenyl}-1-(4-methoxyphenyl)-7-oxo-4,5,6,7-tetrahydro-1H-pyrazolo[3,4-c]pyridine-3-carboxamide N-[2-(aminomethyl)]-1H-imidazole bis(hydrochloric acid)salt (333 mg, 1.96 mmol), the product from Part B of Example 18 (500 mg, 1.2 mmol), CuI (186 mg, 0.98 mmol), K$_2$CO$_3$ (1.082 g, 7.84 mmol) were added together with 6 mL of DMSO. The mixture was degassed and then heated at 130° C. under N$_2$ for 4 h. The mixture was cooled and aqueous NH$_4$OH was added. The mixture was filtered through Celite® and washed with EtOAc. The two layers were separated and the aqueous layer was extracted with EtOAc. The combined EtOAc mixture was washed with brine, dried over MgSO$_4$, concentrated in vacuo, and chromatographed with MeOH:CHCl₃:NH₄OH (20:1000:2 to 20:100:2) to give 30 mg of desired product. MS (ES⁺): 458.4, (M+H)⁺. ¹HNMR (CD₃OD) δ 7.56 (d, 1H), 7.49–7.43 (m, 4H), 7.37 (d, 1H), 7.16 (d, 1H), 6.96 (d, 2H), 4.15 (s, 2H), 3.80 (s, 3H), 3.28 (t, 2H) ppm.

Part C: Preparation of 6-[4-(2-{[ethylcarbonylamino]methyl}-1H-imidazol-1-yl)phenyl]-1-(4-methoxyphenyl)-7-oxo-4,5,6,7-tetrahydro-1H-pyrazolo[3,4-c]pyridine-3-carboxamide, trifluoroacetic acid salt This compound was prepared by the same methods described in Example 7 using the product from Part B as the starting material. MS (ES⁺): 514, (M+H)⁺. ¹HNMR (CD₃OD) δ 7.69 (d, 1H), 7.65–7.52 (m, 5H), 7.49 (d, 2H), 6.97 (d, 2H), 4.52 (s, 2H), 4.17 (t, 2H), 3.81 (s, 3H), 3.33 (t, 2H), 2.16 (q, 2H), 1.02 (t, 2H) ppm.

EXAMPLE 22

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylacetamide trifluoroacetic acid salt

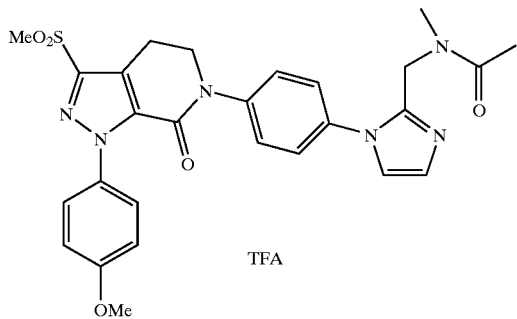

Part A: Preparation of (1Z)-1-[chloro(methylsulfonyl)methylene]-2-(4-methoxyphenyl)hydrazine To a solution of p-anisidine (4.39 g, 3.6 mmol) in con. HCl (9.2 mL) and water (20 mL) at 0° C. was slowly added sodium nitrite (2.58 g, 3.7 mmol) in water (20 mL). The reaction mixture was stirred at 0° C. for 0.5 h. The above mixture was poured into a mixture of 3-chloromethanesulphonyl acetone (Grossert, J S, et al., Can. J. Chem. Vol 62, 1984, 798)(6.1 g, 3.5 mmol), acetone (50 mL), sodium acetate (6.7 g, 8.2 mmol), and water (100 mL). The resulting mixture was stirred for 4 h at rt. The precipitate was filtered-off and dried to afford the hydrazone as a red solid (5.28 g, 57%); ¹HNMR (CDCl₃) δ 8.05 (s, 1H), 7.12 (d, 2H), 6.91 (d, 2H), 3.80 (s, 3H), 3.23 (s, 3H) ppm.

Part B: Preparation of 6-(4-iodophenyl)-1-(4-methoxyphenyl)-3-(methylsulfonyl)-1,4,5,6-tetrahydro-7H-pyrazolo[3,4-c]pyridin-7-one The product of Part A (2.60 g, 10 mol) was stirred with 1-(4-iodophenyl)-3-(4-morpholinyl)-5,6-dihydro-2(1H)-pyridinone (3.80 g, 10 mol) prepared in Part B of Example 1 and triethylamine (2.76 mL, 20 mol) in EtOAc (30 mL). The mixture was heated at 70° C. under N₂ for 12 h. The reaction mixture was cooled to 5° C., aqueous HCl (12.4 mL of 4N) was added dropwise. The cooling bath was removed and the mixture was stirred at RT for 4 h. A small amount of hexane (5 mL) and water (10 mL) were added. The precipitate formed was filtered, washed with water and hexane, and dried to afford 4.15 g (80%) of the desired product. ¹HNMR (CDCl₃) δ 7.66 (d, 2H), 7.44 (d, 2H), 7.05 (d, 2H), 6.90 (d, 2H), 4.08 (t, 2H), 3.80 (s, 3H), 3.35 (t, 2H), 3.28 (s, 3H) ppm.

Part C: Preparation of. 1-(4-methoxyphenyl)-6-(4-{2-[(methylamino)methyl]-1H-imidazol-1-yl}phenyl)-3-(methylsulfonyl)-1,4,5,6-tetrahydro-7H-pyrazolo[3,4-c]pyridin-7-one The product from Part B (4.15 g, 7.94 mmol), 2-(methylaminomethyl)imidazole from Part C of Example 6. (1.93 g, 16.67 mmol), K₂CO₃ (4.39 g, 31.76 mmol), CuI (1.51 g, 7.94 mmol) were added together with 50 mL of DMSO. The mixture was degassed and then heated at 130° C. under N₂ for 4 h. The mixture was cooled, EtOAc and 8% aqueous NH₄OH were added. The mixture was filtered through Celite® and washed with EtOAc. The two layers were separated and the aqueous layer was extracted with EtOAc. The aqueous layer was extracted with CHCl₃ again. The EtOAc and CHCl₃ extracts were washed with water and brine and dried over MgSO₄ separately. They were then combined, concentrated, and chromatographed on silica gel with 1:1 EtOAc/hexane and 8:1 CHCl₃/MeOH to give 2.79 g of the desired product. This material was further purified by reverse phase HPLC (C18 reverse phase column, eluted with a H₂O/CH₃CN gradient with 0.05% TFA) to give 2.5 g of the bis-TFA salt. MS (ES⁺): 507.4, (M+H)⁺. ¹HNMR (DMSO-d₆) δ 7.60–7.02 (m, 10H), 4.28 (s, 2H), 4.16 (t, 2H), 3.82 (s, 3H), 3.38 (s, 3H), 3.25 (t, 2H), 2.65 (s, 3H) ppm.

Part D: Preparation of N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylacetamide trifluoroacetic acid salt Product from Part C (119.0 mg, 0.16 mmol), acetic acid (9.26 µL, 0.16 mmol), triethylamine (79.4 µL, 0.57 mmol), and HBTU (61.5 mg, 0.16 mmol) were added together with DMF (5 mL). The mixture was stirred at RT under N₂ for 12 h. Water was added, followed by aqueous NaOH to adjust the pH to 8–9. It was then extracted with EtOAc. The organic layer was washed with water and brine, concentrated, and purified by reverse phase HPLC (C18 reverse phase column, eluted with a H₂O/CH₃CN gradient with 0.05% TFA) to give the final product as the TFA salt (84 mg). MS (ES⁺): 549.4 (M+H)⁺. ¹HNMR (CD₃OD) δ 7.71–7.60 (m, 6H), 7.49 (d, 2H), 6.98 (d, 2H), 4.72 (s, 2H), 4.22 (t, 2H), 3.83 (s, 3H), 3.33 (t, 2H), 3.30 (s, 3H), 3.00 (s, 3H), 2.04 (s, 3H) ppm.

EXAMPLE 23

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylpropanamide trifluoroacetic acid salt

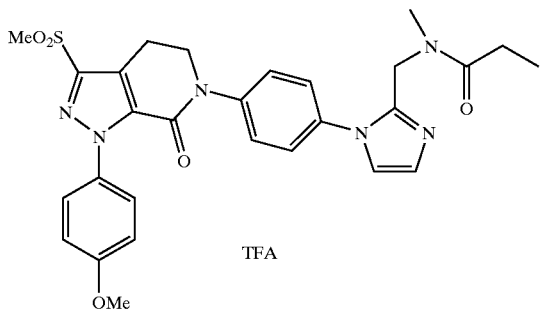

This compound was prepared by the same methods described in Example 22. MS (ES⁺): 563.5 (M+H)⁺. ¹HNMR (CD₃OD) δ 7.71–7.60 (m, 6H), 7.52 (d, 2H), 7.02 (d, 2H), 4.72 (s, 2H), 4.23 (t, 2H), 3.85 (s, 3H), 3.31 (t, 2H), 3.30 (s, 3H), 2.97 (s, 3H), 2.34 (q, 2H), 1.02 (t, 3H) ppm.

EXAMPLE 24

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylbutanamide trifluoroacetic acid salt

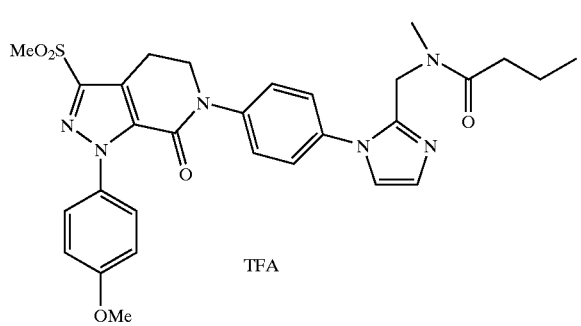

This compound was prepared by the same methods described in Example 22. MS (ES+): 577.3 (M+H)+. ¹HNMR (CD₃OD) δ 7.67–7.57 (m, 6H), 7.48 (d, 2H), 6.96 (d, 2H), 4.68 (s, 2H), 4.19 (t, 2H), 3.81 (s, 3H), 3.27 (t, 2H), 3.26 (s, 3H), 2.93 (s, 3H), 2.24 (t, 2H), 1.50 (m, 2H), 0.87 (t, 3H) ppm.

EXAMPLE 25

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N,2-dimethylpropanamide trifluoroacetic acid salt

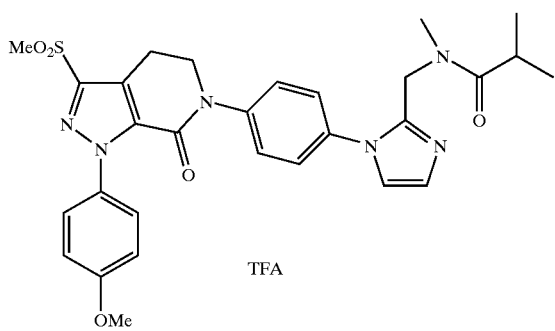

This compound was prepared by the same methods described in Example 22. MS (ES+): 577.3 (M+H)+. ¹HNMR (CD₃OD) δ 7.71–7.62 (m, 6H), 7.51 (d, 2H), 7.00 (d, 2H), 4.70 (s, 2H), 4.23 (t, 2H), 3.85 (s, 3H), 3.34 (t, 2H), 3.29 (s, 3H), 3.04 (s, 3H), 2.84 (m, 1H), 1.01 (d, 6H) ppm.

EXAMPLE 26

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-methylcyclopropanecarboxamide trifluoroacetic acid salt

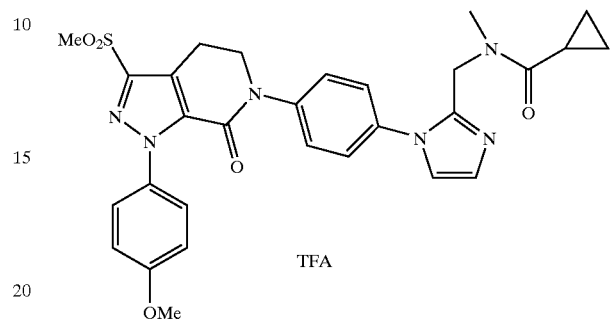

This compound was prepared by the same methods described in Example 22. MS (ES+): 575.5 (M+H)+. ¹HNMR (CD₃OD) δ 7.67–7.59 (m, 6H), 7.47 (d, 2H), 6.97 (d, 2H), 4.70 (s, 2H), 4.19 (t, 2H), 3.81 (s, 3H), 3.31 (t, 2H), 3.26 (s, 3H), 3.11 (s, 3H), 1.82 (m, 1H), 0.79 (m, 4H) ppm.

EXAMPLE 27

Methyl (1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl(methyl)carbamate trifluoroacetic acid salt

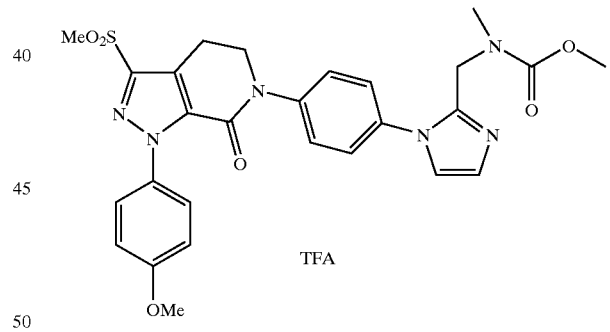

The product from Part C of Example 22 (100 mg, 0.14 mmol) was dissolved in CH₂Cl₂ (5 mL). Triethylamine (0.76 μL, 0.54 mmol) was added, followed by methyl chloroformate (11.6 μL, 0.15 mmol). The mixture was stirred at room temperature under N₂ for ½ h. It was diluted with CH₂Cl₂ and washed with H₂O and brine. The organic solution was then dried over MgSO₄ and concentrated. The crude product was purified by reverse phase HPLC (C18 reverse phase column, eluted with a H₂O/CH₃CN gradient with 0.05% TFA) to give 74 mg of the desired product as the TFA salt. MS (ES+): 565.4, (M+H)+. ¹HNMR (CD₃OH) δ 7.81–7.50 (m, 6H), 7.48 (d, 2H), 6.97 (d, 2H), 4.60 (s, 2H), 4.11 (t, 2H), 3.76 (s, 3H), 3.50–3.36 (d, 3H), 3.32 (s, 3H), 3.19 (t, 2H), 2.71 (s, 3H) ppm.

EXAMPLE 28

N-ethyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide trifluoroacetic acid salt

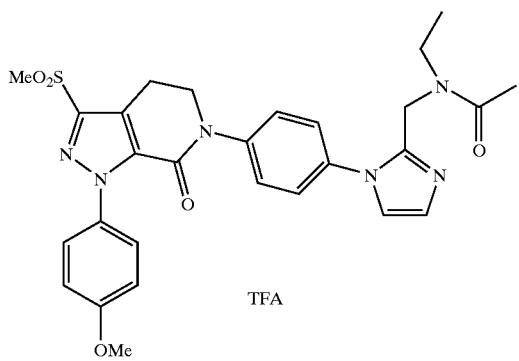

Part A: Preparation of 6-(4-{2-[(ethylamino)methyl]-1H-imidazol-1-yl}phenyl)-1-(4-methoxyphenyl)-3-(methylsulfonyl)-1,4,5,6-tetrahydro-7H-pyrazolo[3,4-c]pyridin-7-one The product from Part B of Example 22 (0.52 g, 1.00 mmol), 2-(ethylaminomethyl)imidazole from Part A of Example 18. (0.26 g, 2.10 mmol), $K_2CO_3$ (0.55 g, 4.00 mmol), CuI (0.19 g, 1.00 mmol) were added together with 6 mL of DMSO. The mixture was degassed and then heated at 130° C. under $N_2$ for 4 h. The mixture was cooled, $CHCl_3$ and 8% aqueous $NH_4OH$ were added. The mixture was filtered through Celite® and washed with $CHCl_3$. The two layers were separated and the aqueous layer was extracted with $CHCl_3$. The organic extract was washed with water and brin, dried over $MgSO_4$, and concentrated. The crude product was chromatographed on silica gel with 1:1 EtOAc/hexane and 8:1 $CHCl_3$/MeOH, then further purified by reverse phase HPLC (C18 reverse phase column, eluted with a $H_2O/CH_3CN$ gradient with 0.05% TFA) to give 351 mg of the bis-TFA salt. MS (ES$^+$): 521.3, (M+H)$^+$. $^1$HNMR (DMSO-$d_6$) δ 7.60–7.02 (m, 10H), 4.28 (s, 2H), 4.16 (t, 2H), 3.82 (s, 3H), 3.38 (s, 3H), 3.25 (t, 2H), 3.04 (q, 2H), 1.18 (t, 3H) ppm.

Part B: Preparation of N-ethyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide trifluoroacetic acid salt Product from Part A (150 mg, 0.20 mmol), acetic acid (11.5 μL, 0.20 mmol), triethylamine (118.0 μL, 0.40 mmol), and HBTU (76.0 mg, 0.20 mmol) were added together with DMF (5 mL). The mixture was stirred at RT under $N_2$ for 30 h. Water was added, followed by aqueous NaOH to adjust the pH to 8–9. It was then extracted with EtOAc. The organic layer was washed with water and brine, concentrated, and purified by reverse phase HPLC (C18 reverse phase column, eluted with a $H_2O/CH_3CN$ gradient with 0.05% TFA) to give the final product as the TFA salt (126 mg). MS (ES$^+$): 563.4 (M+H)$^+$. $^1$HNMR (CD$_3$OD) δ 7.69–7.58 (m, 6H), 7.47 (d, 2H), 6.98 (d, 2H), 4.64 (s, 2H), 4.20 (t, 2H), 3.81 (s, 3H), 3.38–3.25 (m, 7H), 3.28 (s, 3H), 2.05 (s, 3H), 1.10 (t, 3H) ppm.

EXAMPLE 29

N-isopropyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide trifluoroacetic acid salt

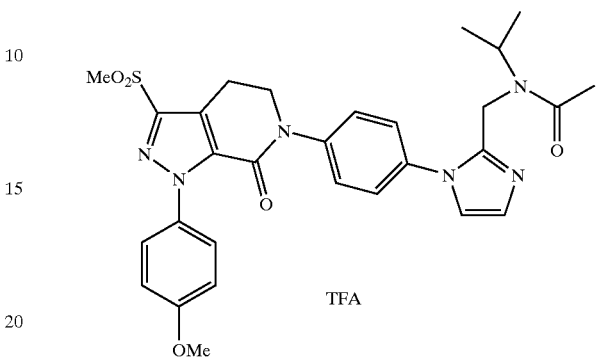

Part A: Preparation of 6-(4-{2-[(isopropylamino)methyl]-1H-imidazol-1-yl}phenyl)-1-(4-methoxyphenyl)-3-(methylsulfonyl)-1,4,5,6-tetrahydro-7H-pyrazolo[3,4-c]pyridin-7-one The product from Part B of Example 22 (0.52 g, 1.00 mmol), 2-(I-propylaminomethyl)imidazole from Part A of Example 20. (0.29 g, 2.10 mmol), $K_2CO_3$ (0.55 g, 4.00 mmol), CuI (0.19 g, 1.00 mmol) were added together with 6 mL of DMSO. The mixture was degassed and then heated at 130° C. under $N_2$ for 4 h. The mixture was cooled, $CHCl_3$ and 8% aqueous $NH_4OH$ were added. The mixture was filtered through Celite® and washed with $CHCl_3$. The two layers were separated and the aqueous layer was extracted with $CHCl_3$. The organic extract was washed with water and brin, dried over $MgSO_4$, and concentrated. The crude product was chromatographed on silica gel with 1:1 EtOAc/hexane and 8:1 $CHCl_3$/MeOH, then further purified by reverse phase HPLC (C18 reverse phase column, eluted with a $H_2O/CH_3CN$ gradient with 0.05% TFA) to give 270 mg of the bis-TFA salt. MS (ES$^+$): 535.5, (M+H)$^+$. $^1$HNMR (DMSO-$d_6$) δ 7.60–7.02 (m, 10H), 4.26 (s, 2H), 4.16 (t, 2H), 3.82 (s, 3H), 3.39 (m, 1H), 3.38 (s, 3H), 3.25 (t, 2H), 1.22 (d, 6H) ppm.

Part B: Preparation of N-isopropyl-N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]acetamide trifluoroacetic acid salt Product from Part A (130 mg, 0.17 mmol), acetic acid (9.8 μL, 0.17 mmol), triethylamine (95 μL, 0.34 mmol), and HBTU (64.6 mg, 0.17 mmol) were added together with DMF (5 mL). The mixture was stirred at RT under $N_2$ for 30 h. Water was added, followed by aqueous NaOH to adjust the pH to 8–9. It was then extracted with EtOAc. The organic layer was washed with water and brine, concentrated, and purified by reverse phase HPLC (C18 reverse phase column, eluted with a $H_2O/CH_3CN$ gradient with 0.05% TFA) to give the final product as the TFA salt (90 mg). MS (ES$^+$): 577.6 (M+H)$^+$. $^1$HNMR (CD$_3$OD) δ 7.65–7.60 (m, 6H), 7.48 (d, 2H), 6.97 (d, 2H), 4.51 (s, 2H), 4.20 (t, 2H), 3.81 (s, 3H), 3.28–3.25 (m, 6H), 2.17 (s, 3H), 1.15 (d, 6H) ppm.

EXAMPLE 30

N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-propylacetamide trifluoroacetic acid salt

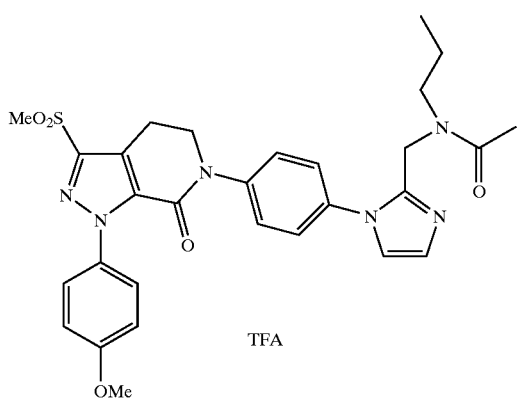

TFA

Part A: Preparation of. 1-(4-methoxyphenyl)-3-(methylsulfonyl)-6-(4-{2-[(propylamino)methyl]-1H-imidazol-1-yl}phenyl)-1,4,5,6-tetrahydro-7H-pyrazolo[3,4-c]pyridin-7-one The product from Part B of Example 22 (0.52 g, 1.00 mmol), 2-(ethylaminomethyl)imidazole from Part A of Example 19.(0.29 g, 2.10 mmol), K₂CO₃ (0.55 g, 4.00 mmol), CuI (0.19 g, 1.00 mmol) were added together with 6 mL of DMSO. The mixture was degassed and then heated at 130° C. under N₂ for 4 h. The mixture was cooled, CHCl₃ and 8% aqueous NH₄OH were added. The mixture was filtered through Celite® and washed with CHCl₃. The two layers were separated and the aqueous layer was extracted with CHCl₃. The organic extract was washed with water and brin, dried over MgSO₄, and concentrated. The crude product was chromatographed on silica gel with 1:1 EtOAc/hexane and 8:1 CHCl₃/MeOH, then further purified by reverse phase HPLC (C18 reverse phase column, eluted with a H₂O/CH₃CN gradient with 0.05% TFA) to give 300 mg of the bis-TFA salt. MS (ES⁺): 535.4, (M+H)⁺. ¹HNMR (DMSO-d₆) δ 7.60–7.02 (m, 10H), 4.28 (s, 2H), 4.16 (t, 2H), 3.82 (s, 3H), 3.38 (s, 3H), 3.25 (t, 2H), 2.95 (t, 2H), 1.60 (m, 2H), 0.87 (t, 3H) ppm.

Part B: Preparation of N-[(1-{4-[1-(4-methoxyphenyl)-3-(methylsulfonyl)-7-oxo-1,4,5,7-tetrahydro-6H-pyrazolo[3,4-c]pyridin-6-yl]phenyl}-1H-imidazol-2-yl)methyl]-N-propylacetamide trifluoroacetic acid salt Product from Part A (150 mg, 0.20 mmol), acetic acid (11.6 μL, 0.20 mmol), triethylamine (110 μL, 0.40 mmol), and HBTU (76.0 mg, 0.20 mmol) were added together with DMF (5 mL). The mixture was stirred at RT under N₂ for 12 h. Water was added, followed by aqueous NaOH to adjust the pH to 8–9.

It was then extracted with EtOAc. The organic layer was washed with water and brine, concentrated, and purified by reverse phase HPLC (C18 reverse phase column, eluted with a H₂O/CH₃CN gradient with 0.05% TFA) to give the final product as the TFA salt (110 mg). MS (ES⁺): 577.6 (M+H)⁺. ¹HNMR (CD3OD) δ 7.69–7.60 (m, 6H), 7.47 (d, 2H), 6.97 (d, 2H), 4.64 (s, 2H), 4.20 (t, 2H), 3.81 (s, 3H), 3.31–3.21 (m, 7H), 2.04 (s, 3H), 1.50 (m, 2H), 0.84 (t, 3H) ppm.

EXAMPLE 31

1-(4-methoxyphenyl)-6-[2'-({methyl[(methylamino)carbonyl]-amino}methyl)-1,1'-biphenyl-4-yl]-7-oxo-4,5,6,7-tetrahydro-1H-pyrazolo[3,4-c]pyridine-3-carboxamide trifluoroacetic acid salt

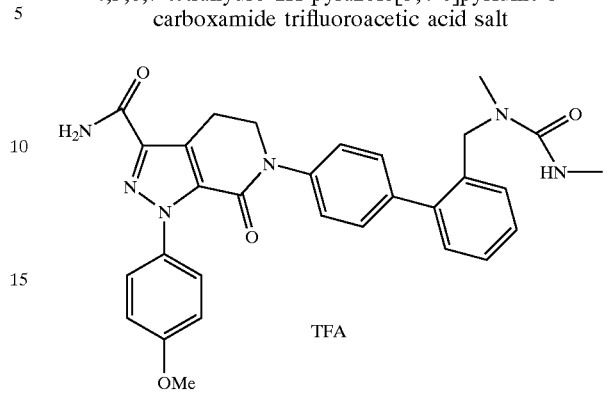

TFA

Part A: Preparation of ethyl 6-(2'-formyl-1,1'-biphenyl-4-yl)-1-(4-methoxyphenyl)-7-oxo-4,5,6,7-tetrahydro-1H-pyrazolo[3,4-c]pyridine-3-carboxylate Ethyl 6-(4-iodophenyl)-1-(4-methoxyphenyl)-7-oxo-4,5,6,7-tetrahydro-1H-pyrazolo[3,4-c]pyridine-3-carboxylate (1.0 g, 1.93 mmol), K₃PO₄ (1.63 g, 7.72 mmol), 2-Formylbenzeneboronic acid (579 mg, 3.86 mmol), and Pd(PPh₃)₄ (116 mg, 0.1 mmol) were added together with 20 mL of 1,4-dioxane. The mixture was degassed and then refluxed for 18 hours. The mixture was cooled and the solvent was removed. The residue was partitioned between EtOAc and H₂O. The EtOAc layer was washed with brine, dried over MgSO₄l concentrated, and chromatographed with 1:1 EtOAc:hexane to afford 490 mg of the desired product (51.3%). MS (ES⁺): 496.4, (M+H)⁺. ¹HNMR (CDCl₃) δ 10.00 (s, 1H), 8.04–8.01 (m, 1H), 7.64–7.61 (m, 1H), 7.53–7.38 (m, 8H), 6.93 (d, 2H), 4.48 (q, 2H), 4.21 (t, 2H), 3.82 (s, 3H), 3.38 (t, 2H), 1.45 (t, 3H) ppm.

Part B: Preparation of ethyl 1-(4-methoxyphenyl)-6-{2'-[(methylamino)methyl]-1,1'-biphenyl-4-yl}-7-oxo-4,5,6,7-tetrahydro-1H-pyrazolo[3,4-c]pyridine-3-carboxylate Ethyl 6-(2'-formyl-1,1'-biphenyl-4-yl)-1-(4-methoxyphenyl)-7-oxo-4,5,6,7-tetrahydro-1H-pyrazolo[3,4-c]pyridine-3-carboxylate (485 mg, 0.98 mmol) and methylamine hydrochloride (135 mg, 2 mmol) were added together in 10 mL of 1:1 MeOH:THF and stirred at room temperature for 15 minutes. Zinc chloride (0.5 M in THF, 1 mL, 0.5 mmol) and Sodium cyanoborohydride (63 mg, 1 mmol) were then added and the mixture was stirred at room temperature for 18 hours. The mixture was diluted with EtOAc and washed with H₂O, brine, dried over MgSO₄, and concentrated to afford 511 mg of desired product (100%). MS (ES⁺): 511.4, (M+H)⁺. ¹HNMR (CDCl₃) δ 7.50–7.41 (m, 3H), 7.39–7.22 (m, 7H), 6.92 (d, 2H), 4.47 (q, 2H), 4.20 (t, 2H), 3.86 (s, 2H), 3.80 (s, 3H) 3.37 (t, 2H), 1.44 (t, 3H) ppm.

Part C: Preparation of ethyl 1-(4-methoxyphenyl)-6-[2'-({methyl[(methylamino)carbonyl]amino}methyl)-1,1'-biphenyl-4-yl]-7-oxo-4,5,6,7-tetrahydro-1H-pyrazolo[3,4-c]pyridine-3-carboxylate Ethyl 1-(4-methoxyphenyl)-6-{2'-[(methylamino)methyl]-1,1'-biphenyl-4-yl}-7-oxo-4,5,6,7-tetrahydro-1H-pyrazolo[3,4-c]pyridine-3-carboxylate (150 mg, 0.29 mmol) and methyl isocyanate (165 mg, 2.9 mmol) were added together in 10 mL of CH₂Cl₂ and the mixture was stirred at room temperature for 18 hours. The mixture was diluted with CH₂Cl₂ and washed with water, brine, dried over MgSO$_4$, concentrated, and chromatographed with 1:1 EtOAc:hexane and then 5% MeOH:CHCl$_3$ to afford 173 mg of desired product (100%). MS (ES$^+$): 568.4, (M+H)$^+$. $^1$HNMR (CDCl$_3$) δ 7.49 (d, 2H), 7.40–7.19 (m, 8H), 6.93 (d, 2H), 4.51–4.44 (m, 4H), 4.19 (t, 2H), 3.82 (s, 3H), 3.36 (t, 2H), 2.77 (d, 3H), 2.72 (s, 3H), 1.44 (t, 3H) ppm.

Part D: Preparation of 1-(4-methoxyphenyl)-6-[2'-({methyl[(methylamino)carbonyl]amino}methyl)-1,1'-biphenyl-4-yl]-7-oxo-4,5,6,7-tetrahydro-1H-pyrazolo[3,4-c]pyridine-3-carboxamide Ethyl 1-(4-methoxyphenyl)-6-[2'-({methyl[(methylamino)carbonyl]amino}methyl)-1,1'-biphenyl-4-yl]-7-oxo-4,5,6,7-tetrahydro-1H-pyrazolo[3,4-c]pyridine-3-carboxylate (130 mg, 0.2 mmol) was dissolved in 7.5 mL of 1,4-dioxane. Concentrated NH$_4$OH (7.5 mL) was added. The reaction vessel was sealed and the mixture was stirred at room temperature for 4 days. The mixture was stripped and chromatographed using 3% MeOH:CHCl$_3$ with 0.1% concentrated NH$_4$OH. The fractions containing desired product were combined and purified by reverse phase HPLC (C18 reverse phase column, eluted with a H$_2$O/CH$_3$CN gradient with 0.05% TFA) to give 71 mg of desired product (48% yield). MS (ES$^+$): 539.4, (M+H)$^+$. $^1$HNMR (CDCl$_3$) δ 7.48 (t, 2H), 7.39–7.19 (m, 9H), 6.95 (m, 3H), 6.00 (bs, 1H), 4.47 (s, 2H), 4.189 (t, 2H), 3.83 (s, 3H), 3.41 (t, 2H), 2.77 (s, 3H), 2.72 (s, 3H) ppm.

EXAMPLE 32

1-(4-methoxyphenyl)-6-(2'-{[methyl(methylsulfonyl)amino]-methyl}-1,1'-biphenyl-4-yl)-7-oxo-4,5,6,7-tetrahydro-1H-pyrazolo[3,4-c]pyridine-3-carboxamide trifluoroacetic acid salt

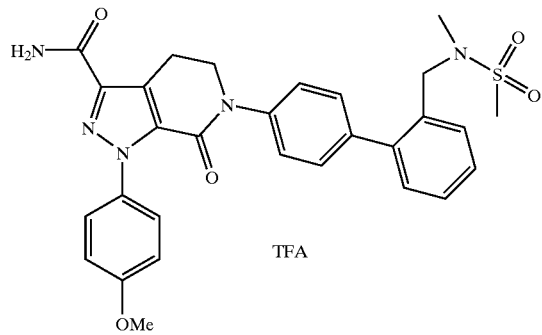

This compound was prepared using similar procedures described in Example 31. MS (ES$^+$): 560.3, (M+H)$^+$. $^1$HNMR (CDCl$_3$) δ 7.61 (d, 1H), 7.49–7.03 (m, 11H), 6.96 (d, 2H), 4.29 (s, 2H), 4.18 (t, 2H), 3.83 (s, 3H), 3.40 (t, 2H), 2.77 (d, 3H), 2.60 (s, 3H) ppm.

EXAMPLE 33

N-[4-(2-{[Acetyl(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide, bis(trifluoroacetic acid)salt

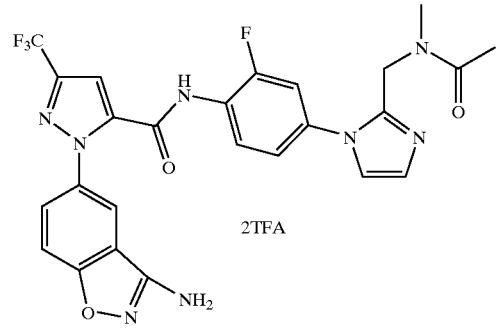

Part A: Preparation benzyl 1H-imidazol-2-ylmethyl(methyl)-carbamate

2-Imidazolecarboxyaldehyde (5.0 g, 52.0 mmol) was suspended in 200 mL of methanol. Methylamine (20 mL of 33% solution in methanol) was added. After stirred for 15 minutes, NaBH$_4$ (3.95 g, 0.10 mol) was added portion-wise. The reaction mixture was then heated at 50° C. for 2 h under N$_2$. The solvent was removed. The solid was washed with CH$_2$Cl$_2$ and filtered. The CH$_2$Cl$_2$ solution was dried over MgSO$_4$, concentrated, and dried under vacuum to give the methylamine as a yellow oil. This oil was dissolved in a 1:1 solution of CH$_2$Cl$_2$ and THF. To it was added Et$_3$N (7.94 mL, 57.0 mmol) and benzylchloroformate (7.4 mL, 52.0 mmol). The mixture was stirred at room temperature under N$_2$ for 1 h. The solvent was removed and the residue was partitioned between EtOAc and H$_2$O. The EtOAc layer was washed with brine, dried over MgSO$_4$, and concentrated. The mixture was refluxed with 15 mL of TFA for 30 minutes to convert most of the bis-acylated byproduct to the desired product. The TFA was removed. It was dissolved in EtOAc and washed with Saturated aqueous NaHCO$_3$ and brine. The mixture was dried over MgSO$_4$, concentrated, and chromatographed with 1:1 EtOAc/hexane to give 6.56 g off-white solid (51.4% yield). MS (AP$^+$): 246.3, (M+H)$^+$. $^1$HNMR (CDCl$_3$): δ 7.35 (s, 6H), 6.90 (s, 1H), 5.14 (s, 2H), 4.48 (s, 2H), 3.00 (s, 3H).

Part B: Preparation of benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate Benzyl 1H-imidazol-2-ylmethyl(methyl)carbamate from Part A (3.60 g, 14.69 mmol), 2-fluoro-4-iodoaniline (3.50 g, 14.69 mmol), K$_2$CO$_3$ (2.23 g, 16.16 mmol), 1,10-phenanthroline (0.13 g, 0.73 mmol), CuI (0.14 g, 0.73 mmol), and DMSO (60 mL) were added together and degassed. The mixture was then heated at 130° C. under N$_2$ for 12 h. The mixture was cooled, 14% aqueous NH$_4$OH (200 mL) and EtOAc (200 mL) were added. The mixture was filtered through Celite® and washed with EtOAc. The filtrate was extracted with EtOAc, the combined organic solution was washed with brine, and dried over MgSO$_4$. It was concentrated and purified by chromatography on silica gel with 50–100% hexane in EtOAc to give 3.46 g of the desired product (67%). MS (ES$^+$): 355.2, (M+H)$^+$.

Part C: Preparation of benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate 1-(3-cyano-4-fluorophenyl)-3-(trifluoromethyl)-1H-pyrazole-5-carboxylic acid prepared as described in WO 98/57951 (1.00 g, 3.34 mmol) was stirred in 20 mL of $CH_2Cl_2$ at room temperature under $N_2$. Oxalyl chloride (0.43 mL, 5.01 mmol) was added, followed by a few drops of DMF. The mixture was stirred for 2 h. The solvent was removed and the resulting solid was dried under vacuum. This solid was then dissolved in 50 mL of $CH_2Cl_2$, benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate from Part B (1.32 g, 3.34 mmol) was added, followed by DMAP (1.02 g, 8.35 mmol). The mixture was stirred at room temperature under $N_2$ for 12 h. It was diluted with $CH_2Cl_2$ washed with water and brine, dried over $MgSO_4$, and concentrated. The crude product was purified by chromatography on silica gel with 50–100% hexane in EtOAc to give 1.10 g of the desired product (52%). MS (ES$^+$): 636.1, (M+H)$^+$.

Part D: Preparation of N-[4-(2-{[(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide Acetohydroxamic acid (0.40 g, 5.34 mmol) was dissolved in 10 mL of DMF. $K_2CO_3$ (0.98 g, 7.12 mmol) was added, followed by 1 mL of water. The mixture was stirred at room temperature under $N_2$ for 30 minutes and a solution of benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate from Part C (1.13 g, 1.78 mmol) in 10 mL of DMF was added. The resulting mixture was stirred at room temperature under $N_2$ for 12 h. Water was added to the reaction mixture. The precipitate formed was filtered and dried. MS (ES$^+$): 647.1, (M–H)$^-$.

The above solid was refluxed with 20 mL of TFA under $N_2$ for 30 minute. The TFA was removed. The residue was purified by reverse phase HPLC (C18 reverse phase column, eluted with a $H_2O/CH_3CN$ gradient with 0.05% TFA) to give 0.61 g of the desired product as the TFA salt. MS (ES$^+$): 515.0, (M+H)$^+$.

Part E: Preparation of N-[4-(2-{[acetyl(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide N-[4-(2-{[(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide from Part D was acylated with acetyl chloride in $CH_2Cl_2$ and triethylamine. The product was purified by reverse phase HPLC (C18 reverse phase column, eluted with a $H_2O/CH_3CN$ gradient with 0.05% TFA) to give the title compounds as the bis-TFA salt. MS (ES$^+$): 557.4 (M+H)$^+$. $^1$HNMR (CD$_3$OD) δ 8.07 (t, 1H), 7.95 (d, 1H), 7.69–7.38 (m, 7H), 4.68 (s, 2H), 2.98 (s, 3H), 2.00 (s, 3H) ppm.

EXAMPLE 34

N-[4-(2-{[Acetyl(methyl)amino]methyl}-1H-imidazol-1-yl)-2-fluorophenyl]-1-(3-amino-1,2-benzisoxazol-5-yl)-3-(methylsulfonyl)-1H-pyrazole-5-carboxamide, bis(trifluoroacetic acid)salt

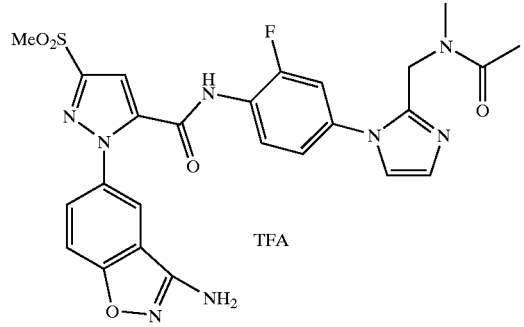

Part A: Preparation of 5-{(2Z)-2-[chloro (methylsulfonyl)methylene]hydrazino}-2-fluorobenzonitrile
This compound was prepared using the same methods as described in Part A of Example 22. MS (ES$^-$): 274.1, 276.1, (M–H)$^-$.
Part B: Preparation of ethyl 1-(3-cyano-4-fluorophenyl)-3-(methylsulfonyl)-4,5-dihydro-1H-pyrazole-5-carboxylate
The product from Part A (3.8 g, 13.8 mmol) was suspended in toluene (50 mL) and cooled in an ice bath. Triethylamine (3.14 g, 31.1 mmol) was added, followed by ethyl acrylate (4.14 g, 41.4 mmol) dropwise. The mixture was stirred at room temperature under $N_2$ for 24 h. The mixture was refluxed for 4 h. The mixture was diluted with EtOAc and washed with $H_2O$ and brine. The organic solution was then dried over $MgSO_4$ and concentrated. The crude product was purified by flash chromatography using EtOAc:Hexane (2:3 to 1:1) to afford 3.79 g of the desired product. MS (ES$^-$): 374.2, (M+Cl)$^-$.
Part C: Preparation of ethyl 1-(3-cyano-4-fluorophenyl)-3-(methylsulfonyl)-1H-pyrazole-5-carboxylate
The product from Part B (3.79 g, 11.2 mmol) was dissolved in THF (50 mL) and cooled in an ice bath. N-Chlorosuccinimide (1.64 g, 12.3 mmol) was added and the mixture was stirred at room temperature under $N_2$ for 1 h. The mixture was diluted with $Et_2O$ and washed with $H_2O$ and brine. The organic solution was then dried over $MgSO_4$ and concentrated in vacuo to afford 3.92 g of the desired product. MS (ES$^+$): 360.2, (M+Na)$^+$.
Part D: Preparation of 1-(3-cyano-4-fluorophenyl)-3-(methylsulfonyl)-1H-pyrazole-5-carboxylic acid
The product from Part C (3.79 g, 11.2 mmol) was dissolved in THF (30 mL) and then diluted with MeOH (10 mL) and $H_2O$ (10 mL). Lithium hyroxide monohyrate (706 mg, 16.8 mmol) was added and the mixture was stirred at room temperature for 2 h. The mixture was quenched with 1.0 N hyrochloric acid (17 mL) and extracted with EtOAc (3×100 mL). The organic layers were combined and washed with $H_2O$ and brine. The organic solution was then dried over $MgSO_4$ and concentrated in vacuo to afford 3.35 g of the desired product. MS (ES$^-$): 308.2, (M–H)$^-$.
Part E: Preparation of benzyl {1-[4-({[1-(3-cyano-4-fluorophenyl)-3-(methylsulfonyl)-1H-pyrazol-5-yl]carbonyl}amino)phenyl]-1H-imidazol-2-yl}methyl(methyl)carbamate
The product from Part D and the product from Part A of Example 33 were coupled using the same methods described in Part C of Example 33 (78% yield). MS (ES$^+$): 526.5 (M+H)$^+$.

Part F: Preparation of 1-(3-amino-1,2-benzisoxazol-5-yl)-N-(4-{2-[(methylamino)methyl]-1H-imidazol-1-yl}phenyl)-3-(methylsulfonyl)-1H-pyrazole-5-carboxamide This compound was prepared using the same methods as described in Part D of Example 33 using the product from Part E as the starting material (yield 12%). MS (ES$^+$): 659.5 (M+H)$^+$, MS (ES$^+$): 525.4 (M+H)$^+$.

Part G: Preparation of N-[4-(2-{[Acetyl(methyl)amino]methyl}-1H-imidazol-1-yl)-2-fluorophenyl]-1-(3-amino-1,2-benzisoxazol-5-yl)-3-(methylsulfonyl)-1H-pyrazole-5-carboxamide, bis(trifluoroacetic acid)salt This compound was prepared using the same methods described in Example 7 using the product from Part F as the starting material (yield 18%). MS (ES$^+$): 567.4 (M+H)$^+$.
$^1$HNMR (CD$_3$OD) δ 8.06 (t, 1H), 7.97 (d, 1H), 7.69–7.37 (m, 7H), 4.67 (s, 2H), 3.29 (s, 3H), 2.98 (s, 3H), 2.00 (s, 3H) ppm.

EXAMPLE 35

N-[4-(2-{[methylsulfonylamino]methyl}-1H-imidazol-i-yl)-2-fluorophenyl]-1-(4-methoxyphenyl)-3-(methylsulfonyl)-1H-pyrazole-5-carboxamide, trifluoroacetic acid salt

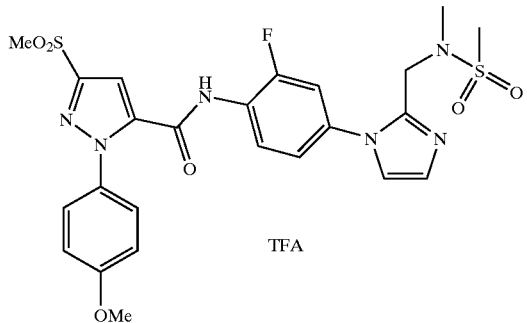

Part A: Preparation of ethyl 1-(4-methoxyphenyl)-3-(methylsulfonyl)-4,5-dihydro-1H-pyrazole-5-carboxylate The product from Part A of example 22 (5 g, 19.1 mmol) was suspended in toluene (50 mL) and cooled in an ice bath. Triethylamine (2.9 g, 28.7 mmol) was added, followed by ethyl acrylate (4.14 mL, 38.2 mmol) dropwise. The mixture was stirred at room temperature under N$_2$ for 24 h. The mixture was diluted with EtOAc and washed with H$_2$O and brine. The organic solution was then dried over MgSO$_4$ and concentrated. The crude product was purified by flash chromatography using EtOAc:Hexane (1:2 to 2:3) to afford 5.21 g of the desired product. MS (ES$^-$): 325.3, (M–H)$^-$.

Part B: Preparation of ethyl 1-(4-methoxyphenyl)-3-(methylsulfonyl)-1H-pyrazole-5-carboxylate The product from Part A (5.2 g, 16 mmol) was dissolved in THF (50 mL) and cooled in a 0 C ice bath. N-Chlorosuccinimide (2.34 g, 17.5 mmol) was added and the mixture was stirred at room temperature under N$_2$ for 1 h. The mixture was diluted with Et$_2$O and washed with H$_2$O and brine. The organic solution was then dried over MgSO$_4$ and concentrated in vacuo to afford 5.32 g of the desired product. MS (ES$^+$): 325.3, (M+H)$^+$.

Part C: Preparation of 1-(4-methoxyphenyl)-3-(methylsulfonyl)-1H-pyrazole-5-carboxylic acid The product from Part B (5.3 g, 16.0 mmol) was dissolved in THF (30 mL) and then diluted with MeOH (10 mL) and H$_2$O (10 mL). Lithium hyroxide monohyrate (1.03 g, 24.5 mmol) was added and the mixture was stirred at room temperature for 3 h. The mixture was quenched with 1.000 N hyrochloric acid (25 mL) and extracted with EtOAc (3×100 mL). The organic layers were combined and washed with H$_2$O and brine. The organic solution was then dried over MgSO$_4$ and concentrated in vacuo to afford 4.76 g of the desired product. MS (ES$^-$): 295.2, (M–H)$^-$.

Part D: Preparation of benzyl {1-[4-({[1-(4-methoxyphenyl)-3-(methylsulfonyl)-1H-pyrazol-5-yl]carbonyl}amino)phenyl]-1H-imidazol-2-yl}methyl(methyl)carbamate The product from Part C (696 mg, 2.35 mmol) was suspended in CH$_2$Cl$_2$ (10 mL). Oxalyl chloride (0.41 mL, 4.7 mmol) was added followed by a drop of DMF and the mixture was stirred at room temperature for 3 h. The mixture was concentrated in vacuo. The residue was dissolved in CH$_2$Cl$_2$ (10 mL) and treated with 4-dimethylaminopyridine (1.73 g, 14.1 mmol) and Part B of Example 33 (1.05 g, 4.23 mmol) and the mixture stirred at room temperature for 18 h. The mixture was diluted with CH$_2$Cl$_2$ and washed with H$_2$O and brine. The organic solution was then dried over MgSO$_4$ and concentrated in vacuo. The residue was purified by flash chromatography using EtOAc:EtOH:Hexane (10:2:10 to 10:3:10) to elute 949 mg of the desired product. MS (ES$^+$): 633.5, (M+H)$^+$.

Part E: Preparation of 1-(4-methoxyphenyl)-N-(4-{2-[(methylamino)methyl]-1H-imidazol-1-yl}phenyl)-3-(methylsulfonyl)-1H-pyrazole-5-carboxamide The product from Part D (940 mg, 1.49 mmol) was dissolved in EtOH (30 mL) and trifluoroacetic acid (0.5 mL) added. 20% Palladium Hydroxide was then added under N$_2$ and the mixture shaken under 55 psi H$_2$ for 18 h. The mixture was filtered through Celite® under a N$_2$ purge and was concentrated in vacuo. The residue was purified by reverse phase HPLC (C18 reverse phase column, eluted with a H$_2$O/CH$_3$CN gradient with 0.05% TFA) to give 76 mg of the desired product as the TFA salt. MS (ES$^+$): 499.4, (M+H)$^+$.

Part F: Preparation of N-[4-(2-{[methylsulfonylamino]methyl}-1H-imidazol-1-yl)-2-fluorophenyl]-1-(4-methoxyphenyl)-3-(methylsulfonyl)-1H-pyrazole-5-carboxamide, trifluoroacetic acid salt AN1315-29 (100 mg, 0.16 mmol) was dissolved in CH$_2$Cl$_2$ (5 mL). Triethylamine (160 mg, 1.6 mmol) was added, followed by methanesulfonyl chloride (37 mg, 0.32 mmol). The mixture was stirred at room temperature under N$_2$ for 18 h. The mixture was diluted with CH$_2$Cl$_2$ and washed with H$_2$O and brine and dried over MgSO$_4$ and the solvent was removed in vacuo. The crude product was purified by reverse phase HPLC (C18 reverse phase column, eluted with a H$_2$O/CH$_3$CN gradient with 0.05% TFA) to give 62 mg of the final product as the TFA salt. MS (ES$^+$): 577.3 (M+H)$^+$, $^1$HNMR (DMSO-d$_6$) δ 10.82 (s, 1H), 7.85 (t, 1H), 7.76 (bs, 1H), 7.70–7.42 (m, 6H), 7.07 (d, 2H), 4.52 (s, 2H), 3.82 (s, 3H), 3.38 (s, 3H), 2.93 (s, 3H), 2.73 (s, 3H) ppm.

EXAMPLE 36

N-[4-(2-{[methylsulfonylamino]methyl}-1H-imidazol-1-yl)-2-fluorophenyl]-1-(4-methoxyphenyl)-3-(aminocarbonyl)-1H-pyrazole-5-carboxamide, trifluoroacetic acid salt

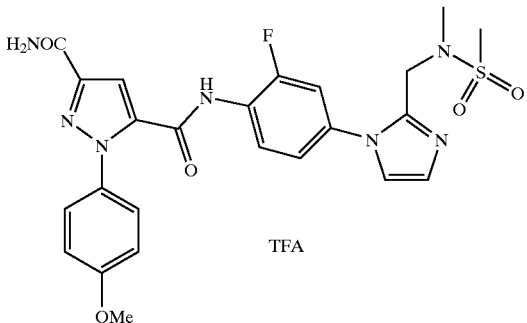

TFA

Part A: Preparation of methyl 4-(2-furyl)-2,4-dioxobutanoate

Sodium Methoxide (25% in methanol, 11.9 g, 55 mmol) was treated dropwise (over 30 minutes) with a solution of 2-acetylfuran (5.01 mL, 50 mmol) and dimethyloxalate (5.14 mL, 50 mmol) in THF. The resulting suspension was stirred at room temperature for 18 h. The solid was filtered, washed with ether, dissolved in EtOAc/$H_2O$, and acidified to pH 2–3 with 10% HCl. The mixture was then extracted with more EtOAc. The organic layers was combined, dried over $MgSO_4$, filtered, concentrated, and dried under vacuum to afford desired product (10.2 g, 95%).

Part B: Preparation of methyl 5-(2-furyl)-1-(4-methoxyphenyl)-1H-pyrazole-3-carboxylate The product from Part A (1.96 g, 10 mmol), p-anisidine (1.23 g 10 mmol), and p-Toluenesulfonic acid (1.90 g, 10 mmol) were dissolved in methanol and the resulting solution refluxed for 3 h. The solvents were removed in vacuo and the residue filtered through a silica gel bed with ethyl acetate. The solvents were removed in vacuo and the residue crystallized from ether/hexane to afford desired product (>85% yield).

Part C: Preparation of 3-(methoxycarbonyl)-1-(4-methoxyphenyl)-1H-pyrazole-5-carboxylic acid The compound from Part B (1.0 g, 3.4 mmol) was dissolved in acetonitrile (10 mL) and cooled in a 0 C ice bath. $NaH_2PO_4$ (2.32 g, 16.8 mmol) in $H_2O$ (4 mL) was then added followed by $NaClO_2$ in $H_2O$ (12 mL) and the mixture stirred at room temperature for 2 h. The mixture was quenched with sat. sodium bisulfite and extracted with EtOAc (2×50 mL). The organic extracts were combined, dried over $MgSO_4$ and concentrated in vacuo. The residue was triturated with $Et_2O$ and the solid collected and dried under vacuum to afford 190 mg of desired product. $^1$HNMR (DMSO-d6) δ 7.40 (m, 3H), 7.05 (d, 2H), 3.83 (s, 3H), 3.82 (s, 3H).

Part D: Preparation of methyl 5-({[4-(2-{[[(benzyloxy)carbonyl](methyl)amino]methyl}-1H-imidazol-1-yl)phenyl]amino}carbonyl)-1-(4-methoxyphenyl)-1H-pyrazole-3-carboxylate The product from Part C and the product from Part B of Example 33 were coupled using the same methods as described in Part D of Example 35. MS (ES$^+$): 613.5 (M+H)$^+$.

Part E: Preparation of methyl 1-(4-methoxyphenyl)-5-{[(4-(2-[(methylamino)methyl]-1H-imidazol-1-yl}phenyl)amino]carbonyl)-1H-pyrazole-3-carboxylate The product from Part D was hydrogenated using the same methods as described in Part E of Example 35. MS (ES$^+$): 479.5 (M+H)$^+$.

Part F: Preparation of methyl 1-(4-methoxyphenyl)-5-({[4-(2-{[methyl(methylsulfonyl)amino]methyl}-1H-imidazol-1-yl)phenyl]amino}carbonyl)-1H-pyrazole-3-carboxylate Product from Part E (100 mg, 0.17 mmol) was dissolved in $CH_2Cl_2$ (10 mL). Triethylamine (170 mg, 1.7 mmol) was added, followed by methanesulfonyl chloride (39 mg, 0.34 mmol). The mixture was stirred at room temperature under $N_2$ for 18 h. The mixture was diluted with $CH_2Cl_2$ and washed with $H_2O$ and brine and the solvent was removed in vacuo. The crude product was purified by flash chromatography using MeOH:$CHCl_3$ (2%) to elute 58 mg of the final product. MS (ES$^+$): 557.4 (M+H)$^+$.

Part G: Preparation of N-[4-(2-{[methylsulfonylamino]methyl}-1H-imidazol-1-yl)-2-fluorophenyl]-1-(4-methoxyphenyl)-3-(aminocarbonyl)-1H-pyrazole-5-carboxamide, trifluoroacetic acid salt (DPC-AN3174-17)

This compound was prepared using the same methods as described in Part G of Example 6. MS (ES$^+$): 542.5 (M+H)$^+$, $^1$HNMR (CDCl$_3$) δ 8.07 (t, 1H), 7.69–7.68 (m, 1H), 7.58–7.37 (m, 6H), 6.99 (d, 2H), 4.56 (s, 2H), 3.81 (s, 3H), 2.85 (s, 3H), 2.80 (s, 3H) ppm.

EXAMPLE 37

5-{[5-(2-{[acetyl(methyl)amino]methyl}-1H-imidazol-1-yl)-2,3-dihydro-1H-indol-1-yl]carbonyl}-1-(3-amino-1,2-benzisoxazol-5-yl)-1H-pyrazole-3-carboxamide trifluoroacetate

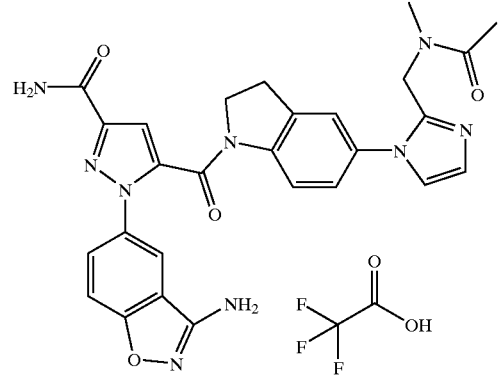

Part A. Preparation of lithium 1-tert-butoxy-4-(2-furyl)-1,4-dioxo-2-buten-2-olate A 1-L flame-dried flask was charged with 130 mL of LiHMDS (130 mmol; 1.0 M in THF) and 410 mL of ethyl ether. The resulting solution was cooled to −78° C. and 2-acetylfuran (14 g, 12 m mmol) was added in one portion. After 5 min, di-tert-butyl oxalate was added dropwise over 1 h as a solution in 100 mL of ether. The resulting mixture was warmed to 23° C. over a period of 3 h and was maintained at room temperature for 20 h. The mixture was then filtered, and the resulting beige precipitate was washed with 100 mL of ether. The filter cake was dried in a vacuum oven for 1 h to afford lithium 1-tert-butoxy-4-(2-furyl)-1,4-dioxo-2-buten-2-olate (25 g, 83%) as a cream colored solid. $^1$HNMR (DMSO-d$_6$) δ 7.75 (t, 1H), 6.96 (m, 1H), 6.56 (m, 1H), 3.34 (s, 2H), 1.46 (s, 9H).

Part B. Preparation of tert-butyl 1-(3-cyano-4-fluorophenyl)-5-(2-furyl)-1H-pyrazole-3-carboxylate To the product (13 g, 54 mmol) from Part A was added 2-fluoro-5-hydrazinobenzonitrile hydrochloride (10 g, 54 mmol) and 250 mL of glacial acetic acid. The resulting orange mixture was maintained at room temperature for 20 h and then concentrated to dryness. The resulting residue was taken up in 30% chloroform in hexanes and filtered to afford tert-butyl 1-(3-cyano-4-fluorophenyl)-5-(2-furyl)-1H-pyrazole-3-carboxylate (18 g, 95%) as a light brown solid. LC/MS (ESI$^+$): 354.2 (M+H)$^+$. $^1$HNMR (CDCl$_3$) δ 7.64–7.78 (m, 3H), 7.42 (s, 1H), 7.05 (s, 1H), 6.45 (s, 1H), 6.30 (s, 1H), 1.61 (s, 9H).

Part C. Preparation of 1-(3-cyano-4-fluorophenyl)-5-(2-furyl)-1H-pyrazole-3-carboxylate To the product from Part B (10 g, 28 mmol) was added 125 mL of dichloromethane and 125 mL of trifluoroacetic acid. The resulting black solution was maintained at room temperature under nitrogen for 2 h and was then concentrated to dryness. The resulting solid was dried in a vacuum oven for 4 h to afford 1-(3-cyano-4-fluorophenyl)-5-(2-furyl)-1H-pyrazole-3-carboxylate (8.4 g, 99%) as a brown solid. LC/MS (ES$^+$): 298.1 (M+H)$^+$. $^1$HNMR (CD$_3$OD) δ 7.90 (m, 1H) 7.75 (m, 1H), 7.51 (s, 1H), 7.46 (t, 1H), 6.98 (s, 1H), 6.47 (m, 1H), 6.35 (m, 1H).

Part D. Preparation of 1-(3-cyano-4-fluorophenyl)-5-(2-furyl)-1H-pyrazole-3-carboxamide To the product (4.1 g, 14 mmol) from Part C was added 23 mL of dichloromethane and 2.0 M oxalyl chloride (10 mL, 21 mmol) in dichloromethane. After dropwise addition of N,N-dimethylformamide (10 drops) to the brown mixture, the mixture became clear over a period of 30 min. When no more gas evolved, the brown solution was concentrated. The resulting residue was redissolved in 100 mL of dichloromethane and 0.5 M ammonia in dioxane (110 mL, 55 mmol) was added via cannula. After 30 min, the resulting suspension was concentrated and poured into water. The aqueous layer was washed with ethyl acetate (3×70 mL), and the combined organic layers were washed with saturated aqueous sodium chloride, dried over sodium sulfate, filtered and concentrated. The resulting residue was dissolved in 10 mL of dichloromethane and 50 mL of hexanes were added. The resulting suspension was filtered, and the filter cake was washed with 50 mL of hexanes. The filter cake was dried in a vacuum oven to afford 1-(3-cyano-4-fluorophenyl)-5-(2-furyl)-1H-pyrazole-3-carboxamide (2.5 g, 62%) as a brown solid. LC/MS (ESI$^+$): 297.1 (M+H)$^+$. $^1$HNMR (CDCl$_3$) δ 7.75 (m, 1H), 7.64 (m, 1H), 7.42 (s, 1H), 7.33 (t, 1H), 7.16 (s, 1H), 6.79 (br s, 1H), 6.46 (m, 1H), 6.36 (m, 1H), 5.50 (br s, 1H).

Part E. Preparation of 3-(aminocarbonyl)-1-(3-cyano-4-fluorophenyl)-1H-pyrazole-5-carboxylic acid To the product (2.5 g, 8.3 mmol) from Part D was added water (51 mL), 5% aqueous sodium dihydrogenphosphate (35 mL), and tert-butanol (51 mL). The resulting mixture was warmed to 60° C., and potassium permanganate (8.0 g, 51 mmol) was added over a period of 10 min. After an additional 10 min, the resulting purple slurry was cooled to 0° C., and the reaction was quenched by the addition of 200 mL of saturated aqueous sodium bisulfite. The resulting mixture was filtered, washed with 300 mL of water, and the filtrate was acidified with concentrated hydrogen chloride. The aqueous layer was extracted with ethyl acetate (6×100 mL) and the combined organic layers were washed with saturated aqueous sodium chloride, dried over sodium sulfate, and filtered. Concentration afforded 3-(aminocarbonyl)-1-(3-cyano-4-fluorophenyl)-1H-pyrazole-5-carboxylic acid (1.6 g, 71%) as a yellow solid. LC/MS (ESI$^+$): 275.1 (M+H)$^+$. $^1$HNMR (CD$_3$OD) δ 8.03 (m, 1H), 7.90 (m, 1H), 7.5 (t, 1H), 7.44 (s, 1H).

Part F. Preparation of N-(1H-imidazol-2-ylmethyl)-N-methylamine

To a flame-dried 500-mL flask was added methanol (200 mL), 2-imidazolecarboxaldehyde (5.0 g, 52 mmol), and 8.0 M methylamine (20 mL, 160 mmol). The reaction was stirred for 45 min, at which time, all carboxaldehyde dissolved. Sodium borohydride (4.0 g, 104 mmol) was added in four equal portions over a period of 2 min, resulting in a vigorous exotherm and a reaction temperature of 45° C. The reaction temperature was increased to 50° C. and maintained at this temperature for 2 h. The reaction was then cooled, concentrated, and dichloromethane (200 mL) was added. The mixture was concentrated, and dichloromethane (200 mL) was again added. The resulting mixture was filtered, the filter cake was washed with dichloromethane (2□50 mL), and the filtrate was concentrated. The resulting viscous yellow oil solidified upon standing to afford N-(1H-imidazol-2-ylmethyl)-N-methylamine as a yellow solid (5.5 g, 95%) which was used without further purification. $^1$HNMR (CDCl$_3$) δ 6.99 (s, 2H), 3.87 (s, 2H), 2.46 (s, 3H)

Part G. Preparation of tert-butyl 5-iodo-1-indolinecarboxylate

Sodium cyanoborohydride (1.54 g, 25 mmol) was added in one portion to a stirring orange solution of 5-iodo-1H-indole (6.0 g, 25 mmol) in glacial acetic acid (350 mL). After 24 h, the orange solution was concentrated. To the resulting red residue was added tetrahydrofuran (250 mL) and di-tert-butyl dicarbonate (16 g, 74 mmol) followed by saturated aqueous sodium bicarbonate (20 mL). The resulting mixture was stirred for 24 h and was then poured into aqueous 1N hydrogen chloride (70 mL). The layers were separated, and the aqueous layer was washed with ethyl acetate (3×50 mL). The combined organic layers were washed with saturated aqueous sodium chloride (50 mL), dried over sodium sulfate and concentrated. The resulting residue was dissolved in THF (100 mL), and benzyl amine (6 mL, 55 mol) was added. The resulting solution was stirred for 1.5 h and was then poured into 1N hydrogen chloride (70 mL). The layers were separated and the aqueous layer was washed with ethyl acetate (3×50 mL). The combined organic layers were washed with saturated aqueous sodium chloride (50 mL), dried over sodium sulfate, and concentrated. Purification of the resulting residue by flash column chromatography (5% ethyl acetate in hexanes) afforded tert-butyl 5-iodo-1-indolinecarboxylate (3.9 g, 45%) as a white solid. LC/MS (ESI$^+$): 346.1 (M+H)$^+$.

Part H. Preparation of tert-butyl 5-{2-[(methylamino)methyl]-1H-imidazol-1-yl}-1-indolinecarboxylate A flame-dried flask was charged with methyl sulfoxide (46 mL), anhydrous potassium carbonate (1.28 g, 9.3 mmol), and N-(1H-imidazol-2-ylmethyl)-N-methylamine (520 mg, 4.6 mmol). The product (0.80 g, 2.3 mmol) from Part G was added, and the mixture was degassed by alternating treatment with vacuum and nitrogen (×3). Copper(I) iodide (440 mg, 2.3 mmol) was added, and the reaction mixture was again degassed. The green mixture was maintained at 130° C. for 2.5 h and was then cooled to room temperature. The mixture was poured into saturated aqueous ammonium hydroxide (100 mL) and the aqueous layer was washed with ethyl acetate (150 mL). The organic layer was washed with saturated aqueous ammonium hydroxide (50 mL), water (2×50 mL), and saturated aqueous sodium chloride (50 mL). The organic layer was then dried over sodium sulfate, concentrated, and the resulting green-black residue was purified by radial chromatography (5% methanol in dichloromethane) to afford tert-butyl 5-{2-[(methylamino)methyl]-1H-imidazol-1-yl}-1-indolinecarboxylate (0.40 g, 52%) as a brown oil. LC/MS (ESI$^+$): 329.3 (M+H)$^+$.

Part I. Preparation of tert-butyl 5-(2-{[acetyl(methyl)-amino]methyl}-1H-imidazol-1-yl)indolinecarboxylate To the product from Part H (0.20 g, 0.61 mmol) was added dichloromethane (6 mL) and triethylamine (0.25 mL, 0.67 mmol). Acetyl chloride (0.048 mL, 0.67 mmol) was added in one portion, and the resulting yellow solution was stirred for 2 h. The reaction was then poured into aqueous 1N hydrogen chloride (10 mL). The layers were separated, and the organic layer was washed with saturated aqueous sodium bicarbonate (10 mL) and saturated aqueous sodium chloride (10 mL), dried over sodium sulfate, and concentrated to give tert-butyl 5-(2-{[acetyl(methyl)-amino]methyl}-1H-imidazol-1-yl)indolinecarboxylate (230 mg, 100%) as a brown oil). LC/MS (ESI+): 371.3 (M+H)+.

Part J. Preparation of N-{[1-(2,3-dihydro-1H-indol-5-yl)-1H-imidazol-2-yl]methyl}-N-methylacetamide To the product from Part I (0.23 mg, 0.62 mmol) was added 50% triflouoroacetic acid in dichloromethane (6 mL). The resulting brown solution was stirred for 2 h and was then concentrated. The resulting residue was poured into saturated aqueous sodium bicarbonate (30 mL), and the aqueous layer was washed with ethyl acetate (4□50 mL). The combined organic layers were washed with saturated aqueous sodium chloride (50 mL), dried over sodium sulfate, and concentrated to give N-{[1-(2,3-dihydro-1H-indol-5-yl)-1H-imidazol-2-yl]methyl}-N-methylacetamide (96 mg, 57%) as a brown oil. LC/MS (ESI+): 271.3 (M+H)+.

Part K. Preparation of 5-{[5-(2-{[acetyl(methyl)-amino]methyl}-1H-imidazol-1-yl)-2,3-dihydro-1H-indol-1-yl]carbonyl}-1-(3-amino-1,2-benzisoxazol-5-yl)-1H-pyrazole-3-carboxamide trifluoroacetate To the product from Part J (96 mg, 0.36 mmol) was added 3-(aminocarbonyl)-1-(3-cyano-4-fluorophenyl)-1H-pyrazole-5-carboxylic acid (107 mg, 0.39 mmol), followed by pyridine (3.2 mL) and N,N-dimethylformamide (0.80 mL). 1,3-Diisopropylcarbodiimide (0.067 mL, 0.43 mmol) was added, and the resulting solution was stirred for 14 h. The red mixture was then poured into 1N aqueous hydrogen chloride (70 mL) and washed with ethyl acetate (3□50 mL). The combined organic layers were washed with saturated aqueous sodium chloride, dried over sodium sulfate, filtered, and concentrated. The resulting residue was purified by preparative LC/MS (C18 reverse phase, eluted with 0.05% TFA in CH$_3$CN/H$_2$O) to give partially pure 5-{[5-(2-{[acetyl(methyl)amino]methyl}-1H-imidazol-1-yl)-2,3-dihydro-1H-indol-1-yl]carbonyl}-1-(3-cyano-4-fluorophenyl)-1H-pyrazole-3-carboxamide (187 mg) as a red residue (LC/MS (ESI+): 527.3 (M+H)+). This material was dissolved in N,N-dimethylformamide (2.8 mL), and potassium carbonate (250 mg, 1.8 mmol) and water (0.70 mL) were added. Acetohydroxamic acid (30 mg, 0.39 mmol) was added in one portion, and the resulting yellow mixture was warmed to 50° C. After 2 h, the reaction was cooled to room temperature and poured into ethyl acetate (40 mL). The organic layer was washed with water (2×50 mL), saturated aqueous sodium chloride, dried over sodium sulfate, filtered, and concentrated. The resulting brown oily residue was purified by radial chromatography (5% methanol in dichloromethane) and preparative LC/MS (C18 reverse phase, eluted with 0.05% TFA in CH$_3$CN/H$_2$O) to give 5-{[5-(2-{[acetyl(methyl)-amino]methyl}-1H-imidazol-1-yl)-2,3-dihydro-1H-indol-1-yl]carbonyl}-1-(3-amino-1,2-benzisoxazol-5-yl)-1H-pyrazole-3-carboxamide trifluoroacetate (13 mg, 5.6%). LC/MS (ESI+): 540.3 (M+H)+. $^1$HNMR (CD$_3$OD) δ 8.29 (br s, 1H), 7.95 (br s, 1H), 7.77 (br s, 1H), 7.65 (d, 2H), 7.30–7.51 (br m, 3H), 7.32 (s, 1H), 4.69 (br s, 2H), 4.21 (t, 2H), 3.22 (br s, 2H), 3.00 (s, 3H), 2.07 (s, 3H).

EXAMPLE 38

1-(3-amino-1,2-benzisoxazol-5-yl)-5-{[5-(2-{[methyl(methylsulfonyl)amino]methyl}-1H-imidazol-1-yl)-2,3-dihydro-1H-indol-1-yl]carbonyl}-1H-pyrazole-3-carboxamide trifluoroacetate

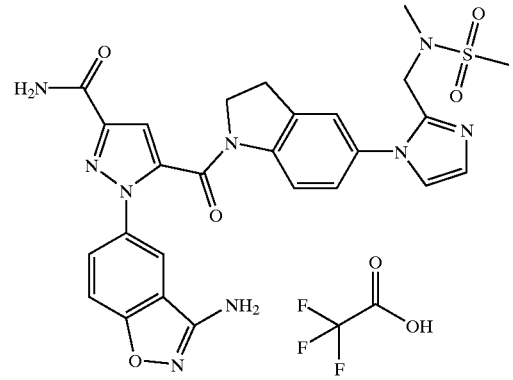

Part A. Preparation of tert-butyl 5-(2-{[methyl(methylsulfonyl)amino]methyl}-1H-imidazol-1-yl)-1-indolinecarboxylate To tert-butyl 5-{2-[(methylamino)methyl]-1H-imidazol-1-yl}-1-indolinecarboxylate (0.20 g, 0.61 mmol; from Part H of Example 37) was added dichloromethane (6 mL) and triethylamine (0.25 mL, 0.67 mmol). Methanesulfonyl chloride (0.052, 0.67 mmol) was added in one portion, and the resulting yellow solution was stirred for 2 h. The reaction was then poured into aqueous 1N hydrogen chloride (10 mL). The layers were separated, and the organic layer was washed with saturated aqueous sodium bicarbonate (10 mL) and saturated aqueous sodium chloride (10 mL), dried over sodium sulfate, and concentrated to give tert-butyl 5-(2-{[methyl(methylsulfonyl)amino]methyl}-1H-imidazol-1-yl)-1-indolinecarboxylate (250 mg, 100%) as a brown oil). LC/MS (ESI+): 407.3 (M+H)+.

Part B. Preparation of N-[{1-(2,3-dihydro-1H-indol-5-yl)-1H-imidazol-2-yl]methyl}-N-methyl methanesulfonamide To the product from Part A (0.25 mg, 0.61 mmol) was added 50% triflouoroacetic acid in dichloromethane (6 mL). The resulting brown solution was stirred for 2 h and was then concentrated. The resulting residue was poured into saturated aqueous sodium bicarbonate (30 mL), and the aqueous layer was washed with ethyl acetate (4×50 mL). The combined organic layers were washed with saturated aqueous sodium chloride (50 mL), dried over sodium sulfate, and concentrated to give N-[{1-(2,3-dihydro-1H-indol-5-yl)-1H-imidazol-2-yl]methyl}-N-methyl methanesulfonamide (150 mg, 78%) as a brown oil. LC/MS (ESI+): 307.3 (M+H)+.

Part C. Preparation of 1-(3-amino-1,2-benzisoxazol-5-yl)-5-{[5-(2-{[methyl(methylsulfonyl)amino]methyl}-1H-imidazol-1-yl)-2,3-dihydro-1H-indol-1-yl]carbonyl}-1H-pyrazole-3-carboxamide trifluoroacetate To the product from Part B (150 mg, 0.48 mmol) was added 3-(aminocarbonyl)-1-(3-cyano-4-fluorophenyl)-1H-pyrazole-5-carboxylic acid (140 mg, 0.52 mmol) followed by pyridine (3.2 mL) and N,N-dimethylformamide (0.80 mL). 1,3-Diisopropylcarbodiimide (0.090 mL, 0.57 mmol) was added, and the resulting solution was stirred for 14 h. The red mixture was then poured into water (70 mL) and washed with EtOAc (3□50 mL). The combined organic layers were washed with aqueous 1N hydrogen chloride (50 mL), and the combined aqueous layers were made basic with saturated aqueous sodium hydrogencarbonate. The aqueous layers were then concentrated. The resulting residue was treated with dichloromethane (3×50 mL) and filtered to afford crude 1-(3-cyano-4-fluorophenyl)-5-{[5-(2-{[methyl (methylsulfonyl)-amino]methyl}-1H-imidazol-1-yl)-2,3-dihydro-1H-indol-1-yl]carbonyl}-1H-pyrazole-3-carboxamide (180 mg) as a pink residue (LC/MS (ESI+): 563.3 (M+H)+). This material was dissolved in N,N-dimethylformamide (2.5 mL), and potassium carbonate (221 mg, 1.6 mmol) and water (0.64 mL) were added. Acetohydroxamic acid (26 mg, 0.35 mmol) was added in one portion, and the resulting yellow mixture was warmed to 50° C. After 2 h, the reaction was cooled to room temperature and half of the reaction mixture was purified by preparative LC/MS (C18 reverse phase, eluted with 0.05% TFA in CH$_3$CN/H$_2$O) to give 1-(3-amino-1,2-benzisoxazol-5-yl)-5-{[5-(2-{[methyl(methylsulfonyl)amino]methyl}-1H-imidazol-1-yl)-2,3-dihydro-1H-indol-1-yl]carbonyl}-1H-pyrazole-3-carboxamide trifluoroacetate (27 mg, 25%). LC/MS (ESI+): 576.3 (M+H)+. $^1$HNMR (CD$_3$OD) δ 8.25 (br s, 1H), 7.95 (br s, 1H), 7.60–7.72 (m, 3H), 7.30–7.51 (br m, 3H), 7.32 (s, 1H), 4.56 (br s, 2H), 4.21 (t, 2H), 3.22 (br s, 2H), 3.89 (s, 3H), 2.81 (s, 3H).

EXAMPLE 39

2-(3-Aminobenzo[d]isoxazol-5-yl)-5-trifluoromethyl-2H-pyrazole-3-carboxylic acid (1-{2-[(acetylmethylamino)-methyl]phenyl}-piperidin-4-yl)amide

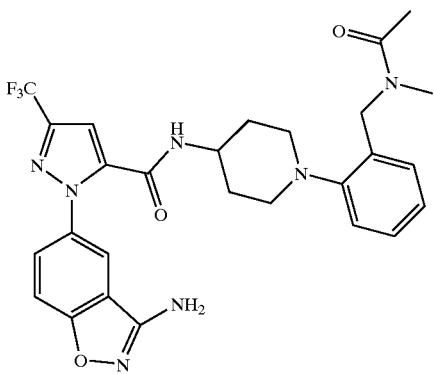

Part A. Preparation of [1-(2-Formylphenyl)-piperidin-4-yl]carbamic acid t-butyl ester A mixture of 4-t-butoxycarbonylaminopiperidine (1 g, 4.99 mmol) 2-fluorobenzaldehyde (0.8 mL, 7.59 mmol) and potassium carbonate (1.38 g, 10 mmol) in DMSO (10 mL) was stirred overnight in an 85–90° C. oil bath under N$_2$. After cooling to room temperature, the reaction mixture was poured into 10 volumes of water, and the product extracted 3× with ethyl acetate. The combined extracts were washed with water and brine, dried over anhydrous Na$_2$SO$_4$, filtered, and evaporated. Purification by flash silica gel chromatography (hexane/ethyl acetate 3:1) provided the product as an off-white solid (0.74 g, 49%). MS (ESI+) m/z 305.1 (M+H)+, 205.1 (M+H-BOC)+. $^1$HNMR (CDCl$_3$) δ 10.24 (1H, s), 7.80 (1H, d, J=12 Hz), 7.52 (1H, t, J=12 Hz), 7.16 (1H, m), 3.65 (1H, m), 3.30 (1H, m), 3.04 (1H, m), 2.09 (2H, m), 1.80–1.48 (4H, m), 1.44 (9H, s).

Part B. Preparation of [1-(2-Methylaminomethylphenyl) piperidin-4-yl]-carbamic acid t-butyl ester A mixture of the product from Part A (0.5 g, 1.64 mmol) and methylamine hydrochloride (0.22 g, 3.28 mmol) in 1,2-dichloroethane (10 mL) was stirred 5–10 min followed by addition of sodium triacetoxyborohydride (0.52 g, 2.46 mmol). The resulting mixture was stirred for 72 h under N$_2$. The reaction was quenched by addition of 2N NaOH and extracted into Et$_2$O. Purification of the resulting residue by rotary prep TLC (silica gel, CH$_2$Cl$_2$-MeOH-NH$_4$OH 95:5:0.5-90:10:1) to remove some alcohol by-product provided the desired N-methylamine product (0.31 g, 58%). MS (ESI+) m/z 320.4 (M+H)+.

Part C. Preparation of (1-{2-[(Acetylmethylamino)methyl] phenyl}piperidin-4-yl)carbamic acid t-butyl ester A solution of the product from Part B (0.1 g, 0.313 mmol) in CH$_2$Cl$_2$ (1 mL) was cooled in an ice bath under N$_2$ with stirring while acetyl chloride (25–30 µl) was added. The whole was stirred overnight at room temperature. The mixture was diluted with additional CH$_2$Cl$_2$ and washed with 5% citric acid solution, saturated NaHCO$_3$ and brine, then dried over anhydrous Na$_2$SO$_4$, filtered, and evaporated. Purification on 5 g silica gel cartridge eluted with hexane-ethyl acetate (1:1) provided the acetamide as a white foam. This was used without purification in Part D below.

Part D. Preparation of N-[2-(4-Aminopiperidin-1-yl) benzyl]-N-methylacetamide, bis(trifluoroacetate)

The product from Part C was dissolved in a mixture of CH$_2$Cl$_2$ (4 mL) and TFA (1 mL) and stirred overnight at room temperature. Mixture was evaporated in vacuo and the residue triturated with Et$_2$O to provide the amine salt as a sticky solid (32 mg, 39% over two steps). MS (ESI+) m/z 262.3 (M+H)+.

Part E. Preparation of 2-(3-Cyano-4-fluorophenyl)-5-trifluoromethyl-2H-pyrazole-3-carboxylic acid (1-{2-[(acetylmethylamino)-methyl]phenyl}piperidin-4-yl)amide A mixture of 2-(3-cyano-4-fluorophenyl)-5-trifluoromethyl-2H-pyrazole-3-carboxylic acid (25 mg, 0.084 mmol), the product from Part D (32 mg, 0.065 mmol), Castro's reagent (43 mg, 0.098 mmol) and N-methylmorpholine (50 µmL, 0.455 mmol) in DMF (1 mL) was stirred overnight at room temperature under N$_2$. The resulting mixture was poured into water and extracted 3× into ethyl acetate. The combined extracts were washed with water, saturated NaHCO$_3$, and brine, then dried over anh. Na$_2$SO$_4$, filtered and evaporated to provide the product (41 mg, 90% crude yield) that was used without purification in Part F below.

Part F. Preparation of 2-(3-Aminobenzo[d]isoxazol-5-yl)-5-trifluoromethyl-2H-pyrazole-3-carboxylic acid (1-{2-[(acetyl-methyl-amino)methyl]phenyl}piperidin-4-yl)amide A mixture of acetoxyhydroxamic acid (38 mg, 0.5 mmol) and K$_2$CO$_3$ (95 mg., 0.7 mmol) in DMF (0.5 mL) was treated with 5 drops of water and stirred for 30 min at room temperature. To the resulting mixture was added a solution of the compound from Part E (41 mg, 0.07 mmol) in DMF (0.5–1.0 mL) and the whole was stirred at room temperature under N$_2$ for 72 h. The mixture was diluted with water and extracted 3× with ethyl acetate. The combined extracts were washed with water and brine, dried over anhydrous Na$_2$CO$_3$, filtered and evaporated. Purification by C18 reverse phase HPLC provided the target compound (20 mg, 43%). MS (ESI+) m/z 556.5 (M+H)+. $^1$HNMR (DMSO-d$_6$) δ 8.05 (1H, s), 7.59 (2H, m), 7.48 (1H, m), 7.32–7.00 (4H, m), 4.55 (2H, m), 2.95 (2H, m), 2.77 (3H, s), 2.70 (2H, m), 2.10 (3H, s), 1.85 (2H, m), 1.63 (2H, m).

EXAMPLE 40

2-(3-Aminobenzo[d]isoxazol-5-yl)-5-trifluoromethyl-2H-pyrazole-3-carboxylic acid (1-{2-[(methanesulfonylmethyl-amino)methyl]phenyl}piperidin-4-yl)amide

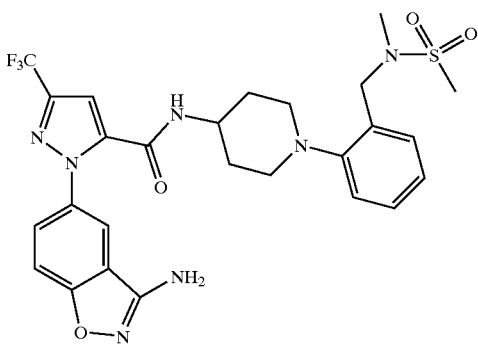

This compound was prepared in analogous fashion to Example 39 above by substituting methanesulfonyl chloride for the acetyl chloride in Part C of Example 39. MS (ESI+) m/z 592.5 (M+H)+. 1HNMR (CD3CN) δ 7.83 (1H, s), 7.60 (1H, d, J=8 Hz), 7.49 (1H, d, J=8 Hz), 7.44–7.26 (5H, m), 7.17 (2H, m), 4.42 (2H, s), 4.03 (1H, m), 3.22 (4H, m), 2.95 (3H, s), 2.69 (3H, s), 2.06 (2H, m), 1.92 (2H, m).

EXAMPLE 41

2-(4-Methoxyphenyl)-5-trifluoromethyl-2H-pyrazole-3-carboxylic acid [1-(2-{[(2-hydroxyethyl)methylamino]-methyl}phenyl)piperidin-4-yl]amide

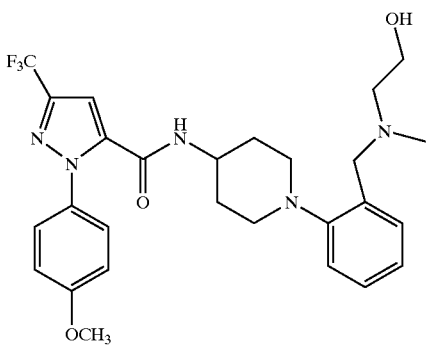

Part A. Preparation of 2-[2-(4-Aminopiperidin-1-yl)benzyl]methyl-aminoethanol

The compound from Part A of Example 39 (0.20 g, 0.66 mmol) was charged to a 25 mL reaction vessel, and sodium triacetoxyborohydride (0.21 g, 1.0 mmol), and 5 mL of 1,2-dichloroethane were added. While stirring under N2 2-aminoethanol (0.04 g, 0.77 mmol) was added. The reaction mixture was stirred for an additional 14 h at room temperature. The mixture was concentrated in vacuo. The crude product was redissolved in 5 mL dioxane and treated with 5 mL of 4N solution of HCl in dioxane. The reaction was stirred under N2 for 2 h and then filtered. The resulting white solid was dried under high vacuum for 14 h to provide the desired product (0.210 g, 95% yield). 1HNMR (DMSO-d6) δ 8.59–8.42 (bs, 2H), 7.59–7.56 (d, 1H), 7.50–7.47 (t, 1H), 7.35–7.32 (d, 1H), 7.29–7.21 (t, 1H), 4.66–4.34 (m, 4H), 3.77 (bs, 1H), 3.24–3.15 (m, 2H), 2.44 (m, 4H), 2.00 (m, 4H); MS (ESI+) m/z 264.3 (M+H)+.

Part B. Preparation of 2-(4-Methoxyphenyl)-5-trifluoromethyl-2H-pyrazole-3-carboxylic acid [1-(2-{[(2-hydroxyethyl)methylamino]-methyl}phenyl)piperidin-4-yl]amide A small reaction vessel was charged with the compound of from Part A (0.053 g, 0.20 mmol), 2-(4-Methoxyphenyl)-5-trifluoromethyl-2H-pyrazole-3-carboxylic acid (0.037 g, 0.13 mmol), 4-methylmorpholine (36 ul, 0.33 mmol) and DMF (3 mL). While stirring under N2, Castro's Reagent (0.089 g, 0.20 mmol) was added and the reaction mixture was allowed to stir at room temperature for 48 h. The reaction was concentrated and purified by prep LC/MS to obtain the target compound. (0.016 g, 23% yield). 1HNMR (DMSO-d6) δ 8.72 (d, 1H), 7.50–7.41 (m, 7H), 7.34–7.23 (t, 1H), 7.08–7.03 (d, 2H), 4.49–4.45 (m, 2H), 3.81 (s, 3H), 3.77 (m, 2H), 3.14 (m, 2H), 2.98 (m, 2H), 2.80 (bs, 4H), 1.89 (m, 2H), 1.71 (m, 2H); MS (ESI+) m/z 532.5, (M+H)+.

EXAMPLES 42 AND 43

N-(2-{4-[3-cyano-1-(4-methoxyphenyl)-7-oxo-1,4,5,7-tetrahydro-6H-pyrazolo[3,4-c]pyridin-6-yl]-1-piperidinyl}benzyl)-N-methylacetamide, trifluoroacetic acid salt and 6-[1-(2-{[acetyl(methyl)amino]methyl}phenyl)-4-piperidinyl]-1-(4-methoxyphenyl)-7-oxo-4,5,6,7-tetrahydro-1N-pyrazolo[3,4-c]pyridine-3-carboxamide, trifluoroacetic acid salt

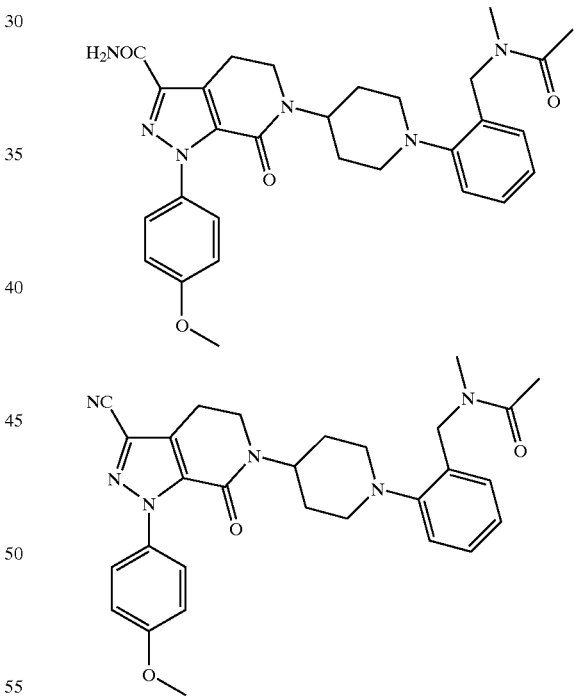

Part A. Preparation of 1'-benzyl-1,4'-bipiperidin-2-one

1-Benzyl-4-aminopiperidine (16.97 g, 89.0 mmol) was stirred in EtOAc (400 mL). Aqueous K2CO3 (20% w/w, 13.56 g in 54 mL H2O, 1.1 eq) was added, followed by dropwise addition of 5-bromovaleryl chloride (19.53 g, 1.1 eq) during a half-hour period at room temperature under N2. The resulting mixture was stirred at room temperature for 1 h. LC-MS showed completion of the reaction. The layers were separated. The aqueous layer was extracted with EtOAc (2×). The combined organic layers were washed with H₂O (2x), brine (2x), dried over MgSO₄, filtered, and concentrated to dryness to yield off-white solids (17.57 g). This compound was stirred in THF (200 mL) at 0° C. under N₂. KO-tBu (7.26 g, 1.3 eq) was added portion wise over 10-min period. The mixture was stirred at 0° C. for 0.5 h. LC-MS showed completion of the reaction. Sat'd NH₄Cl was added, and the mixture was extracted with EtOAc (2x). The organic layer was washed with H₂O (2x), brine (2x), dried over MgSO₄, filtered, and concentrated to dryness to yield the desire product, 1'-benzyl-1,4'-bipiperidin-2-one, as off-white floatable solids (13.38 g, yield: 99%). ¹HNMR (CDCl₃) δ 7.30 (m, 5H), 4.54 (m, 1H), 3.50 (s, 2H), 3.19 (m, 2H), 2.92 (m, 2H), 2.39 (t, J=5.8 Hz, 2H), 2.11 (td, J=11.7, 2.5 Hz, 2H), 1.76 (m, 4H), 1.58 (m, 2H).

Part B. Preparation of 1'-benzyl-3,3-dichloro-1,4'-bipiperidin-2-one

The product from Part A (9.94 g, 36.54 mmol) and PCl₅ (22.80 g, 109.6 mmol) were refluxed in CHCl₃ (100 mL) for 3 h under N₂. LC-MS showed completion of the reaction. The mixture was cooled in an ice bath, and H₂O was added. The product was extracted with CHCl₃, washed with sat'd NaHCO₃, H₂O, brine, dried over MgSO₄, filtered, and concentrated to dryness. The desired product (10.56 g, 85%) was essentially pure 1'-benzyl-3,3-dichloro-1,4'-bipiperidin-2-one, and used directly in the next step. LC/MS (ESI⁺), 341.4 (M+H). ¹HNMR (CDCl₃) δ 7.32 (m, 5H), 4.46 (m, 1H), 3.55 (s, 2H), 3.31 (t, J=6.0 Hz, 2H), 2.99 (m, 2H), 2.76 (m, 2H), 2.16–1.64 (m, 8H).

Part C. Preparation of 1-(1-benzyl-4-piperidinyl)-3-(4-morpholinyl)-5,6-dihydro-2(1H)-pyridinone The product from Part B (10.56 g, 31.06 mmol) was refluxed in morpholine (50 mL) overnight under N₂. LC-MS showed completion of the reaction. Solvent was evaporated. The residue was diluted with EtOAc, washed with H₂O (2x), brine (2x), dried over MgSO₄, and concentrated to yield light tan foam of 1-(1-benzyl-4-piperidinyl)-3-(4-morpholinyl)-5,6-dihydro-2(1H)-pyridinone (9.85 g, 86%). LC/MS (ESI⁺), 356.2 (M+H).

Part D. Preparation of ethyl 6-(1-benzyl-4-piperidinyl)-1-(4-methoxyphenyl)-7-oxo-4,5,6,7-tetrahydro-1H-pyrazolo[3,4-c]pyridine-3-carboxylate The product from Part C (9.75 g, 27.46 mmol) and ethyl 2-chloro[(4-methoxyphenyl)hydrazono]ethanoate (7.03 g, 27.46 mmol) were stirred in toluene (100 mL) room temperature under N₂. Et₃N (7.65 mL, 55.11 mmol) was added. The mixture was stirred overnight at 85° C. It was cooled to room temperature and concentrated. The residue was dissolved in CH₂Cl₂ (100 mL). 4N HCl (35 mL) was added dropwise to the stirred solution. The resulting mixture was stirred at room temperature for 7 h. LC-MS showed completion of the reaction. After cooling, the reaction was basified with 1N NaOH, and extracted with CH₂Cl₂ (3x). The organic layers were washed with H₂O (2x), brine (2x), dried over MgSO₄, filtered, and concentrated to dryness. The residue was purified by Flash column chromatography (silica gel, CH₂Cl₂, then EtOAc, then EtOAc:MeOH:Et₃N= 10:1:0.5) to produce the desired compounds of ethyl 6-(1-benzyl-4-piperidinyl)-1-(4-methoxyphenyl)-7-oxo-4,5,6,7-tetrahydro-1H-pyrazolo[3,4-c]pyridine-3-carboxylate as light-tan solids (5.5 g, yield: 41%). ¹HNMR (CDCl₃) δ 7.45 (d, J=8.7 Hz, 2H), 7.30 (m, 5H), 6.94 (d, J=8.9 Hz, 2H), 4.54 (m, 1H), 4.43 (q, J=7.2 Hz, 2H), 3.83 (s, 3H), 3.58 (t, J=6.7 Hz, 2H), 3.49 (s, 3H), 3.11 (t, J=6.8 Hz, 2H), 2.95 (m, 2H), 2.76 (m, 2H), 2.16–1.64 (m, 8H), 1.40 (t, J=7.2 Hz, 3H). LC/MS (ESI⁺), 489.6 (M+H).

Part E. Preparation of ethyl 1-(4-methoxyphenyl)-7-oxo-6-(4-piperidinyl)-4,5,6,7-tetrahydro-1H-pyrazolo[3,4-c]pyridine-3-carboxylate CH₃COOH (0.1 mL) was added to a mixture of the product from Part D (600 mg, 1.2 mmol), 10% Pd-C (600 mg), and MeOH (10 mL) under an H₂ atmosphere (balloon). The suspension was stirred at room temperature for 3 h and then filtered through a bed of Celite®. The filter cake was washed with methanol and concentrated in vacuo to give ethyl 1-(4-methoxyphenyl)-7-oxo-6-(4-piperidinyl)-4,5,6,7-tetrahydro-1H-pyrazolo[3,4-c]pyridine-3-carboxylate (460 mg, 94%). LC/MS (ESI⁺) 399.6 (M+H). ¹HNMR (CDCl₃) δ 7.42, 6.92 (AA'BB', J=8.9 Hz, 4H), 4.50 (m, 1H), 4.40 (q, J=6.9 Hz, 2H), 3.80 (s, 3H), 3.55 (t, J=6.6 Hz, 2H), 3.08 (m, 4H), 2.03 (m, 2H), 1.71 (m, 2H), 1.60 (m, 2H), 1.35 (t, J=6.9 Hz, 3H).

Part F. Preparation of 1-(4-methoxyphenyl)-7-oxo-6-(4-piperidinyl)-4,5,6,7-tetrahydro-1H-pyrazolo[3,4-c]pyridine-3-carboxamide The product from Part E (400 mg, 1.5 mmol) was heated in 8% NH₃ (g) solution in ethylene glycol (10 mL) in a sealed tube at 85° C. for 2 h. The reaction mixture was then purified by Reverse phase HPLC (20–98% CH₃CN/H₂O 30 min) to obtain the desire product 1-(4-methoxyphenyl)-7-oxo-6-(4-piperidinyl)-4,5,6,7-tetrahydro-1H-pyrazolo[3,4-c]pyridine-3-carboxamide (350 mg, 80%). LC/MS (ESI⁺) 370.6 (M+H). ¹HNMR (CDCl₃) □ 7.20 (AA'BB', J=9.0 Hz, 4H), 4.76 (m, 1H), 4.40 (m, 1H), 3.81 (s, 3H), 3.52 (m, 4H), 3.08 (m, 2H), 2.92 (m, 2H), 2.12 (m, 2H), 1.81 (m, 2H); ¹³C NMR (CDCl₃) δ 164.2, 160.0, 157.4, 133.2, 132.3, 126.7, 125.2, 113.7, 55.6, 47.1, 43.8, 41.8, 26.0, 21.2.

Part G. Preparation of 6-[1-(2-formylphenyl)-4-piperidinyl]-1-(4-methoxyphenyl)-7-oxo-4,5,6,7-tetrahydro-1H-pyrazolo[3,4-c]pyridine-3-carboxamide The product from Part F (350 mg, 0.95 mmol), o-fluorobenzaldehyde (0.15 mL, 1.4 mmol), and K₂CO₃ (262 mg, 1.9 mmol) were heated in anhydrous DMSO (2 mL) at 85° C. for 16 h. The reaction mixture was then partitioned between water and ethyl acetate. The organic layer was washed by sat'd NaHCO₃, brine, dried (Na₂SO₄), filtered, and concentrated in vacuo. The residue was purified by FCC (80% ethyl acetate/Hexane) to produce 6-[1-(2-formylphenyl)-4-piperidinyl]-1-(4-methoxyphenyl)-7-oxo-4,5,6,7-tetrahydro-1H-pyrazolo[3,4-c]pyridine-3-carboxamide (160 mg, 78% based on recovered starting material). LC/MS (ESI⁺) 474.4 (M+H). ¹HNMR (CDCl₃) δ 10.3 (s, 1H), 7.78 (dd, J=7.7, 1.4 Hz, 1H), 7.48 (dd, J=8.0, 1.9 Hz, 1H), 7.44, 6.97 (AA'BB', J=9.0 Hz, 4H), 7.08 (t, J=8.0 Hz, 2H), 4.71 (m, 1H), 3.84 (s, 3H), 3.63 (t, J=6.8 Hz, 2H), 3.35 (m, 2H), 3.21 (t, J=6.8 Hz, 2H), 2.96 (td, J=10.8, 1.8 Hz, 2H), 2.02 (m, 2H), 1.78 (m, 2H). ¹³C NMR (CDCl₃) δ 191.2, 163.8, 159.9, 157.4, 155.4, 140.5, 135.0, 133.8, 132.6, 130.3, 128.5, 127.0, 126.9, 124.9, 122.6, 119.2, 113.7, 55.5, 53.9, 49.5, 42.0, 29.6, 21.2.

Part H. Preparation of 1-(4-methoxyphenyl)-6-(1-{2-[(methylamino)methyl]phenyl}-4-piperidinyl)-7-oxo-4,5,6,7-tetrahydro-1H-pyrazolo[3,4-c]pyridine-3-carboxamide A solution of the product from Part G (100 mg, 0.2 mmol), methyl amine (0.1 mL), NaBH(OAc)₃ (100 mg, 1.2 mmol), and HOAc (0.02 mL) were stirred in anhydrous MeOH/CH₂Cl₂ (3:1, 4 mL) at room temperature for 2 h under N₂. The mixture was then concentrated in vacuo. The residue was purified by prep LC-MS (5–98% CH₃CN/H₂O in a 10-min run) to obtain the product 1-(4-methoxyphenyl)-6-(1-{2-[(methylamino)methyl]phenyl}-4-piperidinyl)-7-oxo-4,5,6,7-tetrahydro-1H-pyrazolo[3,4-c]pyridine-3-carboxamide (85 mg, 86%). LC/MS (ESI⁺) 489.6 (M+H).

¹HNMR δ 9.83 (br, s, NH₂, 2H), 7.45 (dd, J=7.9, 2.2 Hz, 2H), 7.39 (dd, J=7.7, 1.4 Hz, 1H), 7.32 (dd, J 7.7.4, 1.8 Hz, 1H), 7.19 (t, J=7.4 Hz, 2H), 6.99 (d, J=7.9, 2.2 Hz, 2H), 4.67 (m, 1H), 4.21 (br s, 2H), 4.64 (m, 1H), 3.80 (s, 3H), 3.62 (t, J=3.6 Hz, 2H), 3.12 (m, 4H), 2.86 (t, J=11.1 Hz, 2H), 2.58 (m, 3H), 2.03 (m, 2H), 1.77 (m, 2H).

Part I. Preparations of 6-[1-(2-{[acetyl(methyl)amino]methyl}phenyl)-4-piperidinyl]-1-(4-methoxyphenyl)-7-oxo-4,5,6,7-tetrahydro-1H-pyrazolo[3,4-c]pyridine-3-carboxamide and, N-(2-{4-[3-cyano-1-(4-methoxyphenyl)-7-oxo-1,4,5,7-tetrahydro-6H-pyrazolo[3,4-c]pyridin-6-yl]-1-piperidinyl}benzyl)-N-methylacetamide A solution of the product from Part H (17 mg, 0.02 mmol), acetyl chloride (0.05 mL), and pyridine (0.05 mL) in anhydrous CH₂Cl₂ (1 mL) was stirred at room temperature for 2 h under N₂. Two products (1:5) were detected by LC/MS (ESI⁺): 531.6 (M+H) and 513.6 (M+H) for the amide (I-1) and the nitrile (I-2), respectively. The mixture was then concentrated in vacuo, and the residue was purified by prep LC-MS (5–98% CH₃CN/H₂O in a 10-min run) to obtain the product I-1, 6-[1-(2-{[acetyl(methyl)amino]methyl}phenyl)-4-piperidinyl]-1-(4-methoxyphenyl)-7-oxo-4,5,6,7-tetrahydro-1H-pyrazolo[3,4-c]pyridine-3-carboxamide (1.6 mg, 10%). LC/MS (ESI⁺), 531.6 (M+H). And product I-2, N-(2-{4-[3-cyano-1-(4-methoxyphenyl)-7-oxo-1,4,5,7-tetrahydro-6H-pyrazolo[3,4-c]pyridin-6-yl]-1-piperidinyl}benzyl)-N-methylacetamide (8 mg, 50%). LC/MS (ESI⁺), 513.6 (M+H).

EXAMPLE 44

1-(4-methoxyphenyl)-6-[1-(2-{[methyl(methylsulfonyl)amino]methyl}phenyl)-4-piperidinyl]-7-oxo-4,5,6,7-tetrahydro-1H-pyrazolo[3,4-c]pyridine-3-carboxamide, trifluoroacetic acid salt

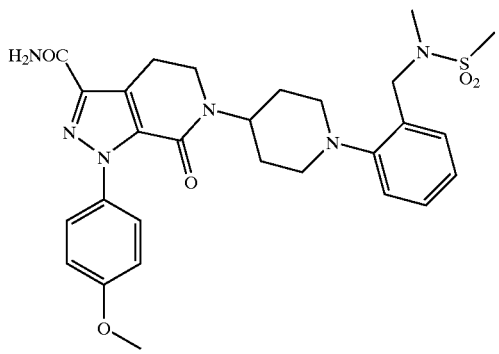

A solution of the product from Part G of Example 42 (12 mg, 0.01 mmol), methanesulfonyl chloride (0.02 mL), and pyridine (0.02 mL) in anhydrous CH₂Cl₂ (1 mL) was stirred at room temperature for 2 h under N₂. The mixture was then concentrated. The residue was purified by prep LC/MS (5–98% acetonitrile/H₂O in a 10-min run) to give 1-(4-methoxyphenyl)-6-[1-(2-{[methyl(methylsulfonyl)amino]methyl}phenyl)-4-piperidinyl]-7-oxo-4,5,6,7-tetrahydro-1H-pyrazolo[3,4-c]pyridine-3-carboxamide (10 mg, 85%). LC/MS (ESI⁺) 567.6 (M+H); ¹HNMR ((CD₃)₂CO) δ 7.50 (dd, J=6.6, 1.8 Hz, 2H), 7.27 (m, 2H), 7.12 (m, 2H), 6.99 (dd, J=7.0, 2.0 Hz, 2H), 4.82 (m, 2H), 4.58 (m, 1H), 3.80 (s, 3H), 3.78 (t, J=5.6 Hz, 2H), 3.20–2.80 (m, 9H), 1.71 (m, 2H).

EXAMPLE 45

6-(4-{2-[(dimethylnitroryl)methyl]-1H-imidazol-1-yl}phenyl)-1-(4-methoxyphenyl)-3-(trifluoromethyl)-1,4,5,6-tetrahydro-7H-pyrazolo[3,4-c]pyridin-7-one

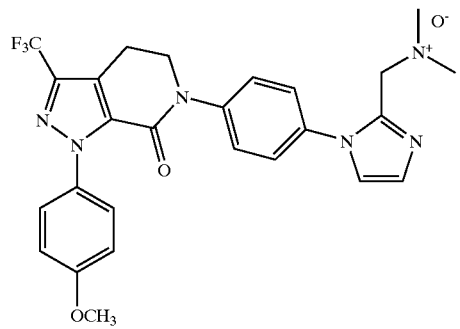

Part A: Preparation of 1-[4-methoxyphenyl]-3-trifluoromethyl-6-[4-iodophenyl]-1,4,5,6-tetrahydropyrazolo-[3,4-c]-pyridin-7-one 3-Hydroxy-1-(4-iodophenyl)-4-(trifluoroacetyl)-5,6-dihydro-2(1H)-pyridinone (10.0 g, 24.3 mmol) and 4-methoxyhydrazine hydrochloride (4.28 g, 24.3 mmol) were dissolved in HCl (1N, 200 mL) and methanol (400 mL) and refluxed overnight. The reaction was cooled to room temperature, quenched with water, extracted with ethyl acetate, washed with brine, and dried (Na₂SO₄). Purification by silica gel chromatography using 0%–100% ethyl acetate/hexane gradient as eluent afforded the desired trimethylpyrazole intermediate 9.28 g (74%); ¹HNMR (CDCl₃) δ 7.69 (d, j=9.4 Hz, 2H), 7.45 (d, j=8.8 Hz, 2H), 7.06 (d, j=8.8 Hz, 2H), 6.92 (d, j=9.2 Hz, 2H), 4.11 (t, j=6.8 Hz, 2H), 3.81 (s, 3H), 3.15 (t, j=6.5 Hz, 2H) ppm; Mass Spec (M+H)⁺ 514.3.

Part B: Preparation of 6-(4-{2-[(dimethylamino)methyl]-1H-imidazol-1-yl}phenyl)-1-(4-methoxyphenyl)-3-(trifluoromethyl)-1,4,5,6-tetrahydro-7H-pyrazolo[3,4-c]pyridin-7-one The product from part A (500 mg, 0.97 mmol), 2-dimethylaminomethyl imidazole (146 mg, 1.17 mmol), cesium carbonate (348 mg, 1.07 mmol), and copper iodide (37 mg, 0.20 mmol) were charged to a flask and flushed with N₂. DMSO (6 mL) was syringed into the flask and the reaction was heated to 120° C. overnight. The reaction was cooled to room temperature, quenched with water and ammonium hydroxide to pH 12, extracted with ethylacetate, washed with brine, and dried (Na₂SO₄). Purification by silica gel chromatography using 0%–100% ethyl acetate/hexane followed by 0%–10% methanol/ethyl acetate as eluents, prep. HPLC and freeze-dying afforded the desired product 268.6 mg (54%). ¹HNMR (CDCl₃) δ 7.53–7.43 (m, 4H), 7.37 (d, j=8.5 Hz, 3H), 7.27 (s, 1H), 6.94 (d, j=9.2 Hz, 2H), 4.49 (s, 2H), 4.24 (t, j=6.6 Hz, 2H), 3.82 (s, 3H), 3.22 (t, j=6.4 Hz, 2H), 2.83 (s, 6H) ppm; Mass Spec (M+H)⁺ 511.5.

Part C: Preparation of 6-(4-{2-[(dimethylnitroryl)methyl]-1H-imidazol-1-yl}phenyl)-1-(4-methoxyphenyl)-3-(trifluoromethyl)-1,4,5,6-tetrahydro-7H-pyrazolo[3,4-c]pyridin-7-one The product from part B (100 mg) was dissolved in dichloromethane (20 mL). To this solution was added 3 equivalents of MCPBA and the reaction mixture was stirred at room temperature overnight. The reaction mixture was quenched with saturated sodium bicarbonate and the organic layer separated and concentrated. The title compound was obtained as colorless crystals by purification va reverse phase HPLC and lyophylization. ESI mass spectrum 527 (M+H); HNMR (CDCl$_3$) δ 7.54 (m, 6H), 7.38 (d, 2H), 6.95 (d, 2H), 5.40 (s), 4.20 (t, 2H), 3.82 (s, 3H), 3.50 (s, 6H), 3.20 (t, 2H) ppm.

EXAMPLE 46

1-(3-amino-1,2-benzisoxazol-5-yl)-6-(2'-{[bis(2-hydroxyethyl)amino]methyl}-1,1'-biphenyl-4-yl)-3-(trifluoromethyl)-1,4,5,6-tetrahydro-7H-pryazolo[3,4-c]pyridin-7-one trifluoroacetic acid salt

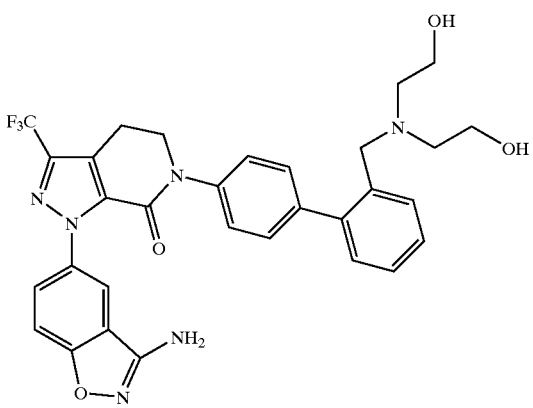

Part A: Preparation of 1-[3-cyano-4-fluorophenyl]-3-trifluoromethyl-6-[4-iodophenyl]-1,4,5,6-tetrahydropyrazolo-[3,4-c]-pyridin-7-one To 1-(4-iodophenyl)-3-(4-morpholinyl)-4-(trifluoroacetyl)-5,6-dihydro-2(1H)-pyridinone (2.2 g, 4.6 mmol) was added 2-fluoro-5-hydrazinobenzonitrile hydrochloride (1.11 g, 6 mmol) and 50% con. HCl (10 mL), acetic acid (25 mL) and MeOH (30 mL). The reaction was heated to reflux for 24 h, then cooled and concentrated. The residue was extracted with ethyl acetate, washed with water, brine, and sat'd NaHCO$_3$, and dried (Na$_2$SO$_4$). Purification by chromatography on silica gel using 3:1 Hexanes/ethyl acetate as eluent afforded 0.68 g (28%) of a yellow foam. Mass Spec (M–H)$^-$ 524.9.

Part B: Preparation of 1-[3-cyano-4-fluorophenyl]-3-trifluoromethyl-6-[2'-formyl-1,1'-biphenyl]-1,4,5,6-tetrahydropyrazolo-[3,4-c]-pyridin-7-one To the iodo compound from Part A (0.67 g, 1.27 mmol) was added 2-formylbenzeneboronic acid (0.29 g, 1.9 mmol), K$_3$PO$_4$ (0.95 g, 4.5 mmol) and dioxane (25 mL) and the mixture was degassed with N$_2$ for 15 min. Tetrakistriphenylphosphine Palladium (73 mg) was added and the reaction was heated to reflux 1.5 h. The reaction was stripped and purification by chromatography on silica gel using 2:1 Hexanes/ethyl acetate as eluent afforded 0.37 g (58%) of a brown foam. MS (M+H$_2$O)$^-$ 522.1.

Part C. Preparation of 1-(3-amino-1,2-benzisoxazol-5-yl)-6-(2'-bromomethyl)-1,1'-biphenyl-4-yl)-3-(trifluoromethyl)-1,4,5,6-tetrahydro-7H-pryazolo[3,4-c]pyridin-7-one To the aldehyde from Part B (2 g, 0.3.8 mmol) in 2:1 THF/MeOH (50 mL) at 0° C. was added NaBH$_4$ (0.17 g, 0.46 mmol) and the reaction was stirred 30 min. The reaction was concentrated and partitioned between CH$_2$Cl$_2$/H2O. The organic layer was washed with brine and dried (MgSO$_4$) to afford crude alcohol. To acetohydroxamic acid (0.89 g, 11.9 mmol) in DMF (5 mL) was added K$_2$CO$_3$ (2.139 g, 15.9 mmol) and several drops of water. After 30 min the above alcohol in DMF (15 mL) was added and the reaction was stirred 24 h. The reaction was concentrated, diluted with water and extracted with ethyl acetate, washed with water and brine and dried (MgSO$_4$) to afford the crude aminobenzisoxazole.

To the above compound in CH$_2$Cl$_2$ (25 mL) was added PBr$_3$ (0.52 mL, 5 mmol) and the reaction was stirred 30 min. The reaction was quenched with water, extracted with CH$_2$Cl$_2$ and dried (Na$_2$SO$_4$). Purification by chromatography on silica gel using 1:1 hexanes/ethyl acetate then 1:1 ethyl acetate/CH$_2$Cl$_2$ as eluent afforded 1.5 g (75%) of a orange foam. $^1$HNMR (CDCl$_3$) δ 7.79 (s, 1H), 7.74 (dd, j=9.2, 1.8 Hz, 1H), 7.53–7.45 (m, 4H), 7.40 (d, j=8.4 Hz, 2H), 7.35 (m, 2H), 7.22 (dd, j=8.4, 1.8 Hz, 1H), 4.43 (s, 4H), 4.26 (t, j=6.6 Hz, 2H), 3.25 (t, j=6.6 Hz, 2H) ppm.

Part D. Preparation of 1-(3-amino-1,2-benzisoxazol-5-yl)-6-(2'-{[bis(2-hydroxyethyl)amino]methyl}-1,1'-biphenyl-4-yl)-3-(trifluoromethyl)-1,4,5,6-tetrahydro-7H-pryazolo[3,4-c]pyridin-7-one trifluoroacetic acid salt The bromide from Part C (0.2 g, 0.344 mmol) was combined with excess diethanolamine (0.5 mL) in 10:1 CH$_3$CN/CHCl$_3$ (20 mL) and the reaction was stirred 24 h. TFA was added and the solvents removed. The residue was purified by HPLC and freeze-dried to afford 70 mg (29%); $^1$HNMR (DMSO-d6) □ 8.79 (m, 1H), 8.11 (d, j=1.8 Hz, 1H), 7.81 (dd, j=8.8,2.2 Hz, 1H), 7.76 (m, 1H), 7.58 (d, j=8.8 Hz, 2H), 7.54 (m, 1H), 7.51 (d, j=8.8 Hz, 2H), 7.40 (d, j=8.4 Hz, 2H), 7.36 (m, 2H), 6.57 (s, 2H), 4.47 (s, 2H), 4.23 (t, j=6.6 Hz, 2H), 3.55 (m, 4H), 3.21 (t, j=6.2 Hz, 2H), 3.03 (m, 4H) ppm; HRMS for C$_{31}$H$_{30}$F$_3$O$_4$N$_6$ (M+H)$^+$ 607.2268.

EXAMPLE 47

1-(3-amino-1,2-benzisoxazol-5-yl)-6-(2'-{[(3-aminopropyl)(methyl)amino]methyl}-1,1'-biphenyl-4-yl)-3-(trifluoromethyl)-1,4,5,6-tetrahydro-7H-pryazolo[3,4-c]pyridin-7-one trifluoroacetic acid salt

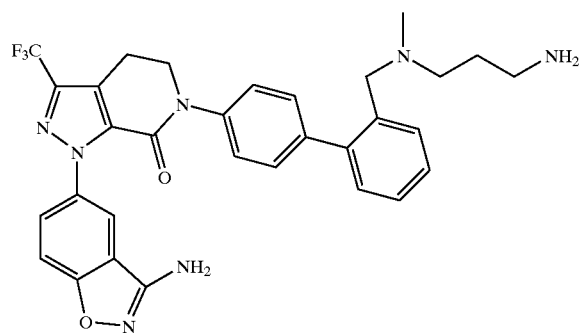

Part A. Preparation of benzyl 3-(methylamino)propylcarbamate

To benzyl chloroformate (1 g, 5.8 mmol) in CH$_2$Cl$_2$ (25 mL) at 0° C. was added dropwise imidazole (0.79 g, 11.7 mmol) in CH$_2$Cl$_2$ (20 mL). After the addition was complete the reaction was stirred at room temperature for 15 min., then washed with 10% citric acid, brine, and dried (MgSO$_4$). The product obtained was combined with N-methyl-1,3-propane diamine (0.6 mL, 5.8 mmol) and DMAP (15 mg) in CH$_2$Cl$_2$ (30 mL) and stirred for 24 h. The reaction was stripped, diluted with ethyl acetate, washed with 5% citric acid and brine and dried (MgSO$_4$). Mass Spec (M+H)$^+$ 223.3

Part B. Preparation of 1-(3-amino-1,2-benzisoxazol-5-yl)-6-(2'-{[(3-aminopropyl)(methyl)amino]methyl}-1,1'-biphenyl-4-yl)-3-(trifluoromethyl)-1,4,5,6-tetrahydro-7H-pryazolo[3,4-c]pyridin-7-one trifluoroacetic acid salt To the product of Part A (0.12 g, 0.54 mmol) was added the bromide (0.157 g, 0.27 mmol) from Part C of Example 46 in CH₃CN and the reaction was stirred 72 h. The solvent was removed and the residue dissolved in ethyl acetate, washed with water and dried (MgSO₄). TFA (5 mL) was added and the reaction was heated to reflux 1 h. The TFA was removed and the crude product was purified by HPLC and freeze-dried to afford 65 mg (29%). ¹HNMR (DMSO-d6) δ 8.11 (d, j=1.9 Hz, 1H), 7.81 (dd, j=2.2,8.8 Hz, 1H), 7.74 (brd s, 4H), 7.58 (d, j=9.2 Hz, 2H), 7.50 (m, 1H), 7.51 (d, j=8.5 Hz, 2H), 7.42 (d, j=9 Hz, 1H), 7.39 (m, 1H), 6.58 (s, 2H), 4.31 (m, 1H), 4.24 (m, 1H), 4.23 (t, j=6.6 Hz, 2H), 3.21 (t, j=6.6 Hz, 2H), 3.10 (m, 1H), 2.89 (m, 1H), 2.72 (m, 2H), 2.50 (s, 3H), 1.75 (m, 2H) ppm; HRMS (M+H)⁺ for $C_{31}H_{31}F_3N_7O_2$ 590.2498.

EXAMPLE 48

6-(2'-{[(2-hydroxyethyl)(methyl)amino]methyl}-1,1'-biphenyl-4-yl)-1-(4-methoxyphenyl)-7-oxo-4,5,6,7-tetrahydro-1H-pryazolo[3,4-c]pyridine-3-carboxamide trifluoroacetic acid salt

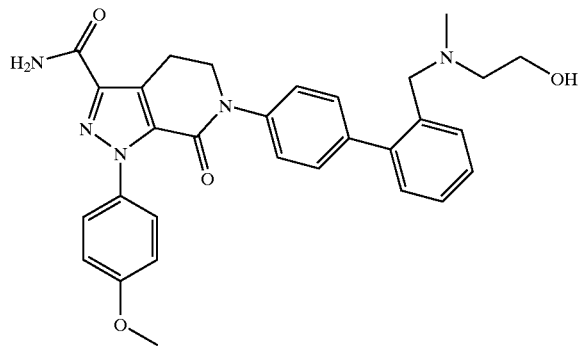

To ethyl 6-(2'-formyl-1,1'-biphenyl-4-yl)-1-(4-methoxyphenyl)-7-oxo-4,5,6,7-tetrahydro-1H-pyrazolo[3,4-c]pyridine-3-carboxylate from Part A of Example 31 (0.46 g, 0.93 mmol) in THF (15 mL) and ethanol(25 mL) was added 2-methylaminoethanol (0.1 5 mL, 1.8 mmol) and the reaction was stirred 15 min. A 0.5M solution of ZnCl₂ in THF (0.93 mL, 0.4 mmol) followed by NaBH₃CN (58 mg, 0.9 mmol) were added. The reaction was stirred 24 h. The reaction was concentrated and partitioned with ethyl acetate and water. Extraction with ethyl acetate and drying (Na₂SO₄) afforded crude ester. The ester was treated with excess NH₄OH in methanol (20 mL) for 24 h. The solvents were removed and purification by silica gel chromatography using 1 to 9% methanol/CH₂Cl₂ (w/1% NH₃) as eluent afforded 0.24 g of free base. The free base was treated with TFA (0.1 mL) in water and CH₃CN and freeze-dried to afford 0.29 g (49%); ¹HNMR (DMSO-d6) δ 7.76 (s, 1H), 7.75 (m, 1H), 7.55 (m, 3H), 7.50 (d, j=8.8 Hz, 4H), 7.38 (d, j=8.8 Hz, 2H), 7.35 (m, 1H), 7.02 (d, j=8.8, 2H), 4.39 (m, 3H), 4.13 (t, j=6.6 Hz, 2H), 3.81 (s, 3H), 3.58 (m, 2H), 3.26 (t, j=6.5 Hz, 2H), 3.05 (m, 1H), 2.90 (m, 1H), 2.59 (s, 3H) ppm; HRMS (M+H)+ for $C_{30}H_{32}N_5O_4$ 526.2470.

EXAMPLE 49

6-(2'-{[bis(2-hydroxyethyl)amino]methyl}-1,1'-biphenyl-4-yl)-1-(4-methoxyphenyl)-7-oxo-4,5,6,7-tetrahydro-1H-pryazolo[3,4-c]pyridine-3-carboxamide trifluoroacetic acid salt

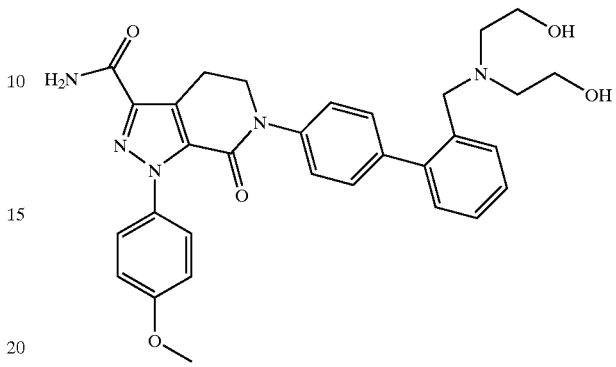

To ethyl 6-(2'-formyl-1,1'-biphenyl-4-yl)-1-(4-methoxyphenyl)-7-oxo-4,5,6,7-tetrahydro-1H-pyrazolo[3,4-c]pyridine-3-carboxylate from Part A of Example 31 (0.4 g, 0.81 mmol) in THF (15 mL) and methanol (25 mL) was added diethanolamine (0.18 mL, 1.8 mmol) and the reaction was stirred 15 min. A 0.5M solution of ZnCl₂ in THF (0.8 mL, 0.4 mmol) followed by NaBH₃CN (50 mg, 0.79 mmol) were added. The reaction was stirred 24 h. The reaction was concentrated and partitioned with ethyl acetate and water. Extraction with ethyl acetate and drying (Na₂SO₄) afforded crude ester. The ester was treated with excess NH₄OH and NH₄Cl in methanol (20 mL) for 72 h. The solvents were removed and purification by silica gel chromatography using 1 to 9% methanol/CH₂Cl₂ (w/1% NH₃) as eluent afforded 0.37 g of free base. The free base was treated with TFA (0.1 mL) in water and CH₃CN and freeze-dried to afford 0.41 g (66%); ¹HNMR (DMSO-d6) δ 7.7 (m, 2H), 7.55 (m, 4H), 7.50 (d, j=9.2 Hz, 4H), 7.39 (d, j=8.4 Hz, 2H), 7.35 (m, 1H), 7.03 (d, j=8.8, 2H), 4.49 (s, 2H), 4.10 (m, 1H), 4.15 (t, j=6.6 Hz, 2H), 3.81 (s, 3H), 3.57 (m, 4H), 3.26 (t, j=6.5 Hz, 2H), 3.04 (m, 4H) ppm; HRMS (M+H)⁺ for $C_{31}H_{34}N_5O_5$ 556.2574.

EXAMPLE 50

6-(2'-{[(3-aminopropyl)(methyl)amino]methyl}-1,1'-biphenyl-4-yl)-1-(4-methoxyphenyl)-7-oxo-4,5,6,7-tetrahydro-1N-pryazolo[3,4-c]pyridine-3-carboxamide trifluoroacetic acid salt

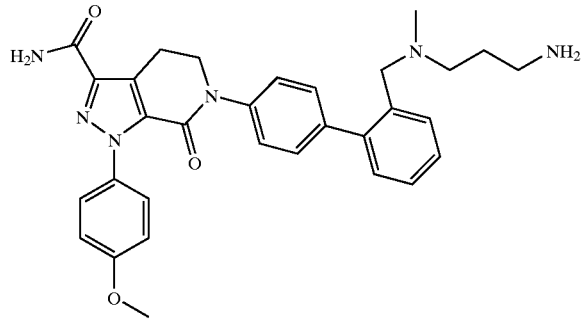

To ethyl 6-(2'-formyl-1,1'-biphenyl-4-yl)-1-(4-methoxyphenyl)-7-oxo-4,5,6,7-tetrahydro-1H-pyrazolo[3, 4-c]pyridine-3-carboxylate from Part A of Example 31 (0.4 g, 0.81 mmol) in THF (15 mL) and ethanol (25 mL) was added the carbobenzyloxy protected amine from Part A of Example 47 (0.54 g, 2.4 mmol). The reaction was stirred for 15 min. A 0.5M solution of $ZnCl_2$ in THF (0.8 mL, 0.4 mmol) followed by $NaBH_3CN$ (50 mg, 0.79 mmol) were added. The reaction was stirred 24 h. The reaction was concentrated and partitioned with ethyl acetate and water. Extraction with ethyl acetate and drying ($Na_2SO_4$) afforded crude ester. The ester was treated with excess $NH_4OH$ and $NH_4Cl$ in methanol (20 mL) for 72 h. The solvents were removed and purification by silica gel chromatography using 0 to 10% methanol/$CH_2Cl_2$ (w/1% $NH_3$) as eluent afforded carbobenzyloxy protected product. The protected product was treated with TFA at reflux for 1 h and purified by HPLC and freeze-dried to afford 0.1 g (16%); $^1$HNMR (DMSO-d6) δ 7.77 (m, 4H), 7.53 (m, 5H), 7.50 (d, j=8.7 Hz, 2H), 7.41 (d, j=8.8 Hz, 2H), 7.30 (m, 1H), 7.03 (d, j=8.8, 2H), 4.45 (m, 1H), 4.25 (m, 1H), 4.15 (t, j=6.6 Hz, 2H), 3.81 (s, 3H), 3.27 (t, j=6.2 Hz, 2H), 3.05 (m, 1H), 2.95 (m, 1H), 2.72 (m, 2H), 2.50 (s, 3H), 1.85 (m, 2H) ppm; HRMS (M+H)$^+$ for $C_{31}H_{35}N_6O_3$ 539.2767.

EXAMPLE 51

6-(2'-{[(2-hydroxyethyl)(methyl)amino]methyl}-1,1'-biphenyl-4-yl)-1-(4-methoxyphenyl)-3-(methylsulfonyl)-1,4,5,6-tetrahydro-1H-pryazolo[3,4-c]pyridin-7-one trifluoroacetic acid salt

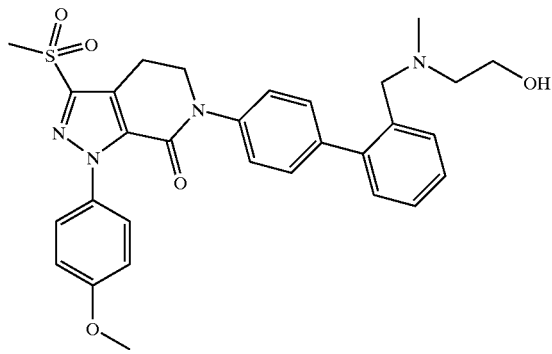

Part A. Preparation of 6-(2'-formyl-1,1'-biphenyl)-1-(4-methoxyphenyl)-3-(methylsulfonyl)-1,4,5,6-tetrahydro-7H-pyrazolo[3,4-c]pyridin-7-one 6-(4-Iodophenyl)-1-(4-methoxyphenyl)-3-(methylsulfonyl)-1,4,5,6-tetrahydro-7H-pyrazolo[3,4-c]pyridin-7-one from Part B of Example 22 (0.41 g, 0.7 mmol) and 2-formyl phenylboronic acid (0.18 g, 1.1 mmol) was added 2M $Na_2CO_3$ (1 mL), ethanol(20 mL) and toluene (30 mL) and the mixture was degassed with $N_2$ for 15 min. Tetrakistriphenylphosphine Palladium(0) (50 mg) was added and the reaction was heated to reflux 24 h. The reaction was cooled, concentrated and the residue extracted with ethyl acetate, washed with water and dried ($MgSO_4$). Purification by silica gel chromatography using 1:1 hexane/ethyl acetate as eluent afforded 0.28 g (71.8%) of an grey solid; Mass Spec (M+Na)$^+$ 524.

Part B. Preparation of 6-(2'-{[(2-hydroxyethyl)(methyl)amino]methyl}-1,1'-biphenyl-4-yl)-1-(4-methoxyphenyl)-3-(methylsulfonyl)-1,4,5,6-tetrahydro-1H-pryazolo[3,4-c]pyridin-7-one trifluoroacetic acid salt To the product of Part A (0.06 g, 0.11 mmol) in THF (10 mL) and methanol (10 mL) was added N-methylethanolamine (27 mg, 0.3 mmol) and the reaction was stirred 15 min. A 0.5M solution of $ZnCl_2$ in THF (0.119 mL, 0.059 mmol) followed by $NaBH_3CN$ (7.5 mg, 0.11 mmol) were added. The reaction was stirred 24 h. The reaction was concentrated and partitioned with ethyl acetate and water. Extraction with ethyl acetate and drying ($Na_2SO_4$) afforded crude amine. Purification by HPLC and freeze-drying afforded 54 mg (66%); $^1$HNMR (DMSO-d6) δ 7.75 (m, 1H), 7.54 (d, j=8.8 Hz, 2H), 7.53 (m, 2H), 7.48 (d, j=8.8 Hz, 2H), 7.38 (d, j=8.5 Hz, 2H), 7.34 (m, 1H), 7.03 (d, j=9.2 Hz, 2H), 4.35 (m, 2H), 4.17 (t, j=6.6 Hz, 2H), 3.80 (s, 3H), 3.56 (m, 2H), 3.36 (s, 3H), 3.24 (t, j=6.6 Hz, 2H), 3.0 (m, 1H), 2.95 (m, 1H), 2.56 (s, 3H) ppm; HRMS (M+H)$^+$ for $C_{30}H_{33}N_4O_5S$ 561.2164.

The following nomenclature is intended for group A in the following tables.

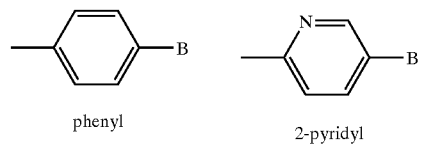

phenyl     2-pyridyl

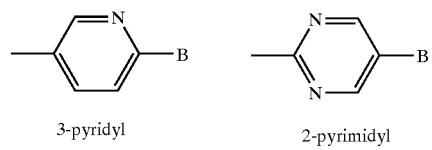

3-pyridyl     2-pyrimidyl

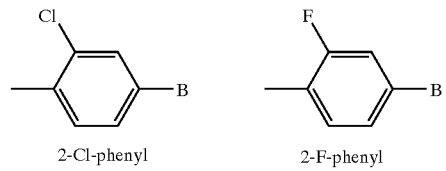

2-Cl-phenyl     2-F-phenyl

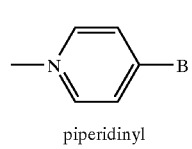

piperidinyl

TABLE 1

R⁴ᵃ = CH₂N(Me)₂O
   = CH₂NHCO₂Me
   = CH₂N(Et)CO₂Me
   = CH₂NHC(O)NHMe
   = CH₂N(Me)CO₂Et
   = CH₂N(Me)CO₂Me
   = CH₂N(Me)C(O)NHMe
   = CH₂NHSO₂Me
   = CH₂NHSO₂Et
   = CH₂N(Me)SO₂Me
   = CH₂N(Me)SO₂Et
   = CH₂N(Me)SO₂Pr
   = CH₂NHC(O)Me
   = CH₂NHC(O)Et
   = CH₂NHC(O)Pr
   = CH₂NHC(O)Bu
   = CH₂N(Me)C(O)Me
   = CH₂N(Me)C(O)Et
   = CH₂N(Me)C(O)Pr
   = CH₂N(Me)C(O)Bu
   = CH₂N(Et)C(O)Me
   = CH₂N(Et)C(O)Et
   = CH₂N(Et)C(O)Pr
   = CH₂N(Et)C(O)Bu
   = CH₂N(Pr)C(O)Me
   = CH₂N(Pr)C(O)Et
   = CH₂N(Pr)C(O)Pr
   = CH₂N(Pr)C(O)Bu
   = CH₂NHC(O)cyclopropyl
   = CH₂N(Me)C(O)cyclopropyl
   = CH₂NHC(O)CH₂cyclopropyl
   = CH₂N(cyclopropyl)C(O)Me
   = CH₂N(CH₂cyclopropyl)C(O)Me
   = CH₂N(Me)C(O)CH₂cyclopropyl
   = CH₂N(cyclopropyl)C(O)Et
   = CH₂N(CH₂cyclopropyl)C(O)Et
   = CH₂N(cyclobutyl)C(O)Me
   = CH₂N(cyclopentyl)C(O)Me R⁴ᵃ = CH₂N(Me)₂O
   = CH₂NHCO₂Me
   = CH₂N(Et)CO₂Me
   = CH₂NHC(O)NHMe
   = CH₂N(Me)CO₂Et
   = CH₂N(Me)CO₂Me
   = CH₂N(Me)C(O)NHMe
   = CH₂NHSO₂Me
   = CH₂NHSO₂Et
   = CH₂N(Me)SO₂Me
   = CH₂N(Me)SO₂Et
   = CH₂N(Me)SO₂Pr
   = CH₂NHC(O)Me
   = CH₂NHC(O)Et
   = CH₂NHC(O)Pr
   = CH₂NHC(O)Bu
   = CH₂N(Me)C(O)Me
   = CH₂N(Me)C(O)Et
   = CH₂N(Me)C(O)Pr
   = CH₂N(Me)C(O)Bu
   = CH₂N(Et)C(O)Me
   = CH₂N(Et)C(O)Et
   = CH₂N(Et)C(O)Pr
   = CH₂N(Et)C(O)Bu
   = CH₂N(Pr)C(O)Me
   = CH₂N(Pr)C(O)Et
   = CH₂N(Pr)C(O)Pr
   = CH₂N(Pr)C(O)Bu
   = CH₂NHC(O)cyclopropyl
   = CH₂N(Me)C(O)cyclopropyl
   = CH₂NHC(O)CH₂cyclopropyl
   = CH₂N(cyclopropyl)C(O)Me
   = CH₂N(CH₂cyclopropyl)C(O)Me
   = CH₂N(Me)C(O)CH₂cyclopropyl
   = CH₂N(cyclopropyl)C(O)Et
   = CH₂N(CH₂cyclopropyl)C(O)Et
   = CH₂N(cyclobutyl)C(O)Me
   = CH₂N(cyclopentyl)C(O)Me R⁴ᵃ = CH₂N(Me)₂O
   = CH₂NHCO₂Me
   = CH₂N(Et)CO₂Me
   = CH₂NHC(O)NHMe
   = CH₂N(Me)CO₂Et
   = CH₂N(Me)CO₂Me
   = CH₂N(Me)C(O)NHMe
   = CH₂NHSO₂Me
   = CH₂NHSO₂Et
   = CH₂N(Me)SO₂Me
   = CH₂N(Me)SO₂Et
   = CH₂N(Me)SO₂Pr
   = CH₂NHC(O)Me
   = CH₂NHC(O)Et
   = CH₂NHC(O)Pr
   = CH₂NHC(O)Bu
   = CH₂N(Me)C(O)Me
   = CH₂N(Me)C(O)Et
   = CH₂N(Me)C(O)Pr
   = CH₂N(Me)C(O)Bu R⁴ᵃ = CH₂N(Me)₂O
   = CH₂NHCO₂Me
   = CH₂N(Et)CO₂Me
   = CH₂NHC(O)NHMe
   = CH₂N(Me)CO₂Et
   = CH₂N(Me)CO₂Me
   = CH₂N(Me)C(O)NHMe
   = CH₂NHSO₂Me
   = CH₂NHSO₂Et
   = CH₂N(Me)SO₂Me
   = CH₂N(Me)SO₂Et
   = CH₂N(Me)SO₂Pr
   = CH₂NHC(O)Me
   = CH₂NHC(O)Et
   = CH₂NHC(O)Pr
   = CH₂NHC(O)Bu
   = CH₂N(Me)C(O)Me
   = CH₂N(Me)C(O)Et
   = CH₂N(Me)C(O)Pr
   = CH₂N(Me)C(O)Bu TABLE 1-continued = CH₂N(Et)C(O)Me
= CH₂N(Et)C(O)Et
= CH₂N(Et)C(O)Pr
= CH₂N(Et)C(O)Bu
= CH₂N(Pr)C(O)Me
= CH₂N(Pr)C(O)Et
= CH₂N(Pr)C(O)Pr
= CH₂N(Pr)C(O)Bu
= CH₂NHC(O)cyclopropyl
= CH₂N(Me)C(O)cyclopropyl
= CH₂NHC(O)CH₂cyclopropyl
= CH₂N(cyclopropyl)C(O)Me
= CH₂N(CH₂cyclopropyl)C(O)Me
= CH₂N(Me)C(O)CH₂cyclopropyl
= CH₂N(cyclopropyl)C(O)Et
= CH₂N(CH₂cyclopropyl)C(O)Et
= CH₂N(cyclobutyl)C(O)Me
= CH₂N(cyclopentyl)C(O)Me = CH₂N(Et)C(O)Me
= CH₂N(Et)C(O)Et
= CH₂N(Et)C(O)Pr
= CH₂N(Et)C(O)Bu
= CH₂N(Pr)C(O)Me
= CH₂N(Pr)C(O)Et
= CH₂N(Pr)C(O)Pr
= CH₂N(Pr)C(O)Bu
= CH₂NHC(O)cyclopropyl
= CH₂N(Me)C(O)cyclopropyl
= CH₂NHC(O)CH₂cyclopropyl
= CH₂N(cyclopropyl)C(O)Me
= CH₂N(CH₂cyclopropyl)C(O)Me
= CH₂N(Me)C(O)CH₂cyclopropyl
= CH₂N(cyclopropyl)C(O)Et
= CH₂N(CH₂cyclopropyl)C(O)Et
= CH₂N(cyclobutyl)C(O)Me
= CH₂N(cyclopentyl)C(O)Me

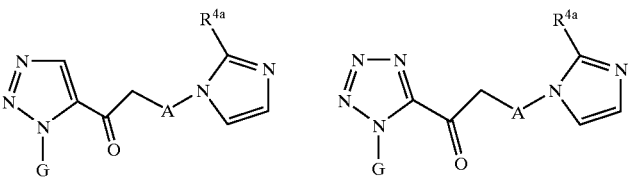

$R^{4a}$ = CH₂N(Me)₂O
= CH₂NHCO₂Me
= CH₂N(Et)CO₂Me
= CH₂NHC(O)NHMe
= CH₂N(Me)CO₂Et
= CH₂N(Me)CO₂Me
= CH₂N(Me)C(O)NHMe
= CH₂NHSO₂Me
= CH₂NHSO₂Et
= CH₂N(Me)SO₂Me
= CH₂N(Me)SO₂Et
= CH₂N(Me)SO₂Pr
= CH₂NHC(O)Me
= CH₂NHC(O)Et
= CH₂NHC(O)Pr
= CH₂NHC(O)Bu
= CH₂N(Me)C(O)Me
= CH₂N(Me)C(O)Et
= CH₂N(Me)C(O)Pr
= CH₂N(Me)C(O)Bu
= CH₂N(Et)C(O)Me
= CH₂N(Et)C(O)Et
= CH₂N(Et)C(O)Pr
= CH₂N(Et)C(O)Bu
= CH₂N(Pr)C(O)Me
= CH₂N(Pr)C(O)Et
= CH₂N(Pr)C(O)Pr
= CH₂N(Pr)C(O)Bu
= CH₂NHC(O)cyclopropyl
= CH₂N(Me)C(O)cyclopropyl
= CH₂NHC(O)CH₂cyclopropyl
= CH₂N(cyclopropyl)C(O)Me
= CH₂N(CH₂cyclopropyl)C(O)Me
= CH₂N(Me)C(O)CH₂cyclopropyl
= CH₂N(cyclopropyl)C(O)Et
= CH₂N(CH₂cyclopropyl)C(O)Et
= CH₂N(cyclobutyl)C(O)Me
= CH₂N(cyclopentyl)C(O)Me $R^{4a}$ = CH₂N(Me)₂O
= CH₂NHCO₂Me
= CH₂N(Et)CO₂Me
= CH₂NHC(O)NHMe
= CH₂N(Me)CO₂Et
= CH₂N(Me)CO₂Me
= CH₂N(Me)C(O)NHMe
= CH₂NHSO₂Me
= CH₂NHSO₂Et
= CH₂N(Me)SO₂Me
= CH₂N(Me)SO₂Et
= CH₂N(Me)SO₂Pr
= CH₂NHC(O)Me
= CH₂NHC(O)Et
= CH₂NHC(O)Pr
= CH₂NHC(O)Bu
= CH₂N(Me)C(O)Me
= CH₂N(Me)C(O)Et
= CH₂N(Me)C(O)Pr
= CH₂N(Me)C(O)Bu
= CH₂N(Et)C(O)Me
= CH₂N(Et)C(O)Et
= CH₂N(Et)C(O)Pr
= CH₂N(Et)C(O)Bu
= CH₂N(Pr)C(O)Me
= CH₂N(Pr)C(O)Et
= CH₂N(Pr)C(O)Pr
= CH₂N(Pr)C(O)Bu
= CH₂NHC(O)cyclopropyl
= CH₂N(Me)C(O)cyclopropyl
= CH₂NHC(O)CH₂cyclopropyl
= CH₂N(cyclopropyl)C(O)Me
= CH₂N(CH₂cyclopropyl)C(O)Me
= CH₂N(Me)C(O)CH₂cyclopropyl
= CH₂N(cyclopropyl)C(O)Et
= CH₂N(CH₂cyclopropyl)C(O)Et
= CH₂N(cyclobutyl)C(O)Me
= CH₂N(cyclopentyl)C(O)Me

| Ex# | A | G |
|---|---|---|
| 1-1. | phenyl | 4-methoxyphenyl |
| 1-2. | 2-pyridyl | 4-methoxyphenyl |
| 1-3. | 3-pyridyl | 4-methoxyphenyl |
| 1-4. | 2-pyrimidyl | 4-methoxyphenyl |
| 1-5. | 2-Cl-phenyl | 4-methoxyphenyl |
| 1-6. | 2-F-phenyl | 4-methoxyphenyl |
| 1-7. | phenyl | 2-aminomethylphenyl |
| 1-8. | 2-pyridyl | 2-aminomethylphenyl |
| 1-9. | 3-pyridyl | 2-aminomethylphenyl |

TABLE 1-continued

| | | |
|---|---|---|
| 1-10. | 2-pyrimidyl | 2-aminomethylphenyl |
| 1-11. | 2-Cl-phenyl | 2-aminomethylphenyl |
| 1-12. | 2-F-phenyl | 2-aminomethylphenyl |
| 1-13. | phenyl | 3-aminomethylphenyl |
| 1-14. | 2-pyridyl | 3-aminomethylphenyl |
| 1-15. | 3-pyridyl | 3-aminomethylphenyl |
| 1-16. | 2-pyrimidyl | 3-aminomethylphenyl |
| 1-17. | 2-Cl-phenyl | 3-aminomethylphenyl |
| 1-18. | 2-F-phenyl | 3-aminomethylphenyl |
| 1-19. | phenyl | 2-amidophenyl |
| 1-20. | 2-pyridyl | 2-amidophenyl |
| 1-21. | 3-pyridyl | 2-amidophenyl |
| 1-22. | 2-pyrimidyl | 2-amidophenyl |
| 1-23. | 2-Cl-phenyl | 2-amidophenyl |
| 1-24. | 2-F-phenyl | 2-amidophenyl |
| 1-25. | phenyl | 2-amido-4-methoxy-phenyl |
| 1-26. | 2-pyridyl | 2-amido-4-methoxy-phenyl |
| 1-27. | 3-pyridyl | 2-amido-4-methoxy-phenyl |
| 1-28. | 2-pyrimidyl | 2-amido-4-methoxy-phenyl |
| 1-29. | 2-Cl-phenyl | 2-amido-4-methoxy-phenyl |
| 1-30. | 2-F-phenyl | 2-amido-4-methoxy-phenyl |
| 1-31. | phenyl | 3-amidophenyl |
| 1-32. | 2-pyridyl | 3-amidophenyl |
| 1-33. | 3-pyridyl | 3-amidophenyl |
| 1-34. | 2-pyrimidyl | 3-amidophenyl |
| 1-35. | 2-Cl-phenyl | 3-amidophenyl |
| 1-36. | 2-F-phenyl | 3-amidophenyl |
| 1-37. | phenyl | 3-chlorophenyl |
| 1-38. | 2-pyridyl | 3-chlorophenyl |
| 1-39. | 3-pyridyl | 3-chlorophenyl |
| 1-40. | 2-pyrimidyl | 3-chlorophenyl |
| 1-41. | 2-Cl-phenyl | 3-chlorophenyl |
| 1-42. | 2-F-phenyl | 3-chlorophenyl |
| 1-43. | phenyl | 3-amino-4-chloro-phenyl |
| 1-44. | 2-pyridyl | 3-amino-4-chloro-phenyl |
| 1-45. | 3-pyridyl | 3-amino-4-chloro-phenyl |
| 1-46. | 2-pyrimidyl | 3-amino-4-chloro-phenyl |
| 1-47. | 2-Cl-phenyl | 3-amino-4-chloro-phenyl |
| 1-48. | 2-F-phenyl | 3-amino-4-chloro-phenyl |
| 1-49. | phenyl | 2-aminosulfonyl-phenyl |
| 1-50. | 2-pyridyl | 2-aminosulfonyl-phenyl |
| 1-51. | 3-pyridyl | 2-aminosulfonyl-phenyl |
| 1-52. | 2-pyrimidyl | 2-aminosulfonyl-phenyl |
| 1-53. | 2-Cl-phenyl | 2-aminosulfonyl-phenyl |
| 1-54. | 2-F-phenyl | 2-aminosulfonyl-phenyl |
| 1-55. | phenyl | 2-aminosulfonyl-4-methoxyphenyl |
| 1-56. | 2-pyridyl | 2-aminosulfonyl-4-methoxyphenyl |
| 1-57. | 3-pyridyl | 2-aminosulfonyl-4-methoxyphenyl |
| 1-58. | 2-pyrimidyl | 2-aminosulfonyl-4-methoxyphenyl |
| 1-59. | 2-Cl-phenyl | 2-aminosulfonyl-4-methoxyphenyl |
| 1-60. | 2-F-phenyl | 2-aminosulfonyl-4-methoxyphenyl |
| 1-61. | phenyl | 3-(1',2',4'-triazolin-5'-on-3'-yl)phenyl |
| 1-62. | 2-pyridyl | 3-(1',2',4'-triazolin-5'-on-3'-yl)phenyl |
| 1-63. | 3-pyridyl | 3-(1',2',4'-triazolin-5'-on-3'-yl)phenyl |
| 1-64. | 2-pyrimidyl | 3-(1',2',4'-triazolin-5'-on-3'-yl)phenyl |
| 1-65. | 2-Cl-phenyl | 3'-(1',2',4'-triazolin-5'-on-3'-yl)phenyl |
| 1-66. | 2-F-phenyl | 3-(1',2',4'-triazolin-5'-on-3'-yl)phenyl |
| 1-67. | phenyl | 1-aminoisoquinolin-6-yl |
| 1-68. | 2-pyridyl | 1-aminoisoquinolin-6-yl |
| 1-69. | 3-pyridyl | 1-aminoisoquinolin-6-yl |
| 1-70. | 2-pyrimidyl | 1-aminoisoquinolin-6-yl |
| 1-71. | 2-Cl-phenyl | 1-aminoisoquinolin-6-yl |
| 1-72. | 2-F-phenyl | 1-aminoisoquinolin-6-yl |
| 1-73. | phenyl | 1-aminoisoquinolin-7-yl |
| 1-74. | 2-pyridyl | 1-aminoisoquinolin-7-yl |
| 1-75. | 3-pyridyl | 1-aminoisoquinolin-7-yl |
| 1-76. | 2-pyrimidyl | 1-aminoisoquinolin-7-yl |

TABLE 1-continued

| | | |
|---|---|---|
| 1-77. | 2-Cl-phenyl | 1-aminoisoquinolin-7-yl |
| 1-78. | 2-F-phenyl | 1-aminoisoquinolin-7-yl |
| 1-79. | phenyl | 4-aminoquinazol-6-yl |
| 1-80. | 2-pyridyl | 4-aminoquinazol-6-yl |
| 1-81. | 3-pyridyl | 4-aminoquinazol-6-yl |
| 1-82. | 2-pyrimidyl | 4-aminoquinazol-6-yl |
| 1-83. | 2-Cl-phenyl | 4-aminoquinazol-6-yl |
| 1-84. | 2-F-phenyl | 4-aminoquinazol-6-yl |
| 1-85. | phenyl | 4-aminoquinazol-7-yl |
| 1-86. | 2-pyridyl | 4-aminoquinazol-7-yl |
| 1-87. | 3-pyridyl | 4-aminoquinazol-7-yl |
| 1-88. | 2-pyrimidyl | 4-aminoquinazol-7-yl |
| 1-89. | 2-Cl-phenyl | 4-aminoquinazol-7-yl |
| 1-90. | 2-F-phenyl | 4-aminoquinazol-7-yl |
| 1-91. | phenyl | 3-aminobenzisoxazol-5-yl |
| 1-92. | 2-pyridyl | 3-aminobenzisoxazol-5-yl |
| 1-93. | 3-pyridyl | 3-aminobenzisoxazol-5-yl |
| 1-94. | 2-pyrimidyl | 3-aminobenzisoxazol-5-yl |
| 1-95. | 2-Cl-phenyl | 3-aminabenzisoxazol-5-yl |
| 1-96. | 2-F-phenyl | 3-aminobenzisoxazol-5-yl |
| 1-97. | phenyl | 3-aminobenzisoxazol-6-yl |
| 1-98. | 2-pyridyl | 3-aminobenzisoxazol-6-yl |
| 1-99. | 3-pyridyl | 3-aminabenzisoxazol-6-yl |
| 1-100. | 2-pyrimidyl | 3-aminobenzisoxazol-6-yl |
| 1-101. | 2-Cl-phenyl | 3-aminobenzisoxazol-6-yl |
| 1-102. | 2-F-phenyl | 3-aminabenzisoxazol-6-yl |
| 1-103. | phenyl | 3-aminoindazol-5-yl |
| 1-104. | 2-pyridyl | 3-aminoindazol-5-yl |
| 1-105. | 3-pyridyl | 3-aminoindazol-5-yl |
| 1-106. | 2-pyrimidyl | 3-aminoindazol-5-yl |
| 1-107. | 2-Cl-phenyl | 3-aminoindazol-5-yl |
| 1-108. | 2-F-phenyl | 3-aminoindazol-5-yl |
| 1-109. | phenyl | 3-aminoindazol-6-yl |
| 1-110. | 2-pyridyl | 3-aminoindazol-6-yl |
| 1-111. | 3-pyridyl | 3-aminoindazol-6-yl |
| 1-112. | 2-pyrimidyl | 3-aminoindazol-6-yl |
| 1-113. | 2-Cl-phenyl | 3-aminoindazol-6-yl |
| 1-114. | 2-F-phenyl | 3-aminoindazol-6-yl |
| 1-115. | phenyl | indolin-5-yl |
| 1-116. | 2-pyridyl | indolin-5-yl |
| 1-117. | 3-pyridyl | indolin-5-yl |
| 1-118. | 2-pyrimidyl | indolin-5-yl |
| 1-119. | 2-Cl-phenyl | indolin-5-yl |
| 1-120. | 2-F-phenyl | indolin-5-yl |
| 1-121. | phenyl | indolin-6-yl |
| 1-122. | 2-pyridyl | indolin-6-yl |
| 1-123. | 3-pyridyl | indolin-6-yl |
| 1-124. | 2-pyrimidyl | indolin-6-yl |
| 1-125. | 2-Ci-phenyl | indolin-6-yl |
| 1-126. | 2-F-phenyl | indolin-6-yl |
| 1-127. | phenyl | 2-naphthyl |
| 1-128. | 2-pyridyl | 2-naphthyl |
| 1-129. | 3-pyridyl | 2-naphthyl |
| 1-130. | 2-pyrimidyl | 2-naphthyl |
| 1-131. | 2-Cl-phenyl | 2-naphthyl |
| 1-132. | 2-F-phenyl | 2-naphthyl |
| 1-133. | phenyl | 3-amida-naphth-2-yl |
| 1-134. | 2-pyridyl | 3-amido-naphth-2-yl |
| 1-135. | 3-pyridyl | 3-amido-naphth-2-yl |
| 1-136. | 2-pyrimidyl | 3-amido-naphth-2-yl |
| 1-137. | 2-Cl-phenyl | 3-amido-naphth-2-yl |
| 1-138. | 2-F-phenyl | 3-amido-naphth-2-yl |
| 1-139. | phenyl | 3-methylsulfonyl-naphth-2-yl |
| 1-140. | 2-pyridyl | 3-methylsulfonyl-naphth-2-yl |
| 1-141. | 3-pyridyl | 3-methylsulfonyl-naphth-2-yl |
| 1-142. | 2-pyrimidyl | 3-methylsulfonyl-naphth-2-yl |
| 1-143. | 2-Cl-phenyl | 3-methylsulfonyl-naphth-2-yl |
| 1-144. | 2-F-phenyl | 3-methylsulfonyl-naphth-2-yl |
| 1-145. | phenyl | 3-aminomethyl-naphth-2-yl |
| 1-146. | 2-pyridyl | 3-aminomethyl-naphth-2-yl |
| 1-147. | 3-pyridyl | 3-aminomethyl-naphth-2-yl |
| 1-148. | 2-pyrimidyl | 3-aminomethyl-naphth-2-yl |
| 1-149. | 2-Cl-phenyl | 3-aminomethyl-naphth-2-yl |
| 1-150. | 2-F-phenyl | 3-aminomethyl-naphth-2-yl |
| 1-151. | phenyl | 3-fluoro-naphth-2-yl |
| 1-152. | 2-pyridyl | 3-fluoro-naphth-2-y1 |
| 1-153. | 3-pyridyl | 3-fluoro-naphth-2-yl |
| 1-154. | 2-pyrimidyl | 3-fluoro-naphth-2-yl |
| 1-155. | 2-Cl-phenyl | 3-fluoro-naphth-2-yl |

TABLE 1-continued

| | | |
|---|---|---|
| 1-156. | 2-F-phenyl | 3-fluoro-naphth-2-yl |
| 1-157. | phenyl | 3-cyano-naphth-2-yl |
| 1-158. | 2-pyridyl | 3-cyano-naphth-2-yl |
| 1-159. | 3-pyridyl | 3-cyano-naphth-2-yl |
| 1-160. | 2-pyrimidyl | 3-cyano-naphth-2-yl |
| 1-161. | 2-Cl-phenyl | 3-cyano-naphth-2-yl |
| 1-162. | 2-F-phenyl | 3-cyano-naphth-2-yl |
| 1-163. | phenyl | 3-aminosulfonyl-naphth-2-yl |
| 1-164. | 2-pyridyl | 3-aminosulfonyl-naphth-2-yl |
| 1-165. | 3-pyridyl | 3-aminosulfonyl-naphth-2-yl |
| 1-166. | 2-pyrimidyl | 3-aminosulfonyl-naphth-2-yl |
| 1-167. | 2-Cl-phenyl | 3-aminosulfonyl-naphth-2-yl |
| 1-168. | 2-F-phenyl | 3-aminosulfonyl-naphth-2-yl |
| 1-169. | phenyl | 6-chloro-naphth-2-yl |
| 1-170. | 2-pyridyl | 6-chloro-naphth-2-yl |
| 1-171. | 3-pyridyl | 6-chloro-naphth-2-yl |
| 1-172. | 2-pyrimidyl | 6-chloro-naphth-2-yl |
| 1-173. | 2-Cl-phenyl | 6-chloro-naphth-2-yl |
| 1-174. | 2-F-phenyl | 6-chloro-naphth-2-yl |

TABLE 2

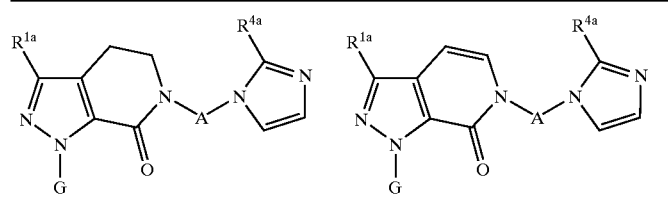

| | |
|---|---|
| $R^{4a}$ = $CH_2N(Me)_2O$ | $R^{4a}$ = $CH_2N(Me)_2O$ |
| = $CH_2NHCO_2Me$ | = $CH_2NHCO_2Me$ |
| = $CH_2N(Et)CO_2Me$ | = $CH_2N(Et)CO_2Me$ |
| = $CH_2NHC(O)NHMe$ | = $CH_2NHC(O)NHMe$ |
| = $CH_2N(Me)CO_2Et$ | = $CH_2N(Me)CO_2Et$ |
| = $CH_2N(Me)CO_2Me$ | = $CH_2N(Me)CO_2Me$ |
| = $CH_2N(Me)C(O)NHMe$ | = $CH_2N(Me)C(O)NHMe$ |
| = $CH_2NHSO_2Me$ | = $CH_2NHSO_2Me$ |
| = $CH_2NHSO_2Et$ | = $CH_2NHSO_2Et$ |
| = $CH_2N(Me)SO_2Me$ | = $CH_2N(Me)SO_2Me$ |
| = $CH_2N(Me)SO_2Et$ | = $CH_2N(Me)SO_2Et$ |
| = $CH_2N(Me)SO_2Pr$ | = $CH_2N(Me)SO_2Pr$ |
| = $CH_2NHC(O)Me$ | = $CH_2NHC(O)Me$ |
| = $CH_2NHC(O)Et$ | = $CH_2NHC(O)Et$ |
| = $CH_2NHC(O)Pr$ | = $CH_2NHC(O)Pr$ |
| = $CH_2NHC(O)Bu$ | = $CH_2NHC(O)Bu$ |
| = $CH_2N(Me)C(O)Me$ | = $CH_2N(Me)C(O)Me$ |
| = $CH_2N(Me)C(O)Et$ | = $CH_2N(Me)C(O)Et$ |
| = $CH_2N(Me)C(O)Pr$ | = $CH_2N(Me)C(O)Pr$ |
| = $CH_2N(Me)C(O)BU$ | = $CH_2N(Me)C(O)Bu$ |
| = $CH_2N(Et)C(O)Me$ | = $CH_2N(Et)C(O)Me$ |
| = $CH_2N(Et)C(O)Et$ | = $CH_2N(Et)C(O)Et$ |
| = $CH_2N(Et)C(O)Pr$ | = $CH_2N(Et)C(O)Pr$ |
| = $CH_2N(Et)C(O)Bu$ | = $CH_2N(Et)C(O)Bu$ |
| = $CH_2N(Pr)C(O)Me$ | = $CH_2N(Pr)C(O)Me$ |
| = $CH_2N(Pr)C(O)Et$ | = $CH_2N(Pr)C(O)Et$ |
| = $CH_2N(Pr)C(O)Pr$ | = $CH_2N(Pr)C(O)Pr$ |
| = $CH_2N(Pr)C(O)Bu$ | = $CH_2N(Pr)C(O)Bu$ |
| = $CH_2NHC(O)cyclopropyl$ | = $CH_2NHC(O)cyclopropyl$ |
| = $CH_2N(Me)C(O)cyclopropyl$ | = $CH_2N(Me)C(O)cyclopropyl$ |
| = $CH_2NHC(O)CH_2cyclopropyl$ | = $CH_2NHC(O)CH_2cyclopropyl$ |
| = $CH_2N(cyclopropyl)C(O)Me$ | = $CH_2N(cyclopropyl)C(O)Me$ |
| = $CH_2N(CH_2cyclopropyl)C(O)Me$ | = $CH_2N(CH_2cyclopropyl)C(O)Me$ |
| = $CH_2N(Me)C(O)CH_2cyclopropyl$ | = $CH_2N(Me)C(O)CH_2cyclopropyl$ |
| = $CH_2N(cyclopropyl)C(O)Et$ | = $CH_2N(cyclopropyl)C(O)Et$ |
| = $CH_2N(CH_2cyclopropyl)C(O)Et$ | = $CH_2N(CH_2cyclopropyl)C(O)Et$ |
| = $CH_2N(cyclobutyl)C(O)Me$ | = $CH_2N(cyclobutyl)C(O)Me$ |
| = $CH_2N(cyclopentyl)C(O)Me$ | = $CH_2N(cyclopentyl)C(O)Me$ |

TABLE 2-continued

[Structure: Pyrazole-C(=O)-NH-A-imidazole with R¹ᵃ, R⁴ᵃ, G substituents]  [Structure: Triazole-C(=O)-NH-A-imidazole with R¹ᵃ, R⁴ᵃ, G substituents]

R⁴ᵃ = CH₂N(Me)₂O
  = CH₂NHCO₂Me
  = CH₂N(Et)CO₂Me
  = CH₂NHC(O)NHMe
  = CH₂N(Me)CO₂Et
  = CH₂N(Me)CO₂Me
  = CH₂N(Me)C(O)NHMe
  = CH₂NHSO₂Me
  = CH₂NHSO₂Et
  = CH₂N(Me)SO₂Me
  = CH₂N(Me)SO₂Et
  = CH₂N(Me)SO₂Pr
  = CH₂NHC(O)Me
  = CH₂NHC(O)Et
  = CH₂NHC(O)Pr
  = CH₂NHC(O)Bu
  = CH₂N(Me)C(O)Me
  = CH₂N(Me)C(O)Et
  = CH₂N(Me)C(O)Pr
  = CH₂N(Me)C(O)Bu
  = CH₂N(Et)C(O)Me
  = CH₂N(Et)C(O)Et
  = CH₂N(Et)C(O)Pr
  = CH₂N(Et)C(O)Bu
  = CH₂N(Pr)C(O)Me
  = CH₂N(Pr)C(O)Et
  = CH₂N(Pr)C(O)Pr
  = CH₂N(Pr)C(O)Bu
  = CH₂NHC(O)cyclopropyl
  = CH₂N(Me)C(O)cyclopropyl
  = CH₂NHC(O)CH₂cyclopropyl
  = CH₂N(cyclopropyl)C(O)Me
  = CH₂N(CH₂cyclopropyl)C(O)Me
  = CH₂N(Me)C(O)CH₂cyclopropyl
  = CH₂N(cyclopropyl)C(O)Et
  = CH₂N(CH₂cyclopropyl)C(O)Et
  = CH₂N(cyclobutyl)C(O)Me
  = CH₂N(cyclopentyl)C(O)Me R⁴ᵃ = CH₂N(Me)₂O
  = CH₂NHCO₂Me
  = CH₂N(Et)CO₂Me
  = CH₂NHC(O)NHMe
  = CH₂N(Me)CO₂Et
  = CH₂N(Me)CO₂Me
  = CH₂N(Me)C(O)NHMe
  = CH₂NHSO₂Me
  = CH₂NHSO₂Et
  = CH₂N(Me)SO₂Me
  = CH₂N(Me)SO₂Et
  = CH₂N(Me)SO₂Pr
  = CH₂NHC(O)Me
  = CH₂NHC(O)Et
  = CH₂NHC(O)Pr
  = CH₂NHC(O)Bu
  = CH₂N(Me)C(O)Me
  = CH₂N(Me)C(O)Et
  = CH₂N(Me)C(O)Pr
  = CH₂N(Me)C(O)Bu
  = CH₂N(Et)C(O)Me
  = CH₂N(Et)C(O)Et
  = CH₂N(Et)C(O)Pr
  = CH₂N(Et)C(O)Bu
  = CH₂N(Pr)C(O)Me
  = CH₂N(Pr)C(O)Et
  = CH₂N(Pr)C(O)Pr
  = CH₂N(Pr)C(O)Bu
  = CH₂NHC(O)cyclopropyl
  = CH₂N(Me)C(O)cyclopropyl
  = CH₂NHC(O)CH₂cyclopropyl
  = CH₂N(cyclopropyl)C(O)Me
  = CH₂N(CH₂cyclopropyl)C(O)Me
  = CH₂N(Me)C(O)CH₂cyclopropyl
  = CH₂N(cyclopropyl)C(O)Et
  = CH₂N(CH₂cyclopropyl)C(O)Et
  = CH₂N(cyclobutyl)C(O)Me
  = CH₂N(cyclopentyl)C(O)Me

[Structure: Pyrazole-C(=O)-CH₂-A-imidazole with R¹ᵃ, R⁴ᵃ, G substituents]  [Structure: Triazole-C(=O)-CH₂-A-imidazole with R¹ᵃ, R⁴ᵃ, G substituents]

R⁴ᵃ = CH₂N(Me)₂O
  = CH₂NHCO₂Me
  = CH₂N(Et)CO₂Me
  = CH₂NHC(O)NHMe
  = CH₂N(Me)CO₂Et
  = CH₂N(Me)CO₂Me
  = CH₂N(Me)C(O)NHMe
  = CH₂NHSO₂Me
  = CH₂NHSO₂Et
  = CH₂N(Me)SO₂Me
  = CH₂N(Me)SO₂Et
  = CH₂N(Me)SO₂Pr
  = CH₂NHC(O)Me
  = CH₂NHC(O)Et
  = CH₂NHC(O)Pr
  = CH₂NHC(O)Bu
  = CH₂N(Me)C(O)Me
  = CH₂N(Me)C(O)Et
  = CH₂N(Me)C(O)Pr
  = CH₂N(Me)C(O)Bu

R⁴ᵃ = CH₂N(Me)₂O
  = CH₂NHCO₂Me
  = CH₂N(Et)CO₂Me
  = CH₂NHC(O)NHMe
  = CH₂N(Me)CO₂Et
  = CH₂N(Me)CO₂Me
  = CH₂N(Me)C(O)NHMe
  = CH₂NHSO₂Me
  = CH₂NHSO₂Et
  = CH₂N(Me)SO₂Me
  = CH₂N(Me)SO₂Et
  = CH₂N(Me)SO₂Pr
  = CH₂NHC(O)Me
  = CH₂NHC(O)Et
  = CH₂NHC(O)Pr
  = CH₂NHC(O)Bu
  = CH₂N(Me)C(O)Me
  = CH₂N(Me)C(O)Et
  = CH₂N(Me)C(O)Pr
  = CH₂N(Me)C(O)Bu

TABLE 2-continued

```
=  CH₂N(Et)C(O)Me              =  CH₂N(Et)C(O)Me
=  CH₂N(Et)C(O)Et              =  CH₂N(Et)C(O)Et
=  CH₂N(Et)C(O)Pr              =  CH₂N(Et)C(O)Pr
=  CH₂N(Et)C(O)Bu              =  CH₂N(Et)C(O)Bu
=  CH₂N(Pr)C(O)Me              =  CH₂N(Pr)C(O)Me
=  CH₂N(Pr)C(O)Et              =  CH₂N(Pr)C(O)Et
=  CH₂N(Pr)C(O)Pr              =  CH₂N(Pr)C(O)Pr
=  CH₂N(Pr)C(O)Bu              =  CH₂N(Pr)C(O)Bu
=  CH₂NHC(O)cyclopropyl        =  CH₂NHC(O)cyclopropyl
=  CH₂N(Me)C(O)cyclopropyl     =  CH₂N(Me)C(O)cyclopropyl
=  CH₂NHC(O)CH₂cyclopropyl     =  CH₂NHC(O)CH₂cyclopropyl
=  CH₂N(cyclopropyl)C(O)Me     =  CH₂N(cyclopropyl)C(O)Me
=  CH₂N(CH₂cyclopropyl)C(O)Me  =  CH₂N(CH₂cyclopropyl)C(O)Me
=  CH₂N(Me)C(O)CH₂cyclopropyl  =  CH₂N(Me)C(O)CH₂cyclopropyl
=  CH₂N(cyclopropyl)C(O)Et     =  CH₂N(cyclopropyl)C(O)Et
=  CH₂N(CH₂cyclopropyl)C(O)Et  =  CH₂N(CH₂cyclopropyl)C(O)Et
=  CH₂N(cyclobutyl)C(O)Me      =  CH₂N(cyclobutyl)C(O)Me
=  CH₂N(cyclopentyl)C(O)Me     =  CH₂N(cyclopentyl)C(O)Me
```
$R^{1a}$ is $CH_3$;

| Ex # | A | G |
|---|---|---|
| 2-1. | phenyl | 4-methoxyphenyl |
| 2-2. | 2-pyridyl | 4-methoxyphenyl |
| 2-3. | 3-pyridyl | 4-methoxyphenyl |
| 2-4. | 2-pyrimidyl | 4-methoxyphenyl |
| 2-5. | 2-Cl-phenyl | 4-methoxyphenyl |
| 2-6. | 2-F-phenyl | 4-methoxyphenyl |
| 2-7. | piperidinyl | 4-methoxyphenyl |
| 2-8. | phenyl | 2-aminomethylphenyl |
| 2-9. | 2-pyridyl | 2-aminomethylphenyl |
| 2-10. | 3-pyridyl | 2-aminomethylphenyl |
| 2-11. | 2-pyrimidyl | 2-aminomethylphenyl |
| 2-12. | 2-Cl-phenyl | 2-aminomethylphenyl |
| 2-13. | 2-F-phenyl | 2-aminomethylphenyl |
| 2-14. | piperidinyl | 2-aminomethylphenyl |
| 2-15. | phenyl | 3-aminomethylphenyl |
| 2-16. | 2-pyridyl | 3-aminomethylphenyl |
| 2-17. | 3-pyridyl | 3-aminomethylphenyl |
| 2-18. | 2-pyrimidyl | 3-aminomethylphenyl |
| 2-19. | 2-Cl-phenyl | 3-aminomethylphenyl |
| 2-20. | 2-F-phenyl | 3-aminomethylphenyl |
| 2-21. | piperidinyl | 3-aminomethylphenyl |
| 2-22. | phenyl | 2-amidophenyl |
| 2-23. | 2-pyridyl | 2-amidophenyl |
| 2-24. | 3-pyridyl | 2-amidophenyl |
| 2-25. | 2-pyrimidyl | 2-amidophenyl |
| 2-26. | 2-Cl-phenyl | 2-amidophenyl |
| 2-27. | 2-F-phenyl | 2-amidophenyl |
| 2-28. | piperidinyl | 2-amidophenyl |
| 2-29. | phenyl | 2-amido-4-methoxy-phenyl |
| 2-30. | 2-pyridyl | 2-amido-4-methoxy-phenyl |
| 2-31. | 3-pyridyl | 2-amido-4-methoxy-phenyl |
| 2-32. | 2-pyrimidyl | 2-amido-4-methoxy-phenyl |
| 2-33. | 2-Cl-phenyl | 2-amido-4-methoxy-phenyl |
| 2-34. | 2-F-phenyl | 2-amido-4-methoxy-phenyl |
| 2-35. | piperidinyl | 2-amido-4-methoxy-phenyl |
| 2-36. | phenyl | 3-amidophenyl |
| 2-37. | 2-pyridyl | 3-amidophenyl |
| 2-38. | 3-pyridyl | 3-amidophenyl |
| 2-39. | 2-pyrimidyl | 3-amidophenyl |
| 2-40. | 2-Cl-phenyl | 3-amidophenyl |
| 2-41. | 2-F-phenyl | 3-amidophenyl |
| 2-42. | piperidinyl | 3-amidophenyl |
| 2-43. | phenyl | 3-chlorophenyl |
| 2-44. | 2-pyridyl | 3-chlorophenyl |
| 2-45. | 3-pyridyl | 3-chlorophenyl |
| 2-46. | 2-pyrimidyl | 3-chlorophenyl |
| 2-47. | 2-Cl-phenyl | 3-chlorophenyl |
| 2-48. | 2-F-phenyl | 3-chlorophenyl |
| 2-49. | piperidinyl | 3-chlorophenyl |
| 2-50. | phenyl | 3-amino-4-chloro-phenyl |
| 2-51. | 2-pyridyl | 3-amino-4-chloro-phenyl |
| 2-52. | 3-pyridyl | 3-amino-4-chloro-phenyl |
| 2-53. | 2-pyrimidyl | 3-amino-4-chloro-phenyl |
| 2-54. | 2-Cl-phenyl | 3-amino-4-chloro-phenyl |
| 2-55. | 2-F-phenyl | 3-amino-4-chloro-phenyl |
| 2-56. | piperidinyl | 3-amino-4-chloro-phenyl |
| 2-57. | phenyl | 2-aminosulfonyl-phenyl |

TABLE 2-continued

| | | |
|---|---|---|
| 2-58. | 2-pyridyl | 2-aminosulfonyl-phenyl |
| 2-59. | 3-pyridyl | 2-aminosulfonyl-phenyl |
| 2-60. | 2-pyrimidyl | 2-aminosulfonyl-phenyl |
| 2-61. | 2-Cl-phenyl | 2-aminosulfonyl-phenyl |
| 2-62. | 2-F-phenyl | 2-aminosulfonyl-phenyl |
| 2-63. | piperidinyl | 2-aminosulfonyl-phenyl |
| 2-64. | phenyl | 2-aminosulfonyl-4-methoxyphenyl |
| 2-65. | 2-pyridyl | 2-aminosulfonyl-4-methoxyphenyl |
| 2-66. | 3-pyridyl | 2-aminosulfonyl-4-methoxyphenyl |
| 2-67. | 2-pyrimidyl | 2-aminosulfonyl-4-methoxyphenyl |
| 2-68. | 2-Cl-phenyl | 2-aminosulfonyl-4-methoxyphenyl |
| 2-69. | 2-F-phenyl | 2-aminosulfonyl-4-methoxyphenyl |
| 2-70. | piperidinyl | 2-aminosulfonyl-4-methoxyphenyl |
| 2-71. | phenyl | 3-(1', 2', 4'-triazolin-5'-on-3'-yl)phenyl |
| 2-72. | 2-pyridyl | 3-(1', 2', 4'-triazolin-5'-on-3'-yl)phenyl |
| 2-73. | 3-pyridyl | 3-(1', 2', 4'-triazolin-5'-on-3'-yl)phenyl |
| 2-74. | 2-pyrimidyl | 3-(1', 2', 4'-triazolin-5'-on-3'-yl)phenyl |
| 2-75. | 2-Cl-phenyl | 3-(1', 2', 4'-triazolin-5'-on-3'-ylphenyl |
| 2-76. | 2-F-phenyl | 3-(1', 2', 4'-triazolin-5'-on-3'-ylphenyl |
| 2-77. | piperidinyl | 3-(1', 2', 4'-triazolin-5'-on-3'-yl)phenyl |
| 2-78. | phenyl | 1-aminoisoquinolin-6-yl |
| 2-79. | 2-pyridyl | 1-aminoisoquinolin-6-yl |
| 2-80. | 3-pyridyl | 1-aminoisoquinolin-6-yl |
| 2-81. | 2-pyrimidyl | 1-aminoisoquinolin-6-yl |
| 2-82. | 2-Cl-phenyl | 1-aminoisoquinolin-6-yl |
| 2-83. | 2-F-phenyl | 1-aminoisoquinolin-6-yl |
| 2-84. | piperidinyl | 1-aminoisoquinolin-6-yl |
| 2-85. | phenyl | 1-aminoisoquinolin-7-yl |
| 2-86. | 2-pyridyl | 1-aminoisoquinolin-7-yl |
| 2-87. | 3-pyridyl | 1-aminoisoquinolin-7-yl |
| 2-88. | 2-pyrimidyl | 1-aminoisoquinolin-7-yl |
| 2-89. | 2-Cl-phenyl | 1-aminoisoquinolin-7-yl |
| 2-90. | 2-F-phenyl | 1-aminoisoquinolin-7-yl |
| 2-91. | piperidinyl | 1-aminoisoquinolin-7-yl |
| 2-92. | phenyl | 4-aminoquinazol-6-yl |
| 2-93. | 2-pyridyl | 4-aminoquinazol-6-yl |
| 2-94. | 3-pyridyl | 4-aminoquinazol-6-yl |
| 2-95. | 2-pyrimidyl | 4-aminoquinazol-6-yl |
| 2-96. | 2-Cl-phenyl | 4-aminoquinazol-6-yl |
| 2-97. | 2-F-phenyl | 4-aminoquinazol-6-yl |
| 2-98. | piperidinyl | 4-aminoquinazol-6-yl |
| 2-99. | phenyl | 4-aminoquinazol-7-yl |
| 2-100. | 2-pyridyl | 4-aminoquinazol-7-yl |
| 2-101. | 3-pyridyl | 4-aminoquinazol-7-yl |
| 2-102. | 2-pyrimidyl | 4-aminoquinazol-7-yl |
| 2-103. | 2-Cl-phenyl | 4-aminoquinazol-7-yl |
| 2-104. | 2-F-phenyl | 4-aminoquinazol-7-yl |
| 2-105. | piperidinyl | 4-aminoquinazol-7-yl |
| 2-106. | phenyl | 3-aminobenzisoxazol-5-yl |
| 2-107. | 2-pyridyl | 3-aminobenzisoxazol-5-yl |
| 2-108. | 3-pyridyl | 3-aminobenzisoxazol-5-yl |
| 2-109. | 2-pyrimidyl | 3-aminobenzisoxazol-5-yl |
| 2-110. | 2-Cl-phenyl | 3-aminobenzisoxazol-5-yl |
| 2-111. | 2-F-phenyl | 3-aminobenzisoxazol-5-yl |
| 2-112. | piperidinyl | 3-aminobenzisoxazol-5-yl |
| 2-113. | phenyl | 3-aminobenzisoxazol-6-yl |
| 2-114. | 2-pyridyl | 3-aminobenzisoxazol-6-yl |
| 2-115. | 3-pyridyl | 3-aminobenzisoxazol-6-yl |
| 2-116. | 2-pyrimidyl | 3-aminobenzisoxazol-6-yl |
| 2-117. | 2-Cl-phenyl | 3-aminobenzisaxazol-6-yl |
| 2-118. | 2-F-phenyl | 3-aminobenzisaxazol-6-yl |
| 2-119. | piperidinyl | 3-aminobenzisoxazol-6-yl |
| 2-120. | phenyl | 3-aminoindazol-5-yl |
| 2-121. | 2-pyridyl | 3-aminoindazol-5-yl |
| 2-122. | 3-pyridyl | 3-aminoindazol-5-yl |

TABLE 2-continued

| | | |
|---|---|---|
| 2-123. | 2-pyrimidyl | 3-aminoindazol-5-yl |
| 2-124. | 2-Cl-phenyl | 3-aminoindazol-5-yl |
| 2-125. | 2-F-phenyl | 3-aminoindazol-5-yl |
| 2-126. | piperidinyl | 3-aminoindazol-5-yl |
| 2-127. | phenyl | 3-aminoindazol-6-yl |
| 2-128. | 2-pyridyl | 3-aminoindazol-6-yl |
| 2-129. | 3-pyridyl | 3-aminoindazol-6-yl |
| 2-130. | 2-pyrimidyl | 3-aminoindazol-6-yl |
| 2-131. | 2-Cl-phenyl | 3-aminoindazol-6-yl |
| 2-132. | 2-F-phenyl | 3-aminoindazol-6-yl |
| 2-133. | piperidinyl | 3-aminoindazol-6-yl |
| 2-134. | phenyl | indolin-5-yl |
| 2-135. | 2-pyridyl | indolin-5-yl |
| 2-136. | 3-pyridyl | indolin-5-yl |
| 2-137. | 2-pyrimidyl | indolin-5-yl |
| 2-138. | 2-Cl-phenyl | indolin-5-yl |
| 2-139. | 2-F-phenyl | indolin-5-yl |
| 2-140. | piperidinyl | indolin-5-yl |
| 2-141. | phenyl | indolin-6-yl |
| 2-142. | 2-pyridyl | indolin-6-yl |
| 2-143. | 3-pyridyl | indolin-6-yl |
| 2-144. | 2-pyrimidyl | indolin-6-yl |
| 2-145. | 2-Cl-phenyl | indolin-6-yl |
| 2-146. | 2-F-phenyl | indoliri-6-yl |
| 2-147. | piperidinyl | indolin-6-yl |
| 2-148. | phenyl | 2-naphthyl |
| 2-149. | 2-pyridyl | 2-naphthyl |
| 2-150. | 3-pyridyl | 2-naphthyl |
| 2-151. | 2-pyrimidyl | 2-naphthyl |
| 2-152. | 2-Cl-phenyl | 2-naphthyl |
| 2-153. | 2-F-phenyl | 2-naphthyl |
| 2-154. | piperidinyl | 2-naphthyl |
| 2-155. | phenyl | 3-amido-naphth-2-yl |
| 2-156. | 2-pyridyl | 3-amido-naphth-2-yl |
| 2-157. | 3-pyridyl | 3-amido-naphth-2-yl |
| 2-158. | 2-pyrimidyl | 3-amido-naphth-2-yl |
| 2-159. | 2-Cl-phenyl | 3-amido-naphth-2-yl |
| 2-160. | 2-F-phenyl | 3-amido-naphth-2-yl |
| 2-161. | piperidinyl | 3-amido-naphth-2-yl |
| 2-162. | phenyl | 3-methylsulfonyl-naphth-2-yl |
| 2-163. | 2-pyridyl | 3-methylsulfonyl-naphth-2-yl |
| 2-164. | 3-pyridyl | 3-methylsulfonyl-naphth-2-yl |
| 2-165. | 2-pyrimidyl | 3-methylsulfonyl-naphth-2-yl |
| 2-166. | 2-Cl-phenyl | 3-methylsulfonyl-naphth-2-yl |
| 2-167. | 2-F-phenyl | 3-methylsulfonyl-naphth-2-yl |
| 2-168. | piperidinyl | 3-methylsulfonyl-naphth-2-yl |
| 2-169. | phenyl | 3-aminomethyl-naphth-2-yl |
| 2-170. | 2-pyridyl | 3-aminomethyl-naphth-2-yl |
| 2-171. | 3-pyridyl | 3-aminomethyl-naphth-2-yl |
| 2-172. | 2-pyrimidyl | 3-aminomethyl-naphth-2-yl |
| 2-173. | 2-Cl-phenyl | 3-aminomethyl-naphth-2-yl |
| 2-174. | 2-F-phenyl | 3-aminomethyl-naphth-2-yl |
| 2-175. | piperidinyl | 3-aminomethyl-naphth-2-yl |
| 2-176. | phenyl | 3-fluoro-naphth-2-yl |
| 2-177. | 2-pyridyl | 3-fluoro-naphth-2-yl |
| 2-178. | 3-pyridyl | 3-fluoro-naphth-2-yl |
| 2-179. | 2-pyrimidyl | 3-fluoro-naphth-2-yl |
| 2-180. | 2-Cl-phenyl | 3-fluoro-naphth-2-yl |
| 2-181. | 2-F-phenyl | 3-fluoro-naphth-2-yl |
| 2-182. | Piperidinyl | 3-fluoro-naphth-2-yl |
| 2-183. | phenyl | 3-cyano-naphth-2-yl |
| 2-184. | 2-pyridyl | 3-cyano-naphth-2-yl |
| 2-185. | 3-pyridyl | 3-cyano-naphth-2-yl |
| 2-186. | 2-pyrimidyl | 3-cyano-naphth-2-yl |
| 2-187. | 2-Cl-phenyl | 3-cyano-naphth-2-yl |
| 2-188. | 2-F-phenyl | 3-cyano-naphth-2-yl |
| 2-189. | Piperidinyl | 3-cyano-naphth-2-yl |
| 2-190. | phenyl | 3-aminosulfonyl-naphth-2-yl |
| 2-191. | 2-pyridyl | 3-aminosulfonyl-naphth-2-yl |
| 2-192. | 3-pyridyl | 3-aminosulfonyl-naphth-2-yl |
| 2-193. | 2-pyrimidyl | 3-aminosulfonyl-naphth-2-yl |
| 2-194. | 2-Cl-phenyl | 3-aminosulfonyl-naphth-2-yl |
| 2-195. | 2-F-phenyl | 3-aminosulfonyl-naphth-2-yl |
| 2-196. | piperidinyl | 3-aminosulfonyl-naphth-2-yl |
| 2-197. | phenyl | 6-chloro-naphth-2-yl |
| 2-198. | 2-pyridyl | 6-chloro-naphth-2-yl |
| 2-199. | 3-pyridyl | 6-chloro-naphth-2-yl |
| 2-200. | 2-pyrimidyl | 6-chloro-naphth-2-yl |
| 2-201. | 2-Cl-phenyl | 6-chloro-naphth-2-yl |

TABLE 2-continued

| | | |
|---|---|---|
| 2-202. | 2-F-phenyl | 6-chloro-naphth-2-yl |
| 2-203. | Piperidinyl | 6-chloro-naphth-2-yl |

TABLE 3

Examples 3-1-through 3-6090 use the structures from Table 2 and the corresponding A and G groups from Examples 1-203 of Table 2:

Examples 3-1 to 3-203, $R^{1a}$ is $CH_2CH_3$;
Examples 3-204 to 3-406, $R^{1a}$ is $CF_3$;
Examples 3-407 to 3-609, $R^{1a}$ is $SCH_3$;
Examples 3-610 to 3-812, $R^{1a}$ is $SOCH_3$;
Examples 3-813 to 3-1015, $R^{1a}$ is $SO_2CH_3$;
Examples 3-1016 to 3-1218, $R^{1a}$ is Cl;
Examples 3-1219 to 3-1421, $R^{1a}$ is F;
Examples 3-1422 to 3-1624, $R^{1a}$ is $CO_2CH_3$;
Examples 3-1625 to 3-1827, $R^{1a}$ is $CH_2OCH_3$;
Examples 3-1828 to 3-2030, $R^{1a}$ is $CONH_2$;
Examples 3-2031 to 3-2233, $R^{1a}$ is –CN;
Examples 3-2234 to 3-2436, $R^{1a}$ is $CH_2NHCH_3$;
Examples 3-2437 to 3-2639, $R^{1a}$ is $CH_2NHSO_2CH_3$;
Examples 3-2640 to 3-2842, $R^{1a}$ is 1-imidazolyl-$CH_2$;
Examples 3-2843 to 3-3045, $R^{1a}$ is Br;

TABLE 3-continued

Examples 3-1-through 3-6090 use the structures from Table 2 and the corresponding A and G groups from Examples 1-203 of Table 2:

Examples 3-3046 to 3-3248, $R^{1a}$ is 5-tetrazolyl;
Examples 3-3249 to 3-3451, $R^{1a}$ is $N(CH_3)_2$;
Examples 3-3452 to 3-3654, $R^{1a}$ is $NHCH_3$;
Examples 3-3655 to 3-3857, $R^{1a}$ is $SO_2NH_2$;
Examples 3-3858 to 3-4060, $R^{1a}$ is 2-pyridine;
Examples 3-4061 to 3-4263, $R^{1a}$ is 3-pyridine;
Examples 3-4264 to 3-4466, $R^{1a}$ is 4-pyridine;
Examples 3-4467 to 3-4872, $R^{1a}$ is 2-pyridine-N-oxide;
Examples 3-4873 to 3-5075, $R^{1a}$ is 3-pyridine-N-oxide;
Examples 3-5076 to 3-5287, $R^{1a}$ is 4-pyridine-N-oxide;
Examples 3-5288 to 3-5481, $R^{1a}$ is $OCH_3$;
Examples 3-5482 to 3-5684, $R^{1a}$ is $CH_2OC(O)NHCH_3$;
Examples 3-5685 to 3-5887, $R^{1a}$ is $CH_2NHCO_2CH_3$;
Examples 3-5888 to 3-6090, $R^{1a}$ is $CH_2NHC(O)NHCH_3$; and,
Examples 3-6091 to 3-6293, $R^{1a}$ is H.

TABLE 4

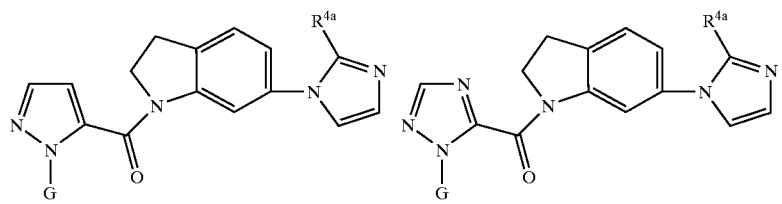

$R^{4a}$ = $CH_2N(Me)_2O$
  = $CH_2NHCO_2Me$
  = $CH_2N(Et)CO_2Me$
  = $CH_2NHC(O)NHMe$
  = $CH_2N(Me)CO_2Et$
  = $CH_2N(Me)CO_2Me$
  = $CH_2N(Me)C(O)NHMe$
  = $CH_2NHSO_2Me$
  = $CH_2NHSO_2Et$
  = $CH_2N(Me)SO_2Me$
  = $CH_2N(Me)SO_2Et$
  = $CH_2N(Me)SO_2Pr$
  = $CH_2NHC(O)Me$
  = $CH_2NHC(O)Et$
  = $CH_2NHC(O)Pr$
  = $CH_2NHC(O)Bu$
  = $CH_2N(Me)C(O)Me$
  = $CH_2N(Me)C(O)Et$
  = $CH_2N(Me)C(O)Pr$
  = $CH_2N(Me)C(O)Bu$
  = $CH_2N(Et)C(O)Me$
  = $CH_2N(Et)C(O)Et$
  = $CH_2N(Et)C(O)Pr$ $R^{4a}$ = $CH_2N(Me)_2O$
  = $CH_2NHCO_2Me$
  = $CH_2N(Et)CO_2Me$
  = $CH_2NHC(O)NHMe$
  = $CH_2N(Me)CO_2Et$
  = $CH_2N(Me)CO_2Me$
  = $CH_2N(Me)C(O)NHMe$
  = $CH_2NHSO_2Me$
  = $CH_2NHSO_2Et$
  = $CH_2N(Me)SO_2Me$
  = $CH_2N(Me)SO_2Et$
  = $CH_2N(Me)SO_2Pr$
  = $CH_2NHC(O)Me$
  = $CH_2NHC(O)Et$
  = $CH_2NHC(O)Pr$
  = $CH_2NHC(O)Bu$
  = $CH_2N(Me)C(O)Me$
  = $CH_2N(Me)C(O)Et$
  = $CH_2N(Me)C(O)Pr$
  = $CH_2N(Me)C(O)Bu$
  = $CH_2N(Et)C(O)Me$
  = $CH_2N(Et)C(O)Et$
  = $CH_2N(Et)C(O)Pr$

TABLE 4-continued

| | |
|---|---|
| = CH₂N(Et)C(O)Bu | = CH₂N(Et)C(O)Bu |
| = CH₂N(Pr)C(O)Me | = CH₂N(Pr)C(O)Me |
| = CH₂N(Pr)C(O)Et | = CH₂N(Pr)C(O)Et |
| = CH₂N(Pr)C(O)Pr | = CH₂N(Pr)C(O)Pr |
| = CH₂N(Pr)C(O)Bu | = CH₂N(Pr)C(O)Bu |
| = CH₂NHC(O)cyclopropyl | = CH₂NHC(O)cyclopropyl |
| = CH₂N(Me)C(O)cyclopropyl | = CH₂N(Me)C(O)cyclopropyl |
| = CH₂NHC(O)CH₂cyclopropyl | = CH₂NHC(O)CH₂cyclopropyl |
| = CH₂N(cyclopropyl)C(O)Me | = CH₂N(cyclopropyl)C(O)Me |
| = CH₂N(CH₂cyclopropyl)C(O)Me | = CH₂N(CH₂cyclopropyl)C(O)Me |
| = CH₂N(Me)C(O)CH₂cyclopropyl | = CH₂N(Me)C(O)CH₂cyclopropyl |
| = CH₂N(cyclopropyl)C(O)Et | = CH₂N(cyclopropyl)C(O)Et |
| = CH₂N(CH₂cyclopropyl)C(O)Et | = CH₂N(CH₂cyclopropyl)C(O)Et |
| = CH₂N(cyclobutyl)C(O)Me | = CH₂N(cyclobutyl)C(O)Me |
| = CH₂N(cyclopentyl)C(O)Me | = CH₂N(cyclopentyl)C(O)Me |

[Structure: triazole-carbonyl linked to indoline-imidazole with R4a substituent, bearing G group] [Structure: tetrazole-carbonyl linked to indoline-imidazole with R4a substituent, bearing G group]

| | |
|---|---|
| R⁴ᵃ = CH₂N(Me)₂O | R⁴ᵃ = CH₂N(Me)₂O |
| = CH₂NHCO₂Me | = CH₂NHCO₂Me |
| = CH₂N(Et)CO₂Me | = CH₂N(Et)CO₂Me |
| = CH₂NHC(O)NHMe | = CH₂NHC(O)NHMe |
| = CH₂N(Me)CO₂Et | = CH₂N(Me)CO₂Et |
| = CH₂N(Me)CO₂Me | = CH₂N(Me)CO₂Me |
| = CH₂N(Me)C(O)NHMe | = CH₂N(Me)C(O)NHMe |
| = CH₂NHSO₂Me | = CH₂NHSO₂Me |
| = CH₂NHSO₂Et | = CH₂NHSO₂Et |
| = CH₂N(Me)SO₂Me | = CH₂N(Me)SO₂Me |
| = CH₂N(Me)SO₂Et | = CH₂N(Me)SO₂Et |
| = CH₂N(Me)SO₂Pr | = CH₂N(Me)SO₂Pr |
| = CH₂NHC(O)Me | = CH₂NHC(O)Me |
| = CH₂NHC(O)Et | = CH₂NHC(O)Et |
| = CH₂NHC(O)Pr | = CH₂NHC(O)Pr |
| = CH₂NHC(O)Bu | = CH₂NHC(O)Bu |
| = CH₂N(Me)C(O)Me | = CH₂N(Me)C(O)Me |
| = CH₂N(Me)C(O)Et | = CH₂N(Me)C(O)Et |
| = CH₂N(Me)C(O)Pr | = CH₂N(Me)C(O)Pr |
| = CH₂N(Me)C(O)Bu | = CH₂N(Me)C(O)Bu |
| = CH₂N(Et)C(O)Me | = CH₂N(Et)C(O)Me |
| = CH₂N(Et)C(O)Et | = CH₂N(Et)C(O)Et |
| = CH₂N(Et)C(O)Pr | = CH₂N(Et)C(O)Pr |
| = CH₂N(Et)C(O)Bu | = CH₂N(Et)C(O)Bu |
| = CH₂N(Pr)C(O)Me | = CH₂N(Pr)C(O)Me |
| = CH₂N(Pr)C(O)Et | = CH₂N(Pr)C(O)Et |
| = CH₂N(Pr)C(O)Pr | = CH₂N(Pr)C(O)Pr |
| = CH₂N(Pr)C(O)Bu | = CH₂N(Pr)C(O)Bu |
| = CH₂NHC(O)cyclopropyl | = CH₂NHC(O)cyclopropyl |
| = CH₂N(Me)C(O)cyclopropyl | = CH₂N(Me)C(O)cyclopropyl |
| = CH₂NHC(O)CH₂cyclopropyl | = CH₂NHC(O)CH₂cyclopropyl |
| = CH₂N(cyclopropyl)C(O)Me | = CH₂N(cyclopropyl)C(O)Me |
| = CH₂N(CH₂cyclopropyl)C(O)Me | = CH₂N(CH₂cyclopropyl)C(O)Me |
| = CH₂N(Me)C(O)CH₂cyclopropyl | = CH₂N(Me)C(O)CH₂cyclopropyl |
| = CH₂N(cyclopropyl)C(O)Et | = CH₂N(cyclopropyl)C(O)Et |
| = CH₂N(CH₂cyclopropyl)C(O)Et | = CH₂N(CH₂cyclopropyl)C(O)Et |
| = CH₂N(cyclobutyl)C(O)Me | = CH₂N(cyclobutyl)C(O)Me |
| = CH₂N(cyclopentyl)C(O)Me | = CH₂N(cyclopentyl)C(O)Me |

| Ex # | G |
|---|---|
| 4-1. | 4-methoxyphenyl |
| 4-2. | 2-aminomethylphenyl |
| 4-3. | 3-aminomethylphenyl |
| 4-4. | 2-amidophenyl |
| 4-5. | 2-amido-4-methoxy-phenyl |
| 4-6. | 3-amidophenyl |
| 4-7. | 3-chlorophenyl |
| 4-8. | 3-amino-4-chloro-phenyl |
| 4-9. | 2-aminosulfonyl-phenyl |
| 4-10. | 2-aminosulfonyl-4-methoxyphenyl |
| 4-11. | 3-(1',2',4'-triazolin-5'-on-3'- |

TABLE 4-continued

| | |
|---|---|
| | yl)phenyl |
| 4-12. | 1-aminoisoquinolin-6-yl |
| 4-13. | 1-aminoisoquinolin-7-yl |
| 4-14. | 4-aminoquinazol-6-yl |
| 4-15. | 4-aminoquinazol-7-yl |
| 4-16. | 3-aminobenzisoxazol-5-yl |
| 4-17. | 3-aminobenzisoxazol-6-yl |
| 4-18. | 3-aminoindazol-5-yl |
| 4-19. | 3-aminoindazol-6-yl |
| 4-20. | indolin-5-yl |
| 4-21. | indolin-6-yl |
| 4-22. | 2-naphthyl |
| 4-23. | 3-amido-naphth-2-yl |
| 4-24. | 3-methylsulfonyl-naphth-2-yl |
| 4-25. | 3-aminomethyl-naphth-2-yl |
| 4-26. | 3-fluoro-naphth-2-yl |
| 4-27. | 3-chloro-naphth-2-yl |
| 4-28. | 3-aminosulfonyl-naphth-2-yl |
| 4-29. | 6-chloro-naphth-2-yl |

TABLE 5

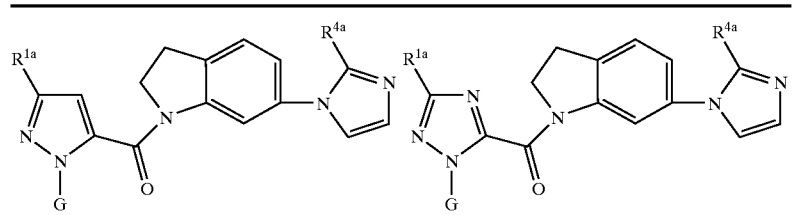

| $R^{4a}$ | | $R^{4a}$ | |
|---|---|---|---|
| = | $CH_2N(Me)_2O$ | = | $CH_2N(Me)_2O$ |
| = | $CH_2NHCO_2Me$ | = | $CH_2NHCO_2Me$ |
| = | $CH_2N(Et)CO_2Me$ | = | $CH_2N(Et)CO_2Me$ |
| = | $CH_2NHC(O)NHMe$ | = | $CH_2NHC(O)NHMe$ |
| = | $CH_2N(Me)CO_2Et$ | = | $CH_2N(Me)CO_2Et$ |
| = | $CH_2N(Me)CO_2Me$ | = | $CH_2N(Me)CO_2Me$ |
| = | $CH_2N(Me)C(O)NHMe$ | = | $CH_2N(Me)C(O)NHMe$ |
| = | $CH_2NHSO_2Me$ | = | $CH_2NHSO_2Me$ |
| = | $CH_2NHSO_2Et$ | = | $CH_2NHSO_2Et$ |
| = | $CH_2N(Me)SO_2Me$ | = | $CH_2N(Me)SO_2Me$ |
| = | $CH_2N(Me)SO_2Et$ | = | $CH_2N(Me)SO_2Et$ |
| = | $CH_2N(Me)SO_2Pr$ | = | $CH_2N(Me)SO_2Pr$ |
| = | $CH_2NHC(O)Me$ | = | $CH_2NHC(O)Me$ |
| = | $CH_2NHC(O)Et$ | = | $CH_2NHC(O)Et$ |
| = | $CH_2NHC(O)Pr$ | = | $CH_2NHC(O)Pr$ |
| = | $CH_2NHC(O)Bu$ | = | $CH_2NHC(O)Bu$ |
| = | $CH_2N(Me)C(O)Me$ | = | $CH_2N(Me)C(O)Me$ |
| = | $CH_2N(Me)C(O)Et$ | = | $CH_2N(Me)C(O)Et$ |
| = | $CH_2N(Me)C(O)Pr$ | = | $CH_2N(Me)C(O)Pr$ |
| = | $CH_2N(Me)C(O)Bu$ | = | $CH_2N(Me)C(O)Bu$ |
| = | $CH_2N(Et)C(O)Me$ | = | $CH_2N(Et)C(O)Me$ |
| = | $CH_2N(Et)C(O)Et$ | = | $CH_2N(Et)C(O)Et$ |
| = | $CH_2N(Et)C(O)Pr$ | = | $CH_2N(Et)C(O)Pr$ |
| = | $CH_2N(Et)C(O)Bu$ | = | $CH_2N(Et)C(O)Bu$ |
| = | $CH_2N(Pr)C(O)Me$ | = | $CH_2N(Pr)C(O)Me$ |
| = | $CH_2N(Pr)C(O)Et$ | = | $CH_2N(Pr)C(O)Et$ |
| = | $CH_2N(Pr)C(O)Pr$ | = | $CH_2N(Pr)C(O)Pr$ |
| = | $CH_2N(Pr)C(O)Bu$ | = | $CH_2N(Pr)C(O)Bu$ |
| = | $CH_2NHC(O)cyclopropyl$ | = | $CH_2NHC(O)cyclopropyl$ |
| = | $CH_2N(Me)C(O)cyclopropyl$ | = | $CH_2N(Me)C(O)cyclopropyl$ |
| = | $CH_2NHC(O)CH_2cyclopropyl$ | = | $CH_2NHC(O)CH_2cyclopropyl$ |
| = | $CH_2N(cyclopropyl)C(O)Me$ | = | $CH_2N(cyclopropyl)C(O)Me$ |
| = | $CH_2N(CH_2cyclopropyl)C(O)Me$ | = | $CH_2N(CH_2cyclopropyl)C(O)Me$ |
| = | $CH_2N(Me)C(O)CH_2cyclopropyl$ | = | $CH_2N(Me)C(O)CH_2cyclopropyl$ |
| = | $CH_2N(cyclopropyl)C(O)Et$ | = | $CH_2N(cyclopropyl)C(O)Et$ |
| = | $CH_2N(CH_2cyclopropyl)C(O)Et$ | = | $CH_2N(CH_2cyclopropyl)C(O)Et$ |
| = | $CH_2N(cyclobutyl)C(O)Me$ | = | $CH_2N(cyclobutyl)C(O)Me$ |
| = | $CH_2N(cyclopentyl)C(O)Me$ | = | $CH_2N(cyclopentyl)C(O)Me$ |

| Ex # | $R^{1a}$ | G |
|---|---|---|
| 5-1. | $CH_3$ | 4-methoxyphenyl |
| 5-2. | $CH_2CH_3$ | 4-methoxyphenyl |
| 5-3. | $CF_3$ | 4-methoxyphenyl |

TABLE 5-continued

| | | |
|---|---|---|
| 5-4. | SCH$_3$ | 4-methoxyphenyl |
| 5-5. | SOCH$_3$ | 4-methoxyphenyl |
| 5-6. | SO$_2$CH$_3$ | 4-methoxyphenyl |
| 5-7. | Cl | 4-methoxyphenyl |
| 5-8. | F | 4-methoxyphenyl |
| 5-9. | CO$_2$CH$_3$ | 4-methoxyphenyl |
| 5-10. | CH$_2$OCH$_3$ | 4-methoxyphenyl |
| 5-11. | CONH$_2$ | 4-methoxyphenyl |
| 5-12. | CN | 4-methoxyphenyl |
| 5-13. | CH$_2$NH$_2$ | 4-methoxyphenyl |
| 5-14. | CH$_2$NHSO$_2$CH$_3$ | 4-methoxyphenyl |
| 5-15. | 1-imidazolyl-CH$_2$ | 4-methoxyphenyl |
| 5-16. | 1-tetrazolyl-CH$_2$— | 4-methoxyphenyl |
| 5-17. | Br | 4-methoxyphenyl |
| 5-18. | 5-tetrazolyl | 4-methoxyphenyl |
| 5-19. | N(CH$_3$)$_2$ | 4-methoxyphenyl |
| 5-20. | NHCH$_3$ | 4-methoxyphenyl |
| 5-21. | SO$_2$NH$_2$ | 4-methoxyphenyl |
| 5-22. | 2-pyridine | 4-methoxyphenyl |
| 5-23. | 3-pyridine | 4-methoxyphenyl |
| 5-24. | 4-pyridine | 4-methoxyphenyl |
| 5-25. | 2-pyridine-N-oxide | 4-methoxyphenyl |
| 5-26. | 3-pyridine-N-oxide | 4-methoxyphenyl |
| 5-27. | 4-pyridine-N-oxide | 4-methoxyphenyl |
| 5-28. | OCH$_3$ | 4-methoxyphenyl |
| 5-29. | CH$_2$OC(O)NHCH$_3$ | 4-methoxyphenyl |
| S-30. | CH$_2$NHCO$_2$CH$_3$ | 4-methoxyphenyl |
| 5-31. | CH$_2$NHC(O)NHCH$_3$ | 4-methoxyphenyl |
| 5-32. | H | 4-methoxyphenyl |

For Examples 5-33 through 5-64, G is 2-aminomethylphenyl and R$^{1a}$ is as shown in Examples 5-1 through 5-32.

For Examples 5-65 through 5-96, G is 3-aminomethylphenyl and R$^{1a}$ is as shown in Examples 5-1 through 5-32.

For Examples 5-97 through 5-128, G is 2-amidophenyl and R$^{1a}$ is as shown in Examples 5-1 through 5-32.

For Examples 5-129 through 5-160, G is 2-amido-4-methoxyphenyl and R$^{1a}$ is as shown in Examples 5-1 through 5-32.

For Examples 5-161 through 5-192, G is 3-amidophenyl and R$^{1a}$ is as shown in Examples 5-1 through 5-32.

For Examples 5-193 through 5-224, G is 3-chlorophenyl and R$^{1a}$ is as shown in Examples 5-1 through 5-32.

For Examples 5-225 through 5-256, G is 3-amino-4-chlorophenyl and R$^{1a}$ is as shown in Examples 5-1 through 5-32.

For Examples 5-257 through 5-288, G is 2-aminosulfonylphenyl and R$^{1a}$ is as shown in Examples 5-1 through 5-32.

For Examples 5-289 through 5-320, G is 2-aminosulfonyl-4-methoxyphenyl and R$^{1a}$ is as shown in Examples 5-1 through 5-32.

For Examples 5-321 through 5-352, G is 3-(1',2',4'-triazolin-5'-on-3'-yl)phenyl and R$^{1a}$ is as shown in Examples 5-1 through 5-32.

For Examples 5-353 through 5-384, G is 1-aminoisoquinolin-6-yl and R$^{1a}$ is as shown in Examples 5-1 through 5-32.

For Examples 5-385 through 5-416, G is 1-aminoisoquinolin-7-yl and R$^{1a}$ is as shown in Examples 5-1 through 5-32.

For Examples 5-417 through 5-448, G is 4-aminoquinazol-6-yl and R$^{1a}$ is as shown in Examples 5-1 through 5-32.

For Examples 5-449 through 5-480, G is 4-aminoquinazol-7-yl and R$^{1a}$ is as shown in Examples 5-1 through 5-32.

For Examples 5-481 through 5-512, G is 3-aminobenzisoxazol-5-yl and R$^{1a}$ is as shown in Examples 5-1 through 5-32.

For Examples 5-513 through 5-544, G is 3-aminobenzisoxazol-6-yl and R$^{1a}$ is as shown in Examples 5-1 through 5-32.

For Examples 5-545 through 5-576, G is 3-aminoindazol-5-yl and R$^{1a}$ is as shown in Examples 5-1 through 5-32.

For Examples 5-577 through 5-608, G is 3-aminoindazol-6-yl and R$^{1a}$ is as shown in Examples 5-1 through 5-32.

For Examples 5-609 through 5-640, G is indolin-5-yl and R$^{1a}$ is as shown in Examples 5-1 through 5-32.

For Examples 5-641 through 5-672, G is indolin-6-yl and R$^{1a}$ is as shown in Examples 5-1 through 5-32.

For Examples 5-673 through 5-704, G is 2-naphthyl and R$^{1a}$ is as shown in Examples 5-1 through 5-32.

For Examples 5-705 through 5-736, G is 3-amido-naphth-2-yl and R$^{1a}$ is as shown in Examples 5-1 through 5-32.

For Examples 5-737 through 5-768, G is 3-methylsulfonyl-naphth-2-yl and R$^{1a}$ is as shown in Examples 5-1 through 5-32.

For Examples 5-769 through 5-800, G is 3-aminomethyl-naphth-2-yl and R$^{1a}$ is as shown in Examples 5-1 through 5-32.

For Examples 5-801 through 5-832, G is 3-flouro-naphth-2-yl and R$^{1a}$ is as shown in Examples 5-1 through 5-32.

For Examples 5-833 through 5-864, G is 3-chloro-naphth-2-yl and R$^{1a}$ is as shown in Examples 5-1 through 5-32.

For Examples 5-865 through 5-896, G is 3-aminosulfonyl-naphth-2-yl and R$^{1a}$ is as shown in Examples 5-1 through 5-32.

For Examples 5-897 through 5-928, G is 6-chloro-naphth-2-yl and R$^{1a}$ is as shown in Examples 5-1 through 5-32.

Numerous modifications and variations of the present invention are possible in light of the above teachings. It is therefore to be understood that within the scope of the appended claims, the invention may be practiced otherwise that as specifically described herein.

What is claimed is:

1. A compound of formula I:

$$P_4\text{—}P\text{-}M\text{-}M_4 \qquad \qquad I$$

or a stereoisomer or pharmaceutically acceptable salt thereof, wherein;

M is pyrazole;

ring M is substituted with 0–3 $R^{1a}$;

ring P is absent and $P_4$ is directly attached to ring M;

one of $P_4$ and $M_4$ is -Z-A-B and the other -$G_1$-G;

G is a group of formula IIa or IIb:

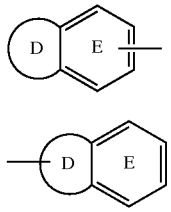

IIa

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–1 carbonyl and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $NHNH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$;

alternatively, when 2 R groups are attached to adjacent atoms, they combine to form methylenedioxy or ethylenedioxy;

A is phenyl substituted with 0–2 $R^4$;

B is imidazolyl substituted with 1 $R^{4a}$ and 0–2 $R^4$;

$G_1$ is absent or is selected from $(CR^3R^{3a})_{1-5}$, $(CR^3R^{3a})_{0-2}$ $CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_u$ $OC(O)(CR^3R^{3a})_w$, $(CR^3R^{3a})_uO(CR^3R^{3a})_w$, $(CR^3R^{3a})_u$ $N^{3b}(CR^3R^{3a})_w$, $(CR^3R^{3a})_uC(O)N^{3b}(CR^3R^{3a})_w$, $(CR^3R^{3a})_uN^{3b}C(O)(CR^3R^{3a})_w$, $(CR^3R^{3a})_uOC(O)N^{3b}$ $(CR^3R^{3a})_w$, $(CR^3R^{3a})_uN^{3b}C(O)O(CR^3R^{3a})_w$, $(CR^3R^{3a})_uN^{3b}C(O)N^{3b}(CR^3R^{3a})_w$, $(CR^3R^{3a})_uN^{3b}C(S)$ $N^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_u$ $S(O)N^{3b}(CR^3R^{3a})_w$, $(CR^3R^{3a})_u N^{3b}S(O)_2(CR^3R^{3a})_w$, $(CR^3R^{3a})_uS(O)_2N^{3b}(CR^3R^{3a})_w$, $(CR^3R^{3a})_uN^{3b}S(O)_2$ $N^{3b}(CR^3R^{3a})_w$, $(CR^3R^{3a})_uNR^{3e}(CR^3R^{3a})_w$, $(CR^3R^{3a})_u$ $C(O)(CR^3R^{3a})_uC(O)(CR^3R^{3a})_w$, $(CR^3R^{3a})_uNR^{3b}$ $(CR^3R^{3a})_uC(O)NR^{3b}(CR^3R^{3a})_w$, $(CR^3R^{3a})_uNR^{3b}C(O)$ $(CR^3R^{3a})_uC(O)(CR^3R^{3a})_w$, $(CR^3R^{3a})_uC(O)(CR^3R^{3a})_u$ $C(O)NR^{3b}(CR^3R^{3a})_w$, $(CR^3R^{3a})_uNR^{3b}C(O)(CR^3R^{3a})_u$ $C(O)NR^{3b}(CR^3R^{3a})_w$, $(CR^3R^{3a})_uS(O)NR^{3b}C(O)$ $(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w total 0, 1, 2, 3, or 4, provided that $G_1$ does not form a N—S, $NCH_2N$, $NCH_2O$, or $NCH_2S$ bond with either group to which it is attached;

Z is selected from C(O)NH and $C(O)CH_2$;

$R^{1a}$, at each occurrence, is selected from H, —$(CR^3R^{3a})_r$ —$R^{1b}$, —$(CR^3R^{3a})_r$—$CR^3R^{1b}R^{1b}$, —$(CR^3R^{3a})_r$—O— $(CR^3R^{3a})_r$—$R^{1b}$, —$(CR^3R^{3a})_r$—$NR^2$—$(CR^3R^{3a})_r$ —$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$ —$C(O)NR^2$—$(CR^3R^{3a})_r$—$R^{1b}$, —$(CR^3R^{3a})_r$—$C(O)_p$ $(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—$C(=NR^{1b})$ $NR^3R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and $S(O)_p$, this ring being substituted with 0–2 $R^{4b}$ and comprising: 0–3 double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_r$ $CO_2R^{2a}$, $S(O)_pR^{2b}$, $NR^2(CH_2)_rOR^2$, $C(=NR^{2c})$ $NR^2R^{2a}$, $NR^2C(O)R^{2b}$, $NR^2C(O)NR^2R^{2a}$, $NR^2C(O)_2$ $R^{2a}$, $OC(O)NR^2R^{2a}$, $C(O)NR^2R^{2a}$, $C(O)NR^2(CH_2)_r$ $OR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond and provided that $S(O)_pR^2$ forms other than $S(O)_2H$ or $S(O)H$;

$R^2$, at each occurrence, is selected from H, $CF_3$, $C_{1-6}$ alkyl, benzyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl, benzyl, —$(CH_2)_rC_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $C_{1-6}$ alkyl substituted with 0–2 $R^{4b}$, $-(CH_2)_r-C_{3-10}$ carbocycle substituted with 0–2 $R^{4b}$, and $-(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, $(CH_2)_r-C_{3-10}$ carbocycle substituted with 0–2 $R^{4b}$, and $-(CH_2)_r$-5–10 membered heterocycle containing from 1–4 heteroatoms selected from the group consisting of N, O, and and substituted with 0–2 $R^{4b}$;

$R^{2d}$, at each occurrence, is selected from H, $R^{4c}$, $C_{1-6}$ alkyl substituted with 0–2 $R^{4c}$, $-(CR^3R^{3a})_r-C_{3-10}$ carbocycle substituted with 0–2 $R^{4c}$, and $-(CR^3R^{3a})_r$-5–10 membered heterocycle consisting of: carbon atoms and 1–4 heteroatoms selected from the group consisting of N, O, and $S(O)_p$ and substituted with 0–2 $R^{4c}$, provided that $R^2d$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-6}$ alkyl substituted with 0–2 $R^{4c}$, $-(CR^3R^{3a})_r-C_{3-10}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $CF_3$, $C_{1-4}$ alkoxy substituted with 0–2 $R^{4b}$, $C_{1-6}$ alkyl substituted with 0–2 $R^{4b}$, $-(CH_2)_r-C_{3-10}$ carbocycle substituted with 0–2 $R^{4b}$, and $-(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $-(CH_2)_r$-3–6 membered carbocycle, and $-(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, F, Cl, Br, I, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_uC(=NR^2)NR^2R^{2a}$, $(CR^3R^{3a})_rC(=NS(O)_2R^{5a})NR^2R^{2a}$, $(CR^3R^{3a})_rNHC(=NR^2)NR^2R^{2a}$, $(CR^3R^{3a})_rC(O)NHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2-C_{1-4}$ alkyl, $(CR^3R^{3a})_rNR^2SO_2R^{5a}$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $N(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$ is selected from $(CR^3R^{3a})_v-NR^{2d}C(O)R^{2e}$, $(CR^3R^{3a})_v-C(O)NR^{2d}R^{2d}$; $(CR^3R^{3g})_v-NR^{2d}C(O)NR^{2d}R^{2d}$, $(CR^3R^{3g})_v-NR^{2d}C(O)OR^{2d}$, $(CR^3R^{3g})_v-SO_2NR^{2d}R^{2d}$, $(CR^3R^{3g})_v-NR^{2d}SO_2NR^{2d}R^{2d}$, $(CR^3R^{3g})_v-C(O)NR^{2d}SO_2R^{2d}$, $(CR^3R^{3g})_v-NR^{2d}SO_2R^{2d}$, and $(CR^3R^{3g})_v-S(O)_pR^{2d}$, provided that $S(O)_pR^{2d}$ forms other than $S(O)_2H$ or $S(O)H$;

alternatively, $R^{4a}$ is selected from $(CR^3R^{3g})_rNR^{2d}R^{2d}$, $NR^{2d}C(O)R^{2e}$, $C(O)NR^{2d}R^{2d}$, $NR^{2d}C(O)NR^{2d}R^{2d}$, $NR^{2d}C(O)OR^{2d}$, $SO_2NR^{2d}R^{2d}$, $NR^{2d}SO_2NR^{2d}R^{2d}$, $C(O)NR^{2d}SO_2R^{2d}$, $NR^{2d}SO_2R^{2d}$, and $S(O)_pR^{2d}$, provided that at least one of $R^{2d}$ and $R^{2e}$ is alkyl substituted with at least one $R^{4c}$ that is other than alkyl;

$R^{4b}$, at each occurrence, is selected from H, $=O$, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_r-C(=NR^3)NR^3R^{3a}$, $(CH_2)_rNR^3C(NR^3)NR^3R^{3a}$, $(CH_2)_rSO_2NR^3R^{3a}$, $(CH_2)_rNR^3SO_2NR^3R^{3a}$, $(CH_2)_rNR^3SO_2-C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p-C_{1-4}$ alkyl, $(CH_2)_rS(O)_p$-phenyl, and $(CH_2)_r(CF_2)_rCF_3$;

$R^{4c}$, at each occurrence, is selected from $=O$, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_r$ $C(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_r$ $NHC(=NR^2)NR^2R^{2a}$, $(CR^3R^{3a})_rSO_2NR^2R^{2a}$, $(CR^3R^{3a})_r$ $NR^2SO_2NR^2R^{2a}$, $(CR^3R^{3a})_rC(O)NHSO_2-$$C_{1-4}$ alkyl, $(CR^3R^{3a})_rNR^2SO_2R^{5a}$, $(CR^3R^{3a})_rS(O)_pR^{5a}$, $(CF_2)_r$ $CF_3$, $(CR^3R^{3a})_rC_{3-10}$ carbocycle substituted with 0–2 $R^{4b}$, and $(CR^3R^{3a})_r$-5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, $C_{1-6}$ alkyl, =O, $(CH_2)_rOR^3$, F, Cl, Br, I, —CN, $NO_2$, $(CH_2)_r$ $NR^3R^{3a}$, $(CH_2)_rC(O)R^3$, $(CH_2)_rC(O)OR^{3c}$, $(CH_2)_r$ $NR^3C(O)R^{3a}$, $(CH_2)_rC(O)NR^3R^{3a}$, $(CH_2)_rNR^3C(O)$ $NR^3R^{3a}$, $(CH_2)_rCH(NOR^{3d})$, $(CH_2)_rC(NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2-C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p-C_{1-4}$ alkyl, $(CH_2)_rS(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted, with 0–2 $R^6$, provided that $R^{5a}$ does not form a S—N or $S(O)_p$—C(O) bond;

$R^6$, at each occurrence, is selected from H, OH, $(CH_2)_r$ $OR^2$, halo, $C_{1-4}$ alkyl, CN, $NO_2$, $(CH_2)_rNR^2R^{2a}$, $(CH_2)_r$ $C(O)R^{2b}$, $NR^2C(O)R^{2b}$, $NR^2C(O)NR^2R^{2a}$, $C(NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-$CH_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, .4, 5, and 6;

t, at each occurrence, is selected from 0, 1, 2, and 3;

v, at each occurrence, is selected from 1, 2, 3, 4, 5, and 6.

2. A compound according to claim 1, wherein:

G is a group of formula IIa or IIb:

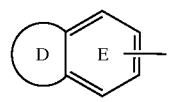

IIa

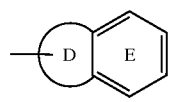

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with 1 R and with a 5 membered heterocycle consisting of: carbon atoms and 1–4 heteroatoms selected from the group consisting of N, O, and $S(O)_p$, wherein the 5 membered heterocycle is substituted with 0–1 carbonyl and 1–2 R and there are 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)$ $NHOH$, $C(=NH)NHOCH_3$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $(CR^8R^9)_rNR^7R^8$, $C(O)$ $NR^7R^8$, $CH_2C(O)NR^7R^8$, $S(O)_2R^3$, $S(O)_pNR^7R^8$, $CH_2S(O)_pNR^7R^8$, and $OCF_3$;

alternatively, when 2 R groups are attached to adjacent atoms, they combine to form methylenedioxy or ethylenedioxy;

$R^{1a}$, at each occurrence, is selected from H, —$(CH_2)_r$—$R^{1b}$, —$(CH(CH_3))_r$—$R^{1b}$, —$C(CH_3)_2)_r$—$R^{1b}$, —O—$(CR^3R^{3a})_r$—$R^{1b}$, —$NR^2(CR^3R^{3a})_u$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_p$ $R^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)$ $NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4a}$ is selected from $(CR^3R^{3a})_v$—$NR^{2d}C(O)R^{2e}$, $(CR^3R^{3a})_v$—$NR^{2d}C(O)NR^{2d}R^{2d}$, $(CR^3R^{3g})_v$—$NR^{2d}C(O)OR^{2d}$, $(CR^3R^{3g})_v$—$NR^{2d}SO_2NR^{2d}R^{2d}$, and $(CR^3R^{3g})_v$—$NR^{2d}SO_2R^{2d}$;

alternatively, $R^{4a}$ is selected from $(CR^3R^{3g})_rNR^{2d}R^{2d}$, $NR^{2d}C(O)R^{2e}$, $NR^{2d}C(O)NR^{2d}R^{2d}$, $NR^{2d}C(O)OR^{2d}$, $NR^{2d}SO_2NR^{2d}R^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^2a$, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$-5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

r, at each occurrence, is selected from 0, 1, and 2; and, v, at each occurrence, is selected from 1, 2, and 3.

3. A compound according to claim 2, wherein:

G is selected from the group:

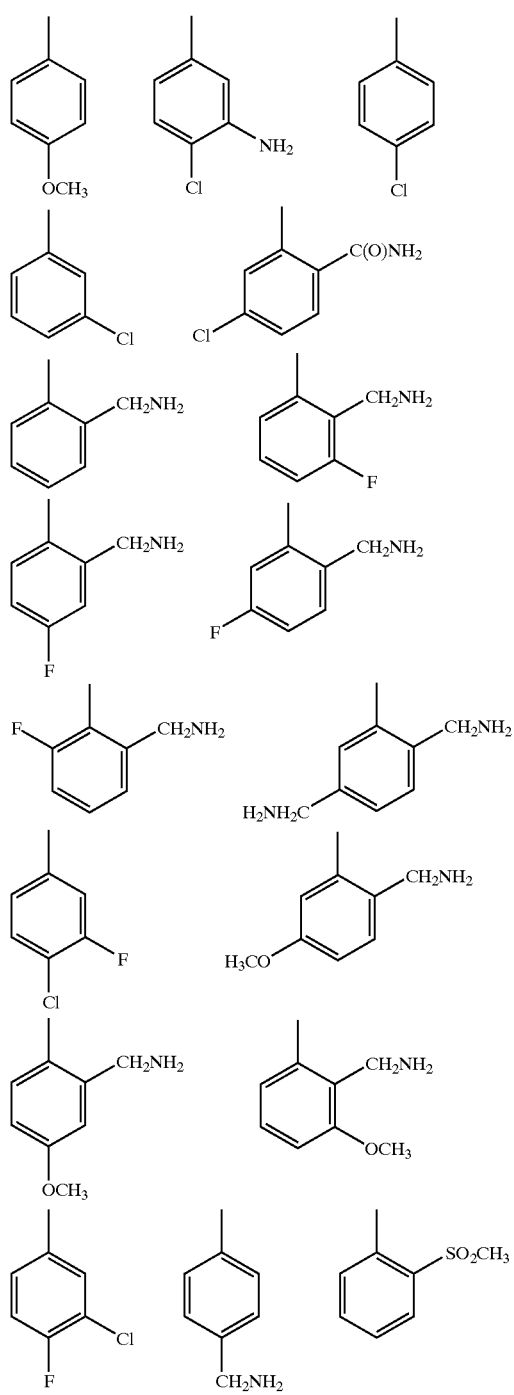

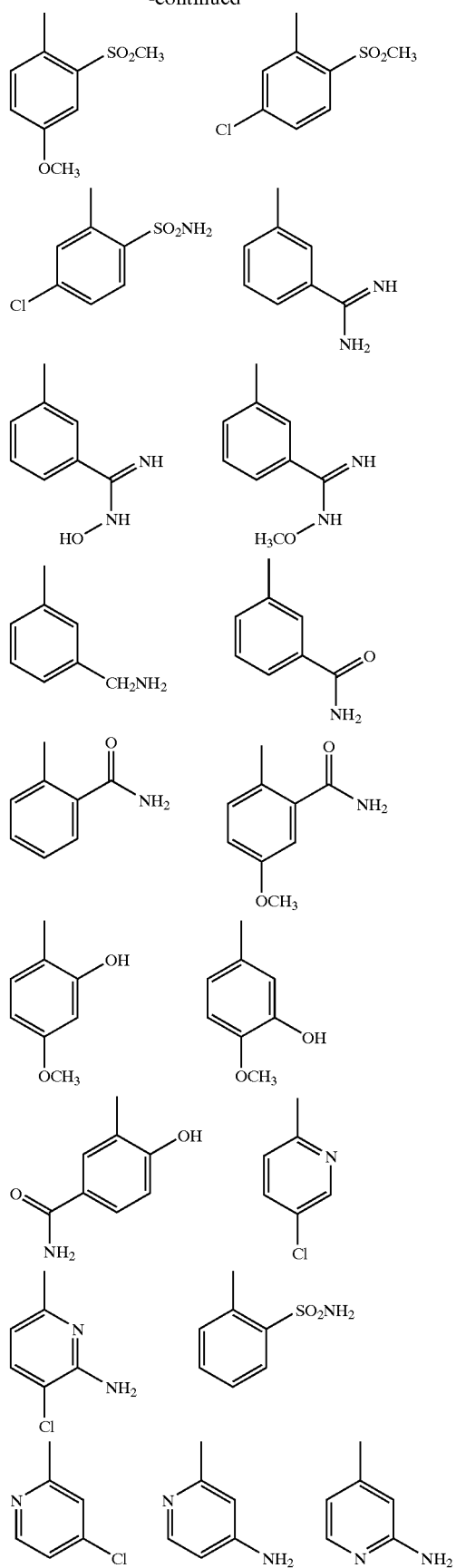

-continued
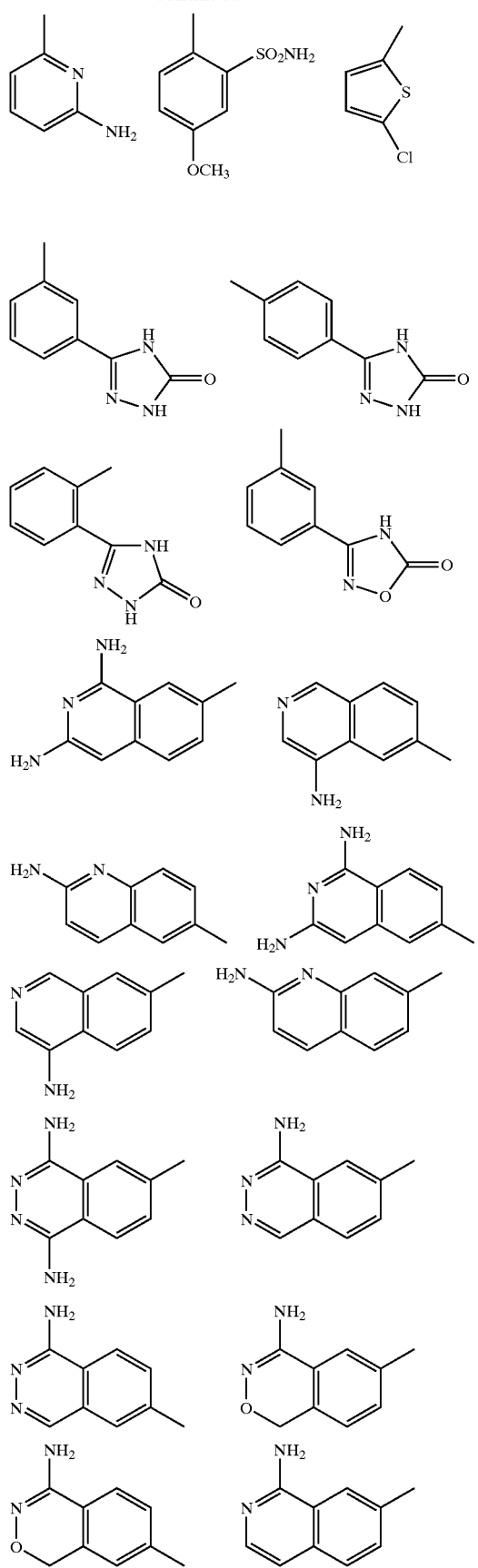
-continued
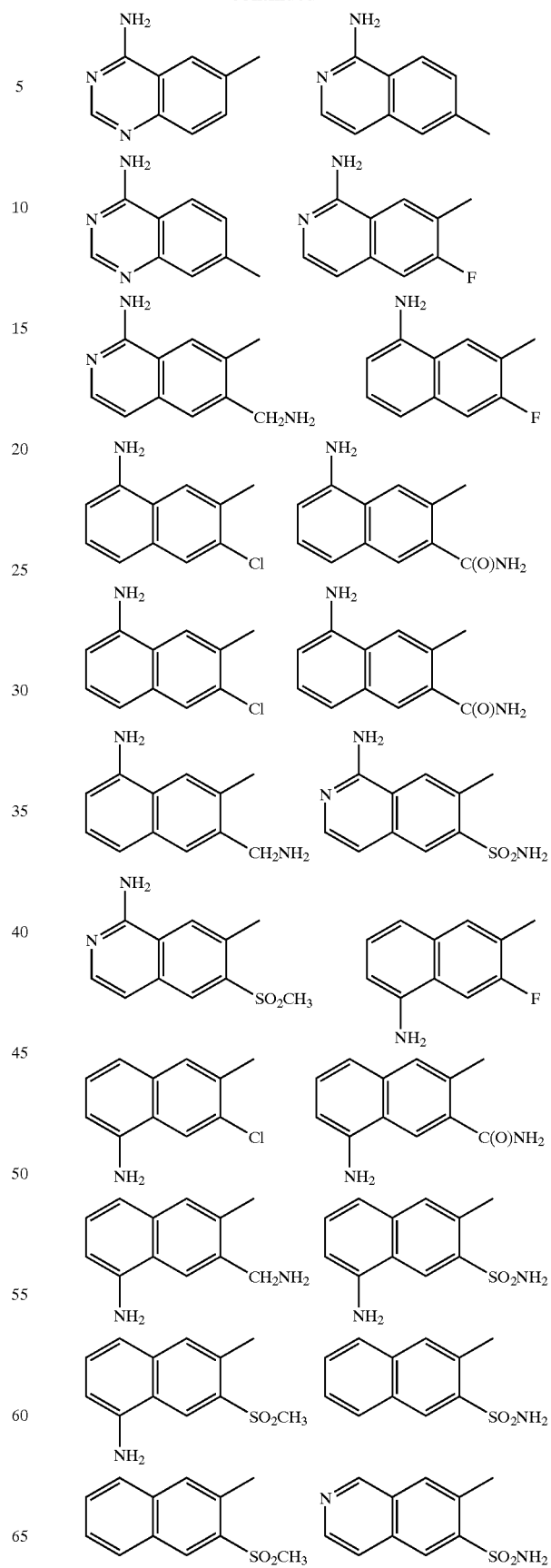

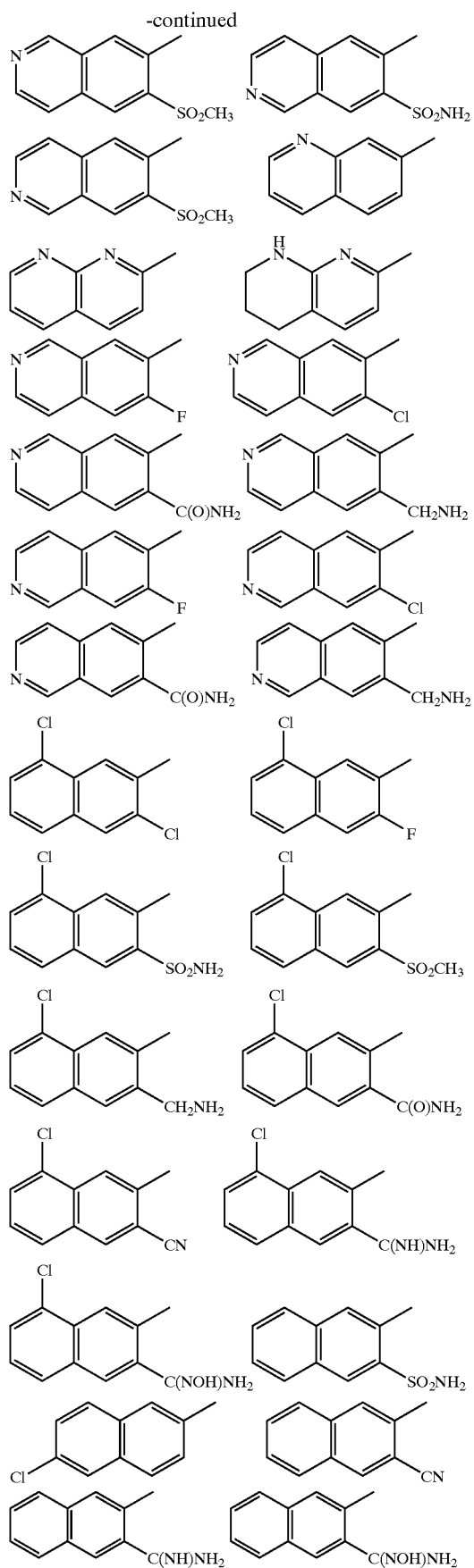
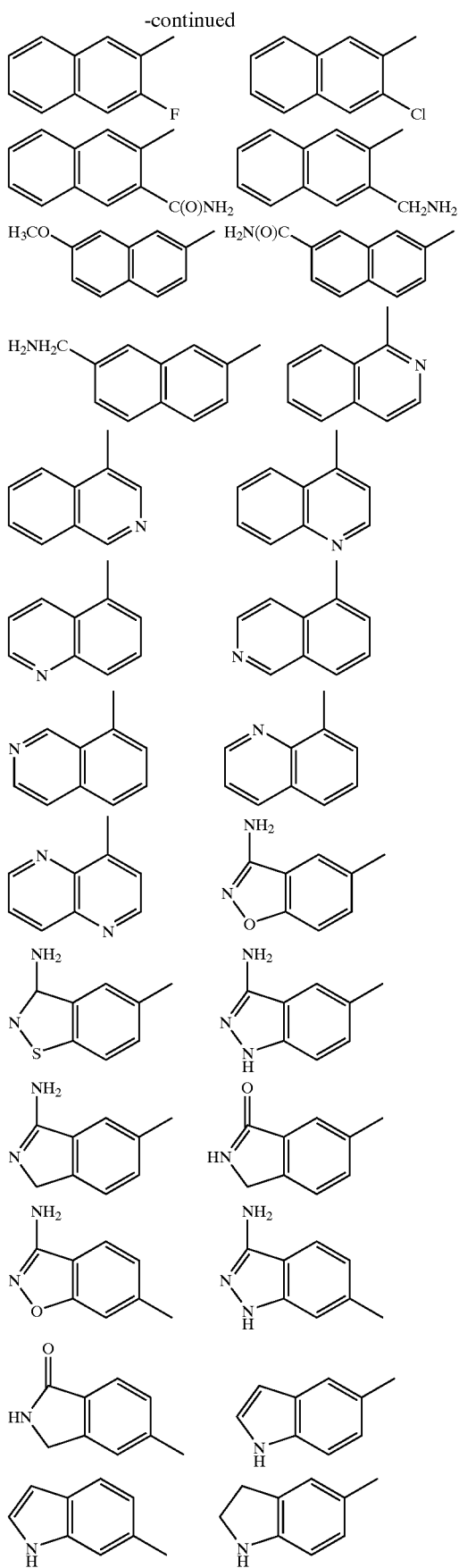

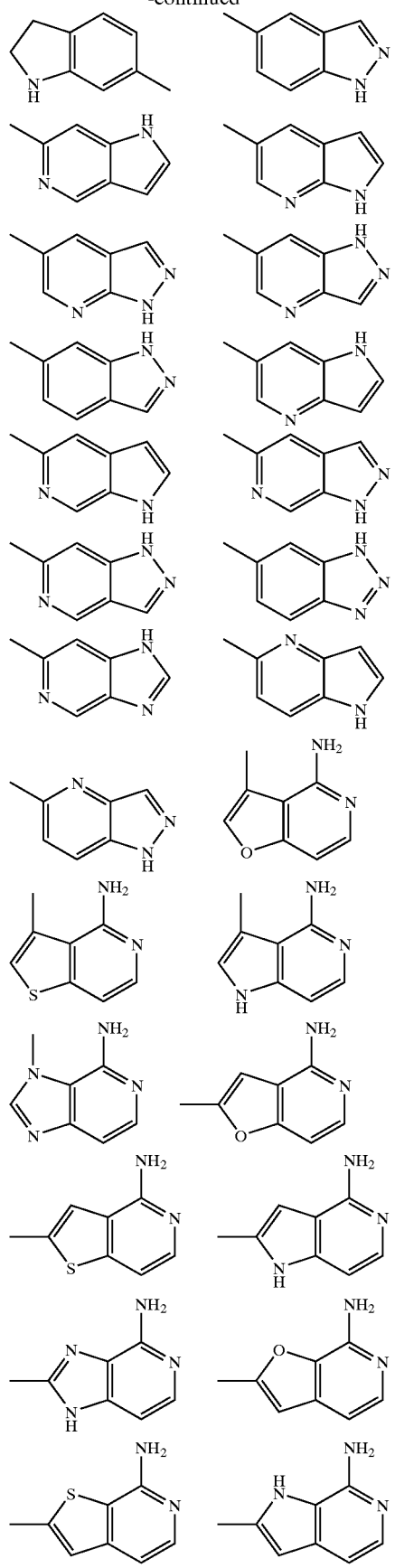
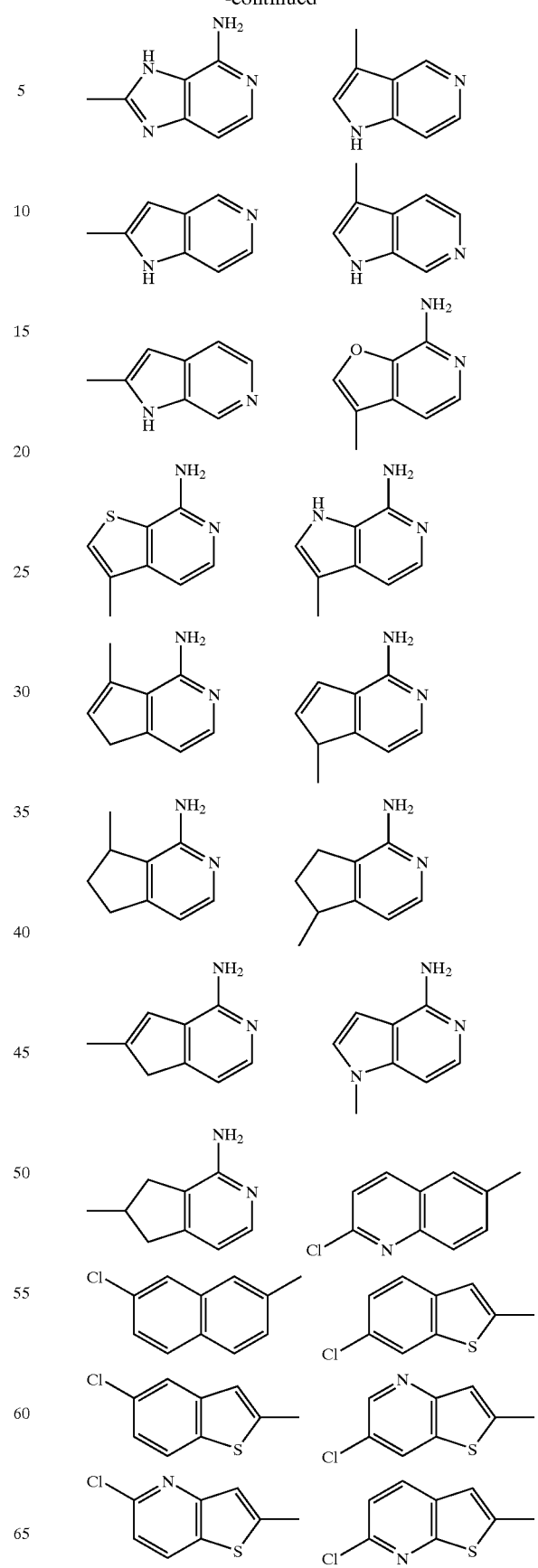

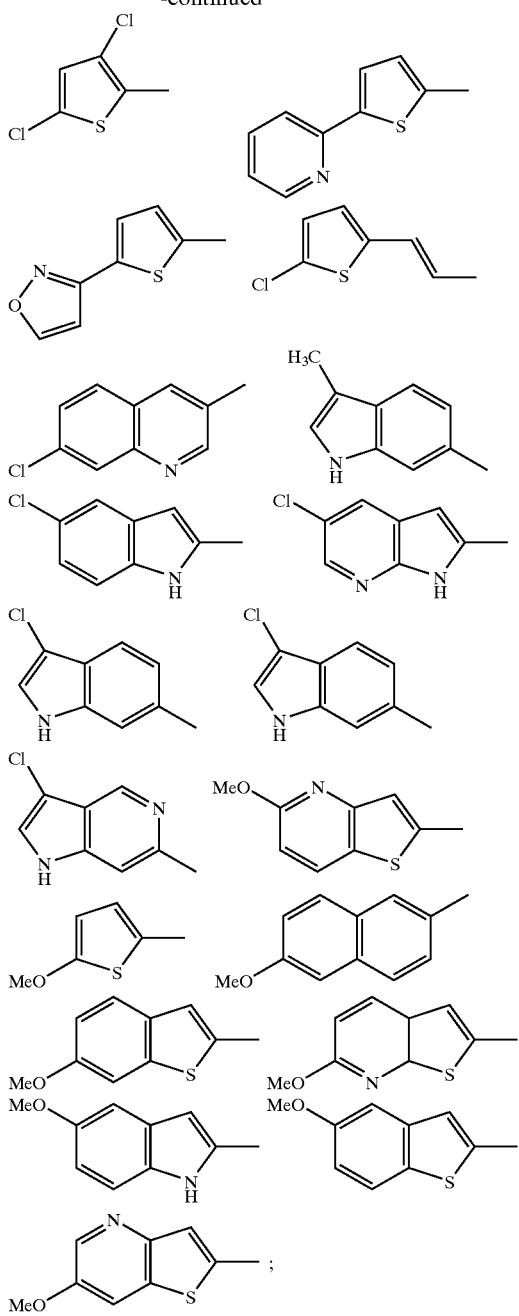

$G_1$ is absent or is selected from $(CR^3R^{3a})_{1-3}$, $(CR^3R^{3a})_u$ $C(O)(CR^3R^{3a})_w$, $(CR^3R^{3a})_uO(CR^3R^{3a})_w$, $(CR^3R^{3a})_u$ $NR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)$ $(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}$ $(CR^3R^{3a})_w$, $(CR^3R^{3a})_u NR^{3b}S(O)_2(CR^3R^{3a})_w$, $(CR^3R^{3a})_uS(O)_2NR^{3b}(CR^3R^{3a})_w$, and $(CR^3R^{3a})_uC(O)$ $NR^{3b}S(O)_2(CR^3R^{3a})_w$, wherein u+w total 0, 1, or 2, provided that $G_1$ does not form a N—S, $NCH_2N$, $NCH_2O$, or $NCH_2S$ bond with either group to which it is attached;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)$ $R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^1$ b forms other than an O—O, N-halo, N—S, or N—CN bond;

B is imidazolyl substituted with 1 $R^{4a}$ and 0–1 $R^4$;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle Consisting of: carbon atoms and 1–4 heteroatoms selected from the group consisting of N, O, and $S(O)_p$ and substituted with 0–2 $R^{4c}$, and —$(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a N-halo, N—C-halo, $S(O)_p$-halo, O-halo, N—S, S—N, $S(O)_p$—$S(O)_p$, S—O, O—N, O—S, or O—O moiety;

$R^{2a}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $(CR^3R^{3a})$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from H, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$ is selected from $(CH_2)_v$—$NR^{2d}C(O)R^{2e}$, $(CH_2)_v$—$NR^{2d}C(O)NR^{2d}R^{2d}$, $(CH_2)_v$—$NR^{2d}C(O)OR^{2d}$, and $(CH_2)_v$—$NR^{2d}SO_2R^{2d}$;

alternatively, $R^{4a}$ is selected from $(CH_2)_rNR^{2d}R^{2d}$, $NR^{2d}C(O)R^{2e}$, $NR^{2d}C(O)NR^{2d}R^{2d}$, $NR^{2d}C(O)OR^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_{2a}C(O)OR^{3c}$, $NR^3C(O)R^{3a}$, $CH_2NR^3C(O)R^{3a}$, $C(O)NR^3R^{3a}$, $CH_{2a}C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})_r$, Br, $(CR^3R^{3a})Br$, Cl, $(CR^3R^{3a})Cl$, $CF_3$, $(CR^3R^{3a})CF_3$, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2$—$C_{1-4}$ alkyl; and, v, at each occurrence, is selected from 1 and 2.

4. A compound according to claim 3, wherein the compound is selected from:

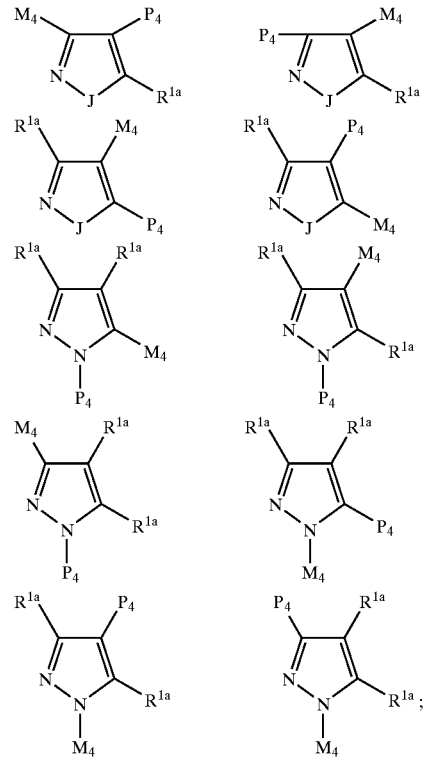

J is selected from NH and $NR^{1a}$;

G is selected from the group:

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, C(O)NH, NHC(O), NHC(O)NH, $C(O)NHS(O)_2$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

$R^{1a}$ is selected from H, $R^{1b}$, $C(CH_3)_2R^{1b}$, and $CH_2R^{1b}$, provided that $R^{1a}$ forms other than an N-halo, N—S, or N—CN bond;

$R^1$ b is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —($CH_2$)-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —($CH_2$)—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —($CH_2$)-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$ is selected from $(CH_2)_v$—$NR^{2d}C(O)R^{2e}$, $(CH_2)_v$—$NR^{2d}C(O)NR^{2d}R^{2d}$, $(CH_2)_v$—$NR^{2d}C(O)OR^{2d}$, and $(CH_2)_v$—$NR^{2d}SO_2R^{2d}$;

alternatively, $R^{4a}$ is selected from $(CH_2)_rNR^{2d}R^{2d}$, $NR^{2d}C(O)R^{2e}$, $NR^{2d}C(O)NR^{2d}R^{2d}$, $NR^{2d}C(O)OR^{2d}$, and $NR^{2d}SO_2R^{2d}$, provided that at least one of $R^{2d}$ and $R^{2e}$ is alkyl substituted with at least one $R^{4c}$ that is other than alkyl;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $C_{1-4}$ alkyl, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, ($CH_2$)$C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and ($CH_2$)-5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^2$a.

5. A compound according to claim 4, wherein the compound is selected from:

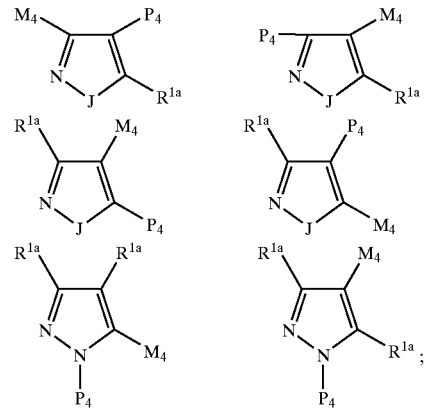

J is selected from NH and $NR^{1a}$;

$P_4$ is -$G_1$-G;

$M_4$ is -Z-A-B;

G is selected from:

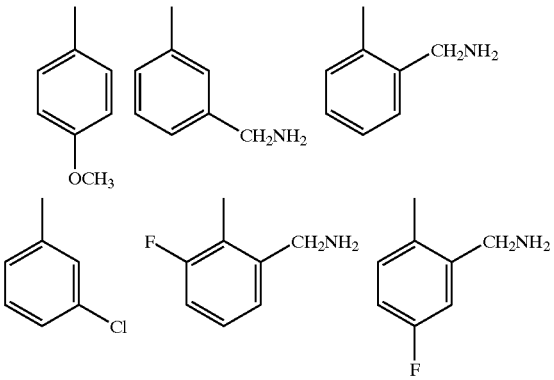

245
-continued
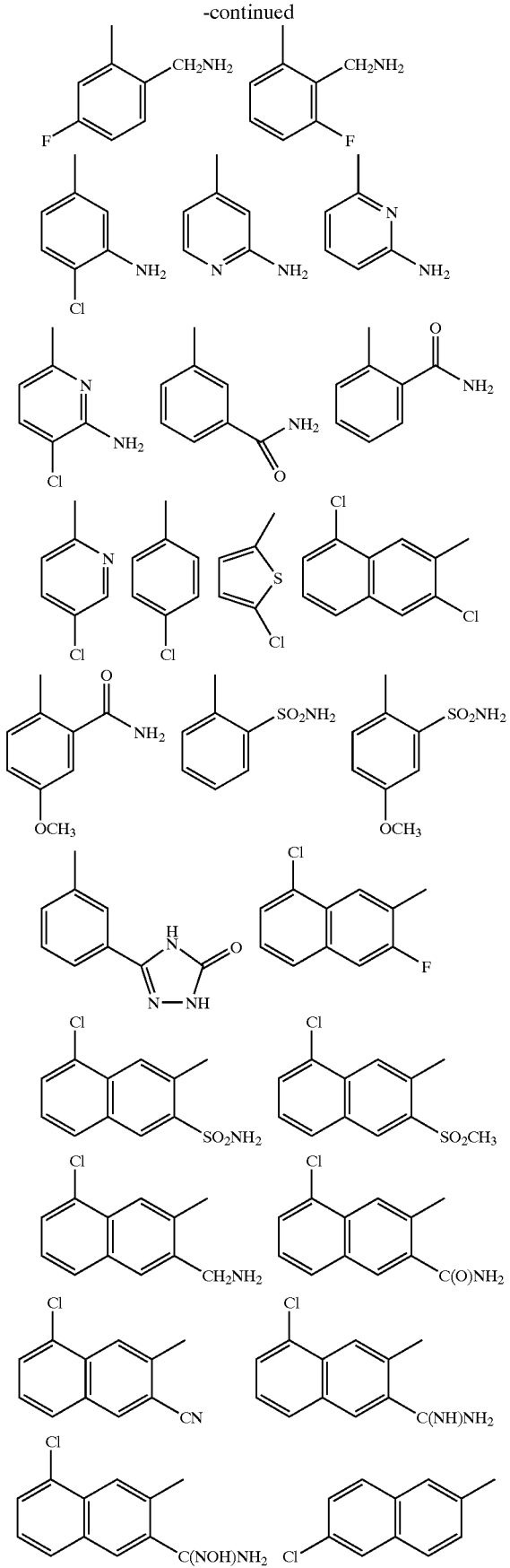
246
-continued
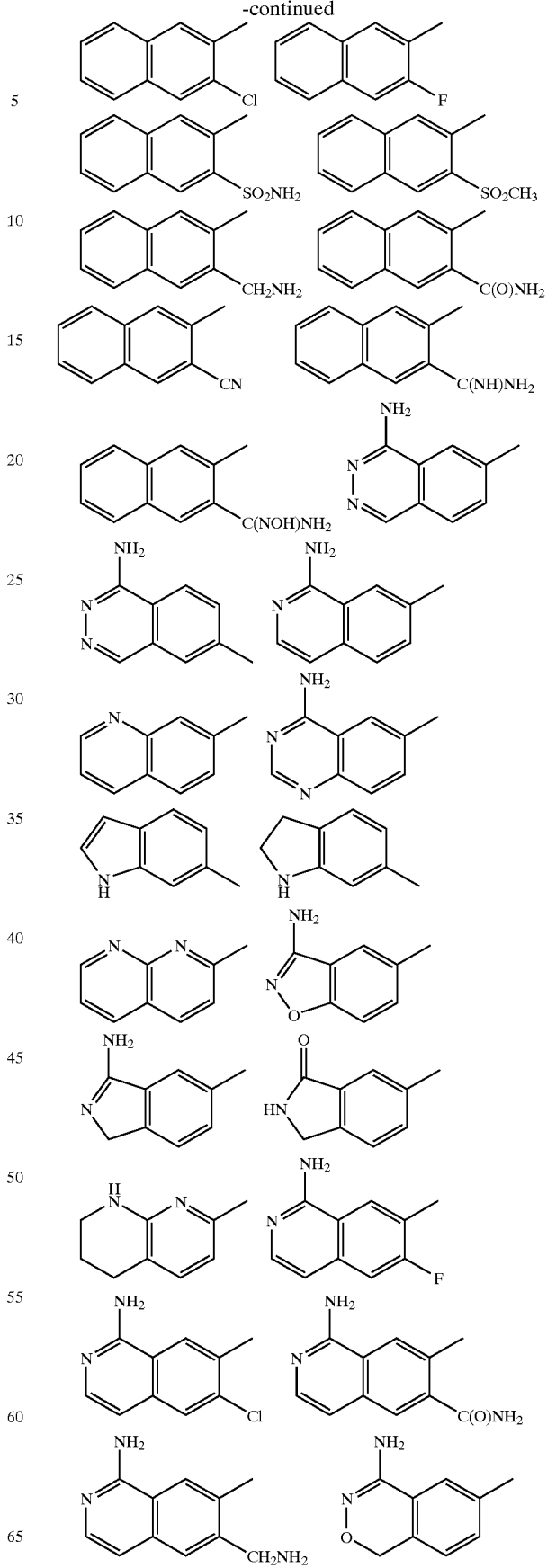

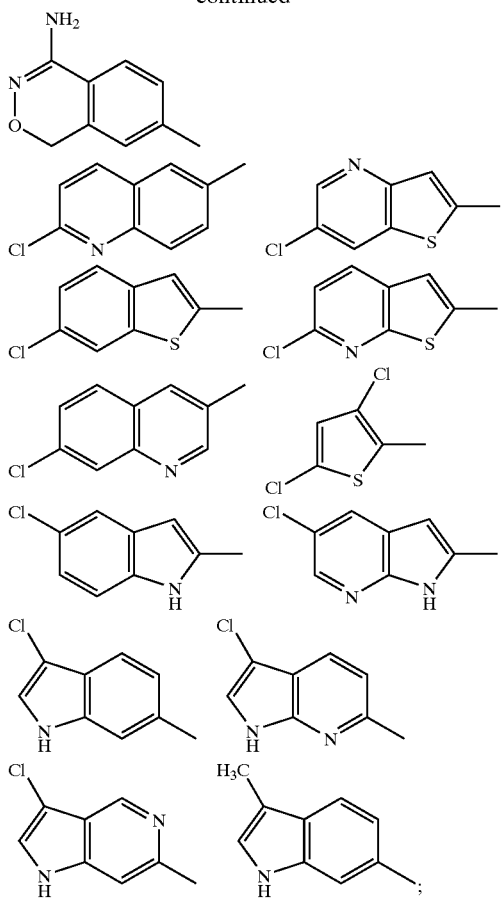

G$_1$ is absent or is selected from CH$_2$NH, NHCH$_2$, CH$_2$C(O), C(O)CH$_2$, C(O)NH, NHC(O), NHC(O)NH, CH$_2$S(O)$_2$, S(O)$_2$(CH$_2$), SO$_2$NH, and NHSO$_2$, provided that G$_1$ does not form a N—S, NCH$_2$N, NCH$_2$O, or NCH$_2$S bond with either group to which it is attached;

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl;

B is imidazolyl substituted with 1 R$^{4a}$;

R$^{1a}$ is selected from H, CH$_3$, CH$_2$CH$_3$, CH$_2$CH$_2$CH$_3$, CH$_2$F, CH$_2$Cl, Br, CH$_2$Br, —CN, CH$_2$CN, CF$_3$, CH$_2$CF$_3$, OCH$_3$, CH$_2$OH, C(CH$_3$)$_2$OH, CH$_2$OCH$_3$, NH$_2$, CH$_2$NH$_2$, NHCH$_3$, CH$_2$NHCH$_3$, N(CH$_3$)$_2$, CH$_2$N(CH$_3$)$_2$, CO$_2$H, COCH$_3$, CO$_2$CH$_3$, CH$_2$CO$_2$CH$_3$, SCH$_3$, CH$_2$SCH$_3$, S(O)CH$_3$, CH$_2$S(O)CH$_3$, S(O)$_2$CH$_3$, CH$_2$S(O)$_2$CH$_3$, C(O)NH$_2$, CH$_2$C(O)NH$_2$, SO$_2$NH$_2$, CH$_2$SO$_2$NH$_2$, NHSO$_2$CH$_3$, CH$_2$NHSO$_2$CH$_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, CH$_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, CH$_2$-1,2,3,4-tetrazol-1-yl, and CH$_2$-1,2,3,4-tetrazol-5-yl, provided that R$^{1a}$ forms other than an N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5 membered aromatic heterocycle consisting of: carbon atoms and 1–4 hereroatoms selected from the group consisting of N, O, and S(O)$_p$ and substituted with 0–1 R$^{4b}$;

R$^{2a}$, at each occurrence, is selected from H, CH$_3$, and CH$_2$CH$_3$;

alternatively, R$^2$ and R$^{2a}$, together with the atom to which they are attached, combine to form a 5 or 6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OH, OCH$_3$, OCH$_2$CH$_3$, CH$_3$, and CH$_2$CH$_3$;

R$^{2c}$, at each occurrence, is selected from OH, OCH$_3$, OCH$_2$CH$_3$, CH$_3$, and CH$_2$CH$_3$;

R$^{2d}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle consisting of: carbon atoms and 1–4 heteroatoms selected from the group consisting of N, O, and S(O)$_p$ and substituted with 0–2 R$^{4c}$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ cycloalkyl substituted with 0–2 R$^{4c}$, phenyl substituted with 0–2 R$^{4c}$, and 5–6 membered aromatic heterocycle consisting of: carbon atoms and 1–4 heteroatoms selected from the group consisting of N, O, and S(O)$_p$ and substituted with 0–2 R$^{4c}$, provided that R$^{2e}$ forms other than a C(O)-halo or C(O)—S(O)$_p$ moiety;

R$^{4a}$ is selected from CH$_2$NR$^{2d}$C(O)R$^{2e}$, CH$_2$NR$^{2d}$C(O)NR$^{2d}$R$^{2d}$, CH$_2$NR$^{2d}$C(O)OR$^{2d}$, and CH$_2$NR$^{2d}$SO$_2$R$^{2d}$;

R$^{4b}$, at each occurrence, is selected from H, =O, OR$^3$, CH$_2$OR$^3$, F, Cl, CH$_3$, CH$_2$CH$_3$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$-phenyl, S(O)$_2$CH$_3$, S(O)$_2$-phenyl, and CF$_3$;

R$^{4c}$, at each occurrence, is selected from =O, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, CH$_2$OH, CH$_2$OCH$_3$, CH$_2$OCH$_2$CH$_3$, CH$_2$OCH$_2$CH$_2$CH$_3$, CH$_2$OCH(CH$_3$)$_2$, F, Br, Cl, CF$_3$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O)R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, cyclopropyl substituted with 0–1 R$^{4b}$, cyclobutyl substituted with 0–1 R$^{4b}$, cyclopentyl substituted with 0–1 R$^{4b}$, phenyl substituted with 0–1 R$^{4b}$, —CH$_2$-cyclopropyl substituted with 0–1 R$^{4b}$, —CH$_2$-cyclobutyl substituted with 0–1 R$^{4b}$, —CH$_2$-cyclopentyl substituted with 0–1 R$^{4b}$, benzyl substituted with 0–2 R$^{4b}$, 5–6 membered aromatic heterocycle consisting of carbon atoms and from 1–4 heteroatoms selected from the group consisting of N, O, and S(O)$_p$ and substituted with 0–2 R$^{4b}$, and (CH$_2$)-5–6 membered aromatic heterocycle consisting of carbon atoms and from 1–4 heteroatoms selected from the group consisting of N, O, and S(O)$_p$ and substituted with 0–2 R$^{4b}$;

R$^5$, at each occurrence, is selected from H, =O, CH$_3$, CH$_2$CH$_3$, OR$^3$, CH$_2$OR$^3$, F, Cl, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_2$—CH$_3$, S(O)$_2$-phenyl, CF$_3$, phenyl substituted with 0–2 R$^6$, naphthyl substituted with 0–2 R$^6$, and benzyl substituted with 0–2 R$^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

6. A compound according to claim 5, wherein the compound is selected from:

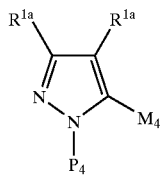 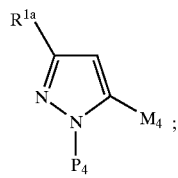

G is selected from:

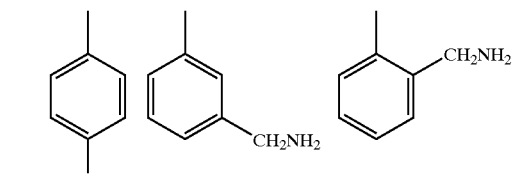

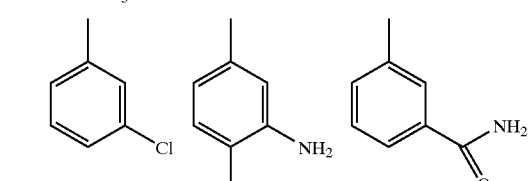

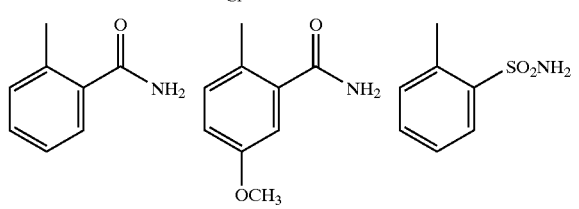

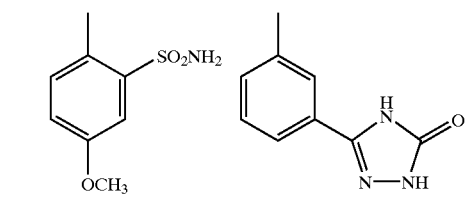

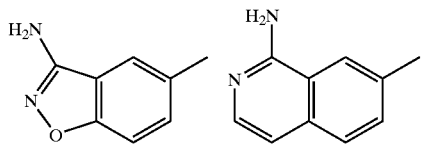

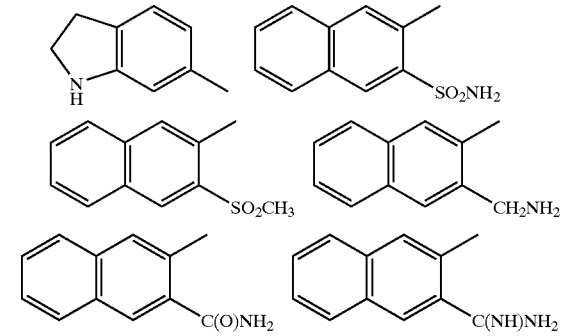

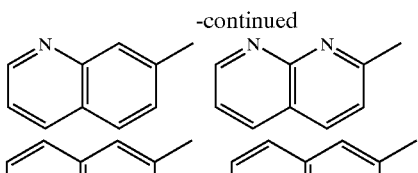

A-B is selected from:

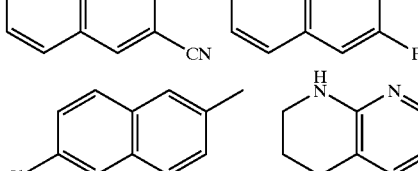

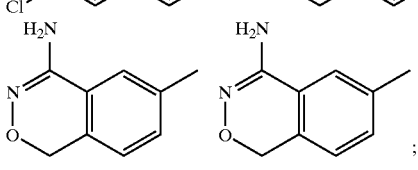

$R^{2d}$, at each occurrence, is selected from H, $C_{1-4}$ alkyl substituted with 0–1 $R^{4c}$, $C_{3-6}$ cycloalkyl substituted with 0–2 $R^{4a}$, phenyl substituted with 0–2 $R^{4c}$, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $C_{1-4}$ alkyl substituted with 0–1 $R^{4c}$, $C_{3-6}$ cycloalkyl substituted with 0–2 $R^{4c}$, phenyl, substituted with 0–2 $R^{4c}$, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety;

$R^{4a}$ is selected from $CH_2NR^{2d}C(O)R^{2e}$, $CH_2NR^{2d}C(O)OR^{2d}$, and $CH_2NR^{2d}SO_2R^{2d}$; and, $R^{4c}$ is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, and $CH_2S(O)_pR^{5a}$.

7. A compound according to claim 6, wherein the compound is selected from:

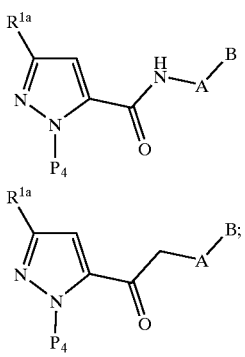

$P_4$ is -G; and

A-B is selected from:

$R^{2d}$, at each occurrence, is selected from H, $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl; and, $R^{2e}$, at each occurrence, is selected from $CH_3$, $CH_2CH_3$, $CH_2CH_2CH_3$, $CH(CH_3)_2$, $CH_2CH(CH_3)_2$, $CH_2CH_2CH(CH_3)_2$, $CH_2$-cyclopropyl, cyclopropyl, and cyclopentyl.

8. A compound according to claim 1, wherein the compound is selected from the group:

N-[4-(2-{[acetyl(methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide;

N-[4-(2-{[acetyl(methyl)amino]methyl}-1H-imidazol-1-yl)-2-fluorophenyl]-1-(3-amino-1,2-benzisoxazol-5-yl)-3-(methylsulfonyl)-1H-pyrazole-5-carboxamide;

N-[4-(2-{[methylsulfonylamino]methyl}-1H-imidazol-1-yl)-2-fluorophenyl]-1-(4-methoxyphenyl)-3-(methylsulfonyl)-1H-pyrazole-5-carboxamide;

N-[4-(2-{[methylsulfonylamino]methyl}-1H-imidazol-1-yl)-2-fluorophenyl]-1-(4-methoxyphenyl)-3-(aminocarbonyl)-1H-pyrazole-5-carboxamide;

or a pharmaceutically acceptable salt form thereof.

9. A pharmaceutical composition, comprising: a pharmaceutically acceptable carrier and a therapeutically effective amount of a compound of claim 1 or a pharmaceutically acceptable salt form thereof.

10. A method for treating a thromboembolic disorder, comprising: administering to a patient in need thereof a therapeutically effective amount of a compound of claim 1 or a pharmaceutically acceptable salt form thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart.

12. A method according to claim 10, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A pharmaceutical composition, comprising: a pharmaceutically acceptable carrier and a therapeutically effective amount of a compound of claim 2 or a pharmaceutically acceptable salt form thereof.

14. A pharmaceutical composition, comprising: a pharmaceutically acceptable carrier and a therapeutically effective amount of a compound of claim 3 or a pharmaceutically acceptable salt form thereof.

15. A pharmaceutical composition, comprising: a pharmaceutically acceptable carrier and a therapeutically effective amount of a compound of claim 4 or a pharmaceutically acceptable salt form thereof.

16. A pharmaceutical composition, comprising: a pharmaceutically acceptable carrier and a therapeutically effective amount of a compound of claim 5 or a pharmaceutically acceptable salt form thereof.

17. A pharmaceutical composition, comprising: a pharmaceutically acceptable carrier and a therapeutically effective amount of a compound of claim 6 or a pharmaceutically acceptable salt form thereof.

18. A pharmaceutical composition, comprising: a pharmaceutically acceptable carrier and a therapeutically effective amount of a compound of claim 7 or a pharmaceutically acceptable salt form thereof.

19. A pharmaceutical composition, comprising: a pharmaceutically acceptable carrier and a therapeutically effective amount of a compound of claim 8 or a pharmaceutically acceptable salt form thereof.

20. A method for treating a thromboembolic disorder, comprising: administering to a patient in need thereof a therapeutically effective amount of a compound of claim 2 or a pharmaceutically acceptable salt form thereof.

21. A method according to claim 20, wherein the thromboembolic disorder is selected from the group consisting of arterial cardiovascular thromboembolic disorders, venous cardiovascular thromboembolic disorders, and thromboembolic disorders in the chambers of the heart.

22. A method according to claim 20, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

23. A method for treating a thromboembolic disorder, comprising: administering to a patient in need thereof a therapeutically effective amount of a compound of claim 3 or a pharmaceutically acceptable salt form thereof.

24. A method according to claim 23, wherein the thromboembolic disorder is selected from the group consisting of arterial cardiovascular thromboembolic disorders, venous cardiovascular thromboembolic disorders, and thromboembolic disorders in the chambers of the heart.

25. A method according to claim 23, the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

26. A method for treating a thromboembolic disorder, comprising: administering to a patient in need thereof a therapeutically effective amount of a compound of claim 4 or a pharmaceutically acceptable salt form thereof.

27. A method according to claim 26, wherein the thromboembolic disorder is selected from the group consisting of arterial cardiovascular thromboembolic disorders, venous cardiovascular thromboembolic disorders, and thromboembolic disorders in the chambers of the heart.

28. A method according to claim 26, wherein the disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

29. A method for treating a thromboembolic disorder, comprising: administering to a patient in need thereof a therapeutically effective amount of a compound of claim 5 or a pharmaceutically acceptable salt form thereof.

30. A method according to claim 29, wherein the thromboembolic disorder is selected from the group consisting of arterial cardiovascular thromboembolic disorders, venous cardiovascular thromboembolic disorders, and thromboembolic disorders in the chambers of the heart.

31. A method according to claim 29, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

32. A method for treating a thromboembolic disorder, comprising: administering to a patient in need thereof a therapeutically effective amount of a compound of claim 6 or a pharmaceutically acceptable salt form thereof.

33. A method according to claim 32, wherein the thromboembolic disorder is selected from the group consisting of arterial cardiovascular thromboembolic disorders, venous cardiovascular thromboembolic disorders, and thromboembolic disorders in the chambers of the heart.

34. A method according to claim 32, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

35. A method for treating a thromboembolic disorder, comprising: administering to a patient in need thereof a therapeutically effective amount of a compound of claim 7 or a pharmaceutically acceptable salt form thereof.

36. A method according to claim 35, wherein the thromboembolic disorder is selected from the group consisting of arterial cardiovascular thromboembolic disorders, venous cardiovascular thromboembolic disorders, and thromboembolic disorders in the chambers of the heart.

37. A method according to claim 35, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

38. A method for treating a thromboembolic disorder, comprising: administering to a patient in need thereof a therapeutically effective amount of a compound of claim 8 or a pharmaceutically acceptable salt form thereof.

39. A method according to claim 38, wherein the thromboembolic disorder is selected from the group consisting of arterial cardiovascular thromboembolic disorders, venous cardiovascular thromboembolic disorders, and thromboembolic disorders in the chambers of the heart.

40. A method according to claim 38, wherein the thromboembolic disorder is selected from unstable angina, an acute coronary syndrome, first myocardial infarction, recurrent myocardial infarction, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *

UNITED STATES PATENT AND TRADEMARK OFFICE
CERTIFICATE OF CORRECTION

PATENT NO. : 6,949,550 B2  Page 1 of 6
APPLICATION NO. : 10/304810
DATED : September 27, 2005
INVENTOR(S) : Mimi L. Quan and Ruth R. Wexler It is certified that error appears in the above-identified patent and that said Letters Patent is hereby corrected as shown below:

Column 223,
Line 26, delete the "with 1-2R;" and insert -- with 1-2R; --;

Column 225,
Line 12, delete the "N, O, and and substituted" and insert -- N, O, and substituted --;

Column 225,
Line 20, delete the "$R^2d$" and insert -- $R^{2d}$ --;

Column 230,
Line 49, delete the "$(CR^3R^{3a})_rNR^2SO_2NR^2R^2a$" and insert -- $(CR^3R^{3a})_rNR^2SO_2NR^2R^{2a}$ --;

Column 240,
Line 15, delete the "that $R^1$ b forms" and insert -- that $R^{1b}$ forms --;

Column 242,
Line 35, delete the "G is selected from the group:" and insert -- G is selected from the group:

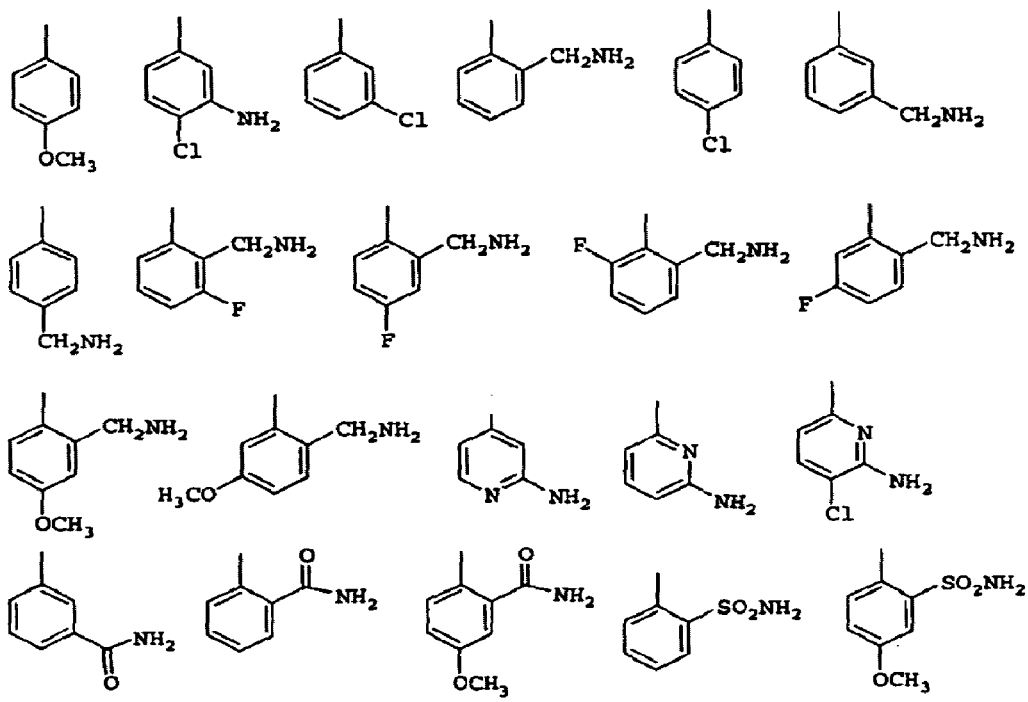

UNITED STATES PATENT AND TRADEMARK OFFICE
CERTIFICATE OF CORRECTION

PATENT NO. : 6,949,550 B2
APPLICATION NO. : 10/304810
DATED : September 27, 2005
INVENTOR(S) : Mimi L. Quan and Ruth R. Wexler Page 2 of 6

It is certified that error appears in the above-identified patent and that said Letters Patent is hereby corrected as shown below:

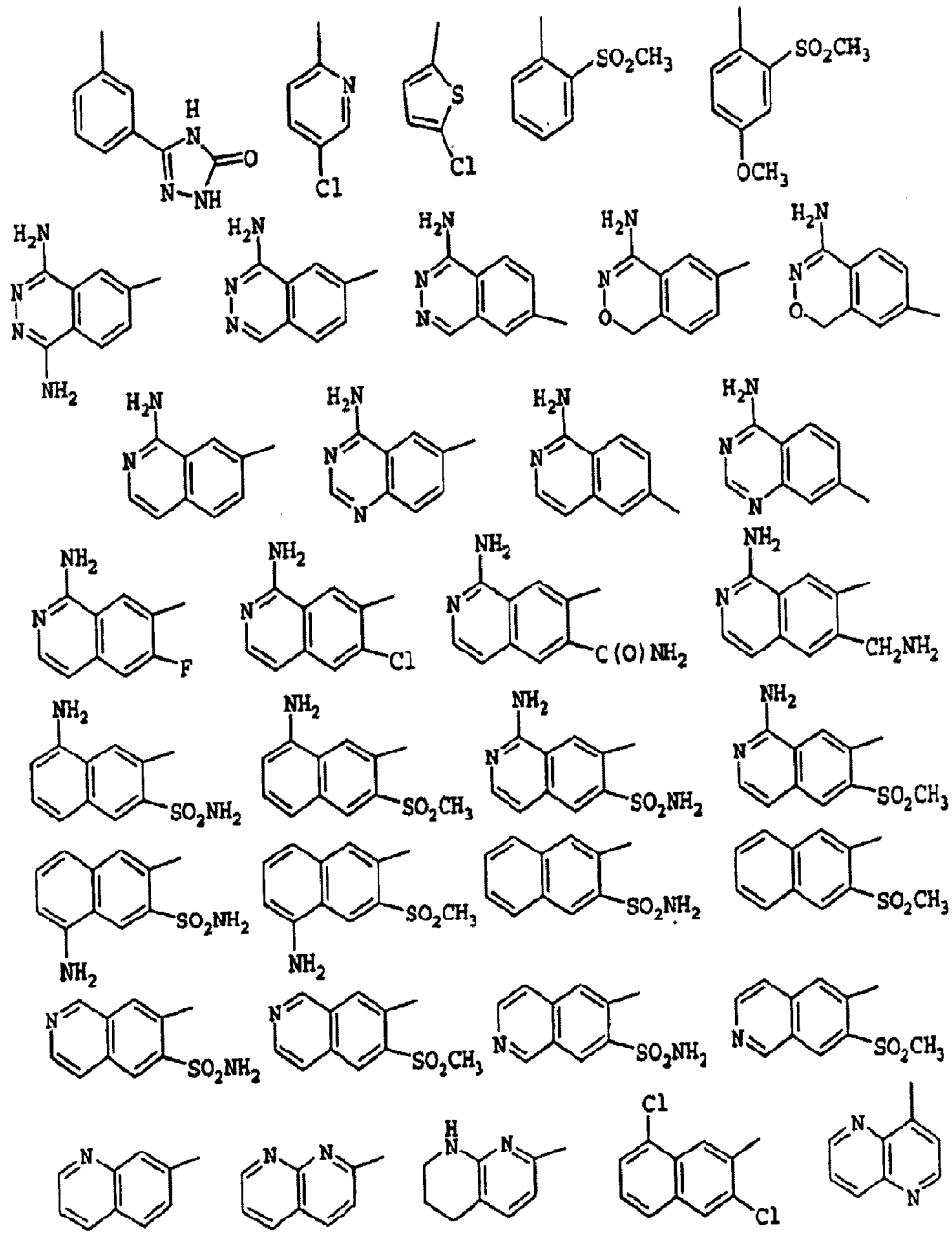

UNITED STATES PATENT AND TRADEMARK OFFICE
CERTIFICATE OF CORRECTION

PATENT NO. : 6,949,550 B2
APPLICATION NO. : 10/304810
DATED : September 27, 2005
INVENTOR(S) : Mimi L. Quan and Ruth R. Wexler It is certified that error appears in the above-identified patent and that said Letters Patent is hereby corrected as shown below:

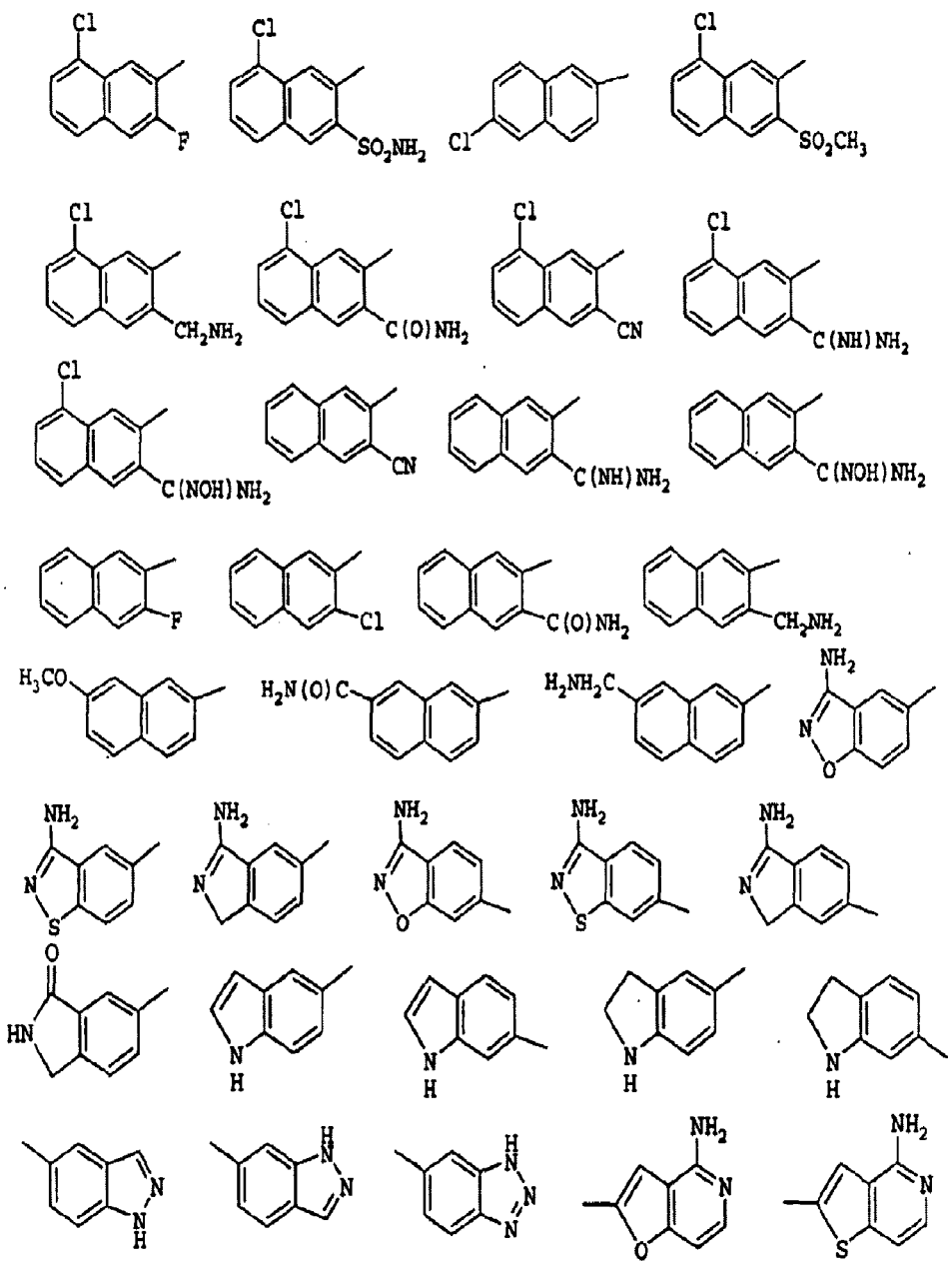

UNITED STATES PATENT AND TRADEMARK OFFICE
CERTIFICATE OF CORRECTION

PATENT NO.       : 6,949,550 B2
APPLICATION NO.  : 10/304810
DATED            : September 27, 2005
INVENTOR(S)      : Mimi L. Quan and Ruth R. Wexler It is certified that error appears in the above-identified patent and that said Letters Patent is hereby corrected as shown below:

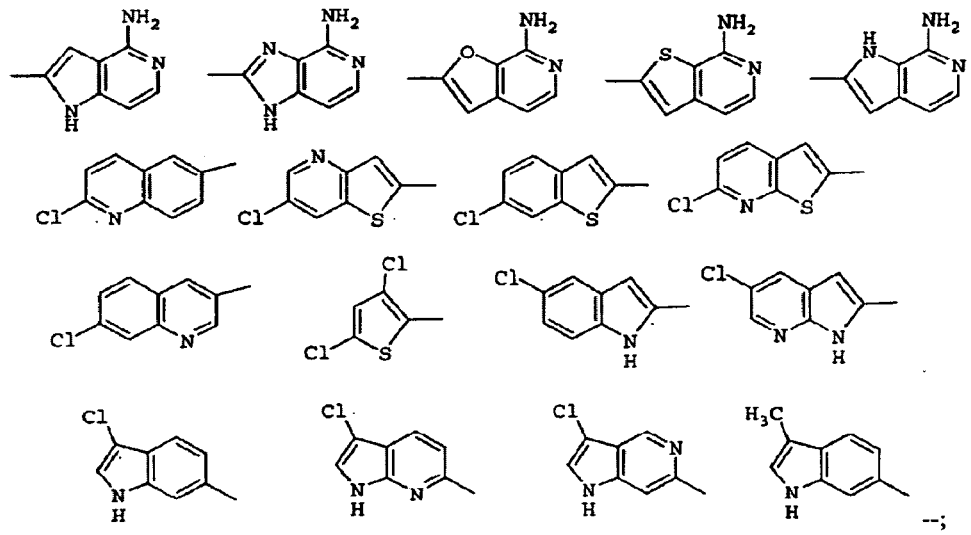

Column 242,
Line 46, delete the "R$^1$ b is selected from" and insert -- R$^{1b}$ is selected from --;

Column 251,
Line 18, delete the "A-B is selected from:" and insert -- A-B is selected from:

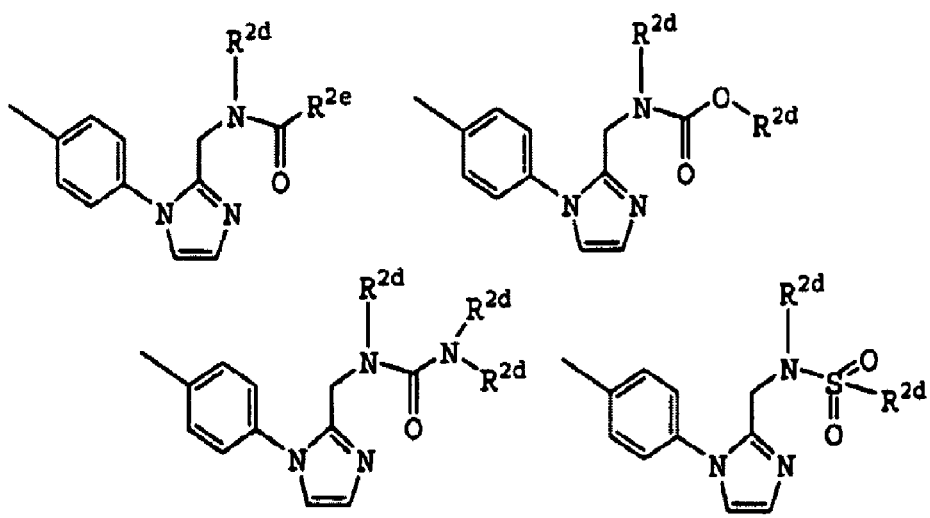

UNITED STATES PATENT AND TRADEMARK OFFICE
CERTIFICATE OF CORRECTION

PATENT NO.      : 6,949,550 B2
APPLICATION NO. : 10/304810
DATED           : September 27, 2005
INVENTOR(S)     : Mimi L. Quan and Ruth R. Wexler It is certified that error appears in the above-identified patent and that said Letters Patent is hereby corrected as shown below:

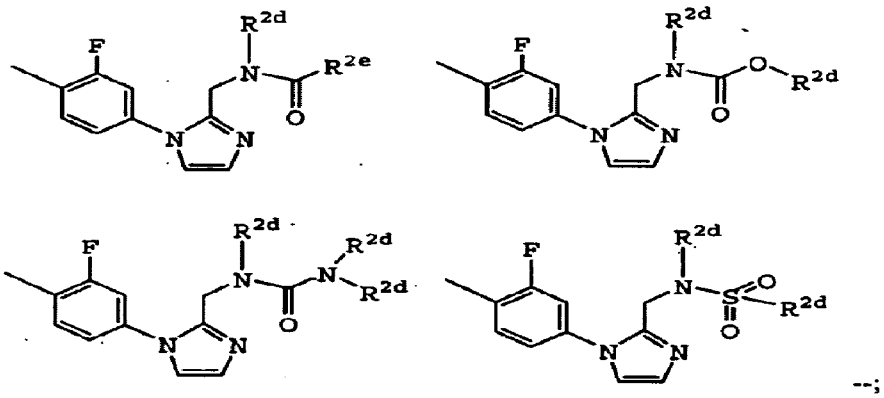

--;

Column 251,
Line 60, delete the "thrombophiebitis," and insert -- thrombophlebitis, --;

Column 252,
Line 43, delete the "thrombophiebitis," and insert -- thrombophlebitis, --;

Column 252,
Line 65, delete the "thrombophiebitis," and insert -- thrombophlebitis, --;

Column 253,
Line 20, delete the "thrombophiebitis," and insert -- thrombophlebitis, --;

Column 253,
Line 42, delete the "thrombophiebitis," and insert -- thrombophlebitis, --;

Column 254,
Line 6, delete the "thrombophiebitis," and insert -- thrombophlebitis, --;

UNITED STATES PATENT AND TRADEMARK OFFICE
CERTIFICATE OF CORRECTION

PATENT NO. : 6,949,550 B2
APPLICATION NO. : 10/304810
DATED : September 27, 2005
INVENTOR(S) : Mimi L. Quan and Ruth R. Wexler It is certified that error appears in the above-identified patent and that said Letters Patent is hereby corrected as shown below:

<u>Column 254,</u>
Line 28, delete the "thrombophiebitis," and insert -- thrombophlebitis, --;

<u>Column 254,</u>
Line 49, delete the "thrombophiebitis," and insert -- thrombophlebitis, --;

Signed and Sealed this

Seventeenth Day of October, 2006

JON W. DUDAS
*Director of the United States Patent and Trademark Office*